United States Patent
Woo et al.

(10) Patent No.: US 11,912,664 B2
(45) Date of Patent: Feb. 27, 2024

(54) DETERMINING SMALL MOLECULE-PROTEIN AND PROTEIN-PROTEIN INTERACTIONS

(71) Applicant: President and Fellows of Harvard College, Cambridge, MA (US)

(72) Inventors: Christina M. Woo, Cambridge, MA (US); Jinxu Gao, Somerville, MA (US); Yuka Amako, Watertown, MA (US); Chia Fu Chang, Cambridge, MA (US); Zhi Lin, Cambridge, MA (US); Hung-Yi Wu, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 880 days.

(21) Appl. No.: 16/620,372

(22) PCT Filed: Jun. 6, 2018

(86) PCT No.: PCT/US2018/036256
§ 371 (c)(1),
(2) Date: Dec. 6, 2019

(87) PCT Pub. No.: WO2018/226828
PCT Pub. Date: Dec. 13, 2018

(65) Prior Publication Data
US 2020/0140388 A1 May 7, 2020

Related U.S. Application Data

(60) Provisional application No. 62/651,599, filed on Apr. 2, 2018, provisional application No. 62/628,372, filed on Feb. 9, 2018, provisional application No. 62/515,846, filed on Jun. 6, 2017.

(51) Int. Cl.
*C07D 229/02* (2006.01)
*C07D 401/12* (2006.01)
*C07D 487/14* (2006.01)
*G01N 33/68* (2006.01)

(52) U.S. Cl.
CPC ......... *C07D 229/02* (2013.01); *C07D 401/12* (2013.01); *C07D 487/14* (2013.01); *G01N 33/6803* (2013.01); *G01N 33/6845* (2013.01)

(58) Field of Classification Search
CPC ... C07D 229/02; C07D 401/12; C07D 487/14
See application file for complete search history.

(56) References Cited

U.S. PATENT DOCUMENTS

2017/0115280 A1    4/2017   Hazen et al.

FOREIGN PATENT DOCUMENTS

WO    WO 2016-085659 A1    6/2016
WO    WO 2018/136555 A2 *  7/2018

OTHER PUBLICATIONS

Gao et al., Small Molecule Interactome Mapping by Photoaffinity Labeling Reveals Binding Site Hotspots for the NSAIDs, JACS, vol. 140, No. 12, pp. 4259-4268 (Mar. 15, 2018).*
Hulikal, Deuterium Labeled Compounds in Drug Discovery Process, Abstract, 2010.*
Pimlott, PubMed Abstract (Nucl Med Commun., 26(3):183-8), 2005.*
Invitation to Pay Additional Fees in connection with Application No. PCT/US2018/036256 dated Oct. 10, 2018.
International Search Report and Written Opinion in connection with Application No. PCT/US2018/036256 dated Jan. 10, 2019.
International Preliminary Report on Patentability in connection with Application No. PCT/US2018/036256 dated Dec. 19, 2019.
Brunner et al., 3-Trifluoromethyl-3-phenyldiazirine. A newcarbene generating group for photolabeling reagents. J Biol Chem. Apr. 25, 1980;255(8):3313-8.
Brunner, New photolabeling and crosslinking methods. Annu Rev Biochem. 1993;62:483-514.
Chandna et al., Synthesis of novel celecoxib analogues by bioisosteric replacement of sulfonamide as potent anti-inflammatory agents and cyclooxygenase inhibitors. Bioorg Med Chem. Aug. 1, 2013;21(15):4581-90.
Das, Aliphatic diazirines as photoaffinity probes for proteins: recent developments. Chem Rev. Aug. 10, 2011;111(8):4405-17.
Doerr et al., (2012) Mass spectrometry of intact protein complexes. Nature Methods, 10, doi: 10.1038/nmeth.2298.
Dubnisky et al., Diazirine based photoaffinity labeling. Bioorg Med Chem. Jan. 15, 2012;20(2):554-70.
Flaxman et al., Mapping the Small Molecule Interactome by Mass Spectrometry. Biochemistry. Jan. 16, 2018;57(2):186-193.
Gertsik et al., Mapping the Binding Site of BMS-708163 on γ-Secretase with Cleavable Photoprobes. Cell Chem Biol. Jan. 19, 2017;24(1):3-8. Extended PDF.
Gree et al., Effect of fluorine or oxygen atom(s) in propargylic position on the reactivity in click chemistry. Tet Lett. 2010; 51:2218-2221.

(Continued)

*Primary Examiner* — Deepak R Rao
(74) *Attorney, Agent, or Firm* — Wolf, Greenfield & Sacks, P.C.

(57) ABSTRACT

Provided herein are methods, systems, kits, and compositions useful for determining small molecule-protein interactions and protein-protein interactions. The photo-click tags provided herein can be conjugated to a small molecule or amino acid analog to provide compounds that can be integrated into a protein through photo-conjugation, allowing for identification of a small molecule-protein interaction or protein-protein interaction to elucidate the small molecules mechanism of action or the protein targeted by the small molecule. In some embodiments, the photo-click tags comprise a photo-conjugation moiety and a click chemistry handle, allowing for the attachment of various functional groups (e.g., affinity tags) to the small molecule or amino acid analog.

17 Claims, 40 Drawing Sheets
Specification includes a Sequence Listing.

(56) References Cited

OTHER PUBLICATIONS

Gundry et al., Preparation of proteins and peptides for mass spectrometry analysis in abottom-up proteomics workflow. Curr Protoc Mol Biol. Oct. 2009;Chapter10:Unit10.25.

Hatanaka, Development and leading-edge application of innovative photoaffinity labeling. Chem Pharm Bull (Tokyo). 2015;63(1):1-12.

Hein et al., Click chemistry, a powerful tool for pharmaceutical sciences. Pharm Res. Oct. 2008;25(10):2216-30.

Hein et al., Copper-catalyzed azide-alkyne cycloaddition (CuAAC) and beyond: new reactivity of copper(I) acetylides. Chem Soc Rev. Apr. 2010;39(4):1302-15.

Kalgutkar et al., Biochemically based design of cyclooxygenase-2 (COX-2) inhibitors: facile conversion of nonsteroidal antiinflammatory drugs to potent and highly selective COX-2 inhibitors. Proc Natl Acad Sci U S A. Jan. 18, 2000;97(2):925-30.

Keiser, Predicting new molecular targets for known drugs. Nature. Nov. 12, 2009;462(7270):175-81.

Kolb et al., The growing impact of click chemistry on drugdiscovery. Drug Discov Today. Dec. 15, 2003;8(24):1128-37.

Kolb et al., Click Chemistry: Diverse Chemical Function from a Few Good Reactions. Angew Chem Int Ed Engl. Jun. 1, 2001;40(11):2004-2021.

Krishnamurty et al., Active site profiling reveals coupling between domains in SRC-family kinases. Nat Chem Biol. 2013;9(1):43-50.

Kumar et al., Design and synthesis of an all-in-one 3-(1,1-difluoroprop-2-ynyl)-3H-diazirin-3-yl functional group for photo-affinity labeling. Bioorg Med Chem. Aug. 1, 2009;17(15):5388-95.

Lee et al., A potent and highly selective inhibitor of human alpha-1,3-ucosyltransferase via click chemistry. J Am Chem Soc. Aug. 13, 2003;125(32):9588-9.

Lewis et al., Click chemistry in situ: acetylcholinesterase as a reaction vessel for the selective assembly of a femtomolar inhibitor from an array of building blocks. Angew Chem Int Ed Engl. Mar. 15, 2002;41(6):1053-7.

Li et al., Design and synthesis of minimalist terminal alkyne-containing diazirine photo-crosslinkers and their incorporation into kinase inhibitors for cell- and tissue-based proteome profiling. Angew Chem Int Ed Engl. Aug. 12, 2013;52(33):8551-6.

Li et al., Design and synthesis of minimalist terminal alkyne-containing diazirine photo-crosslinkers and their incorporation into kinase inhibitors for cell- and tissue-based proteome profiling. Angew Chem Int Ed Engl. Jun. 10, 2013. doi: 10.1002/anie. 201300683. Supporting Information and Abstract Only. 9 pages.

Mackinnon et al., Target Identification by Diazirine Photo-Cross-linking and Click Chemistry. Curr Protoc Chem Biol. Dec. 2009;1:55-73.

Manetsch et al., In situ click chemistry: enzyme inhibitors made to their own specifications. J Am Chem Soc. Oct. 13, 2004;126(40):12809-18.

Mocharla et al., In situ click chemistry: enzyme-generated inhibitors of carbonic anhydrase II. Angew Chem Int Ed Engl. Dec. 17, 2004;44(1):116-20.

Palaniappan et al., Isotopic signature transfer and mass pattern prediction (IsoStamp): an enabling technique for chemically-directed proteomics. ACS Chem Biol. Aug. 19, 2011;6(8):829-36.

Pan et al., A Suite of "Minimalist" Photo-Crosslinkers for Live-Cell Imaging and Chemical Proteomics: Case Study with BRD4 Inhibitors. Angew Chem Int Ed Engl. 2017;56(39):11816-11821.

Parker et al., Ligand and Target Discovery by Fragment-Based Screening in Human Cells. Cell. Jan. 26, 2017;168(3):527-541.e29.

Ranjitkar et al., Affinity-based probes based on type II kinase inhibitors [published correction appears in J Am Chem Soc. Jan. 16, 2013;135(2):948. Swaney, Daniel L [corrected to Swaney, Danielle L]]. J Am Chem Soc. 2012;134(46):19017-19025.

Rostovtsev et al., A stepwise huisgencycloaddition process: copper(I)-catalyzed regioselective "ligation" of azides and terminal alkynes. Angew Chem Int Ed Engl. Jul. 15, 2002;41(14):2596-9.

Shi et al., Proteome profiling reveals potential cellular targets of staurosporine using a clickable cell-permeable probe. Chem Commun (Camb). 2011;47(40):11306-11308.

Shi et al., Cell-based proteome profiling of potential dasatinib targets by use of affinity-based probes. J Am Chem Soc. 2012;134(6):3001-3014.

Sinz, Investigation of protein-ligand interactions by mass spectrometry. ChemMedChem. Apr. 2007;2(4):425-31.

Su et al., Multiplex imaging and cellular target identification of kinase inhibitors via an affinity-based proteome profiling approach. Sci Rep. Jan. 12, 2015;5:7724.

Thul et al., A subcellular map of the human proteome. Science. May 26, 2017;356(6340).

Tomoe et al., Peptidotriazoles on solid phase:[1,2,3]-triazoles by regiospecific copper(i)-catalyzed 1,3-dipolar cycloadditions of terminal alkynes to azides. J Org Chem. May 3, 2002;67(9):3057-64.

Wang et al., Bioconjugation by copper(I)-catalyzed azide-alkyne [3+2] cycloaddition. J Am Chem Soc. Mar. 19, 2003;125(11):3192-3.

Woo et al., Isotope-targeted glycoproteomics (IsoTaG): a mass-independent platform for intact N- and O-glycopeptide discovery and analysis. Nat Methods. Jun. 2015;12(6):561-7.

Woo et al., Development of IsoTaG, a Chemical Glycoproteomics Technique for Profiling Intact N- and O-Glycopeptides from Whole Cell Proteomes. J ProteomeRes. Apr. 7, 2017;16(4):1706-1718.

Zhang et al., Refinements to label free proteome quantitation: how to deal with peptides shared by multiple proteins. Anal Chem. Mar. 15, 2010;82(6):2272-81.

Ziegler et al., Target identification for smallbioactive molecules: finding the needle in the haystack. Angew Chem Int Ed Engl. Mar. 4, 2013;52(10):2744-92.

Partial European Search Report for Application No. EP18813499.3, dated Sep. 28, 2020.

Extended European Search Report for Application No. EP18813499. 3, dated Jan. 19, 2021.

Head et al., Antifungal drug itraconazole targets VDAC1 to modulate the AMPK/mTOR signaling axis in endothelial cells. Proc Natl Acad Sci U S A. Dec. 29, 2015;112(52):E7276-85. doi: 10.1073/pnas.1512867112. Epub Dec. 10, 2015.

Wang et al., Fluorescein Derivatives as Bifunctional Molecules for the Simultaneous Inhibiting and Labeling of FTO Protein. J Am Chem Soc. Nov. 4, 2015;137(43):13736-9. doi: 10.1021/jacs. 5b06690. Epub Oct. 20, 2015.

Zhu et al., In Situ Proteome Profiling and Bioimaging Applications of Small-Molecule Affinity-Based Probes Derived From DOTIL Inhibitors. Chemistry. Jun. 1, 2016;22(23):7824-36. doi: 10.1002/chem.201600259. Epub Apr. 26, 2016.

\* cited by examiner

| Photo-NSAIDs | | NSAIDs | |
|---|---|---|---|
| Inhibitor | $IC_{50}$ (µM) | Inhibitor | $IC_{50}$ (µM) |
| Photo-naproxen (4) | 36.00 | Naproxen (1) | 11.35 |
| Photo-celecoxib (5) | 0.0366 | Celecoxib (2) | 0.0291 |
| Photo-indomethacin (6) | 33.53 | Indomethacin (3) | 15.43 |

| Photo-NSAIDs | | NSAIDs | |
|---|---|---|---|
| Inhibitor | IC$_{50}$ (μM) | Inhibitor | IC$_{50}$ (μM) |
| Photo-naproxen (4) | 23.598 | Naproxen (1) | 42.957 |
| Photo-celecoxib (5) | 21.157 | Celecoxib (2) | 40.936 |
| Photo-indomethacin (6) | 216.04 | Indomethacin (3) | 148.63 |
| Celecoxib analog 9 | >1000 | | |

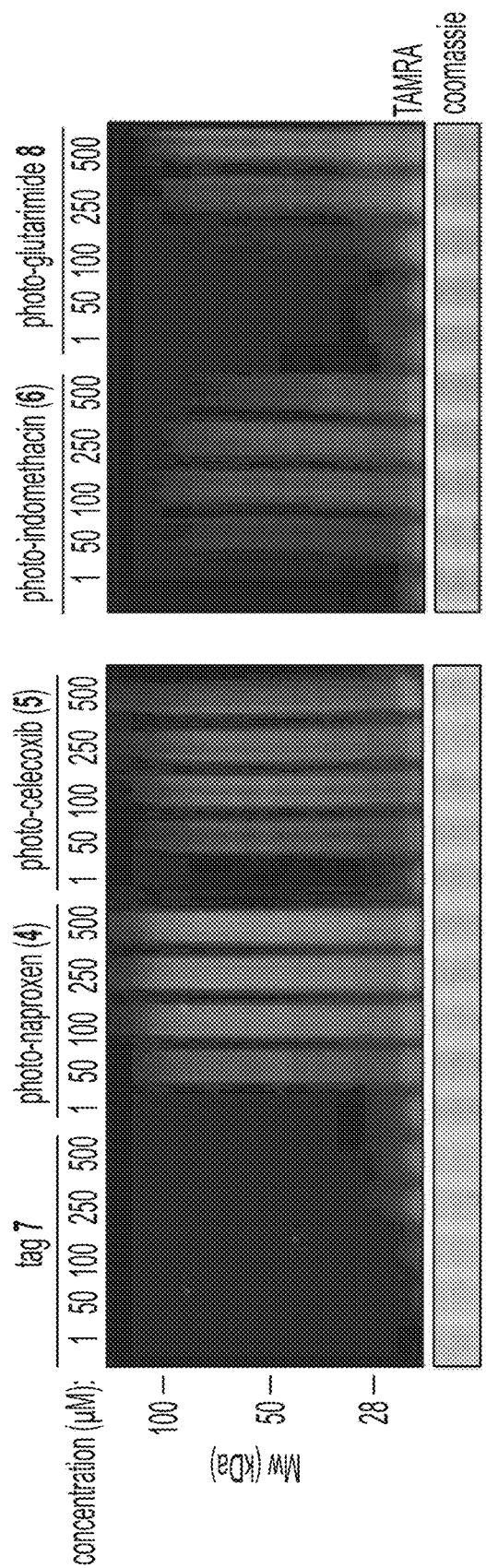
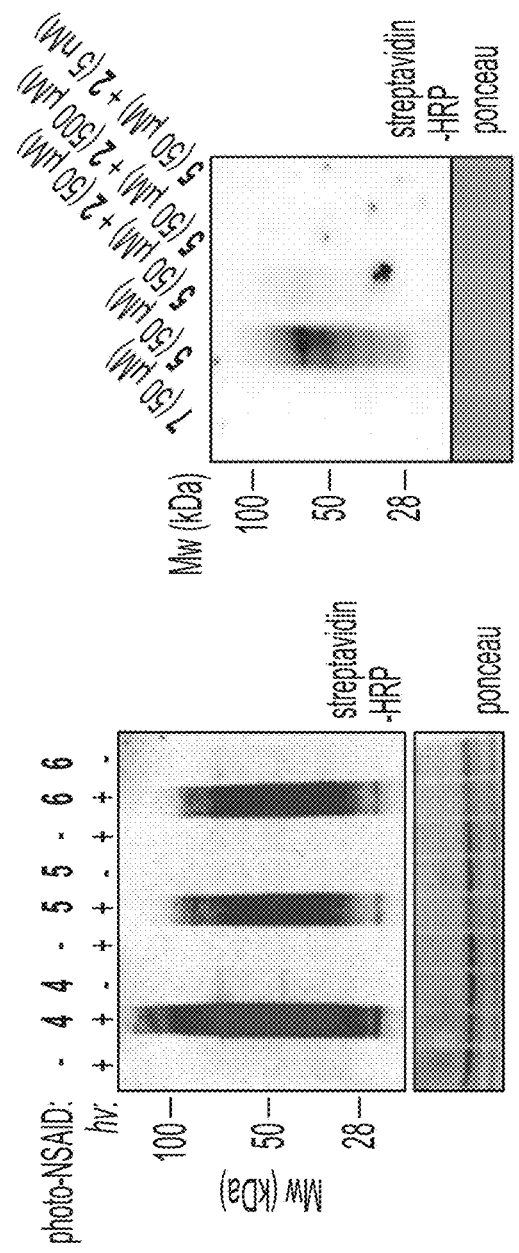
FIG. 18A
FIG. 18B
FIG. 18C

```
                         SEQUENCE LISTING

<160> NUMBER OF SEQ ID NOS: 624

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 1

Ala Met Gly Ile Met Asn Ser Phe Val Asn Asp Ile Phe Glu Arg
1               5                   10                  15

<210> SEQ ID NO 2
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 2

Val Gly Ala Gly Ala Pro Val Tyr Leu Ala Ala Val Leu Glu Tyr Leu
1               5                   10                  15

Thr Ala Glu Ile Leu Glu Leu Ala Gly Asn Ala Ala Arg
            20                  25

<210> SEQ ID NO 3
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 3

Val Ala Pro Glu Glu His Pro Val Leu Leu Thr Glu Ala Pro Leu Asn
1               5                   10                  15

Pro Lys

<210> SEQ ID NO 4
<211> LENGTH: 29
<212> TYPE: PRT
<213> ORGANISM: Artificial Sequence
```

-continued

```
<220> FEATURE:
<223> OTHER INFORMATION: Synthetic polypeptide

<400> SEQUENCE: 4

Val Gly Ala Gly Ala Pro Val Tyr Met Ala Ala Val Leu Glu Tyr Leu
1               5                   10                  15

Thr Ala Glu Ile Leu Glu Leu Ala Gly Asn Ala Ala Arg
            20                  25

<210> SEQ ID NO 5
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 5

Met Ser Val Gln Pro Thr Val Ser Leu Gly Gly Phe Glu Ile Thr Pro
1               5                   10                  15

Pro Val Val Leu Arg
            20

<210> SEQ ID NO 6
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 6

Asn Leu Glu Ala Leu Ala Leu Asp Leu Met Glu Pro Glu Gln Ala Val
1               5                   10                  15

Asp Leu Thr Leu Pro Lys
            20

<210> SEQ ID NO 7
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 7

Ile His Phe Pro Leu Ala Thr Tyr Ala Pro Val Ile Ser Ala Glu Lys
1               5                   10                  15

<210> SEQ ID NO 8
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 8

Val Gly Ala Gly Ala Pro Val Tyr Leu Ala Ala Val Leu Glu Tyr Leu
1               5                   10                  15

Thr Ala Glu Ile Leu Glu Leu Ala Gly Asn Ala Ala Arg Asp Asn Lys
            20                  25                  30

Lys

<210> SEQ ID NO 9
<211> LENGTH: 10
<212> TYPE: PRT
<213> ORGANISM: Artificial Sequence
```

```
<220> FEATURE:
<223> OTHER INFORMATION: Synthetic polypeptide

<400> SEQUENCE: 9

Ile Ser Gly Leu Ile Tyr Glu Glu Thr Arg
1               5                   10

<210> SEQ ID NO 10
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 10

Val Glu Thr Gly Val Leu Lys Pro Gly Met Val Val Thr Phe Ala Pro
1               5                   10                  15

Val Asn Val Thr Thr Glu Val Lys
            20

<210> SEQ ID NO 11
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 11

Ala Ile Gly Ala Val Pro Leu Ile Gln Gly Glu Tyr Met Ile Pro Cys
1               5                   10                  15

Glu Lys

<210> SEQ ID NO 12
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 12

Gly Leu Asn Asp Ile Phe Glu Ala Gln Lys Ile Glu Trp His Glu
1               5                   10                  15

<210> SEQ ID NO 13
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 13

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 14
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 14

Glu Glu Glu Glu Glu Glu
```

```
<210> SEQ ID NO 15
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 15

Gly Ala Pro Val Pro Tyr Pro Asp Pro Leu Glu Pro Arg
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 16

Asp Tyr Lys Asp Asp Asp Asp Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 17

Tyr Pro Tyr Asp Val Pro Asp Tyr Ala
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 18

His His His His His His
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 19

Glu Gln Lys Leu Ile Ser Glu Glu Asp Leu
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 20

Thr Lys Glu Asn Pro Arg Ser Asn Gln Glu Glu Ser Tyr Asp Asp Asn
1               5                   10                  15
```

Glu Ser

<210> SEQ ID NO 21
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 21

Lys Glu Thr Ala Ala Ala Lys Phe Glu Arg Gln His Met Asp Ser
1               5                   10                  15

<210> SEQ ID NO 22
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 22

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 23
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 23

Ser Leu Ala Glu Leu Leu Asn Ala Gly Leu Gly Gly Ser
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 24

Thr Gln Asp Pro Ser Arg Val Gly
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 25

Trp Ser His Pro Gln Phe Glu Lys
1               5

<210> SEQ ID NO 26
<211> LENGTH: 6
<212> TYPE: PRT
<213> ORGANISM: Artificial Sequence

```
<220> FEATURE:
<223> OTHER INFORMATION: Synthetic polypeptide

<400> SEQUENCE: 26

Cys Cys Pro Gly Cys Cys
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 27

Glu Val His Thr Asn Gln Asp Pro Leu Asp
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 28

Gly Lys Pro Ile Pro Asn Pro Leu Leu Gly Leu Asp Ser Thr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 29

Tyr Thr Asp Ile Glu Met Asn Arg Leu Gly Lys
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 30

Asp Leu Tyr Asp Asp Asp Asp Lys
1               5

<210> SEQ ID NO 31
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 31

Thr Asp Lys Asp Met Thr Ile Thr Phe Thr Asn Lys Lys Asp Ala Glu
1               5                   10                  15

<210> SEQ ID NO 32
<211> LENGTH: 13
<212> TYPE: PRT
<213> ORGANISM: Artificial Sequence
<220> FEATURE:
```

<223> OTHER INFORMATION: Synthetic polypeptide

<400> SEQUENCE: 32

Ala His Ile Val Met Val Asp Ala Tyr Lys Pro Thr Lys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 33

Lys Leu Gly Asp Ile Glu Phe Ile Lys Val Asn Lys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 34

Lys Leu Gly Ser Ile Glu Phe Ile Lys Val Asn Lys
1               5                   10

<210> SEQ ID NO 35
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 35

Asp Ile Pro Ala Thr Tyr Glu Phe Thr Asp Gly Lys His Tyr Ile Thr
1               5                   10                  15

Asn Glu Pro Ile Pro Pro Lys
            20

<210> SEQ ID NO 36
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 36

Gln Leu Pro Asp Ser Asn Glu Ile Val Glu Lys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 37

Tyr Gln Ile Ile Asp Gly Glu Met Tyr Pro Pro Thr Val Lys
1               5                   10

<210> SEQ ID NO 38
<211> LENGTH: 16
<212> TYPE: PRT

```
<213> ORGANISM: Artificial Sequence
<220> FEATURE:
<223> OTHER INFORMATION: Synthetic polypeptide

<400> SEQUENCE: 38

Leu Ile Leu Ile Gly Glu Thr Ile Lys Ile Val Ile Glu Asp Tyr Val
1               5                   10                  15

<210> SEQ ID NO 39
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 39

Tyr Gln Ser Phe Asn Glu Tyr Arg
1               5

<210> SEQ ID NO 40
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 40

Arg Phe Met Leu Lys Pro Tyr Glu Ser Phe Glu Glu Leu Thr Gly Glu
1               5                   10                  15

Lys Glu Met Ser Ala
            20

<210> SEQ ID NO 41
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 41

Gly Cys Pro Phe Thr Ser Phe Ser Val Pro Asp Pro Glu Leu Ile Lys
1               5                   10                  15

Thr Val Thr Ile Asn Ala Ser Ser Ser Arg Ser Gly Leu Asp Asp
            20                  25                  30

<210> SEQ ID NO 42
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 42

Leu Phe Leu Lys Pro Thr Pro Asn Thr Val His Tyr Ile Leu Thr His
1               5                   10                  15

Phe Lys

<210> SEQ ID NO 43
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 43
```

```
Ile Leu Thr His Phe Lys Gly Phe Trp Asn Val Val Asn Asn Ile Pro
1               5                   10                  15

Phe Leu Arg
```

<210> SEQ ID NO 44
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 44

```
Pro Pro Thr Tyr Asn Ala Asp Tyr Gly Tyr Lys
1               5                   10
```

<210> SEQ ID NO 45
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 45

```
Leu Ile Leu Ile Gly Glu Thr Ile Lys Ile Val Ile Glu Asp Tyr Val
1               5                   10                  15

Gln His Leu Ser Gly Tyr His Phe Lys Leu Lys Phe
            20                  25
```

<210> SEQ ID NO 46
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 46

```
Val Ile Glu Asp Tyr Val Gln His Leu Ser Gly Tyr His Phe Lys
1               5                   10                  15
```

<210> SEQ ID NO 47
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 47

```
Ser Phe Thr Arg Gln Ile Ala Gly Arg Val Ala Gly Gly Arg
1               5                   10
```

<210> SEQ ID NO 48
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 48

```
Thr Val Thr Ile Asn Ala Ser Ser Ser Arg Ser
1               5                   10
```

<210> SEQ ID NO 49
<211> LENGTH: 12
<212> TYPE: PRT
<213> ORGANISM: Artificial Sequence
<220> FEATURE:

```
<223> OTHER INFORMATION: Synthetic polypeptide

<400> SEQUENCE: 49

Ser Gly Leu Asp Asp Ile Asn Pro Thr Val Leu Leu
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 50

Arg Leu Glu Gly Leu Thr Asp Glu Ile Asn Phe Leu Arg Gln
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 51

Arg Leu Glu Gly Leu Thr Asp Glu Ile Asn Phe Leu Arg Gln
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 52

Arg Leu Glu Gly Leu Thr Asp Glu Ile Asn Phe Leu Arg Gln
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 53

Lys Leu Ser Glu Leu Glu Ala Ala Leu Gln Arg Ala
1               5                   10

<210> SEQ ID NO 54
<211> LENGTH: 14
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Nap_SiC2N3

<400> SEQUENCE: 54

Arg Leu Glu Gly Leu Thr Asp Glu Ile Asn Phe Leu Arg Gln
1               5                   10

<210> SEQ ID NO 55
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by Carbamidomethyl
<220> FEATURE:
<221> NAME/KEY: Misc_feature
<222> LOCATION: (23)..(23)
<223> OTHER INFORMATION: modified by CW_minimalist_Si2N3

<400> SEQUENCE: 55

Arg Cys Glu Lys Gln Ser Pro Gly Val Ala Asn Glu Leu Leu Lys Glu
1               5                   10                  15

Tyr Leu Val Thr Leu Ala Lys Gly
            20

<210> SEQ ID NO 56
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 56

Lys Ile Glu Asp Leu Ser Gln Gln Ala Gln Leu Ala Ala Ala Glu Lys
1               5                   10                  15

Phe

<210> SEQ ID NO 57
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 57

Lys Ile Glu Asp Leu Ser Gln Gln Ala Gln Leu Ala Ala Ala Glu Lys
1               5                   10                  15

Phe

<210> SEQ ID NO 58
<211> LENGTH: 17
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Nap_SiC2N3

<400> SEQUENCE: 58

Lys Ile Glu Asp Leu Ser Gln Gln Ala Gln Leu Ala Ala Ala Glu Lys
1               5                   10                  15

Phe

<210> SEQ ID NO 59
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3

<400> SEQUENCE: 59

Lys Ile Glu Asp Leu Ser Gln Gln Ala Gln Leu Ala Ala Ala Glu Lys
1               5                   10                  15

Phe

<210> SEQ ID NO 60
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 60

Lys Ile Glu Asp Leu Ser Gln Gln Ala Gln Leu Ala Ala Ala Glu Lys
1               5                   10                  15

Phe

<210> SEQ ID NO 61
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_miniGL_SiON3

<400> SEQUENCE: 61

Arg Gly Ile Ser Asp Pro Leu Thr Val Phe Glu Gln Thr Glu Ala Ala
1               5                   10                  15

Ala Arg Glu

<210> SEQ ID NO 62
<211> LENGTH: 8
<212> TYPE: PRT
<213> ORGANISM: Artificial Sequence
<220> FEATURE:
<223> OTHER INFORMATION: Synthetic polypeptide
```

```
<220> FEATURE:
<221> NAME/KEY: Misc_feature
<222> LOCATION: (3)..(3)
<223> OTHER INFORMATION: modified by CW_Nap_SiC0N3

<400> SEQUENCE: 62

Arg Arg Leu Gly Leu Glu Arg Asn
1               5

<210> SEQ ID NO 63
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_minimalist_Si2N3
<220> FEATURE:
<221> NAME/KEY: Misc_feature
<222> LOCATION: (9)..(9)
<223> OTHER INFORMATION: modified by CW_minimalist_Si2N3

<400> SEQUENCE: 63

Arg Gly Glu Leu Pro Asp Phe Gln Asp Gly Thr Lys Ala Thr Phe His
1               5                   10                  15

Tyr Arg Thr Leu His Ser Asp Asp Glu Gly Thr Val Leu Asp Asp Ser
            20                  25                  30

Arg Ala

<210> SEQ ID NO 64
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 64

Arg Leu Glu Glu Pro Ser Leu Arg Cys Val Glu Leu Val His Glu Glu
1               5                   10                  15

Met Gln Arg Ile
            20

<210> SEQ ID NO 65
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 65

Lys Tyr Pro Ala Ser Thr Val Gln Ile Leu Gly Ala Glu Lys Ala
1               5                   10                  15

<210> SEQ ID NO 66
<211> LENGTH: 27
<212> TYPE: PRT
<213> ORGANISM: Artificial Sequence
<220> FEATURE:
```

```
<223> OTHER INFORMATION: Synthetic polypeptide
<220> FEATURE:
<221> NAME/KEY: Misc_feature
<222> LOCATION: (16)..(16)
<223> OTHER INFORMATION: modified by Oxidation
<220> FEATURE:
<221> NAME/KEY: Misc_feature
<222> LOCATION: (26)..(26)
<223> OTHER INFORMATION: modified by CW_miniGL_Si0N3

<400> SEQUENCE: 66

Lys Met Trp Val Asp Arg Tyr Leu Ala Phe Thr Glu Glu Lys Ala Met
1               5                   10                  15

Gly Met Thr Asn Leu Pro Ala Val Gly Arg Lys
            20                  25

<210> SEQ ID NO 67
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 67

Lys Glu Ala Ile Arg Ile Ser Pro Thr Phe Ala Asp Ala Tyr Ser Asn
1               5                   10                  15

Met Gly Asn Thr Leu Lys Glu
            20

<210> SEQ ID NO 68
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Nap_SiC2N3

<400> SEQUENCE: 68

Lys Asn Ala Gly Asn Cys Leu Ser Pro Ala Val Ile Val Gly Leu Leu
1               5                   10                  15

Lys Glu

<210> SEQ ID NO 69
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Nap_SiC2N3

<400> SEQUENCE: 69

Lys Asn Ala Gly Asn Cys Leu Ser Pro Ala Val Ile Val Gly Leu Leu
1               5                   10                  15

Lys Glu

<210> SEQ ID NO 70
<211> LENGTH: 17
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Cele_SiC2N3

<400> SEQUENCE: 70

Lys Leu Gln Leu Asp Ser Pro Glu Asp Ala Glu Phe Ile Val Ala Lys
1               5                   10                  15

Ala

<210> SEQ ID NO 71
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Nap_SiC0N3

<400> SEQUENCE: 71

Lys Asp Glu Lys Gln Asn Leu Leu Ser Val Gly Asp Tyr Arg His
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Cele_SiC2N3

<400> SEQUENCE: 72

Lys Thr Met Leu Glu Thr Glu Glu Gly Ile Leu Leu Leu Val Arg Ala
1               5                   10                  15

<210> SEQ ID NO 73
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 73

Lys Gln Val His Pro Asp Thr Gly Ile Ser Ser Lys Ala
1               5                   10

<210> SEQ ID NO 74
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
```

```
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (12)..(12)
<223> OTHER INFORMATION: modified by CW_Cele_SiC2N3

<400> SEQUENCE: 74

Lys Ala Met Gly Ile Met Asn Ser Phe Val Asn Asp Ile Phe Glu Arg
1               5                   10                  15

Ile

<210> SEQ ID NO 75
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (16)..(16)
<223> OTHER INFORMATION: modified by CW_Cele_SiC2N3

<400> SEQUENCE: 75

Lys Ala Met Gly Ile Met Asn Ser Phe Val Asn Asp Ile Phe Glu Arg
1               5                   10                  15

Ile

<210> SEQ ID NO 76
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (14)..(14)
<223> OTHER INFORMATION: modified by CW_Cele_SiC2N3

<400> SEQUENCE: 76

Lys Ala Met Gly Ile Met Asn Ser Phe Val Asn Asp Ile Phe Glu Arg
1               5                   10                  15

Ile

<210> SEQ ID NO 77
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
```

```
<223> OTHER INFORMATION: modified by Oxidation
<220> FEATURE:
<221> NAME/KEY: Misc_feature
<222> LOCATION: (12)..(12)
<223> OTHER INFORMATION: modified by CW_Cele_SiC2N3

<400> SEQUENCE: 77

Lys Ala Met Gly Ile Met Asn Ser Phe Val Asn Asp Ile Phe Glu Arg
1               5                   10                  15

Ile

<210> SEQ ID NO 78
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (16)..(16)
<223> OTHER INFORMATION: modified by CW_Cele_SiC2N3

<400> SEQUENCE: 78

Lys Ala Met Gly Ile Met Asn Ser Phe Val Asn Asp Ile Phe Glu Arg
1               5                   10                  15

Ile

<210> SEQ ID NO 79
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (12)..(12)
<223> OTHER INFORMATION: modified by CW_Cele_SiC2N3

<400> SEQUENCE: 79

Lys Ala Met Gly Ile Met Asn Ser Phe Val Asn Asp Ile Phe Glu Arg
1               5                   10                  15

Ile

<210> SEQ ID NO 80
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (16)..(16)
<223> OTHER INFORMATION: modified by CW_Nap_SiC2N3
```

-continued

<400> SEQUENCE: 80

Lys Ala Met Gly Ile Met Asn Ser Phe Val Asn Asp Ile Phe Glu Arg
1               5                   10                  15

Ile

<210> SEQ ID NO 81
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 81

Lys Ala Met Gly Ile Met Asn Ser Phe Val Asn Asp Ile Phe Glu Arg
1               5                   10                  15

Ile

<210> SEQ ID NO 82
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (16)..(16)
<223> OTHER INFORMATION: modified by CW_Nap_SiC2N3

<400> SEQUENCE: 82

Lys Ala Met Gly Ile Met Asn Ser Phe Val Asn Asp Ile Phe Glu Arg
1               5                   10                  15

Ile

<210> SEQ ID NO 83
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (15)..(15)

<223> OTHER INFORMATION: modified by CW_Nap_SiC2N3

<400> SEQUENCE: 83

Lys Ala Met Gly Ile Met Asn Ser Phe Val Asn Asp Ile Phe Glu Arg
1               5                   10                  15

Ile

<210> SEQ ID NO 84
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 84

Lys Ala Met Gly Ile Met Asn Ser Phe Val Asn Asp Ile Phe Glu Arg
1               5                   10                  15

Ile

<210> SEQ ID NO 85
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 85

Lys Ala Met Gly Ile Met Asn Ser Phe Val Asn Asp Ile Phe Glu Arg
1               5                   10                  15

Ile

<210> SEQ ID NO 86
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (6)..(6)
<223> OTHER INFORMATION: modified by Oxidation
<220> FEATURE:

```
<221> NAME/KEY: Misc_feature
<222> LOCATION: (12)..(12)
<223> OTHER INFORMATION: modified by CW_Nap_SiC2N3

<400> SEQUENCE: 86

Lys Ala Met Gly Ile Met Asn Ser Phe Val Asn Asp Ile Phe Glu Arg
1               5                   10                  15

Ile

<210> SEQ ID NO 87
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (16)..(16)
<223> OTHER INFORMATION: modified by CW_Nap_SiC2N3

<400> SEQUENCE: 87

Lys Ala Met Gly Ile Met Asn Ser Phe Val Asn Asp Ile Phe Glu Arg
1               5                   10                  15

Ile

<210> SEQ ID NO 88
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 88

Lys Ala Met Gly Ile Met Asn Ser Phe Val Asn Asp Ile Phe Glu Arg
1               5                   10                  15

Ile

<210> SEQ ID NO 89
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 89

Lys Ala Met Gly Ile Met Asn Ser Phe Val Asn Asp Ile Phe Glu Arg
1               5                   10                  15

Ile
```

```
<210> SEQ ID NO 90
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 90

Lys Ala Met Gly Ile Met Asn Ser Phe Val Asn Asp Ile Phe Glu Arg
1               5                   10                  15

Ile

<210> SEQ ID NO 91
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (16)..(16)
<223> OTHER INFORMATION: modified by CW_Nap_SiC2N3

<400> SEQUENCE: 91

Lys Ala Met Gly Ile Met Asn Ser Phe Val Asn Asp Ile Phe Glu Arg
1               5                   10                  15

Ile

<210> SEQ ID NO 92
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (14)..(14)
<223> OTHER INFORMATION: modified by CW_Nap_SiC2N3

<400> SEQUENCE: 92

Lys Ala Met Gly Ile Met Asn Ser Phe Val Asn Asp Ile Phe Glu Arg
1               5                   10                  15

Ile

<210> SEQ ID NO 93
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
```

```
<222> LOCATION: (3)..(3)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 93

Lys Ala Met Gly Ile Met Asn Ser Phe Val Asn Asp Ile Phe Glu Arg
1               5                   10                  15

Ile

<210> SEQ ID NO 94
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (12)..(12)
<223> OTHER INFORMATION: modified by CW_Nap_SiC2N3

<400> SEQUENCE: 94

Lys Ala Met Gly Ile Met Asn Ser Phe Val Asn Asp Ile Phe Glu Arg
1               5                   10                  15

Ile

<210> SEQ ID NO 95
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (16)..(16)
<223> OTHER INFORMATION: modified by CW_Nap_SiC2N3

<400> SEQUENCE: 95

Lys Ala Met Gly Ile Met Asn Ser Phe Val Asn Asp Ile Phe Glu Arg
1               5                   10                  15

Ile

<210> SEQ ID NO 96
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (12)..(12)
<223> OTHER INFORMATION: modified by CW_Nap_SiC2N3

<400> SEQUENCE: 96

Lys Ala Met Gly Ile Met Asn Ser Phe Val Asn Asp Ile Phe Glu Arg
```

<210> SEQ ID NO 97
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 97

Lys Ala Met Gly Ile Met Asn Ser Phe Val Asn Asp Ile Phe Glu Arg
1               5                   10                  15

Ile

<210> SEQ ID NO 98
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 98

Lys Ala Met Gly Ile Met Asn Ser Phe Val Asn Asp Ile Phe Glu Arg
1               5                   10                  15

Ile

<210> SEQ ID NO 99
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 99

Lys Ala Met Gly Ile Met Asn Ser Phe Val Asn Asp Ile Phe Glu Arg
1               5                   10                  15

Ile

<210> SEQ ID NO 100
<211> LENGTH: 17
<212> TYPE: PRT
<213> ORGANISM: Artificial Sequence
<220> FEATURE:

<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (16)..(16)
<223> OTHER INFORMATION: modified by CW_Nap_SiC2N3

<400> SEQUENCE: 100

Lys Ala Met Gly Ile Met Asn Ser Phe Val Asn Asp Ile Phe Glu Arg
1               5                   10                  15

Ile

<210> SEQ ID NO 101
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Nap_SiC2N3

<400> SEQUENCE: 101

Lys Ala Met Gly Ile Met Asn Ser Phe Val Asn Asp Ile Phe Glu Arg
1               5                   10                  15

Ile

<210> SEQ ID NO 102
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Nap_SiC2N3

<400> SEQUENCE: 102

Lys Ala Met Gly Ile Met Asn Ser Phe Val Asn Asp Ile Phe Glu Arg
1               5                   10                  15

Ile

<210> SEQ ID NO 103
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 103

Lys Ala Met Gly Ile Met Asn Ser Phe Val Asn Asp Ile Phe Glu Arg
1               5                   10                  15

Ile

<210> SEQ ID NO 104
<211> LENGTH: 17
<212> TYPE: PRT
<213> ORGANISM: Artificial Sequence

```
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (12)..(12)
<223> OTHER INFORMATION: modified by oxidation CW_Cele_SiC2N3

<400> SEQUENCE: 104

Lys Ala Met Gly Ile Met Asn Ser Phe Val Asn Asp Ile Phe Glu Arg
1               5                   10                  15

Ile

<210> SEQ ID NO 105
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (12)..(12)
<223> OTHER INFORMATION: modified by oxidation CW_Cele_SiC2N3

<400> SEQUENCE: 105

Lys Ala Met Gly Ile Met Asn Ser Phe Val Asn Asp Ile Phe Glu Arg
1               5                   10                  15

Ile

<210> SEQ ID NO 106
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (12)..(12)
<223> OTHER INFORMATION: modified by oxidation CW_Cele_SiC2N3

<400> SEQUENCE: 106

Lys Ala Met Gly Ile Met Asn Ser Phe Val Asn Asp Ile Phe Glu Arg
1               5                   10                  15

Ile

<210> SEQ ID NO 107
<211> LENGTH: 17
<212> TYPE: PRT
<213> ORGANISM: Artificial Sequence
<220> FEATURE:
<223> OTHER INFORMATION: Synthetic polypeptide
```

```
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (8)..(8)
<223> OTHER INFORMATION: modified by oxidation CW_Cele_SiC2N3

<400> SEQUENCE: 107

Lys Ala Met Gly Ile Met Asn Ser Phe Val Asn Asp Ile Phe Glu Arg
1               5                   10                  15

Ile

<210> SEQ ID NO 108
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (12)..(12)
<223> OTHER INFORMATION: modified by oxidation CW_Cele_SiC2N3

<400> SEQUENCE: 108

Lys Ala Met Gly Ile Met Asn Ser Phe Val Asn Asp Ile Phe Glu Arg
1               5                   10                  15

Ile

<210> SEQ ID NO 109
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (10)..(10)
<223> OTHER INFORMATION: modified by oxidation CW_Cele_SiC2N3

<400> SEQUENCE: 109

Lys Ala Met Gly Ile Met Asn Ser Phe Val Asn Asp Ile Phe Glu Arg
1               5                   10                  15

Ile

<210> SEQ ID NO 110
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
```

```
<222> LOCATION: (19)..(19)
<223> OTHER INFORMATION: modified by oxidation CW_Cele_SiC2N3

<400> SEQUENCE: 110

Lys Ala Met Gly Ile Met Asn Ser Phe Val Asn Asp Ile Phe Glu Arg
1               5                   10                  15

Ile Ala Gly Glu Ala Ser Arg Leu
            20

<210> SEQ ID NO 111
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Cele_SiC2N3

<400> SEQUENCE: 111

Lys Gln Val His Pro Asp Thr Gly Ile Ser Ser Lys Ala
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (5)..(5)
<223> OTHER INFORMATION: modified by CW_Indo_SiC2N3
<220> FEATURE:
<221> NAME/KEY: Misc_feature
<222> LOCATION: (6)..(6)
<223> OTHER INFORMATION: modified by oxidation

<400> SEQUENCE: 112

Lys Ala Met Gly Ile Met Asn Ser Phe Val Asn Asp Ile Phe Glu Arg
1               5                   10                  15

Ile

<210> SEQ ID NO 113
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (16)..(16)
<223> OTHER INFORMATION: modified by CW_Nap_SiC2N3

<400> SEQUENCE: 113

Lys Ala Met Gly Ile Met Asn Ser Phe Val Asn Asp Ile Phe Glu Arg
1               5                   10                  15
```

-continued

Ile

<210> SEQ ID NO 114
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 114

Lys Ala Met Gly Ile Met Asn Ser Phe Val Asn Asp Ile Phe Glu Arg
1               5                   10                  15

Ile

<210> SEQ ID NO 115
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 115

Lys Ala Met Gly Ile Met Asn Ser Phe Val Asn Asp Ile Phe Glu Arg
1               5                   10                  15

Ile

<210> SEQ ID NO 116
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 116

```
Lys Ala Met Gly Ile Met Asn Ser Phe Val Asn Asp Ile Phe Glu Arg
1               5                   10                  15

Ile

<210> SEQ ID NO 117
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (16)..(16)
<223> OTHER INFORMATION: modified by CW_Nap_SiC2N3

<400> SEQUENCE: 117

Lys Ala Met Gly Ile Met Asn Ser Phe Val Asn Asp Ile Phe Glu Arg
1               5                   10                  15

Ile

<210> SEQ ID NO 118
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 118

Lys Ala Met Gly Ile Met Asn Ser Phe Val Asn Asp Ile Phe Glu Arg
1               5                   10                  15

Ile

<210> SEQ ID NO 119
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (16)..(16)
<223> OTHER INFORMATION: modified by CW_Nap_SiC2N3

<400> SEQUENCE: 119

Lys Ala Met Gly Ile Met Asn Ser Phe Val Asn Asp Ile Phe Glu Arg
1               5                   10                  15

Ile

<210> SEQ ID NO 120
<211> LENGTH: 17
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by oxidation
<220> FEATURE:
<221> NAME/KEY: Misc_feature
<222> LOCATION: (14)..(14)
<223> OTHER INFORMATION: modified by CW_Nap_SiC2N3

<400> SEQUENCE: 120

Lys Ala Met Gly Ile Met Asn Ser Phe Val Asn Asp Ile Phe Glu Arg
1               5                   10                  15

Ile

<210> SEQ ID NO 121
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (15)..(15)
<223> OTHER INFORMATION: modified by CW_Nap_SiC2N3

<400> SEQUENCE: 121

Lys Ala Met Gly Ile Met Asn Ser Phe Val Asn Asp Ile Phe Glu Arg
1               5                   10                  15

Ile

<210> SEQ ID NO 122
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 122

Lys Ala Met Gly Ile Met Asn Ser Phe Val Asn Asp Ile Phe Glu Arg
1               5                   10                  15

Ile

<210> SEQ ID NO 123
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 123

Lys Ala Met Gly Ile Met Asn Ser Phe Val Asn Asp Ile Phe Glu Arg
1               5                   10                  15

Ile
```

```
<210> SEQ ID NO 124
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 124

Lys Ala Met Gly Ile Met Asn Ser Phe Val Asn Asp Ile Phe Glu Arg
1               5                   10                  15

Ile

<210> SEQ ID NO 125
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 125

Lys Ala Met Gly Ile Met Asn Ser Phe Val Asn Asp Ile Phe Glu Arg
1               5                   10                  15

Ile

<210> SEQ ID NO 126
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 126

Lys Ala Met Gly Ile Met Asn Ser Phe Val Asn Asp Ile Phe Glu Arg
1               5                   10                  15

Ile

<210> SEQ ID NO 127
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by oxidation
<220> FEATURE:
<221> NAME/KEY: Misc_feature
<222> LOCATION: (16)..(16)
<223> OTHER INFORMATION: modified by CW_Nap_SiC2N3

<400> SEQUENCE: 127

Lys Ala Met Gly Ile Met Asn Ser Phe Val Asn Asp Ile Phe Glu Arg
1               5                   10                  15

Ile
```

```
<210> SEQ ID NO 128
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Nap_SiC2N3

<400> SEQUENCE: 128

Lys Ala Met Gly Ile Met Asn Ser Phe Val Asn Asp Ile Phe Glu Arg
1               5                   10                  15

Ile

<210> SEQ ID NO 129
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 129

Lys Ala Met Gly Ile Met Asn Ser Phe Val Asn Asp Ile Phe Glu Arg
1               5                   10                  15

Ile

<210> SEQ ID NO 130
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Indo_SiC2N3

<400> SEQUENCE: 130

Lys Glu Glu Leu Glu Gln Lys Cys Lys Ser Val Asn Thr Arg Leu
1               5                   10                  15

<210> SEQ ID NO 131
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Cele_SiC0N3

<400> SEQUENCE: 131

Arg Leu Val Ser Pro Gly Ser Ala Asn Glu Thr Ser Ser Ile Leu Val
1               5                   10                  15

Glu Ser Val Thr Arg Ser
                20

<210> SEQ ID NO 132
<211> LENGTH: 23
```

-continued

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (22)..(22)
<223> OTHER INFORMATION: modified by CW_Cele_SiC0N3

<400> SEQUENCE: 132

Lys Ser Ser Thr Ala Ile Ser Ser Ile Ala Ala Asp Gly Glu Phe Leu
1               5                   10                  15

His Glu Leu Glu Glu Lys Met
            20

<210> SEQ ID NO 133
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Nap_SiC0N3
<220> FEATURE:
<221> NAME/KEY: Misc_feature
<222> LOCATION: (10)..(10)
<223> OTHER INFORMATION: modified by oxidation
<220> FEATURE:
<221> NAME/KEY: Misc_feature
<222> LOCATION: (20)..(20)
<223> OTHER INFORMATION: modified by oxidation

<400> SEQUENCE: 133

Lys Val Gln Gln Arg Leu Ile Gly Phe Met Arg Pro Glu Asn Gly Asn
1               5                   10                  15

Pro Gln Gln Met Gln Gln Glu Leu Gln Arg Lys
            20                  25

<210> SEQ ID NO 134
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC0N3

<400> SEQUENCE: 134

Lys Ser Gly Asn Gly Glu Val Thr Phe Glu Asn Val Lys Glu
1               5                   10

<210> SEQ ID NO 135
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Indo_SiC2N3

<400> SEQUENCE: 135

Arg Arg Asp Leu Asp Pro Asn Glu Val Trp Glu Ile Val Gly Glu Leu
1               5                   10                  15
```

Gly Asp Gly Ala Phe Gly Lys Val
            20

<210> SEQ ID NO 136
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Nap_SiC2N3
<220> FEATURE:
<221> NAME/KEY: Misc_feature
<222> LOCATION: (28)..(28)
<223> OTHER INFORMATION: modified by carbamidomethyl

<400> SEQUENCE: 136

Lys Phe Lys Ser Ser Leu Glu Val Met Met Leu Cys Ser Glu Cys Pro
1               5                   10                  15

Thr Val Phe Val Asp Ala Glu Thr Leu Met Ser Cys Gly Leu Leu Glu
            20                  25                  30

Thr Leu Lys Phe
        35

<210> SEQ ID NO 137
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (18)..(18)
<223> OTHER INFORMATION: modified by CW_Cele_SiC0N3
<220> FEATURE:
<221> NAME/KEY: Misc_feature
<222> LOCATION: (22)..(22)
<223> OTHER INFORMATION: modified by CW_Cele_SiC0N3

<400> SEQUENCE: 137

Arg Gly Val Ala Leu Leu Arg Pro Glu Pro Leu His Arg Gly Thr Ala
1               5                   10                  15

Asp Thr Leu Leu Asn Arg Val
            20

<210> SEQ ID NO 138
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by oxidation
<220> FEATURE:
<221> NAME/KEY: Misc_feature
<222> LOCATION: (10)..(10)
<223> OTHER INFORMATION: modified by CW_minimalist_Si2N3
<220> FEATURE:
<221> NAME/KEY: Misc_feature
<222> LOCATION: (15)..(15)
<223> OTHER INFORMATION: modified by CW_minimalist_Si2N3

<400> SEQUENCE: 138

Arg Asp Asp Gly Ser Thr Leu Met Glu Ile Asp Gly Asp Lys Gly Lys
1               5                   10                  15

Gln

```
<210> SEQ ID NO 139
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Nap_SiC2N3

<400> SEQUENCE: 139

Lys Gln Val Val Glu Ser Ala Tyr Glu Val Ile Lys Leu
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3

<400> SEQUENCE: 140

Lys Gln Val Val Glu Ser Ala Tyr Glu Val Ile Lys Leu
1               5                   10

<210> SEQ ID NO 141
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 141

Arg Leu Lys Asn Asp Gln Ala Asn Tyr Ser Leu Asn Thr Asp Asp Pro
1               5                   10                  15

Leu Ile Phe Lys Ser
            20

<210> SEQ ID NO 142
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Cele_SiC2N3

<400> SEQUENCE: 142

Arg Leu Lys Asn Asp Gln Ala Asn Tyr Ser Leu Asn Thr Asp Asp Pro
1               5                   10                  15

Leu Ile Phe Lys Ser
            20

<210> SEQ ID NO 143
<211> LENGTH: 19
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 143

Lys Asn Asp Gln Ala Asn Tyr Ser Leu Asn Thr Asp Asp Pro Leu Ile
1               5                   10                  15

Phe Lys Ser

<210> SEQ ID NO 144
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Cele_SiC2N3

<400> SEQUENCE: 144

Lys Asn Asp Gln Ala Asn Tyr Ser Leu Asn Thr Asp Asp Pro Leu Ile
1               5                   10                  15

Phe Lys Ser

<210> SEQ ID NO 145
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 145

Lys Ile Ser Thr Gln Ala Asp Thr Ile Gly Thr Glu Thr Leu Glu Arg
1               5                   10                  15

Leu

<210> SEQ ID NO 146
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Cele_SiC2N3

<400> SEQUENCE: 146

Lys Ile Ser Thr Gln Ala Asp Thr Ile Gly Thr Glu Thr Leu Glu Arg
1               5                   10                  15

Leu

<210> SEQ ID NO 147
<211> LENGTH: 17
<212> TYPE: PRT
<213> ORGANISM: Artificial Sequence
<220> FEATURE:
```

```
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Cele_SiC2N3

<400> SEQUENCE: 147

Lys Ile Ser Thr Gln Ala Asp Thr Ile Gly Thr Glu Thr Leu Glu Arg
1               5                   10                  15

Leu

<210> SEQ ID NO 148
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Nap_SiC2N3

<400> SEQUENCE: 148

Lys Ile Ser Thr Gln Ala Asp Thr Ile Gly Thr Glu Thr Leu Glu Arg
1               5                   10                  15

Leu

<210> SEQ ID NO 149
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 149

Lys Ile Ser Thr Gln Ala Asp Thr Ile Gly Thr Glu Thr Leu Glu Arg
1               5                   10                  15

Leu

<210> SEQ ID NO 150
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Nap_SiC2N3

<400> SEQUENCE: 150

Lys Ile Ser Thr Gln Ala Asp Thr Ile Gly Thr Glu Thr Leu Glu Arg
1               5                   10                  15

Leu

<210> SEQ ID NO 151
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
```

```
<222> LOCATION: (11)..(11)
<223> OTHER INFORMATION: modified by CW_Nap_SiC2N3

<400> SEQUENCE: 151

Lys Ile Ser Thr Gln Ala Asp Thr Ile Gly Thr Glu Thr Leu Glu Arg
1               5                   10                  15

Leu

<210> SEQ ID NO 152
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by carbamidomethyl
<220> FEATURE:
<221> NAME/KEY: Misc_feature
<222> LOCATION: (9)..(9)
<223> OTHER INFORMATION: modified by carbamidomethyl
<220> FEATURE:
<221> NAME/KEY: Misc_feature
<222> LOCATION: (18)..(18)
<223> OTHER INFORMATION: modified by CW_Cele_SiC2N3

<400> SEQUENCE: 152

Arg Lys Glu Ala Glu Ser Cys Asp Cys Leu Gln Gly Phe Gln Leu Thr
1               5                   10                  15

His Ser Leu Gly Gly Gly Thr Gly Ser Gly Met Gly Thr Leu Leu Ile
            20                  25                  30

Ser Lys Ile
        35

<210> SEQ ID NO 153
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3
<220> FEATURE:
<221> NAME/KEY: Misc_feature
<222> LOCATION: (7)..(7)
<223> OTHER INFORMATION: modified by carbamidomethyl
<220> FEATURE:
<221> NAME/KEY: Misc_feature
<222> LOCATION: (9)..(9)
<223> OTHER INFORMATION: modified by carbamidomethyl

<400> SEQUENCE: 153

Arg Lys Glu Ala Glu Ser Cys Asp Cys Leu Gln Gly Phe Gln Leu Thr
1               5                   10                  15

His Ser Leu Gly Gly Gly Thr Gly Ser Gly Met Gly Thr Leu Leu Ile
            20                  25                  30

Ser Lys Ile
        35

<210> SEQ ID NO 154
<211> LENGTH: 27
<212> TYPE: PRT
<213> ORGANISM: Artificial Sequence
<220> FEATURE:
<223> OTHER INFORMATION: Synthetic polypeptide
```

```
<220> FEATURE:
<221> NAME/KEY: Misc_feature
<222> LOCATION: (3)..(3)
<223> OTHER INFORMATION: modified by CW_Nap_SiC2N3

<400> SEQUENCE: 154

Lys Leu Thr Thr Pro Thr Tyr Gly Asp Leu Asn His Leu Val Ser Ala
1               5                   10                  15

Thr Met Ser Gly Val Thr Thr Cys Leu Arg Phe
            20                  25

<210> SEQ ID NO 155
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 155

Lys Leu Thr Thr Pro Thr Tyr Gly Asp Leu Asn His Leu Val Ser Ala
1               5                   10                  15

Thr Met Ser Gly Val Thr Thr Cys Leu Arg Phe
            20                  25

<210> SEQ ID NO 156
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Nap_SiC2N3

<400> SEQUENCE: 156

Lys Leu Thr Thr Pro Thr Tyr Gly Asp Leu Asn His Leu Val Ser Ala
1               5                   10                  15

Thr Met Ser Gly Val Thr Thr Cys Leu Arg Phe
            20                  25

<210> SEQ ID NO 157
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Cele_SiC0N3
<220> FEATURE:
<221> NAME/KEY: Misc_feature
<222> LOCATION: (14)..(14)
<223> OTHER INFORMATION: modified by oxidation

<400> SEQUENCE: 157

Lys Val Ile His Asp Asn Phe Gly Ile Val Glu Gly Leu Met Thr Thr
1               5                   10                  15

Val His Ala Ile Thr Ala Thr Gln Lys Thr
            20                  25

<210> SEQ ID NO 158
```

```
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Nap_SiC2N3

<400> SEQUENCE: 158

Arg Ala Pro Trp Ile Glu Gln Glu Gly Pro Glu Tyr Trp Asp Gln Glu
1               5                   10                  15

Thr Arg Asn

<210> SEQ ID NO 159
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Nap_SiC2N3

<400> SEQUENCE: 159

Arg Leu Pro Glu Glu Trp Ser Gln Trp Leu Gly Gly Ser Ser Trp Pro
1               5                   10                  15

Gly Tyr Val Arg Pro Leu Pro Pro Ala Ala Ile Glu Ser Pro Ala Val
            20                  25                  30

Ala Ala Pro Ala Tyr Ser Arg Ala
        35                  40

<210> SEQ ID NO 160
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Nap_SiC2N3

<400> SEQUENCE: 160

Lys Tyr Leu Ala Ile Leu Gly Ser Val Thr Phe Leu Ala Gly Asn Arg
1               5                   10                  15

Met

<210> SEQ ID NO 161
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3

<400> SEQUENCE: 161

Arg Ile Ser Leu Val Leu Gly Gly Asp His Ser Leu Ala Ile Gly Ser
1               5                   10                  15

Ile Ser Gly His Ala Arg Val
            20
```

<210> SEQ ID NO 162
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 162

Arg Glu Gly Asn Asp Leu Tyr His Glu Met Ile Glu Ser Gly Val Ile
1               5                   10                  15

Asn Leu Lys Asp
            20

<210> SEQ ID NO 163
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 163

Arg Glu Gly Asn Asp Leu Tyr His Glu Met Ile Glu Ser Gly Val Ile
1               5                   10                  15

Asn Leu Lys Asp
            20

<210> SEQ ID NO 164
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 164

Arg Ala Ile Ala Glu Leu Gly Ile Tyr Pro Ala Val Asp Pro Leu Asp
1               5                   10                  15

Ser Thr Ser Arg Ile
            20

<210> SEQ ID NO 165
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 165

Arg Ala Ile Ala Glu Leu Gly Ile Tyr Pro Ala Val Asp Pro Leu Asp
1               5                   10                  15

Ser Thr Ser Arg Ile
            20

<210> SEQ ID NO 166
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 166

Arg Ala Ile Ala Glu Leu Gly Ile Tyr Pro Ala Val Asp Pro Leu Asp
1               5                   10                  15

Ser Thr Ser Arg Ile
            20

<210> SEQ ID NO 167
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 167

Arg Ala Ile Ala Glu Leu Gly Ile Tyr Pro Ala Val Asp Pro Leu Asp
1               5                   10                  15

Ser Thr Ser Arg Ile
            20

<210> SEQ ID NO 168
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 168

Arg Ala Ile Ala Glu Leu Gly Ile Tyr Pro Ala Val Asp Pro Leu Asp
1               5                   10                  15

Ser Thr Ser Arg Ile
            20

<210> SEQ ID NO 169
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 169

Arg Ala Ile Ala Glu Leu Gly Ile Tyr Pro Ala Val Asp Pro Leu Asp
1               5                   10                  15

Ser Thr Ser Arg Ile

20

<210> SEQ ID NO 170
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Nap_SiC2N3

<400> SEQUENCE: 170

Arg Ala Ile Ala Glu Leu Gly Ile Tyr Pro Ala Val Asp Pro Leu Asp
1               5                   10                  15

Ser Thr Ser Arg Ile
            20

<210> SEQ ID NO 171
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Nap_SiC2N3

<400> SEQUENCE: 171

Arg Ala Ile Ala Glu Leu Gly Ile Tyr Pro Ala Val Asp Pro Leu Asp
1               5                   10                  15

Ser Thr Ser Arg Ile
            20

<210> SEQ ID NO 172
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by oxidation
<220> FEATURE:
<221> NAME/KEY: Misc_feature
<222> LOCATION: (11)..(11)
<223> OTHER INFORMATION: modified by CW_Cele_SiC2N3

<400> SEQUENCE: 172

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 173
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Cele_SiC2N3

<400> SEQUENCE: 173

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 174
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Cele_SiC2N3

<400> SEQUENCE: 174

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 175
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Cele_SiC2N3

<400> SEQUENCE: 175

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 176
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Cele_SiC2N3

<400> SEQUENCE: 176

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 177
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Cele_SiC2N3

<400> SEQUENCE: 177

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 178
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Cele_SiC2N3

<400> SEQUENCE: 178

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 179
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Indo_SiC2N3

<400> SEQUENCE: 179

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 180
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3

<400> SEQUENCE: 180

Lys Val Asp Asn Asp Glu Asn Glu His Gln Leu Ser Leu Arg Thr
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 181

Lys Val Asp Asn Asp Glu Asn Glu His Gln Leu Ser Leu Arg Thr
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Nap_SiC2N3

<400> SEQUENCE: 182

Lys Val Asp Asn Asp Glu Asn Glu His Gln Leu Ser Leu Arg Thr
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 183

Lys Val Asp Asn Asp Glu Asn Glu His Gln Leu Ser Leu Arg Thr
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 184

Lys Val Asp Asn Asp Glu Asn Glu His Gln Leu Ser Leu Arg Thr
1               5                   10                  15

<210> SEQ ID NO 185
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by oxidation
<220> FEATURE:
<221> NAME/KEY: Misc_feature
<222> LOCATION: (14)..(14)
<223> OTHER INFORMATION: modified by CW_Nap_SiC2N3

<400> SEQUENCE: 185

Lys Met Ser Val Gln Pro Thr Val Ser Leu Gly Gly Phe Glu Ile Thr
1               5                   10                  15

Pro Pro Val Val Leu Arg Leu
            20

```
<210> SEQ ID NO 186
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by oxidation
<220> FEATURE:
<221> NAME/KEY: Misc_feature
<222> LOCATION: (14)..(14)
<223> OTHER INFORMATION: modified by CW_Nap_SiC2N3

<400> SEQUENCE: 186

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 187
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Nap_SiC2N3

<400> SEQUENCE: 187

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 188
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Nap_SiC2N3

<400> SEQUENCE: 188

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 189
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Nap_SiC2N3

<400> SEQUENCE: 189

Lys Met Ser Val Gln Pro Thr Val Ser Leu Gly Gly Phe Glu Ile Thr
1               5                   10                  15
```

Pro Pro Val Val Leu Arg Leu
            20

<210> SEQ ID NO 190
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Nap_SiC2N3

<400> SEQUENCE: 190

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 191
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC2N3

<400> SEQUENCE: 191

Lys Met Ser Val Gln Pro Thr Val Ser Leu Gly Gly Phe Glu Ile Thr
1               5                   10                  15

Pro Pro Val Val Leu Arg Leu
            20

<210> SEQ ID NO 192
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Cele_SiC2N3
<220> FEATURE:
<221> NAME/KEY: Misc_feature
<222> LOCATION: (17)..(17)
<223> OTHER INFORMATION: modified by carbamidomethyl

<400> SEQUENCE: 192

Lys Ala Ile Gly Ala Val Pro Leu Ile Gln Gly Glu Tyr Met Ile Pro
1               5                   10                  15

Cys Glu Lys Val
            20

<210> SEQ ID NO 193
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

-continued

```
<220> FEATURE:
<221> NAME/KEY: Misc_feature
<222> LOCATION: (17)..(17)
<223> OTHER INFORMATION: modified by carbamidomethyl

<400> SEQUENCE: 193

Lys Ala Ile Gly Ala Val Pro Leu Ile Gln Gly Glu Tyr Met Ile Pro
1               5                   10                  15

Cys Glu Lys Val
            20

<210> SEQ ID NO 194
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Indo_SiC2N3
<220> FEATURE:
<221> NAME/KEY: Misc_feature
<222> LOCATION: (14)..(14)
<223> OTHER INFORMATION: modified by oxidation
<220> FEATURE:
<221> NAME/KEY: Misc_feature
<222> LOCATION: (17)..(17)
<223> OTHER INFORMATION: modified by carbamidomethyl

<400> SEQUENCE: 194

Lys Ala Ile Gly Ala Val Pro Leu Ile Gln Gly Glu Tyr Met Ile Pro
1               5                   10                  15

Cys Glu Lys Val
            20

<210> SEQ ID NO 195
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Indo_SiC2N3
<220> FEATURE:
<221> NAME/KEY: Misc_feature
<222> LOCATION: (14)..(14)
<223> OTHER INFORMATION: modified by oxidation
<220> FEATURE:
<221> NAME/KEY: Misc_feature
<222> LOCATION: (17)..(17)
<223> OTHER INFORMATION: modified by carbamidomethyl

<400> SEQUENCE: 195

Lys Ala Ile Gly Ala Val Pro Leu Ile Gln Gly Glu Tyr Met Ile Pro
1               5                   10                  15

Cys Glu Lys Val
            20

<210> SEQ ID NO 196
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
```

```
<223> OTHER INFORMATION: modified by CW_Indo_SiC2N3
<220> FEATURE:
<221> NAME/KEY: Misc_feature
<222> LOCATION: (17)..(17)
<223> OTHER INFORMATION: modified by carbamidomethyl

<400> SEQUENCE: 196

Lys Ala Ile Gly Ala Val Pro Leu Ile Gln Gly Glu Tyr Met Ile Pro
1               5                   10                  15

Cys Glu Lys Val
            20

<210> SEQ ID NO 197
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Nap_SiC2N3
<220> FEATURE:
<221> NAME/KEY: Misc_feature
<222> LOCATION: (14)..(14)
<223> OTHER INFORMATION: modified by oxidation
<220> FEATURE:
<221> NAME/KEY: Misc_feature
<222> LOCATION: (17)..(17)
<223> OTHER INFORMATION: modified by carbamidomethyl

<400> SEQUENCE: 197

Lys Ala Ile Gly Ala Val Pro Leu Ile Gln Gly Glu Tyr Met Ile Pro
1               5                   10                  15

Cys Glu Lys Val
            20

<210> SEQ ID NO 198
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Nap_SiC2N3
<220> FEATURE:
<221> NAME/KEY: Misc_feature
<222> LOCATION: (14)..(14)
<223> OTHER INFORMATION: modified by oxidation
<220> FEATURE:
<221> NAME/KEY: Misc_feature
<222> LOCATION: (17)..(17)
<223> OTHER INFORMATION: modified by carbamidomethyl

<400> SEQUENCE: 198

Lys Ala Ile Gly Ala Val Pro Leu Ile Gln Gly Glu Tyr Met Ile Pro
1               5                   10                  15

Cys Glu Lys Val
            20

<210> SEQ ID NO 199
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
```

```
<222> LOCATION: (10)..(10)
<223> OTHER INFORMATION: modified by CW_Nap_SiC2N3
<220> FEATURE:
<221> NAME/KEY: Misc_feature
<222> LOCATION: (14)..(14)
<223> OTHER INFORMATION: modified by oxidation
<220> FEATURE:
<221> NAME/KEY: Misc_feature
<222> LOCATION: (17)..(17)
<223> OTHER INFORMATION: modified by carbamidomethyl

<400> SEQUENCE: 199

Lys Ala Ile Gly Ala Val Pro Leu Ile Gln Gly Glu Tyr Met Ile Pro
1               5                   10                  15

Cys Glu Lys Val
            20

<210> SEQ ID NO 200
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Nap_SiC2N3
<220> FEATURE:
<221> NAME/KEY: Misc_feature
<222> LOCATION: (17)..(17)
<223> OTHER INFORMATION: modified by carbamidomethyl

<400> SEQUENCE: 200

Lys Ala Ile Gly Ala Val Pro Leu Ile Gln Gly Glu Tyr Met Ile Pro
1               5                   10                  15

Cys Glu Lys Val
            20

<210> SEQ ID NO 201
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Cele_SiC2N3

<400> SEQUENCE: 201

Arg Ala Leu Thr Val Pro Glu Leu Thr Gln Gln Val Phe Asp Ala Lys
1               5                   10                  15

Asn

<210> SEQ ID NO 202
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3
<220> FEATURE:
<221> NAME/KEY: Misc_feature
<222> LOCATION: (12)..(12)
<223> OTHER INFORMATION: modified by oxidation

<400> SEQUENCE: 202
```

```
Arg Ala Ile Leu Val Asp Leu Glu Pro Gly Thr Met Asp Ser Val Arg
1               5                   10                  15

Ser

<210> SEQ ID NO 203
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Indo_SiC2N3

<400> SEQUENCE: 203

Arg Ala Leu Thr Val Pro Glu Leu Thr Gln Gln Val Phe Asp Ala Lys
1               5                   10                  15

Asn

<210> SEQ ID NO 204
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Indo_SiC2N3

<400> SEQUENCE: 204

Arg Ala Leu Thr Val Pro Glu Leu Thr Gln Gln Val Phe Asp Ala Lys
1               5                   10                  15

Asn

<210> SEQ ID NO 205
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Indo_SiC2N3

<400> SEQUENCE: 205

Arg Ala Leu Thr Val Pro Glu Leu Thr Gln Gln Val Phe Asp Ala Lys
1               5                   10                  15

Asn

<210> SEQ ID NO 206
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Indo_SiC2N3

<400> SEQUENCE: 206

Arg Ala Leu Thr Val Pro Glu Leu Thr Gln Gln Val Phe Asp Ala Lys
1               5                   10                  15
```

Asn

<210> SEQ ID NO 207
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Indo_SiC2N3

<400> SEQUENCE: 207

Arg Ala Leu Thr Val Pro Glu Leu Thr Gln Gln Val Phe Asp Ala Lys
1               5                   10                  15

Asn

<210> SEQ ID NO 208
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 208

Lys Thr Phe Val Asn Ile Thr Pro Ala Glu Val Gly Val Leu Val Gly
1               5                   10                  15

Lys Asp

<210> SEQ ID NO 209
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 209

Lys Thr Phe Val Asn Ile Thr Pro Ala Glu Val Gly Val Leu Val Gly
1               5                   10                  15

Lys Asp

<210> SEQ ID NO 210
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by carbamidomethyl
<220> FEATURE:
<221> NAME/KEY: Misc_feature
<222> LOCATION: (23)..(23)
<223> OTHER INFORMATION: modified by CW_Nap_SiC0N3

<400> SEQUENCE: 210

Lys Ser Leu Cys Ile Pro Phe Lys Pro Leu Cys Glu Leu Gln Pro Gly

Ala Lys Cys Val Cys Gly Lys Asn
            20

<210> SEQ ID NO 211
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 211

Lys Ile Asn Glu Ala Val Glu Cys Leu Leu Ser Leu Lys Ala Gln Tyr
1               5                   10                  15

Lys Glu Lys Thr
            20

<210> SEQ ID NO 212
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 212

Lys Ile Asn Glu Ala Val Glu Cys Leu Leu Ser Leu Lys Ala Gln Tyr
1               5                   10                  15

Lys Glu Lys Thr
            20

<210> SEQ ID NO 213
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Nap_SiC2N3

<400> SEQUENCE: 213

Lys Leu Gly Leu Gly Ile Asp Glu Asp Glu Val Ala Ala Glu Glu Pro
1               5                   10                  15

Asn Ala Ala Val Pro Asp Glu Ile Pro Pro Leu Glu Gly Asp Glu Asp
            20                  25                  30

Ala Ser Arg Met
        35

<210> SEQ ID NO 214
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC2N3

<400> SEQUENCE: 214

Lys Leu Gly Leu Gly Ile Asp Glu Asp Glu Val Ala Ala Glu Glu Pro
1               5                   10                  15

Asn Ala Ala Val Pro Asp Glu Ile Pro Pro Leu Glu Gly Asp Glu Asp
            20                  25                  30

Ala Ser Arg Met
        35

<210> SEQ ID NO 215
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 215

Arg Ala Ile Val Ala Ile Glu Asn Pro Ala Asp Val Ser Val Ile Ser
1               5                   10                  15

Ser Arg Asn

<210> SEQ ID NO 216
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Cele_SiC2N3

<400> SEQUENCE: 216

Arg Ala Ile Val Ala Ile Glu Asn Pro Ala Asp Val Ser Val Ile Ser
1               5                   10                  15

Ser Arg Asn

<210> SEQ ID NO 217
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by carbamidomethyl
<220> FEATURE:
<221> NAME/KEY: Misc_feature
<222> LOCATION: (7)..(7)
<223> OTHER INFORMATION: modified by CW_minimalist_Si2N3
<220> FEATURE:
<221> NAME/KEY: Misc_feature
<222> LOCATION: (8)..(8)
<223> OTHER INFORMATION: modified by oxidation
<220> FEATURE:
<221> NAME/KEY: Misc_feature
<222> LOCATION: (15)..(15)
<223> OTHER INFORMATION: modified by CW_minimalist_Si2N3

<400> SEQUENCE: 217

Lys Glu Asn Cys Asn Gly Lys Met Ala Thr Leu Ser Val Gly Gly Lys
1               5                   10                  15

Thr

```
<210> SEQ ID NO 218
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 218

Lys Asp Gln Gln Glu Ala Ala Leu Val Asp Met Val Asn Asp Gly Val
1               5                   10                  15

Glu Asp Leu Arg Cys
            20

<210> SEQ ID NO 219
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 219

Lys Asp Gln Gln Glu Ala Ala Leu Val Asp Met Val Asn Asp Gly Val
1               5                   10                  15

Glu Asp Leu Arg Cys
            20

<210> SEQ ID NO 220
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Nap_SiC2N3

<400> SEQUENCE: 220

Lys Ala Phe Leu Ala Ser Pro Glu Tyr Val Asn Leu Pro Ile Asn Gly
1               5                   10                  15

Asn Gly Lys Gln
            20

<210> SEQ ID NO 221
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC2N3

<400> SEQUENCE: 221

Lys Ala Phe Leu Ala Ser Pro Glu Tyr Val Asn Leu Pro Ile Asn Gly
1               5                   10                  15
```

Asn Gly Lys Gln
         20

<210> SEQ ID NO 222
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Nap_SiC2N3

<400> SEQUENCE: 222

Lys Ala Phe Leu Ala Ser Pro Glu Tyr Val Asn Leu Pro Ile Asn Gly
1               5                   10                  15

Asn Gly Lys Gln
         20

<210> SEQ ID NO 223
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC2N3

<400> SEQUENCE: 223

Lys Ala Phe Leu Ala Ser Pro Glu Tyr Val Asn Leu Pro Ile Asn Gly
1               5                   10                  15

Asn Gly Lys Gln
         20

<210> SEQ ID NO 224
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 224

Arg Gly Asp Glu Glu Leu Asp Ser Leu Ile Lys Ala
1               5                   10

<210> SEQ ID NO 225
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Cele_SiC2N3

<400> SEQUENCE: 225

Arg Gly Asp Glu Glu Leu Asp Ser Leu Ile Lys Ala
1               5                   10

<210> SEQ ID NO 226

```
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 226

Arg Val Gly Ala Thr Ala Ala Val Tyr Ser Ala Ala Ile Leu Glu Tyr
1               5                   10                  15

Leu Thr Ala Glu Val Leu Glu Leu Ala Gly Asn Ala Ser Lys Asp
            20                  25                  30

<210> SEQ ID NO 227
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 227

Arg Val Gly Ala Thr Ala Ala Val Tyr Ser Ala Ala Ile Leu Glu Tyr
1               5                   10                  15

Leu Thr Ala Glu Val Leu Glu Leu Ala Gly Asn Ala Ser Lys Asp
            20                  25                  30

<210> SEQ ID NO 228
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by oxidation
<220> FEATURE:
<221> NAME/KEY: Misc_feature
<222> LOCATION: (20)..(20)
<223> OTHER INFORMATION: modified by CW_Nap_SiC2N3

<400> SEQUENCE: 228

Lys Leu Asp Met Leu Val Ala Ser Val Gly Thr Gly Gly Thr Ile Thr
1               5                   10                  15

Gly Ile Ala Arg Lys
            20

<210> SEQ ID NO 229
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 229

Lys Leu Glu Val Gln Ala Thr Asp Arg Glu Glu Asn Lys Gln
1               5                   10
```

```
<210> SEQ ID NO 230
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Nap_SiC2N3

<400> SEQUENCE: 230

Arg Gly Ile Trp His Asn Asp Asn Lys Thr Phe Leu Val Trp Val Asn
1               5                   10                  15

Glu Glu Asp His Leu Arg Val
            20

<210> SEQ ID NO 231
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Cele_SiC2N3

<400> SEQUENCE: 231

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 232
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 232

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 233
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 233

Arg Asn Leu Glu Ala Leu Ala Leu Asp Leu Met Glu Pro Glu Gln Ala
1               5                   10                  15

Val Asp Leu Thr Leu Pro Lys Val
            20
```

```
<210> SEQ ID NO 234
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_miniGL_Si2N3

<400> SEQUENCE: 234

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 235
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_miniGL_Si2N3

<400> SEQUENCE: 235

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 236
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3
<220> FEATURE:
<221> NAME/KEY: Misc_feature
<222> LOCATION: (11)..(11)
<223> OTHER INFORMATION: modified by oxidation

<400> SEQUENCE: 236

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 237
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3
<220> FEATURE:
<221> NAME/KEY: Misc_feature
<222> LOCATION: (11)..(11)
```

<223> OTHER INFORMATION: modified by oxidation

<400> SEQUENCE: 237

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 238
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 238

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 239
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC0N3

<400> SEQUENCE: 239

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 240
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Nap_SiC2N3

<400> SEQUENCE: 240

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 241
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Nap_SiC2N3

<400> SEQUENCE: 241

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 242
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3

<400> SEQUENCE: 242

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 243
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_minimalist_Si2N3
<220> FEATURE:
<221> NAME/KEY: Misc_feature
<222> LOCATION: (11)..(11)
<223> OTHER INFORMATION: modified by oxidation

<400> SEQUENCE: 243

Arg Asn Leu Glu Ala Leu Ala Leu Asp Leu Met Glu Pro Glu Gln Ala
1               5                   10                  15

Val Asp Leu Thr Leu Pro Lys Val
            20

<210> SEQ ID NO 244
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC2N3

<400> SEQUENCE: 244

Arg Gly His Val Phe Glu Glu Ser Gln Val Ala Gly Thr Pro Met Phe
1               5                   10                  15

Val Val Lys Ala
            20

<210> SEQ ID NO 245
<211> LENGTH: 20
<212> TYPE: PRT

```
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Nap_SiC2N3

<400> SEQUENCE: 245

Arg Gly His Val Phe Glu Glu Ser Gln Val Ala Gly Thr Pro Met Phe
1               5                   10                  15
Val Val Lys Ala
            20

<210> SEQ ID NO 246
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC2N3

<400> SEQUENCE: 246

Arg Gly His Val Phe Glu Glu Ser Gln Val Ala Gly Thr Pro Met Phe
1               5                   10                  15
Val Val Lys Ala
            20

<210> SEQ ID NO 247
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (25)..(25)
<223> OTHER INFORMATION: modified by CW_Indo_SiC2N3

<400> SEQUENCE: 247

Arg Gln Phe Val Thr Ala Thr Asp Val Val Arg Gly Asn Pro Lys Leu
1               5                   10                  15
Asn Leu Ala Phe Ile Ala Asn Leu Phe Asn Arg Tyr
            20                  25

<210> SEQ ID NO 248
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Indo_SiC2N3

<400> SEQUENCE: 248

Arg Glu Leu Ile Ser Asn Ala Ser Asp Ala Leu Asp Lys Ile
1               5                   10

<210> SEQ ID NO 249
<211> LENGTH: 14
<212> TYPE: PRT
<213> ORGANISM: Artificial Sequence
<220> FEATURE:
```

```
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 249

Arg Glu Leu Ile Ser Asn Ala Ser Asp Ala Leu Asp Lys Ile
1               5                   10

<210> SEQ ID NO 250
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by oxidation
<220> FEATURE:
<221> NAME/KEY: Misc_feature
<222> LOCATION: (11)..(11)
<223> OTHER INFORMATION: modified by CW_Nap_SiC2N3
<220> FEATURE:
<221> NAME/KEY: Misc_feature
<222> LOCATION: (17)..(17)
<223> OTHER INFORMATION: modified by oxidation

<400> SEQUENCE: 250

Arg Gln Asp Ser Leu Glu Ser Met Lys Phe Gly Asp Ser Asn Thr Val
1               5                   10                  15

Met Arg Phe

<210> SEQ ID NO 251
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 251

Lys Ala Leu Ala Ala Ala Gly Tyr Asp Val Glu Lys Asn
1               5                   10

<210> SEQ ID NO 252
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Cele_SiC2N3

<400> SEQUENCE: 252

Lys Ala Leu Ala Ala Ala Gly Tyr Asp Val Glu Lys Asn
1               5                   10

<210> SEQ ID NO 253
<211> LENGTH: 14
<212> TYPE: PRT
<213> ORGANISM: Artificial Sequence
<220> FEATURE:
<223> OTHER INFORMATION: Synthetic polypeptide
```

-continued

```
<220> FEATURE:
<221> NAME/KEY: Misc_feature
<222> LOCATION: (8)..(8)
<223> OTHER INFORMATION: modified by CW_Nap_SiC2N3

<400> SEQUENCE: 253

Lys Ala Ser Gly Pro Pro Val Ser Glu Leu Ile Thr Lys Ala
1               5                   10

<210> SEQ ID NO 254
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 254

Lys Asp Thr Glu Glu Pro Leu Pro Val Lys Glu
1               5                   10

<210> SEQ ID NO 255
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 255

Arg Trp Thr Glu Tyr Gly Leu Thr Phe Thr Glu Lys Trp
1               5                   10

<210> SEQ ID NO 256
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Cele_SiC2N3

<400> SEQUENCE: 256

Arg Gln Glu Met Gln Glu Val Gln Ser Ser Arg Ser
1               5                   10

<210> SEQ ID NO 257
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC0N3

<400> SEQUENCE: 257

Lys Gly Lys Gly Phe Gly Phe Ile Lys Leu Glu Ser Arg Ala
1               5                   10
```

```
<210> SEQ ID NO 258
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 258

Arg Leu Glu Glu Thr Val Gln Ala Lys
1               5

<210> SEQ ID NO 259
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Indo_SiC2N3

<400> SEQUENCE: 259

Arg Ala Thr Glu Asn Asp Ile Ala Asn Phe Phe Ser Pro Leu Asn Pro
1               5                   10                  15

Ile Arg Val

<210> SEQ ID NO 260
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Indo_SiC2N3

<400> SEQUENCE: 260

Arg Ala Thr Glu Asn Asp Ile Ala Asn Phe Phe Ser Pro Leu Asn Pro
1               5                   10                  15

Ile Arg Val

<210> SEQ ID NO 261
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Indo_SiC2N3

<400> SEQUENCE: 261

Arg Lys Ala Thr Glu Asn Asp Ile Tyr Asn Phe Phe Ser Pro Leu Asn
1               5                   10                  15

Pro Val Arg Val
            20

<210> SEQ ID NO 262
<211> LENGTH: 16
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_minimalist_Si2N3

<400> SEQUENCE: 262

Lys Tyr Glu Ile Ala Val Glu Thr Glu Met Lys Lys Glu Ser Lys Leu
1               5                   10                  15

<210> SEQ ID NO 263
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 263

Lys Ile Ala Gln Leu Glu Glu Gln Leu Asp Asn Glu Thr Lys Glu
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 264

Lys Ile Ala Gln Leu Glu Glu Gln Leu Asp Asn Glu Thr Lys Glu
1               5                   10                  15

<210> SEQ ID NO 265
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 265

Lys Leu Gln Val Glu Leu Asp Asn Val Thr Gly Leu Leu Ser Gln Ser
1               5                   10                  15

Asp Ser Lys Ser
            20

<210> SEQ ID NO 266
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_minimalist_Si2N3

<400> SEQUENCE: 266
```

```
Arg Ser Thr Ala Pro Ala Ser Leu Ser Arg Ser
1               5                   10

<210> SEQ ID NO 267
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC0N3
<220> FEATURE:
<221> NAME/KEY: Misc_feature
<222> LOCATION: (14)..(14)
<223> OTHER INFORMATION: modified by CW_Nap_SiC0N3
<220> FEATURE:
<221> NAME/KEY: Misc_feature
<222> LOCATION: (15)..(15)
<223> OTHER INFORMATION: modified by CW_Nap_SiC0N3

<400> SEQUENCE: 267

Arg Ala Cys Glu Ala Ile Thr Val Gly Lys Val Asp Leu Ser Ser Trp
1               5                   10                  15

Arg Glu

<210> SEQ ID NO 268
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Nap_SiC2N3

<400> SEQUENCE: 268

Lys Gly Ser Ala Asp Pro Leu Asn Ser Ala Phe His Leu Thr Tyr Asn
1               5                   10                  15

Met Val Leu Asn Leu Leu Arg Val
            20

<210> SEQ ID NO 269
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 269

Arg Asn Asn Phe Ala Val Gly Tyr Arg Thr
1               5                   10

<210> SEQ ID NO 270
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3
```

```
<400> SEQUENCE: 270

Lys Asn Glu Thr Gly Gly Gly Glu Gly Ile Glu Val Leu Lys Asn
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 271

Lys Asn Glu Thr Gly Gly Gly Glu Gly Ile Glu Val Leu Lys Asn
1               5                   10                  15

<210> SEQ ID NO 272
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_minimalist_Si2N3

<400> SEQUENCE: 272

Lys Arg Pro Glu Ala Ala Gln Leu Leu Glu Asp Val Gln Ala Ala Leu
1               5                   10                  15

Lys Pro Phe Ser Val Lys Leu
            20

<210> SEQ ID NO 273
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (25)..(25)
<223> OTHER INFORMATION: modified by CW_Nap_SiC0N3

<400> SEQUENCE: 273

Lys Tyr Ser His Val Asp Leu Val Val Met Val Asp Gly Phe Glu Gly
1               5                   10                  15

Glu Lys Gly Ala Val Val Ala Gly Ser Arg Gly
            20                  25

<210> SEQ ID NO 274
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (23)..(23)
<223> OTHER INFORMATION: modified by CW_Nap_SiC0N3

<400> SEQUENCE: 274

Lys Tyr Ser His Val Asp Leu Val Val Met Val Asp Gly Phe Glu Gly
1               5                   10                  15
```

Glu Lys Gly Ala Val Val Ala Gly Ser Arg Gly
            20              25

<210> SEQ ID NO 275
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Nap_SiC2N3

<400> SEQUENCE: 275

Arg Phe Gly Pro Tyr Tyr Thr Glu Pro Val Ile Ala Gly Leu Asp Pro
1               5                   10                  15

Lys Thr

<210> SEQ ID NO 276
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Nap_SiC2N3

<400> SEQUENCE: 276

Arg Phe Gly Pro Tyr Tyr Thr Glu Pro Val Ile Ala Gly Leu Asp Pro
1               5                   10                  15

Lys Thr

<210> SEQ ID NO 277
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Nap_SiC2N3

<400> SEQUENCE: 277

Arg Phe Gly Pro Tyr Tyr Thr Glu Pro Val Ile Ala Gly Leu Asp Pro
1               5                   10                  15

Lys Thr

<210> SEQ ID NO 278
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 278

Lys Tyr Leu Pro Lys Leu Ala Ser Gly Glu Thr Val Ala Ala Phe Cys
1               5                   10                  15

Leu Thr Glu Pro Ser Ser Gly Ser Asp Ala Ala Ser Ile Arg Thr

<210> SEQ ID NO 279
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by Oxidation
<220> FEATURE:
<221> NAME/KEY: Misc_feature
<222> LOCATION: (9)..(9)
<223> OTHER INFORMATION: modified by CW_Indo_SiC2N3

<400> SEQUENCE: 279

Arg Ala Phe Ala Asp Ala Met Glu Val Ile Pro Ser Thr Leu Ala Glu
1               5                   10                  15

Asn Ala Gly Leu Asn Pro Ile Ser Thr Val Thr Glu Leu Arg Asn
            20                  25                  30

<210> SEQ ID NO 280
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Nap_SiC2N3

<400> SEQUENCE: 280

Arg Ala Phe Ala Asp Ala Met Glu Val Ile Pro Ser Thr Leu Ala Glu
1               5                   10                  15

Asn Ala Gly Leu Asn Pro Ile Ser Thr Val Thr Glu Leu Arg Asn
            20                  25                  30

<210> SEQ ID NO 281
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Nap_SiC2N3

<400> SEQUENCE: 281

Arg Ala Phe Ala Asp Ala Met Glu Val Ile Pro Ser Thr Leu Ala Glu
1               5                   10                  15

Asn Ala Gly Leu Asn Pro Ile Ser Thr Val Thr Glu Leu Arg Asn
            20                  25                  30

<210> SEQ ID NO 282
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Nap_SiC2N3

<400> SEQUENCE: 282

-continued

```
Arg Ala Phe Ala Asp Ala Met Glu Val Ile Pro Ser Thr Leu Ala Glu
1               5                   10                  15

Asn Ala Gly Leu Asn Pro Ile Ser Thr Val Thr Glu Leu Arg Asn
            20                  25                  30

<210> SEQ ID NO 283
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Nap_SiC2N3

<400> SEQUENCE: 283

Arg Ala Phe Ala Asp Ala Met Glu Val Ile Pro Ser Thr Leu Ala Glu
1               5                   10                  15

Asn Ala Gly Leu Asn Pro Ile Ser Thr Val Thr Glu Leu Arg Asn
            20                  25                  30

<210> SEQ ID NO 284
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Nap_SiC2N3

<400> SEQUENCE: 284

Arg Ala Phe Ala Asp Ala Met Glu Val Ile Pro Ser Thr Leu Ala Glu
1               5                   10                  15

Asn Ala Gly Leu Asn Pro Ile Ser Thr Val Thr Glu Leu Arg Asn
            20                  25                  30

<210> SEQ ID NO 285
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Cele_SiC2N3

<400> SEQUENCE: 285

Arg Ala Glu Glu Tyr Glu Phe Leu Thr Pro Val Glu Glu Ala Pro Lys
1               5                   10                  15

Gly

<210> SEQ ID NO 286
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Cele_SiC2N3

<400> SEQUENCE: 286
```

Arg Ala Glu Glu Tyr Glu Phe Leu Thr Pro Val Glu Ala Pro Lys
1               5                   10                  15

Gly

<210> SEQ ID NO 287
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (28)..(28)
<223> OTHER INFORMATION: modified by CW_minimalist_Si2N3

<400> SEQUENCE: 287

Met Ala Glu Gln Glu Pro Thr Ala Glu Gln Leu Ala Gln Ile Ala Ala
1               5                   10                  15

Glu Asn Glu Glu Asp Glu His Ser Val Asn Tyr Lys Pro Pro Ala Gln
            20                  25                  30

Lys Ser

<210> SEQ ID NO 288
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by Oxidation
<220> FEATURE:
<221> NAME/KEY: Misc_feature
<222> LOCATION: (23)..(23)
<223> OTHER INFORMATION: modified by CW_Cele_SiC2N3

<400> SEQUENCE: 288

Lys Ala Thr Phe Met Val Gly Ser Tyr Gly Pro Arg Pro Glu Glu Tyr
1               5                   10                  15

Glu Phe Leu Thr Pro Val Glu Glu Ala Pro Lys Gly
            20                  25

<210> SEQ ID NO 289
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (25)..(25)
<223> OTHER INFORMATION: modified by CW_Cele_SiC2N3

<400> SEQUENCE: 289

Lys Ala Thr Phe Met Val Gly Ser Tyr Gly Pro Arg Pro Glu Glu Tyr
1               5                   10                  15

Glu Phe Leu Thr Pro Val Glu Glu Ala Pro Lys Gly
            20                  25

<210> SEQ ID NO 290
<211> LENGTH: 28
<212> TYPE: PRT
<213> ORGANISM: Artificial Sequence
<220> FEATURE:
<223> OTHER INFORMATION: Synthetic polypeptide

```
<220> FEATURE:
<221> NAME/KEY: Misc_feature
<222> LOCATION: (5)..(5)
<223> OTHER INFORMATION: modified by Oxidation
<220> FEATURE:
<221> NAME/KEY: Misc_feature
<222> LOCATION: (22)..(22)
<223> OTHER INFORMATION: modified by CW_Nap_SiC2N3

<400> SEQUENCE: 290

Lys Ala Thr Phe Met Val Gly Ser Tyr Gly Pro Arg Pro Glu Glu Tyr
1               5                   10                  15

Glu Phe Leu Thr Pro Val Glu Glu Ala Pro Lys Gly
            20                  25

<210> SEQ ID NO 291
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by Oxidation
<220> FEATURE:
<221> NAME/KEY: Misc_feature
<222> LOCATION: (21)..(21)
<223> OTHER INFORMATION: modified by CW_Nap_SiC2N3

<400> SEQUENCE: 291

Lys Ala Thr Phe Met Val Gly Ser Tyr Gly Pro Arg Pro Glu Glu Tyr
1               5                   10                  15

Glu Phe Leu Thr Pro Val Glu Glu Ala Pro Lys Gly
            20                  25

<210> SEQ ID NO 292
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Nap_SiC2N3

<400> SEQUENCE: 292

Lys Ala Thr Phe Met Val Gly Ser Tyr Gly Pro Arg Pro Glu Glu Tyr
1               5                   10                  15

Glu Phe Leu Thr Pro Val Glu Glu Ala Pro Lys Gly
            20                  25

<210> SEQ ID NO 293
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 293

Lys Phe Tyr Glu Glu Val His Asp Leu Glu Arg Lys
1               5                   10
```

```
<210> SEQ ID NO 294
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Nap_SiC2N3

<400> SEQUENCE: 294

Lys Phe Tyr Glu Glu Val His Asp Leu Glu Arg Lys
1               5                   10

<210> SEQ ID NO 295
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Nap_SiC2N3

<400> SEQUENCE: 295

Lys Phe Tyr Glu Glu Val His Asp Leu Glu Arg Lys
1               5                   10

<210> SEQ ID NO 296
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Nap_SiC2N3

<400> SEQUENCE: 296

Lys Phe Tyr Glu Glu Val His Asp Leu Glu Arg Lys
1               5                   10

<210> SEQ ID NO 297
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC0N3

<400> SEQUENCE: 297

Arg Arg Leu Leu Glu Gly Arg Arg
1               5

<210> SEQ ID NO 298
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3
```

-continued

<400> SEQUENCE: 298

Arg Val Ala Pro Glu Glu His Pro Val Leu Leu Thr Glu Ala Pro Leu
1               5                   10                  15

Asn Pro Lys Ala
            20

<210> SEQ ID NO 299
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 299

Arg Val Ala Pro Glu Glu His Pro Val Leu Leu Thr Glu Ala Pro Leu
1               5                   10                  15

Asn Pro Lys Ala
            20

<210> SEQ ID NO 300
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 300

Arg Val Ala Pro Glu Glu His Pro Val Leu Leu Thr Glu Ala Pro Leu
1               5                   10                  15

Asn Pro Lys Ala
            20

<210> SEQ ID NO 301
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Cele_SiC2N3

<400> SEQUENCE: 301

Arg Val Ala Pro Glu Glu His Pro Val Leu Leu Thr Glu Ala Pro Leu
1               5                   10                  15

Asn Pro Lys Ala
            20

<210> SEQ ID NO 302
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Cele_SiC2N3

-continued

```
<400> SEQUENCE: 302

Arg Val Ala Pro Glu Glu His Pro Val Leu Leu Thr Glu Ala Pro Leu
1               5                   10                  15

Asn Pro Lys Ala
            20

<210> SEQ ID NO 303
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Cele_SiC2N3

<400> SEQUENCE: 303

Arg Val Ala Pro Glu Glu His Pro Val Leu Leu Thr Glu Ala Pro Leu
1               5                   10                  15

Asn Pro Lys Ala
            20

<210> SEQ ID NO 304
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Cele_SiC2N3

<400> SEQUENCE: 304

Arg Val Ala Pro Glu Glu His Pro Val Leu Leu Thr Glu Ala Pro Leu
1               5                   10                  15

Asn Pro Lys Ala
            20

<210> SEQ ID NO 305
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 305

Arg Val Ala Pro Glu Glu His Pro Val Leu Leu Thr Glu Ala Pro Leu
1               5                   10                  15

Asn Pro Lys Ala
            20

<210> SEQ ID NO 306
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
```

```
<223> OTHER INFORMATION: modified by CW_Cele_SiC2N3

<400> SEQUENCE: 306

Arg Val Ala Pro Glu Glu His Pro Val Leu Leu Thr Glu Ala Pro Leu
1               5                   10                  15

Asn Pro Lys Ala
            20

<210> SEQ ID NO 307
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by Oxidation
<220> FEATURE:
<221> NAME/KEY: Misc_feature
<222> LOCATION: (23)..(23)
<223> OTHER INFORMATION: modified by CW_Cele_SiC2N3

<400> SEQUENCE: 307

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 308
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by Oxidation
<220> FEATURE:
<221> NAME/KEY: Misc_feature
<222> LOCATION: (11)..(11)
<223> OTHER INFORMATION: modified by CW_Cele_SiC2N3

<400> SEQUENCE: 308

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 309
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3)

<400> SEQUENCE: 309

Arg Val Ala Pro Glu Glu His Pro Val Leu Leu Thr Glu Ala Pro Leu
1               5                   10                  15

Asn Pro Lys Ala
            20
```

-continued

```
<210> SEQ ID NO 310
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Cele_SiC2N3

<400> SEQUENCE: 310

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 311
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 311

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 312
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 312

Arg Val Ala Pro Glu Glu His Pro Val Leu Leu Thr Glu Ala Pro Leu
1               5                   10                  15

Asn Pro Lys Ala
            20

<210> SEQ ID NO 313
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 313

Arg Val Ala Pro Glu Glu His Pro Val Leu Leu Thr Glu Ala Pro Leu
1               5                   10                  15

Asn Pro Lys Ala
            20
```

```
<210> SEQ ID NO 314
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 314

Arg Val Ala Pro Glu Glu His Pro Val Leu Leu Thr Glu Ala Pro Leu
1               5                   10                  15

Asn Pro Lys Ala
            20

<210> SEQ ID NO 315
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Cele_SiC2N3

<400> SEQUENCE: 315

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 316
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 316

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 317
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC2N3

<400> SEQUENCE: 317

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30
```

```
<210> SEQ ID NO 318
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Cele_SiC2N3

<400> SEQUENCE: 318

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 319
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 319

Lys Gln Glu Tyr Asp Glu Ser Gly Pro Ser Ile Val His Arg Lys
1               5                   10                  15

<210> SEQ ID NO 320
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 320

Arg Val Ala Pro Glu Glu His Pro Val Leu Leu Thr Glu Ala Pro Leu
1               5                   10                  15

Asn Pro Lys Ala
            20

<210> SEQ ID NO 321
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Indo_SiC2N3

<400> SEQUENCE: 321

Arg Val Ala Pro Glu Glu His Pro Val Leu Leu Thr Glu Ala Pro Leu
1               5                   10                  15

Asn Pro Lys Ala
            20
```

```
<210> SEQ ID NO 322
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by Oxidation
<220> FEATURE:
<221> NAME/KEY: Misc_feature
<222> LOCATION: (8)..(8)
<223> OTHER INFORMATION: modified by CW_Indo_SiC2N3

<400> SEQUENCE: 322

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 323
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Indo_SiC2N3

<400> SEQUENCE: 323

Arg Val Ala Pro Glu Glu His Pro Val Leu Leu Thr Glu Ala Pro Leu
1               5                   10                  15

Asn Pro Lys Ala
            20

<210> SEQ ID NO 324
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Indo_SiC2N3

<400> SEQUENCE: 324

Arg Val Ala Pro Glu Glu His Pro Val Leu Leu Thr Glu Ala Pro Leu
1               5                   10                  15

Asn Pro Lys Ala
            20

<210> SEQ ID NO 325
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by Oxidation
<220> FEATURE:
<221> NAME/KEY: Misc_feature
<222> LOCATION: (8)..(8)
<223> OTHER INFORMATION: modified by CW_Indo_SiC2N3
```

-continued

<400> SEQUENCE: 325

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 326
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Indo_SiC2N3
<220> FEATURE:
<221> NAME/KEY: Misc_feature
<222> LOCATION: (15)..(15)
<223> OTHER INFORMATION: modified by Oxidation

<400> SEQUENCE: 326

Lys Asp Leu Tyr Ala Asn Thr Val Leu Ser Gly Gly Thr Thr Met Tyr
1               5                   10                  15

Pro Gly Ile Ala Asp Arg Met
            20

<210> SEQ ID NO 327
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Indo_SiC2N3
<220> FEATURE:
<221> NAME/KEY: Misc_feature
<222> LOCATION: (15)..(15)
<223> OTHER INFORMATION: modified by Oxidation

<400> SEQUENCE: 327

Lys Asp Leu Tyr Ala Asn Thr Val Leu Ser Gly Gly Thr Thr Met Tyr
1               5                   10                  15

Pro Gly Ile Ala Asp Arg Met
            20

<210> SEQ ID NO 328
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Nap_SiC2N3

<400> SEQUENCE: 328

Arg Val Ala Pro Glu Glu His Pro Val Leu Leu Thr Glu Ala Pro Leu
1               5                   10                  15

Asn Pro Lys Ala
            20

<210> SEQ ID NO 329
<211> LENGTH: 20

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Nap_SiC2N3

<400> SEQUENCE: 329

Arg Val Ala Pro Glu Glu His Pro Val Leu Leu Thr Glu Ala Pro Leu
1               5                   10                  15

Asn Pro Lys Ala
            20

<210> SEQ ID NO 330
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Nap_SiC2N3

<400> SEQUENCE: 330

Arg Val Ala Pro Glu Glu His Pro Val Leu Leu Thr Glu Ala Pro Leu
1               5                   10                  15

Asn Pro Lys Ala
            20

<210> SEQ ID NO 331
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Nap_SiC2N3

<400> SEQUENCE: 331

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 332
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 332

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 333
```

```
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 333

Lys Ser Tyr Glu Leu Pro Asp Gly Gln Val Ile Thr Ile Gly Asn Glu
1               5                   10                  15

Arg Phe

<210> SEQ ID NO 334
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 334

Lys Ser Tyr Glu Leu Pro Asp Gly Gln Val Ile Thr Ile Gly Asn Glu
1               5                   10                  15

Arg Phe

<210> SEQ ID NO 335
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 335

Lys Ser Tyr Glu Leu Pro Asp Gly Gln Val Ile Thr Ile Gly Asn Glu
1               5                   10                  15

Arg Phe

<210> SEQ ID NO 336
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 336

Lys Ser Tyr Glu Leu Pro Asp Gly Gln Val Ile Thr Ile Gly Asn Glu
1               5                   10                  15

Arg Phe

<210> SEQ ID NO 337
<211> LENGTH: 13
<212> TYPE: PRT
<213> ORGANISM: Artificial Sequence
```

-continued

```
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 337

Lys Glu Ile Thr Ala Leu Ala Pro Ser Thr Met Lys Ile
1               5                   10

<210> SEQ ID NO 338
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Indo_SiC2N3

<400> SEQUENCE: 338

Lys Ser Tyr Glu Leu Pro Asp Gly Gln Val Ile Thr Ile Gly Asn Glu
1               5                   10                  15

Arg Phe

<210> SEQ ID NO 339
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Indo_SiC2N3

<400> SEQUENCE: 339

Lys Ser Tyr Glu Leu Pro Asp Gly Gln Val Ile Thr Ile Gly Asn Glu
1               5                   10                  15

Arg Phe

<210> SEQ ID NO 340
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Indo_SiC2N3

<400> SEQUENCE: 340

Lys Glu Ile Thr Ala Leu Ala Pro Ser Thr Met Lys Ile
1               5                   10

<210> SEQ ID NO 341
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC2N3
```

-continued

```
<400> SEQUENCE: 341

Lys Ala Gly Phe Ala Gly Asp Asp Ala Pro Arg Ala
1               5                   10

<210> SEQ ID NO 342
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Nap_SiC2N3

<400> SEQUENCE: 342

Lys Ala Gly Phe Ala Gly Asp Asp Ala Pro Arg Ala
1               5                   10

<210> SEQ ID NO 343
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 343

Lys Arg Ser Tyr Glu Leu Pro Asp Gly Gln Val Ile Thr Ile Gly Asn
1               5                   10                  15

Glu Arg Phe

<210> SEQ ID NO 344
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 344

Lys Arg Ser Tyr Glu Leu Pro Asp Gly Gln Val Ile Thr Ile Gly Asn
1               5                   10                  15

Glu Arg Phe

<210> SEQ ID NO 345
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 345

Lys Arg Ser Tyr Glu Leu Pro Asp Gly Gln Val Ile Thr Ile Gly Asn
1               5                   10                  15

Glu Arg Phe
```

-continued

```
<210> SEQ ID NO 346
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 346

Lys Arg Ser Tyr Glu Leu Pro Asp Gly Gln Val Ile Thr Ile Gly Asn
1               5                   10                  15

Glu Arg Phe

<210> SEQ ID NO 347
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Indo_SiC2N3

<400> SEQUENCE: 347

Lys Arg Ser Tyr Glu Leu Pro Asp Gly Gln Val Ile Thr Ile Gly Asn
1               5                   10                  15

Glu Arg Phe

<210> SEQ ID NO 348
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Indo_SiC2N3

<400> SEQUENCE: 348

Lys Arg Ser Tyr Glu Leu Pro Asp Gly Gln Val Ile Thr Ile Gly Asn
1               5                   10                  15

Glu Arg Phe

<210> SEQ ID NO 349
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Indo_SiC2N3

<400> SEQUENCE: 349

Lys Arg Ser Tyr Glu Leu Pro Asp Gly Gln Val Ile Thr Ile Gly Asn
1               5                   10                  15

Glu Arg Phe

<210> SEQ ID NO 350
<211> LENGTH: 19
```

-continued

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3

<400> SEQUENCE: 350

Lys Arg Ser Tyr Glu Leu Pro Asp Gly Gln Val Ile Thr Ile Gly Asn
1               5                   10                  15

Glu Arg Phe

<210> SEQ ID NO 351
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by Carbamidomethyl
<220> FEATURE:
<221> NAME/KEY: Misc_feature
<222> LOCATION: (12)..(12)
<223> OTHER INFORMATION: modified by CW_Nap_SiC0N3
<220> FEATURE:
<221> NAME/KEY: Misc_feature
<222> LOCATION: (22)..(22)
<223> OTHER INFORMATION: modified by Oxidation

<400> SEQUENCE: 351

Arg Ile Asn Asn Ala Cys Phe Glu Ala Val Val Val Thr Asn Thr Ile
1               5                   10                  15

Pro Gln Glu Asp Lys Met Lys His Cys Ser Lys Ile
            20                  25

<210> SEQ ID NO 352
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 352

Arg Leu Ile Leu Ile Glu Ser Arg Ile
1               5

<210> SEQ ID NO 353
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 353

Arg Leu Ile Leu Ile Glu Ser Arg Ile
1               5
```

```
<210> SEQ ID NO 354
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 354

Arg Asp Ala Val Thr Tyr Thr Glu His Ala Lys Arg
1               5                   10

<210> SEQ ID NO 355
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 355

Arg Asp Ala Val Thr Tyr Thr Glu His Ala Lys Arg
1               5                   10

<210> SEQ ID NO 356
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 356

Arg Asp Ala Val Thr Tyr Thr Glu His Ala Lys Arg
1               5                   10

<210> SEQ ID NO 357
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 357

Arg Asp Ala Val Thr Tyr Thr Glu His Ala Lys Arg
1               5                   10

<210> SEQ ID NO 358
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3
```

```
<400> SEQUENCE: 358

Arg Asp Ala Val Thr Tyr Thr Glu His Ala Lys Arg
1               5                   10

<210> SEQ ID NO 359
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Cele_SiC2N3

<400> SEQUENCE: 359

Arg Asp Ala Val Thr Tyr Thr Glu His Ala Lys Arg
1               5                   10

<210> SEQ ID NO 360
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 360

Arg Ile Ser Gly Leu Ile Tyr Glu Glu Thr Arg Gly
1               5                   10

<210> SEQ ID NO 361
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 361

Arg Ile Ser Gly Leu Ile Tyr Glu Glu Thr Arg Gly
1               5                   10

<210> SEQ ID NO 362
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 362

Arg Ile Ser Gly Leu Ile Tyr Glu Glu Thr Arg Gly
1               5                   10

<210> SEQ ID NO 363
<211> LENGTH: 12
<212> TYPE: PRT
<213> ORGANISM: Artificial Sequence
<220> FEATURE:
```

<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Cele_SiC2N3

<400> SEQUENCE: 363

Arg Ile Ser Gly Leu Ile Tyr Glu Glu Thr Arg Gly
1               5                   10

<210> SEQ ID NO 364
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 364

Arg Ile Ser Gly Leu Ile Tyr Glu Glu Thr Arg Gly
1               5                   10

<210> SEQ ID NO 365
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 365

Arg Ile Ser Gly Leu Ile Tyr Glu Glu Thr Arg Gly
1               5                   10

<210> SEQ ID NO 366
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 366

Arg Ile Ser Gly Leu Ile Tyr Glu Glu Thr Arg Gly
1               5                   10

<210> SEQ ID NO 367
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 367

Arg Ile Ser Gly Leu Ile Tyr Glu Glu Thr Arg Gly
1               5                   10

<210> SEQ ID NO 368
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 368

Arg Ile Ser Gly Leu Ile Tyr Glu Glu Thr Arg Gly
1               5                   10

<210> SEQ ID NO 369
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Cele_SiC2N3

<400> SEQUENCE: 369

Arg Ile Ser Gly Leu Ile Tyr Glu Glu Thr Arg Gly
1               5                   10

<210> SEQ ID NO 370
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 370

Lys Val Phe Leu Glu Asn Val Ile Arg Asp
1               5                   10

<210> SEQ ID NO 371
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 371

Lys Val Phe Leu Glu Asn Val Ile Arg Asp
1               5                   10

<210> SEQ ID NO 372
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

```
<400> SEQUENCE: 372

Arg Asp Ala Val Thr Tyr Thr Glu His Ala Lys Arg
1               5                   10

<210> SEQ ID NO 373
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 373

Arg Asp Ala Val Thr Tyr Thr Glu His Ala Lys Arg
1               5                   10

<210> SEQ ID NO 374
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 374

Arg Asp Ala Val Thr Tyr Thr Glu His Ala Lys Arg
1               5                   10

<210> SEQ ID NO 375
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 375

Arg Asp Ala Val Thr Tyr Thr Glu His Ala Lys Arg
1               5                   10

<210> SEQ ID NO 376
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 376

Arg Asp Ala Val Thr Tyr Thr Glu His Ala Lys Arg
1               5                   10

<210> SEQ ID NO 377
<211> LENGTH: 13
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 377

Lys Arg Ile Ser Gly Leu Ile Tyr Glu Glu Thr Arg Gly
1               5                   10

<210> SEQ ID NO 378
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 378

Lys Arg Ile Ser Gly Leu Ile Tyr Glu Glu Thr Arg Gly
1               5                   10

<210> SEQ ID NO 379
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 379

Lys Arg Ile Ser Gly Leu Ile Tyr Glu Glu Thr Arg Gly
1               5                   10

<210> SEQ ID NO 380
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 380

Lys Arg Ile Ser Gly Leu Ile Tyr Glu Glu Thr Arg Gly
1               5                   10

<210> SEQ ID NO 381
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Indo_SiC2N3

<400> SEQUENCE: 381

Arg Ile Ser Gly Leu Ile Tyr Glu Glu Thr Arg Gly
1               5                   10
```

```
<210> SEQ ID NO 382
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Nap_SiC2N3

<400> SEQUENCE: 382

Arg Ile Ser Gly Leu Ile Tyr Glu Glu Thr Arg Gly
1               5                   10

<210> SEQ ID NO 383
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Nap_SiC2N3

<400> SEQUENCE: 383

Arg Ile Ser Gly Leu Ile Tyr Glu Glu Thr Arg Gly
1               5                   10

<210> SEQ ID NO 384
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Nap_SiC2N3

<400> SEQUENCE: 384

Lys Val Phe Leu Glu Asn Val Ile Arg Asp
1               5                   10

<210> SEQ ID NO 385
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Nap_SiC2N3

<400> SEQUENCE: 385

Lys Val Phe Leu Glu Asn Val Ile Arg Asp
1               5                   10

<210> SEQ ID NO 386
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
```

<223> OTHER INFORMATION: modified by CW_Nap_SiC2N3

<400> SEQUENCE: 386

Lys Val Phe Leu Glu Asn Val Ile Arg Asp
1               5                   10

<210> SEQ ID NO 387
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by Carbamidomethyl
<220> FEATURE:
<221> NAME/KEY: Misc_feature
<222> LOCATION: (24)..(24)
<223> OTHER INFORMATION: modified by CW_Nap_SiC2N3

<400> SEQUENCE: 387

Arg Asp Ala Arg Lys Ala Cys Ala Asp Ala Thr Leu Ser Gln Ile Thr
1               5                   10                  15

Asn Asn Ile Asp Pro Val Gly Arg Ile
            20                  25

<210> SEQ ID NO 388
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by Carbamidomethyl
<220> FEATURE:
<221> NAME/KEY: Misc_feature
<222> LOCATION: (6)..(6)
<223> OTHER INFORMATION: modified by CW_Cele_SiC2N3

<400> SEQUENCE: 388

Lys Ser Tyr Cys Ala Glu Ile Ala His Asn Val Ser Ser Lys Asn
1               5                   10                  15

<210> SEQ ID NO 389
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by Oxidation
<220> FEATURE:
<221> NAME/KEY: Misc_feature
<222> LOCATION: (9)..(9)
<223> OTHER INFORMATION: modified by CW_Cele_SiC0N3

<400> SEQUENCE: 389

Lys Thr Val Ala Asn Met Ile Lys Gly Lys Thr Pro Glu Glu Ile Arg
1               5                   10                  15

Lys

<210> SEQ ID NO 390
<211> LENGTH: 20
<212> TYPE: PRT

-continued

```
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Cele_SiC2N3

<400> SEQUENCE: 390

Arg Val Ala Pro Glu Glu His Pro Thr Leu Leu Thr Glu Ala Pro Leu
1               5                   10                  15

Asn Pro Lys Ala
            20

<210> SEQ ID NO 391
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 391

Lys Tyr Pro Ile Glu His Gly Ile Ile Thr Asn Trp Asp Asp Met Glu
1               5                   10                  15

Lys Ile

<210> SEQ ID NO 392
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Indo_SiC0N3

<400> SEQUENCE: 392

Arg Val Ala Pro Glu Glu His Pro Thr Leu Leu Thr Glu Ala Pro Leu
1               5                   10                  15

Asn Pro Lys Ala
            20

<210> SEQ ID NO 393
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by Oxidation
<220> FEATURE:
<221> NAME/KEY: Misc_feature
<222> LOCATION: (16)..(16)
<223> OTHER INFORMATION: modified by Oxidation
<220> FEATURE:
<221> NAME/KEY: Misc_feature
<222> LOCATION: (17)..(17)
<223> OTHER INFORMATION: modified by Carbamidomethyl
<220> FEATURE:
<221> NAME/KEY: Misc_feature
<222> LOCATION: (20)..(20)
<223> OTHER INFORMATION: modified by CW_Cele_SiC2N3
```

-continued

<400> SEQUENCE: 393

Lys Ser Gly Asp Ala Ala Ile Val Asp Met Val Pro Gly Lys Pro Met
1               5                   10                  15

Cys Val Glu Ser Phe Ser Asp Tyr Pro Pro Leu Gly Arg Phe
            20                  25                  30

<210> SEQ ID NO 394
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3
<220> FEATURE:
<221> NAME/KEY: Misc_feature
<222> LOCATION: (10)..(10)
<223> OTHER INFORMATION: modified by Oxidation
<220> FEATURE:
<221> NAME/KEY: Misc_feature
<222> LOCATION: (17)..(17)
<223> OTHER INFORMATION: modified by Carbamidomethyl

<400> SEQUENCE: 394

Lys Ser Gly Asp Ala Ala Ile Val Asp Met Val Pro Gly Lys Pro Met
1               5                   10                  15

Cys Val Glu Ser Phe Ser Asp Tyr Pro Pro Leu Gly Arg Phe
            20                  25                  30

<210> SEQ ID NO 395
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 395

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 396
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Cele_SiC2N3

<400> SEQUENCE: 396

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 397
<211> LENGTH: 30

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3
<220> FEATURE:
<221> NAME/KEY: Misc_feature
<222> LOCATION: (17)..(17)
<223> OTHER INFORMATION: modified by Carbamidomethyl

<400> SEQUENCE: 397

Lys Ser Gly Asp Ala Ala Ile Val Asp Met Val Pro Gly Lys Pro Met
1               5                   10                  15

Cys Val Glu Ser Phe Ser Asp Tyr Pro Pro Leu Gly Arg Phe
            20                  25                  30

<210> SEQ ID NO 398
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 398

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 399
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (24)..(24)
<223> OTHER INFORMATION: modified by CW_Cele_SiC2N3

<400> SEQUENCE: 399

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 400
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by Oxidation
<220> FEATURE:
<221> NAME/KEY: Misc_feature
<222> LOCATION: (16)..(16)
<223> OTHER INFORMATION: modified by Oxidation
<220> FEATURE:
<221> NAME/KEY: Misc_feature
<222> LOCATION: (17)..(17)
```

<223> OTHER INFORMATION: modified by Carbamidomethyl
<220> FEATURE:
<221> NAME/KEY: Misc_feature
<222> LOCATION: (21)..(21)
<223> OTHER INFORMATION: modified by CW_Cele_SiC2N3

<400> SEQUENCE: 400

Lys Ser Gly Asp Ala Ala Ile Val Asp Met Val Pro Gly Lys Pro Met
1               5                   10                  15

Cys Val Glu Ser Phe Ser Asp Tyr Pro Pro Leu Gly Arg Phe
            20                  25                  30

<210> SEQ ID NO 401
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by Oxidation
<220> FEATURE:
<221> NAME/KEY: Misc_feature
<222> LOCATION: (11)..(11)
<223> OTHER INFORMATION: modified by CW_Cele_SiC2N3
<220> FEATURE:
<221> NAME/KEY: Misc_feature
<222> LOCATION: (16)..(16)
<223> OTHER INFORMATION: modified by Oxidation
<220> FEATURE:
<221> NAME/KEY: Misc_feature
<222> LOCATION: (17)..(17)
<223> OTHER INFORMATION: modified by Carbamidomethyl

<400> SEQUENCE: 401

Lys Ser Gly Asp Ala Ala Ile Val Asp Met Val Pro Gly Lys Pro Met
1               5                   10                  15

Cys Val Glu Ser Phe Ser Asp Tyr Pro Pro Leu Gly Arg Phe
            20                  25                  30

<210> SEQ ID NO 402
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3
<220> FEATURE:
<221> NAME/KEY: Misc_feature
<222> LOCATION: (11)..(11)
<223> OTHER INFORMATION: modified by Oxidation

<400> SEQUENCE: 402

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 403
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature

```
<222> LOCATION: (3)..(3)
<223> OTHER INFORMATION: modified by CW_Cele_SiC2N3
<220> FEATURE:
<221> NAME/KEY: Misc_feature
<222> LOCATION: (11)..(11)
<223> OTHER INFORMATION: modified by Oxidation

<400> SEQUENCE: 403

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 404
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by Oxidation
<220> FEATURE:
<221> NAME/KEY: Misc_feature
<222> LOCATION: (24)..(24)
<223> OTHER INFORMATION: modified by CW_Cele_SiC2N3

<400> SEQUENCE: 404

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 405
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by Carbamidomethyl
<220> FEATURE:
<221> NAME/KEY: Misc_feature
<222> LOCATION: (19)..(19)
<223> OTHER INFORMATION: modified by CW_Cele_SiC2N3

<400> SEQUENCE: 405

Lys Ser Gly Asp Ala Ala Ile Val Asp Met Val Pro Gly Lys Pro Met
1               5                   10                  15

Cys Val Glu Ser Phe Ser Asp Tyr Pro Pro Leu Gly Arg Phe
            20                  25                  30

<210> SEQ ID NO 406
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by Oxidation
<220> FEATURE:
<221> NAME/KEY: Misc_feature
<222> LOCATION: (24)..(24)
<223> OTHER INFORMATION: modified by CW_Nap_SiC2N3
```

```
<400> SEQUENCE: 406

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 407
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3
<220> FEATURE:
<221> NAME/KEY: Misc_feature
<222> LOCATION: (11)..(11)
<223> OTHER INFORMATION: modified by Oxidation

<400> SEQUENCE: 407

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 408
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by Oxidation
<220> FEATURE:
<221> NAME/KEY: Misc_feature
<222> LOCATION: (12)..(12)
<223> OTHER INFORMATION: modified by CW_Nap_SiC2N3

<400> SEQUENCE: 408

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 409
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by Oxidation
<220> FEATURE:
<221> NAME/KEY: Misc_feature
<222> LOCATION: (25)..(25)
<223> OTHER INFORMATION: modified by CW_Nap_SiC2N3

<400> SEQUENCE: 409

Arg Val Glu Thr Gly Val Leu Lys Pro Gly Met Val Val Thr Phe Ala
1               5                   10                  15

Pro Val Asn Val Thr Thr Glu Val Lys Ser
            20                  25
```

```
<210> SEQ ID NO 410
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (24)..(24)
<223> OTHER INFORMATION: modified by CW_Nap_SiC2N3

<400> SEQUENCE: 410

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 411
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by Oxidation
<220> FEATURE:
<221> NAME/KEY: Misc_feature
<222> LOCATION: (15)..(15)
<223> OTHER INFORMATION: modified by CW_Cele_SiC2N3

<400> SEQUENCE: 411

Arg Phe Gln Ser Ser Ala Val Met Ala Leu Gln Glu Ala Cys Glu Ala
1               5                   10                  15

Tyr Leu Val Gly Leu Phe Glu Asp Thr Asn Leu Cys Ala Ile His Ala
            20                  25                  30

Lys Arg

<210> SEQ ID NO 412
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 412

Lys Val Gly Ala His Ala Gly Glu Tyr Gly Ala Glu Ala Leu Glu Arg
1               5                   10                  15

Met

<210> SEQ ID NO 413
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 413
```

Lys Val Gly Ala His Ala Gly Glu Tyr Gly Ala Glu Ala Leu Glu Arg
1               5                   10                  15

Met

<210> SEQ ID NO 414
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 414

Lys Val Gly Ala His Ala Gly Glu Tyr Gly Ala Glu Ala Leu Glu Arg
1               5                   10                  15

Met

<210> SEQ ID NO 415
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Cele_SiC2N3

<400> SEQUENCE: 415

Lys Val Gly Ala His Ala Gly Glu Tyr Gly Ala Glu Ala Leu Glu Arg
1               5                   10                  15

Met

<210> SEQ ID NO 416
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 416

Lys Val Gly Ala His Ala Gly Glu Tyr Gly Ala Glu Ala Leu Glu Arg
1               5                   10                  15

Met

<210> SEQ ID NO 417
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Cele_SiC2N3

<400> SEQUENCE: 417

Lys Val Gly Ala His Ala Gly Glu Tyr Gly Ala Glu Ala Leu Glu Arg
1               5                   10                  15

Met

<210> SEQ ID NO 418
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Cele_SiC2N3

<400> SEQUENCE: 418

Lys Val Gly Ala His Ala Gly Glu Tyr Gly Ala Glu Ala Leu Glu Arg
1               5                   10                  15

Met

<210> SEQ ID NO 419
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Nap_SiC2N3

<400> SEQUENCE: 419

Arg Lys Gln Val Glu Glu Leu Phe Glu Arg Lys
1               5                   10

<210> SEQ ID NO 420
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 420

Arg Tyr Arg Pro Gly Thr Val Ala Leu Arg Glu
1               5                   10

<210> SEQ ID NO 421
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Cele_SiC2N3

<400> SEQUENCE: 421

Arg Glu Ile Ala Gln Asp Phe Lys Thr Asp Leu Arg Phe
1               5                   10

<210> SEQ ID NO 422
<211> LENGTH: 9
<212> TYPE: PRT
<213> ORGANISM: Artificial Sequence
<220> FEATURE:

<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 422

Lys Ser Thr Glu Leu Leu Ile Arg Lys
1               5

<210> SEQ ID NO 423
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Cele_SiC2N3

<400> SEQUENCE: 423

Arg Phe Lys Glu Gln Leu Thr Pro Ser Gln Ile Met Ser Leu Glu Lys
1               5                   10                  15

Glu

<210> SEQ ID NO 424
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 424

Lys Asn Glu Thr Gly Gly Gly Glu Gly Val Glu Val Leu Val Asn Glu
1               5                   10                  15

Pro Tyr Glu Lys Asp
            20

<210> SEQ ID NO 425
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 425

Lys Asn Glu Thr Gly Gly Gly Glu Gly Val Glu Val Leu Val Asn Glu
1               5                   10                  15

Pro Tyr Glu Lys Asp
            20

<210> SEQ ID NO 426
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature

```
<222> LOCATION: (11)..(11)
<223> OTHER INFORMATION: modified by CW_minimalist_Si2N3
<220> FEATURE:
<221> NAME/KEY: Misc_feature
<222> LOCATION: (13)..(13)
<223> OTHER INFORMATION: modified by CW_minimalist_Si2N3

<400> SEQUENCE: 426

Lys Glu Met Asn Asp Ala Ala Met Phe Tyr Thr Asn Arg Val
1               5                   10

<210> SEQ ID NO 427
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3
<220> FEATURE:
<221> NAME/KEY: Misc_feature
<222> LOCATION: (24)..(24)
<223> OTHER INFORMATION: modified by Oxidation

<400> SEQUENCE: 427

Arg Gly Met Pro Pro Pro Leu Arg Gly Gly Pro Gly Gly Pro Gly Gly
1               5                   10                  15

Pro Gly Gly Pro Met Gly Arg Met Gly Gly Arg Gly
            20                  25

<210> SEQ ID NO 428
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (4)..(4)
<223> OTHER INFORMATION: modified by CW_Nap_SiC2N3
<220> FEATURE:
<221> NAME/KEY: Misc_feature
<222> LOCATION: (6)..(6)
<223> OTHER INFORMATION: modified by CW_Nap_SiC2N3

<400> SEQUENCE: 428

Lys Thr His Ile Asn Ile Val Val Ile Gly His Val Asp Ser Gly Lys
1               5                   10                  15

Ser

<210> SEQ ID NO 429
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (19)..(19)
<223> OTHER INFORMATION: modified by CW_Nap_SiC2N3

<400> SEQUENCE: 429

Lys Val Glu Glu Gln Glu Pro Glu Leu Thr Ser Thr Pro Asn Phe Val
1               5                   10                  15

Val Glu Val Ile Lys Asn
            20
```

<210> SEQ ID NO 430
<211> LENGTH: 33
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by Oxidation
<220> FEATURE:
<221> NAME/KEY: Misc_feature
<222> LOCATION: (32)..(32)
<223> OTHER INFORMATION: modified by CW_Cele_SiC2N3

<400> SEQUENCE: 430

Arg Glu Arg Ser Thr Pro Ser Leu Pro Cys Met Val Ser Ala Gln Asp
1               5                   10                  15

Ala Pro Leu Pro Lys Gly Ala Asp Leu Ile Glu Ala Ala Ser Arg
            20                  25                  30

Ile

<210> SEQ ID NO 431
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (19)..(19)
<223> OTHER INFORMATION: modified by CW_Cele_SiC0N3

<400> SEQUENCE: 431

Lys His Asn Ala Val Asn Ala Thr Leu Ile Asp Ser Trp Val Asp Ile
1               5                   10                  15

Ala Ile Phe Gln Leu Lys Glu Gly Ser Ser Lys Glu Lys Ala
            20                  25                  30

<210> SEQ ID NO 432
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 432

Lys Glu Gly Ser Val Val Val Asp Leu Ala Ala Glu Ala Gly Gly Asn
1               5                   10                  15

Phe Glu Thr Thr Lys Pro Gly Glu Leu Tyr Ile His Lys Gly
            20                  25                  30

<210> SEQ ID NO 433
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Cele_SiC2N3
<220> FEATURE:
<221> NAME/KEY: Misc_feature

```
<222> LOCATION: (22)..(22)
<223> OTHER INFORMATION: modified by Oxidation

<400> SEQUENCE: 433

Arg Ser Leu Gly Val Gly Tyr Ala Ala Val Asp Asn Pro Ile Phe Tyr
1               5                   10                  15

Lys Pro Asn Thr Ala Met Leu Leu Gly Asp Ala Lys Lys Thr
            20                  25                  30

<210> SEQ ID NO 434
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Cele_SiC2N3

<400> SEQUENCE: 434

Lys Ser Val Cys Lys Ala Pro Glu Leu Leu Ala Lys Tyr
1               5                   10

<210> SEQ ID NO 435
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3
<220> FEATURE:
<221> NAME/KEY: Misc_feature
<222> LOCATION: (9)..(9)
<223> OTHER INFORMATION: modified by Oxidation

<400> SEQUENCE: 435

Arg Ser Leu Gly Tyr Asp Leu Pro Met Val Glu Glu Gly Glu Pro Asp
1               5                   10                  15

Pro Glu Phe Glu Ala Ile Leu Asp Thr Val Asp Pro Asn Arg Asp
            20                  25                  30

<210> SEQ ID NO 436
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 436

Arg Ala Ile Leu Val Asp Leu Glu Pro Gly Thr Met Asp Ser Val Arg
1               5                   10                  15

Ser

<210> SEQ ID NO 437
<211> LENGTH: 17
<212> TYPE: PRT
<213> ORGANISM: Artificial Sequence
<220> FEATURE:
<223> OTHER INFORMATION: Synthetic polypeptide
<220> FEATURE:
```

<221> NAME/KEY: Misc_feature
<222> LOCATION: (6)..(6)
<223> OTHER INFORMATION: modified by CW_Cele_SiC2N3

<400> SEQUENCE: 437

Arg Ala Ile Leu Val Asp Leu Glu Pro Gly Thr Met Asp Ser Val Arg
1               5                   10                  15

Ser

<210> SEQ ID NO 438
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (25)..(25)
<223> OTHER INFORMATION: modified by CW_Nap_SiC2N3

<400> SEQUENCE: 438

Lys Leu Thr Thr Pro Thr Tyr Gly Asp Leu Asn His Leu Val Ser Ala
1               5                   10                  15

Thr Met Ser Gly Val Thr Thr Cys Leu Arg Phe
            20                  25

<210> SEQ ID NO 439
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Nap_SiC2N3

<400> SEQUENCE: 439

Lys Leu Thr Thr Pro Thr Tyr Gly Asp Leu Asn His Leu Val Ser Ala
1               5                   10                  15

Thr Met Ser Gly Val Thr Thr Cys Leu Arg Phe
            20                  25

<210> SEQ ID NO 440
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (26)..(26)
<223> OTHER INFORMATION: modified by CW_Nap_SiC2N3

<400> SEQUENCE: 440

Lys Leu Thr Thr Pro Thr Tyr Gly Asp Leu Asn His Leu Val Ser Ala
1               5                   10                  15

Thr Met Ser Gly Val Thr Thr Cys Leu Arg Phe
            20                  25

<210> SEQ ID NO 441
<211> LENGTH: 27
<212> TYPE: PRT
<213> ORGANISM: Artificial Sequence
<220> FEATURE:
<223> OTHER INFORMATION: Synthetic polypeptide
<220> FEATURE:

<221> NAME/KEY: Misc_feature
<222> LOCATION: (14)..(14)
<223> OTHER INFORMATION: modified by CW_Nap_SiC2N3

<400> SEQUENCE: 441

Lys Leu Thr Thr Pro Thr Tyr Gly Asp Leu Asn His Leu Val Ser Ala
1               5                   10                  15

Thr Met Ser Gly Val Thr Thr Cys Leu Arg Phe
            20                  25

<210> SEQ ID NO 442
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (26)..(26)
<223> OTHER INFORMATION: modified by CW_Nap_SiC2N3

<400> SEQUENCE: 442

Lys Leu Thr Thr Pro Thr Tyr Gly Asp Leu Asn His Leu Val Ser Ala
1               5                   10                  15

Thr Met Ser Gly Val Thr Thr Cys Leu Arg Phe
            20                  25

<210> SEQ ID NO 443
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_miniGL_Si0N3
<220> FEATURE:
<221> NAME/KEY: Misc_feature
<222> LOCATION: (13)..(13)
<223> OTHER INFORMATION: modified by Oxidation

<400> SEQUENCE: 443

Lys Gln Thr Asp Val Leu Gln Gln Leu Ser Ile Gln Met Ala Asn Ala
1               5                   10                  15

Lys Phe

<210> SEQ ID NO 444
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_minimalist_Si2N3

<400> SEQUENCE: 444

Lys Asp Asn Gln Gln Lys Ala Asn Glu Val Glu Gln Met Ile Arg Asp
1               5                   10                  15

<210> SEQ ID NO 445
<211> LENGTH: 25
<212> TYPE: PRT
<213> ORGANISM: Artificial Sequence
<220> FEATURE:
<223> OTHER INFORMATION: Synthetic polypeptide

```
-continued

<220> FEATURE:
<221> NAME/KEY: Misc_feature
<222> LOCATION: (6)..(6)
<223> OTHER INFORMATION: modified by CW_Nap_SiC2N3
<220> FEATURE:
<221> NAME/KEY: Misc_feature
<222> LOCATION: (8)..(8)
<223> OTHER INFORMATION: modified by CW_Nap_SiC0N3

<400> SEQUENCE: 445

Arg Glu Gln Trp Glu Pro Val Phe Gln Asn Gly Lys Met Ala Leu Leu
1               5                   10                  15

Ala Ser Asn Ser Cys Phe Ile Arg Cys
            20                  25

<210> SEQ ID NO 446
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Nap_SiC2N3
<220> FEATURE:
<221> NAME/KEY: Misc_feature
<222> LOCATION: (8)..(8)
<223> OTHER INFORMATION: modified by CW_Nap_SiC0N3

<400> SEQUENCE: 446

Arg Glu Gln Trp Glu Pro Val Phe Gln Asn Gly Lys Met Ala Leu Leu
1               5                   10                  15

Ala Ser Asn Ser Cys Phe Ile Arg Cys
            20                  25

<210> SEQ ID NO 447
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Nap_SiC2N3

<400> SEQUENCE: 447

Lys Ser Glu Lys Phe Gln Glu Ala Gly Glu Leu Tyr Asn Arg Met
1               5                   10                  15

<210> SEQ ID NO 448
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC2N3

<400> SEQUENCE: 448

Arg Glu Ser Glu Glu Lys Leu Lys Gln Gln Gln Gln Glu Ser Ala Arg
1               5                   10                  15

Arg

<210> SEQ ID NO 449
```

```
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (19)..(19)
<223> OTHER INFORMATION: modified by CW_minimalist_Si2N3

<400> SEQUENCE: 449

Arg His Ser Gln Glu Leu Pro Ala Ile Leu Asp Asp Thr Thr Leu Ser
1               5                   10                  15

Gly Ser Asp Arg Asn
            20

<210> SEQ ID NO 450
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC0N3

<400> SEQUENCE: 450

Arg Ser Ser Ile Ala Gly Leu Leu Leu Lys Ala Thr Asn Glu Lys Leu
1               5                   10                  15

<210> SEQ ID NO 451
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (18)..(18)
<223> OTHER INFORMATION: modified by CW_minimalist_Si2N3

<400> SEQUENCE: 451

Arg Ser Met Val Glu Glu Gly Thr Gly Leu Arg Leu Leu Glu Ala Ala
1               5                   10                  15

Ala Gln Ser Thr Lys Gly Tyr Tyr Ser Pro Tyr Ser Val Ser Gly Ser
            20                  25                  30

Gly Ser Thr Ala Gly Ser Arg Thr
        35                  40

<210> SEQ ID NO 452
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_minimalist_Si2N3

<400> SEQUENCE: 452

Arg Ser Met Val Glu Glu Gly Thr Gly Leu Arg Leu Leu Glu Ala Ala
1               5                   10                  15

Ala Gln Ser Thr Lys Gly Tyr Tyr Ser Pro Tyr Ser Val Ser Gly Ser
            20                  25                  30

Gly Ser Thr Ala Gly Ser Arg Thr
```

<210> SEQ ID NO 453
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 453

Arg Glu Lys Leu Glu Met Glu Met Glu Ala Ala Arg His
1               5                   10

<210> SEQ ID NO 454
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (24)..(24)
<223> OTHER INFORMATION: modified by CW_Nap_SiC2N3

<400> SEQUENCE: 454

Arg Cys Ser Gly Ile Ala Ser Ala Ala Ala Ala Val Glu Ala Ala
1               5                   10                  15

Arg Gly Ala Gly Trp Thr Gly His Val Ala Gly Thr Arg Lys Thr
            20                  25                  30

<210> SEQ ID NO 455
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Nap_SiC2N3
<220> FEATURE:
<221> NAME/KEY: Misc_feature
<222> LOCATION: (7)..(7)
<223> OTHER INFORMATION: modified by Carbamidomethyl

<400> SEQUENCE: 455

Arg Asn Ile Glu Leu Ile Cys Gln Glu Asn Glu Gly Glu Asn Asp Pro
1               5                   10                  15

Val Leu Gln Arg Ile
            20

<210> SEQ ID NO 456
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Nap_SiC2N3
<220> FEATURE:
<221> NAME/KEY: Misc_feature
<222> LOCATION: (7)..(7)
<223> OTHER INFORMATION: modified by Carbamidomethyl

<400> SEQUENCE: 456

Arg Asn Ile Glu Leu Ile Cys Gln Glu Asn Glu Gly Glu Asn Asp Pro
1               5                   10                  15

Val Leu Gln Arg Ile
            20

<210> SEQ ID NO 457
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_minimalist_Si2N3

<400> SEQUENCE: 457

Lys Ala Phe Gly Asn Glu Trp Lys Gln Ala Gly Gly His Lys Asp
1               5                   10                  15

<210> SEQ ID NO 458
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 458

Arg Leu Pro Ala Ile Pro Arg Ser Ala Thr Asn Gly Lys Ser Glu Thr
1               5                   10                  15

Ile Thr Ala Asp Val Asn His Asn Leu Lys Asp
            20                  25

<210> SEQ ID NO 459
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Nap_SiC0N3

<400> SEQUENCE: 459

Lys Glu Gly Glu Glu Ala Gly Pro Gly Asp Pro Leu Leu Glu Ala Val
1               5                   10                  15

Pro Lys Thr Gly Asp Glu Lys Asp
            20

<210> SEQ ID NO 460
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_miniGL_Si0N3

<400> SEQUENCE: 460

```
Lys Asp Val Ala Arg Val Glu Ser Lys Thr Val Ile Val Thr Pro Ser
1               5                   10                  15

Gln Arg Asp

<210> SEQ ID NO 461
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 461

Arg Asp Glu Gly Trp Leu Ala Glu His Met Leu Ile Leu Gly Ile Thr
1               5                   10                  15

Ser Pro Ala Gly Lys Lys
            20

<210> SEQ ID NO 462
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Cele_SiC2N3

<400> SEQUENCE: 462

Arg Val Ala Pro Asp Glu His Pro Ile Leu Leu Thr Glu Ala Pro Leu
1               5                   10                  15

Asn Pro Lys Ile
            20

<210> SEQ ID NO 463
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3

<400> SEQUENCE: 463

Arg Leu Ala His Tyr Asn Lys Arg Ser
1               5

<210> SEQ ID NO 464
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by Oxidation
<220> FEATURE:
<221> NAME/KEY: Misc_feature
<222> LOCATION: (14)..(14)
<223> OTHER INFORMATION: modified by CW_Cele_SiC0N3

<400> SEQUENCE: 464
```

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 465
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by Oxidation
<220> FEATURE:
<221> NAME/KEY: Misc_feature
<222> LOCATION: (21)..(21)
<223> OTHER INFORMATION: modified by CW_Cele_SiC0N3

<400> SEQUENCE: 465

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 466
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Cele_SiC0N3

<400> SEQUENCE: 466

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 467
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC0N3

<400> SEQUENCE: 467

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 468
<211> LENGTH: 31
<212> TYPE: PRT
<213> ORGANISM: Artificial Sequence
<220> FEATURE:
<223> OTHER INFORMATION: Synthetic polypeptide
<220> FEATURE:

<221> NAME/KEY: Misc_feature
<222> LOCATION: (20)..(20)
<223> OTHER INFORMATION: modified by CW_Cele_SiC0N3

<400> SEQUENCE: 468

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 469
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 469

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 470
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 470

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 471
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (22)..(22)
<223> OTHER INFORMATION: modified by CW_Cele_SiC0N3

<400> SEQUENCE: 471

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 472
<211> LENGTH: 31
<212> TYPE: PRT
<213> ORGANISM: Artificial Sequence
<220> FEATURE:
<223> OTHER INFORMATION: Synthetic polypeptide

```
<220> FEATURE:
<221> NAME/KEY: Misc_feature
<222> LOCATION: (20)..(20)
<223> OTHER INFORMATION: modified by CW_Cele_SiC0N3

<400> SEQUENCE: 472

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 473
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 473

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 474
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 474

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 475
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 475

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 476
<211> LENGTH: 31
```

-continued

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 476

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 477
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by Oxidation
<220> FEATURE:
<221> NAME/KEY: Misc_feature
<222> LOCATION: (11)..(11)
<223> OTHER INFORMATION: modified by CW_Indo_SiC2N3

<400> SEQUENCE: 477

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 478
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by Oxidation
<220> FEATURE:
<221> NAME/KEY: Misc_feature
<222> LOCATION: (20)..(20)
<223> OTHER INFORMATION: modified by CW_Indo_SiC2N3

<400> SEQUENCE: 478

Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 479
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Indo_SiC2N3

<400> SEQUENCE: 479
```

```
Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30
```

<210> SEQ ID NO 480
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Indo_SiC2N3

<400> SEQUENCE: 480

```
Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30
```

<210> SEQ ID NO 481
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (19)..(19)
<223> OTHER INFORMATION: modified by CW_Indo_SiC2N3

<400> SEQUENCE: 481

```
Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp
            20                  25                  30
```

<210> SEQ ID NO 482
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Nap_SiC0N3

<400> SEQUENCE: 482

```
Arg Val Gly Ala Gly Ala Pro Val Tyr Met Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35
```

<210> SEQ ID NO 483
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)

<223> OTHER INFORMATION: modified by CW_Nap_SiC0N3

<400> SEQUENCE: 483

```
Arg Val Gly Ala Gly Ala Pro Val Tyr Met Ala Ala Val Leu Glu Tyr
1               5                   10                  15
Leu Thr Ala Glu Ile Leu Glu Leu Ala Gly Asn Ala Ala Arg Asp
            20                  25                  30
```

<210> SEQ ID NO 484
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Nap_SiC0N3

<400> SEQUENCE: 484

```
Arg Val Gly Ala Gly Ala Pro Val Tyr Met Ala Ala Val Leu Glu Tyr
1               5                   10                  15
Leu Thr Ala Glu Ile Leu Glu Leu Ala Gly Asn Ala Ala Arg Asp
            20                  25                  30
```

<210> SEQ ID NO 485
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by Oxidation
<220> FEATURE:
<221> NAME/KEY: Misc_feature
<222> LOCATION: (14)..(14)
<223> OTHER INFORMATION: modified by CW_Cele_SiC2N3
<220> FEATURE:
<221> NAME/KEY: Misc_feature
<222> LOCATION: (28)..(28)
<223> OTHER INFORMATION: modified by Carbamidomethyl

<400> SEQUENCE: 485

```
Arg Phe Gln Ser Ser Ala Val Met Ala Leu Gln Glu Ala Ser Glu Ala
1               5                   10                  15
Tyr Leu Val Gly Leu Phe Glu Asp Thr Asn Leu Cys Ala Ile His Ala
            20                  25                  30
Lys Arg
```

<210> SEQ ID NO 486
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 486

```
Arg Ala Val Phe Val Asp Leu Glu Pro Thr Val Ile Asp Glu Val Arg
1               5                   10                  15
Thr
```

```
<210> SEQ ID NO 487
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 487

Arg Ala Val Phe Val Asp Leu Glu Pro Thr Val Ile Asp Glu Val Arg
1               5                   10                  15
Thr

<210> SEQ ID NO 488
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Cele_SiC2N3

<400> SEQUENCE: 488

Arg Ala Val Phe Val Asp Leu Glu Pro Thr Val Ile Asp Glu Val Arg
1               5                   10                  15
Thr

<210> SEQ ID NO 489
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 489

Arg Ala Val Phe Val Asp Leu Glu Pro Thr Val Ile Asp Glu Val Arg
1               5                   10                  15
Thr

<210> SEQ ID NO 490
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Cele_SiC2N3

<400> SEQUENCE: 490

Lys Thr Ile Gly Gly Gly Asp Asp Ser Phe Asn Thr Phe Phe Ser Glu
1               5                   10                  15
Thr Gly Ala Gly Lys His
            20

<210> SEQ ID NO 491
```

```
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC2N3

<400> SEQUENCE: 491

Arg Ala Val Phe Val Asp Leu Glu Pro Thr Val Ile Asp Glu Val Arg
1               5                   10                  15

Thr

<210> SEQ ID NO 492
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 492

Arg Ala Val Phe Val Asp Leu Glu Pro Thr Val Ile Asp Glu Val Arg
1               5                   10                  15

Thr

<210> SEQ ID NO 493
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 493

Arg Ala Val Phe Val Asp Leu Glu Pro Thr Val Ile Asp Glu Val Arg
1               5                   10                  15

Thr

<210> SEQ ID NO 494
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 494

Arg Ala Val Phe Val Asp Leu Glu Pro Thr Val Ile Asp Glu Val Arg
1               5                   10                  15

Thr

<210> SEQ ID NO 495
<211> LENGTH: 17
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Indo_SiC2N3

<400> SEQUENCE: 495

Arg Ala Val Phe Val Asp Leu Glu Pro Thr Val Ile Asp Glu Val Arg
1               5                   10                  15

Thr

<210> SEQ ID NO 496
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Indo_SiC2N3

<400> SEQUENCE: 496

Arg Ala Val Phe Val Asp Leu Glu Pro Thr Val Ile Asp Glu Val Arg
1               5                   10                  15

Thr

<210> SEQ ID NO 497
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Nap_SiC2N3

<400> SEQUENCE: 497

Lys Thr Ile Gly Gly Gly Asp Asp Ser Phe Asn Thr Phe Phe Ser Glu
1               5                   10                  15

Thr Gly Ala Gly Lys His
            20

<210> SEQ ID NO 498
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Nap_SiC2N3

<400> SEQUENCE: 498

Lys Thr Ile Gly Gly Gly Asp Asp Ser Phe Asn Thr Phe Phe Ser Glu
1               5                   10                  15

Thr Gly Ala Gly Lys His
            20

<210> SEQ ID NO 499
<211> LENGTH: 22
<212> TYPE: PRT
<213> ORGANISM: Artificial Sequence
<220> FEATURE:
```

<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Nap_SiC2N3

<400> SEQUENCE: 499

Lys Thr Ile Gly Gly Gly Asp Asp Ser Phe Asn Thr Phe Phe Ser Glu
1               5                   10                  15

Thr Gly Ala Gly Lys His
            20

<210> SEQ ID NO 500
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 500

Arg Ile His Phe Pro Leu Ala Thr Tyr Ala Pro Val Ile Ser Ala Glu
1               5                   10                  15

Lys Ala

<210> SEQ ID NO 501
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 501

Arg Ile His Phe Pro Leu Ala Thr Tyr Ala Pro Val Ile Ser Ala Glu
1               5                   10                  15

Lys Ala

<210> SEQ ID NO 502
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 502

Arg Ile His Phe Pro Leu Ala Thr Tyr Ala Pro Val Ile Ser Ala Glu
1               5                   10                  15

Lys Ala

<210> SEQ ID NO 503
<211> LENGTH: 18
<212> TYPE: PRT
<213> ORGANISM: Artificial Sequence
<220> FEATURE:
<223> OTHER INFORMATION: Synthetic polypeptide
<220> FEATURE:

<221> NAME/KEY: Misc_feature
<222> LOCATION: (16)..(16)
<223> OTHER INFORMATION: modified by CW_Cele_SiC2N3

<400> SEQUENCE: 503

Arg Ile His Phe Pro Leu Ala Thr Tyr Ala Pro Val Ile Ser Ala Glu
1               5                   10                  15

Lys Ala

<210> SEQ ID NO 504
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 504

Arg Ile His Phe Pro Leu Ala Thr Tyr Ala Pro Val Ile Ser Ala Glu
1               5                   10                  15

Lys Ala

<210> SEQ ID NO 505
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 505

Arg Ile His Phe Pro Leu Ala Thr Tyr Ala Pro Val Ile Ser Ala Glu
1               5                   10                  15

Lys Ala

<210> SEQ ID NO 506
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 506

Arg Ile His Phe Pro Leu Ala Thr Tyr Ala Pro Val Ile Ser Ala Glu
1               5                   10                  15

Lys Ala

<210> SEQ ID NO 507
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

-continued

<400> SEQUENCE: 507

Arg Ile His Phe Pro Leu Ala Thr Tyr Ala Pro Val Ile Ser Ala Glu
1               5                   10                  15

Lys Ala

<210> SEQ ID NO 508
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 508

Arg Ile His Phe Pro Leu Ala Thr Tyr Ala Pro Val Ile Ser Ala Glu
1               5                   10                  15

Lys Ala

<210> SEQ ID NO 509
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Cele_SiC2N3

<400> SEQUENCE: 509

Lys Val Gly Ile Asn Tyr Gln Pro Pro Thr Val Val Pro Gly Gly Asp
1               5                   10                  15

Leu Ala Lys Val
            20

<210> SEQ ID NO 510
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC2N3

<400> SEQUENCE: 510

Arg Ile His Phe Pro Leu Ala Thr Tyr Ala Pro Val Ile Ser Ala Glu
1               5                   10                  15

Lys Ala

<210> SEQ ID NO 511
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 511

Arg Ile His Phe Pro Leu Ala Thr Tyr Ala Pro Val Ile Ser Ala Glu
1               5                   10                  15

Lys Ala

<210> SEQ ID NO 512
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 512

Arg Ile His Phe Pro Leu Ala Thr Tyr Ala Pro Val Ile Ser Ala Glu
1               5                   10                  15

Lys Ala

<210> SEQ ID NO 513
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC2N3

<400> SEQUENCE: 513

Arg Ile His Phe Pro Leu Ala Thr Tyr Ala Pro Val Ile Ser Ala Glu
1               5                   10                  15

Lys Ala

<210> SEQ ID NO 514
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (19)..(19)
<223> OTHER INFORMATION: modified by CW_Indo_SiC2N3

<400> SEQUENCE: 514

Lys Val Gly Ile Asn Tyr Gln Pro Pro Thr Val Val Pro Gly Gly Asp
1               5                   10                  15

Leu Ala Lys Val
            20

<210> SEQ ID NO 515
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by Carbamidomethyl
<220> FEATURE:
<221> NAME/KEY: Misc_feature
<222> LOCATION: (21)..(21)
<223> OTHER INFORMATION: modified by CW_Nap_SiC2N3

<400> SEQUENCE: 515

Lys Ser Ala Thr Leu Cys Ser Leu Pro Ser Cys Pro Pro Phe Ile Pro
1               5                   10                  15

Leu Asn Phe Glu Ala Thr Pro Ile Val Arg Val
            20                  25

<210> SEQ ID NO 516
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Cele_SiC2N3

<400> SEQUENCE: 516

Arg Glu Ala Gln Ala Ala Leu Ala Glu Ala Gln Glu Asp Leu Glu Ser
1               5                   10                  15

Glu Arg Val Ala Arg Thr Lys Ala
            20

<210> SEQ ID NO 517
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Cele_SiC2N3

<400> SEQUENCE: 517

Arg Thr Glu Leu Gly Leu Asp Leu Gly Leu Glu Pro Lys Arg
1               5                   10

<210> SEQ ID NO 518
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Nap_SiC0N3
<220> FEATURE:
<221> NAME/KEY: Misc_feature
<222> LOCATION: (21)..(21)
<223> OTHER INFORMATION: modified by Carbamidomethyl
<220> FEATURE:
<221> NAME/KEY: Misc_feature
<222> LOCATION: (22)..(22)
<223> OTHER INFORMATION: modified by CW_Nap_SiC0N3

<400> SEQUENCE: 518

Lys Arg Ala Ser Tyr Gly His Ser Met Val Val Asp Pro Trp Gly Thr
1               5                   10                  15

Val Val Ala Arg Cys Ser Glu Gly Pro Gly Leu Cys Leu Ala Arg Ile
            20                  25                  30

<210> SEQ ID NO 519
<211> LENGTH: 32
<212> TYPE: PRT
<213> ORGANISM: Artificial Sequence

```
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Nap_SiC0N3
<220> FEATURE:
<221> NAME/KEY: Misc_feature
<222> LOCATION: (21)..(21)
<223> OTHER INFORMATION: modified by Carbamidomethyl
<220> FEATURE:
<221> NAME/KEY: Misc_feature
<222> LOCATION: (22)..(22)
<223> OTHER INFORMATION: modified by CW_Nap_SiC0N3

<400> SEQUENCE: 519

Lys Arg Ala Ser Tyr Gly His Ser Met Val Val Asp Pro Trp Gly Thr
1               5                   10                  15

Val Val Ala Arg Cys Ser Glu Gly Pro Gly Leu Cys Leu Ala Arg Ile
            20                  25                  30

<210> SEQ ID NO 520
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Cele_SiC0N3

<400> SEQUENCE: 520

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 521
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 521

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 522
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
```

<223> OTHER INFORMATION: modified by CW_Cele_SiC0N3

<400> SEQUENCE: 522

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys

<210> SEQ ID NO 523
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiC0N3

<400> SEQUENCE: 523

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys

<210> SEQ ID NO 524
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by CW_Cele_SiC0N3

<400> SEQUENCE: 524

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 525
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (18)..(18)
<223> OTHER INFORMATION: modified by CW_Cele_SiC0N3

<400> SEQUENCE: 525

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 526
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Cele_SiC0N3

<400> SEQUENCE: 526

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 527
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 527

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 528
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 528

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 529
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 529

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 530
<211> LENGTH: 31
<212> TYPE: PRT

<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiCON3

<400> SEQUENCE: 530

Arg Val Gly Ala Gly Ala Pro Val Tyr Leu Ala Ala Val Leu Glu Tyr
1               5                   10                  15
Leu Thr Ala Glu Ile Leu Glu Leu Ala Gly Asn Ala Ala Arg Asp
            20                  25                  30

<210> SEQ ID NO 531
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiCON3

<400> SEQUENCE: 531

Arg Val Gly Ala Gly Ala Pro Val Tyr Leu Ala Ala Val Leu Glu Tyr
1               5                   10                  15
Leu Thr Ala Glu Ile Leu Glu Leu Ala Gly Asn Ala Ala Arg Asp
            20                  25                  30

<210> SEQ ID NO 532
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiCON3

<400> SEQUENCE: 532

Arg Val Gly Ala Gly Ala Pro Val Tyr Leu Ala Ala Val Leu Glu Tyr
1               5                   10                  15
Leu Thr Ala Glu Ile Leu Glu Leu Ala Gly Asn Ala Ala Arg Asp
            20                  25                  30

<210> SEQ ID NO 533
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Cele_SiCON3

<400> SEQUENCE: 533

Arg Val Gly Ala Gly Ala Pro Val Tyr Leu Ala Ala Val Leu Glu Tyr
1               5                   10                  15
Leu Thr Ala Glu Ile Leu Glu Leu Ala Gly Asn Ala Ala Arg Asp
            20                  25                  30

<210> SEQ ID NO 534
<211> LENGTH: 31

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 534

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 535
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 535

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 536
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC2N3

<400> SEQUENCE: 536

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 537
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 537

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35
```

<210> SEQ ID NO 538
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (22)..(22)
<223> OTHER INFORMATION: modified by CW_Cele_SiC0N3

<400> SEQUENCE: 538

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 539
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 539

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 540
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 540

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 541
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature

```
<222> LOCATION: (20)..(20)
<223> OTHER INFORMATION: modified by CW_Cele_SiCON3

<400> SEQUENCE: 541

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 542
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiCON3

<400> SEQUENCE: 542

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys

<210> SEQ ID NO 543
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Cele_SiCON3

<400> SEQUENCE: 543

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 544
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiCON3

<400> SEQUENCE: 544

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 545
<211> LENGTH: 31
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 545

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 546
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 546

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 547
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Cele_SiC2N3

<400> SEQUENCE: 547

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 548
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC2N3

<400> SEQUENCE: 548

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 549
```

```
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC2N3

<400> SEQUENCE: 549

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 550
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC2N3

<400> SEQUENCE: 550

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 551
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (18)..(18)
<223> OTHER INFORMATION: modified by CW_Cele_SiC2N3

<400> SEQUENCE: 551

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 552
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Cele_SiC0N3

<400> SEQUENCE: 552

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30
```

```
<210> SEQ ID NO 553
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC2N3

<400> SEQUENCE: 553

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 554
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC2N3

<400> SEQUENCE: 554

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 555
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Cele_SiC2N3

<400> SEQUENCE: 555

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 556
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (16)..(16)
<223> OTHER INFORMATION: modified by CW_Cele_SiC0N3

<400> SEQUENCE: 556

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30
```

<210> SEQ ID NO 557
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3

<400> SEQUENCE: 557

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 558
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (15)..(15)
<223> OTHER INFORMATION: modified by CW_Cele_SiC0N3

<400> SEQUENCE: 558

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 559
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (22)..(22)
<223> OTHER INFORMATION: modified by CW_Indo_SiC2N3

<400> SEQUENCE: 559

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 560
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (22)..(22)
<223> OTHER INFORMATION: modified by CW_Indo_SiC2N3

<400> SEQUENCE: 560

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 561
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (18)..(18)
<223> OTHER INFORMATION: modified by CW_Indo_SiC2N3

<400> SEQUENCE: 561

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 562
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Indo_SiC2N3

<400> SEQUENCE: 562

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 563
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (18)..(18)
<223> OTHER INFORMATION: modified by CW_Indo_SiC2N3

<400> SEQUENCE: 563

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 564
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Indo_SiC2N3

<400> SEQUENCE: 564

Arg Val Gly Ala Gly Ala Pro Val Tyr Leu Ala Ala Val Leu Glu Tyr

```
            1               5                  10                  15
Leu Thr Ala Glu Ile Leu Glu Leu Ala Gly Asn Ala Ala Arg Asp
            20                  25                  30
```

<210> SEQ ID NO 565
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Indo_SiC2N3

<400> SEQUENCE: 565

```
Arg Val Gly Ala Gly Ala Pro Val Tyr Leu Ala Ala Val Leu Glu Tyr
1               5                  10                  15
Leu Thr Ala Glu Ile Leu Glu Leu Ala Gly Asn Ala Ala Arg Asp
            20                  25                  30
```

<210> SEQ ID NO 566
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Indo_SiC2N3

<400> SEQUENCE: 566

```
Arg Val Gly Ala Gly Ala Pro Val Tyr Leu Ala Ala Val Leu Glu Tyr
1               5                  10                  15
Leu Thr Ala Glu Ile Leu Glu Leu Ala Gly Asn Ala Ala Arg Asp
            20                  25                  30
```

<210> SEQ ID NO 567
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (19)..(19)
<223> OTHER INFORMATION: modified by CW_Indo_SiC2N3

<400> SEQUENCE: 567

```
Arg Val Gly Ala Gly Ala Pro Val Tyr Leu Ala Ala Val Leu Glu Tyr
1               5                  10                  15
Leu Thr Ala Glu Ile Leu Glu Leu Ala Gly Asn Ala Ala Arg Asp
            20                  25                  30
```

<210> SEQ ID NO 568
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (14)..(14)
<223> OTHER INFORMATION: modified by CW_Nap_SiC0N3

<400> SEQUENCE: 568

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 569
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Nap_SiC0N3

<400> SEQUENCE: 569

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 570
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Nap_SiC0N3

<400> SEQUENCE: 570

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys

<210> SEQ ID NO 571
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Nap_SiC0N3

<400> SEQUENCE: 571

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 572

```
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (21)..(21)
<223> OTHER INFORMATION: modified by CW_Nap_SiC0N3

<400> SEQUENCE: 572

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 573
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (18)..(18)
<223> OTHER INFORMATION: modified by CW_Nap_SiC0N3

<400> SEQUENCE: 573

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 574
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Nap_SiC0N3

<400> SEQUENCE: 574

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp Asn
            20                  25                  30

Lys Lys Thr
        35

<210> SEQ ID NO 575
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Nap_SiC0N3

<400> SEQUENCE: 575

Arg Val Gly Ala Gly Ala Pro Val Tyr Leu Ala Ala Val Leu Glu Tyr
1               5                   10                  15
```

1               5                   10                  15

Leu Thr Ala Glu Ile Leu Glu Leu Ala Gly Asn Ala Ala Arg Asp
            20                  25                  30

<210> SEQ ID NO 576
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Nap_SiC0N3

<400> SEQUENCE: 576

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 577
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Nap_SiC0N3

<400> SEQUENCE: 577

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 578
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Nap_SiC0N3

<400> SEQUENCE: 578

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 579
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Nap_SiC0N3

<400> SEQUENCE: 579

-continued

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 580
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Nap_SiC0N3

<400> SEQUENCE: 580

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 581
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Nap_SiC0N3

<400> SEQUENCE: 581

Arg Val Gly Ala Gly Ala Pro Val Tyr Leu Ala Ala Val Leu Glu Tyr
1               5                   10                  15

Leu Thr Ala Glu Ile Leu Glu Leu Ala Gly Asn Ala Ala Arg Asp
            20                  25                  30

<210> SEQ ID NO 582
<211> LENGTH: 29
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Carbamidomethyl
<220> FEATURE:
<221> NAME/KEY: Misc_feature
<222> LOCATION: (7)..(7)
<223> OTHER INFORMATION: modified by CW_Cele_SiC2N3
<220> FEATURE:
<221> NAME/KEY: Misc_feature
<222> LOCATION: (19)..(19)
<223> OTHER INFORMATION: modified by Oxidation

<400> SEQUENCE: 582

Lys Asn Cys Leu Leu Leu Leu Thr Tyr Leu Ile Ser Glu Leu Glu Ala
1               5                   10                  15

Ala Arg Met Leu Cys Val Asn Ala Pro Pro Lys Lys Ala
            20                  25

<210> SEQ ID NO 583
<211> LENGTH: 14
<212> TYPE: PRT
<213> ORGANISM: Artificial Sequence -continued

```
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 583

Lys Asn Ala Ser Asp Met Pro Glu Thr Ile Thr Ser Arg Asp
1               5                   10

<210> SEQ ID NO 584
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 584

Lys Asn Ala Ser Asp Met Pro Glu Thr Ile Thr Ser Arg Asp
1               5                   10

<210> SEQ ID NO 585
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 585

Lys Asn Ala Ser Asp Met Pro Glu Thr Ile Thr Ser Arg Asp
1               5                   10

<210> SEQ ID NO 586
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Indo_SiC2N3

<400> SEQUENCE: 586

Lys Asn Ala Ser Asp Met Pro Glu Thr Ile Thr Ser Arg Asp
1               5                   10

<210> SEQ ID NO 587
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_miniGL_Si0N3

<400> SEQUENCE: 587

Lys Glu Asp Glu Ile Ser Leu Glu Asp Leu Ile Glu Arg Glu Arg Ser
1               5                   10                  15
```

<210> SEQ ID NO 588
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_Nap_SiC2N3
<220> FEATURE:
<221> NAME/KEY: Misc_feature
<222> LOCATION: (8)..(8)
<223> OTHER INFORMATION: modified by CW_Nap_SiC0N3

<400> SEQUENCE: 588

Arg Glu Asp Ser Asn Leu Glu Ser Ser Gln Leu Thr Val Gln Ala Glu
1               5                   10                  15

Phe Asp Met Ser Ala Ile Pro Arg Lys
            20                  25

<210> SEQ ID NO 589
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Indo_SiC2N3

<400> SEQUENCE: 589

Lys Leu Asp Pro Thr Lys Thr Thr Leu Leu Lys Met Ala Asp Cys Gly
1               5                   10                  15

Gly Leu Pro Gln Ile Ser Gln Pro Ala Lys Leu
            20                  25

<210> SEQ ID NO 590
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Nap_SiC0N3

<400> SEQUENCE: 590

Arg Thr Leu Gly Asp Leu Val Arg Lys Leu Gly Glu Lys Ile
1               5                   10

<210> SEQ ID NO 591
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC0N3

<400> SEQUENCE: 591

Arg Thr Leu Gly Asp Leu Val Arg Lys Leu Gly Glu Lys Ile
1               5                   10

```
<210> SEQ ID NO 592
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (9)..(9)
<223> OTHER INFORMATION: modified by CW_Indo_SiC2N3

<400> SEQUENCE: 592

Arg Ala Thr Glu Lys Ala Phe Gly Gln Asn Ser Gly Trp Leu Phe Leu
1               5                   10                  15

Asp Ser Ser Thr Ser Met Phe Ile Asn Ala Arg Ala
            20                  25

<210> SEQ ID NO 593
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (10)..(10)
<223> OTHER INFORMATION: modified by CW_Nap_SiC2N3

<400> SEQUENCE: 593

Lys Asp Phe Ile Ile Leu Ser Cys Val Arg Ala Asn Glu His Gln Gly
1               5                   10                  15

Ile Gly Phe Leu Asn Asp Pro Arg Arg
            20                  25

<210> SEQ ID NO 594
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Indo_SiC2N3

<400> SEQUENCE: 594

Arg Glu Ser Val Phe Thr Val Glu Gly Gly His Arg Ala
1               5                   10

<210> SEQ ID NO 595
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by CW_Indo_SiC2N3
<220> FEATURE:
<221> NAME/KEY: Misc_feature
<222> LOCATION: (5)..(5)
<223> OTHER INFORMATION: modified by CW_Indo_SiC0N3

<400> SEQUENCE: 595

Lys Ser Val Val Ala Lys Phe Asn Ala Ser Gln Leu Ile Thr Gln Arg
1               5                   10                  15

Ala
```

```
<210> SEQ ID NO 596
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (22)..(22)
<223> OTHER INFORMATION: modified by CW_Indo_SiC0N3

<400> SEQUENCE: 596

Lys Val Ala Val Pro Ser Thr Ile His Cys Asp His Leu Ile Glu Ala
1               5                   10                  15

Gln Val Gly Gly Glu Lys Asp
            20

<210> SEQ ID NO 597
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_miniGL_Si0N3

<400> SEQUENCE: 597

Arg Ala Trp Asn Ser Val Arg Met Ala Ser Ser Gly Met Thr Arg Arg
1               5                   10                  15

<210> SEQ ID NO 598
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (17)..(17)
<223> OTHER INFORMATION: modified by CW_Indo_SiC2N3

<400> SEQUENCE: 598

Arg Ser Gly Pro Phe Gly Gln Leu Phe Arg Pro Asp Asn Phe Ile Phe
1               5                   10                  15

Gly Gln Thr Gly Ala Gly Asn Asn Trp Ala Lys Gly
            20                  25

<210> SEQ ID NO 599
<211> LENGTH: 29
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (12)..(12)
<223> OTHER INFORMATION: modified by Oxidation
<220> FEATURE:
<221> NAME/KEY: Misc_feature
<222> LOCATION: (18)..(18)
<223> OTHER INFORMATION: modified by Oxidation
<220> FEATURE:
<221> NAME/KEY: Misc_feature
<222> LOCATION: (22)..(22)
<223> OTHER INFORMATION: modified by Carbamidomethyl
<220> FEATURE:
<221> NAME/KEY: Misc_feature
```

<222> LOCATION: (26)..(26)
<223> OTHER INFORMATION: modified by CW_Nap_SiC0N3

<400> SEQUENCE: 599

Arg Ala Leu Thr Val Pro Glu Leu Thr Gln Gln Met Phe Asp Ala Arg
1               5                   10                  15

Asn Met Met Ala Ala Cys Asp Pro Arg His Gly Arg Tyr
            20                  25

<210> SEQ ID NO 600
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by Oxidation
<220> FEATURE:
<221> NAME/KEY: Misc_feature
<222> LOCATION: (23)..(23)
<223> OTHER INFORMATION: modified by CW_Indo_SiC0N3
<220> FEATURE:
<221> NAME/KEY: Misc_feature
<222> LOCATION: (25)..(25)
<223> OTHER INFORMATION: modified by Oxidation

<400> SEQUENCE: 600

Lys Ile Gly Glu Met Pro Leu Thr Asp Ser Ile Leu Cys Asp Gly Leu
1               5                   10                  15

Thr Asp Ala Phe His Asn Cys His Met Gly Ile Thr Ala Glu Asn Val
            20                  25                  30

Ala Lys Lys Trp
        35

<210> SEQ ID NO 601
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_miniGL_Si0N3

<400> SEQUENCE: 601

Lys Lys Glu Tyr Ser Leu Asp Thr Arg Gly
1               5                   10

<210> SEQ ID NO 602
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Cele_SiC0N3

<400> SEQUENCE: 602

Arg Ser Val Gly Val Ile Ser Pro Tyr Arg Lys Gln
1               5                   10

<210> SEQ ID NO 603
<211> LENGTH: 10

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Indo_SiC2N3

<400> SEQUENCE: 603

Lys Gln Val Val Lys His Leu Pro Lys Ala
1               5                   10

<210> SEQ ID NO 604
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Indo_SiC2N3

<400> SEQUENCE: 604

Lys Gln Val Val Lys His Leu Pro Lys Ala
1               5                   10

<210> SEQ ID NO 605
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Nap_SiC2N3

<400> SEQUENCE: 605

Arg Gln Tyr Glu Asn His Ile Phe Val Gly Ser Lys Thr Ala Asp Pro
1               5                   10                  15

Cys Cys Tyr Gly His Thr Gln Phe His Leu Leu Pro Asp Lys Leu
            20                  25                  30

<210> SEQ ID NO 606
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (2)..(2)
<223> OTHER INFORMATION: modified by CW_minimalist_Si2N3
<220> FEATURE:
<221> NAME/KEY: Misc_feature
<222> LOCATION: (12)..(12)
<223> OTHER INFORMATION: modified by Oxidation

<400> SEQUENCE: 606

Arg Ser Asp Ala Gly Leu Glu Ser Asp Thr Ala Met Lys Lys Gly Glu
1               5                   10                  15

Thr Leu Arg Lys
            20

<210> SEQ ID NO 607
<211> LENGTH: 18
<212> TYPE: PRT
```

<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Indo_SiC2N3
<220> FEATURE:
<221> NAME/KEY: Misc_feature
<222> LOCATION: (17)..(17)
<223> OTHER INFORMATION: modified by CW_Indo_SiC0N3

<400> SEQUENCE: 607

Arg Ser Gly Ala Pro Ala Ala Glu Ser Lys Glu Ile Val Arg Gly Tyr
1               5                   10                  15

Lys Trp

<210> SEQ ID NO 608
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (23)..(23)
<223> OTHER INFORMATION: modified by CW_Indo_SiC0N3

<400> SEQUENCE: 608

Lys Gly Ser Glu Lys Pro Leu Glu Gln Thr Phe Ala Thr Met Val Ser
1               5                   10                  15

Ser Leu Gly Ser Gly Met Met Arg Tyr Ile Ala Phe Asp Phe His Lys
            20                  25                  30

Glu Cys Lys Asn
        35

<210> SEQ ID NO 609
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_miniGL_Si0N3
<220> FEATURE:
<221> NAME/KEY: Misc_feature
<222> LOCATION: (17)..(17)
<223> OTHER INFORMATION: modified by Carbamidomethyl

<400> SEQUENCE: 609

Arg Ala Leu Glu Phe Gly Glu Pro Val Leu Leu Val Gly Asp Thr Gly
1               5                   10                  15

Cys Gly Lys Thr
            20

<210> SEQ ID NO 610
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (11)..(11)
<223> OTHER INFORMATION: modified by CW_Nap_SiC2N3

<400> SEQUENCE: 610

-continued

Lys Ser Pro Gly Ile Ile Phe Ile Pro Gly Tyr Leu Ser Tyr Met Asn
1               5                   10                  15

Gly Thr Lys Ala
            20

<210> SEQ ID NO 611
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (7)..(7)
<223> OTHER INFORMATION: modified by CW_Nap_SiC2N3

<400> SEQUENCE: 611

Lys Ser Pro Gly Ile Ile Phe Ile Pro Gly Tyr Leu Ser Tyr Met Asn
1               5                   10                  15

Gly Thr Lys Ala
            20

<210> SEQ ID NO 612
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (3)..(3)
<223> OTHER INFORMATION: modified by Oxidation
<220> FEATURE:
<221> NAME/KEY: Misc_feature
<222> LOCATION: (16)..(16)
<223> OTHER INFORMATION: modified by Carbamidomethyl
<220> FEATURE:
<221> NAME/KEY: Misc_feature
<222> LOCATION: (18)..(18)
<223> OTHER INFORMATION: modified by CW_Nap_SiC0N3

<400> SEQUENCE: 612

Arg Ala Met Lys Leu Gly Glu Glu Ala Phe Phe Tyr His Ser Asn Cys
1               5                   10                  15

Lys Glu Pro Gly Ile Ala Gly Leu Met Lys Ile
            20                  25

<210> SEQ ID NO 613
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (6)..(6)
<223> OTHER INFORMATION: modified by CW_Nap_SiC2N3
<220> FEATURE:
<221> NAME/KEY: Misc_feature
<222> LOCATION: (7)..(7)
<223> OTHER INFORMATION: modified by Oxidation
<220> FEATURE:
<221> NAME/KEY: Misc_feature
<222> LOCATION: (15)..(15)
<223> OTHER INFORMATION: modified by Oxidation

<400> SEQUENCE: 613

Arg Ile Thr Asp Gly Thr Met Leu Gln Ala Ile Glu Arg Tyr Met Lys
1               5                   10                  15

Gln

<210> SEQ ID NO 614
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (13)..(13)
<223> OTHER INFORMATION: modified by CW_Cele_SiC2N3

<400> SEQUENCE: 614

Arg Ala Phe Asp Gln Gly Ala Asp Ala Ile Tyr Asp His Ile Asn Glu
1               5                   10                  15

Gly Lys Leu

<210> SEQ ID NO 615
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Nap_SiC0N3

<400> SEQUENCE: 615

Lys Glu Asn Ser Glu Gly Ala Gly Ala Lys Ala Ser Ser Ala Gly Val
1               5                   10                  15

Leu Val Ser

<210> SEQ ID NO 616
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Nap_SiC0N3

<400> SEQUENCE: 616

Lys Glu Asn Ser Glu Gly Ala Gly Ala Lys Ala Ser Ser Ala Gly Val
1               5                   10                  15

Leu Val Ser

<210> SEQ ID NO 617
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 617

Lys Ala Ser Tyr Gly Val Glu Asp Pro Glu Tyr Ala Val Thr Gln Leu
1               5                   10                  15

Ala Gln Thr Thr Met Arg Ser
            20

<210> SEQ ID NO 618
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_Cele_SiC2N3

<400> SEQUENCE: 618

Lys Ala Ser Tyr Gly Val Glu Asp Pro Glu Tyr Ala Val Thr Gln Leu
1               5                   10                  15

Ala Gln Thr Thr Met Arg Ser
            20

<210> SEQ ID NO 619
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (20)..(20)
<223> OTHER INFORMATION: modified by CW_Cele_SiC0N3
<220> FEATURE:
<221> NAME/KEY: Misc_feature
<222> LOCATION: (22)..(22)
<223> OTHER INFORMATION: modified by Oxidation

<400> SEQUENCE: 619

Lys Ile Asp Gln Gln Gln Gln Lys Val Ala Ala Ser Met Pro Leu
1               5                   10                  15

Ser Pro Gly Gly Gln Met Glu Glu Val Ala Gly Ala Val Lys Gln
            20                  25                  30

<210> SEQ ID NO 620
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_miniGL_Si0N3
<220> FEATURE:
<221> NAME/KEY: Misc_feature
<222> LOCATION: (14)..(14)
<223> OTHER INFORMATION: modified by CW_miniGL_Si0N3
<220> FEATURE:
<221> NAME/KEY: Misc_feature
<222> LOCATION: (16)..(16)
<223> OTHER INFORMATION: modified by CW_miniGL_Si2N3

<400> SEQUENCE: 620

Arg Gly Tyr Lys Ser Ile Met Glu Leu Met Asn Val Leu Glu Leu Arg
1               5                   10                  15

Lys

<210> SEQ ID NO 621
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_miniGL_Si0N3
<220> FEATURE:
<221> NAME/KEY: Misc_feature
<222> LOCATION: (23)..(23)
<223> OTHER INFORMATION: modified by CW_miniGL_Si0N3

<400> SEQUENCE: 621

Arg Ile Ser Ala Ser Gly Pro Glu Ser Leu Leu Gly Gly Pro Gly Gly
1               5                   10                  15

Ala Ser Ala Ala Pro Ala Ala Gly Ser Lys Val
            20                  25

<210> SEQ ID NO 622
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (8)..(8)
<223> OTHER INFORMATION: modified by CW_miniGL_Si0N3
<220> FEATURE:
<221> NAME/KEY: Misc_feature
<222> LOCATION: (23)..(23)
<223> OTHER INFORMATION: modified by CW_miniGL_Si0N3

<400> SEQUENCE: 622

Arg Ile Ser Ala Ser Gly Pro Glu Ser Leu Leu Gly Gly Pro Gly Gly
1               5                   10                  15

Ala Ser Ala Ala Pro Ala Ala Gly Ser Lys Val
            20                  25

<210> SEQ ID NO 623
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

<400> SEQUENCE: 623

Lys Val Leu Gln His Tyr Gln Glu Ser Asp Lys Gly Glu Glu Leu Gly
1               5                   10                  15

Pro Gly Asn Val Gln Lys Glu
            20

<210> SEQ ID NO 624
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (5)..(5)
<223> OTHER INFORMATION: modified by CW_Cele_SiC2N3

```
<400> SEQUENCE: 624

Lys Val Leu Gln His Tyr Gln Glu Ser Asp Lys Gly Glu Glu Leu Gly
1               5                   10                  15

Pro Gly Asn Val Gln Lys Glu
            20
```

DETERMINING SMALL MOLECULE-PROTEIN AND PROTEIN-PROTEIN INTERACTIONS

RELATED APPLICATIONS

This application is a national stage filing under 35 U.S.C. § 371 of international PCT application, PCT/US2018/036256, filed Jun. 6, 2018, which claims priority under 35 U.S.C. § 119(e) to U.S. Provisional Applications, U.S. Ser. No. 62/515,846, filed Jun. 6, 2017, U.S. Ser. No. 62/628,372, filed Feb. 9, 2018, and U.S. Ser. No. 62/651,599, filed Apr. 2, 2018, each of which is incorporated herein by reference.

BACKGROUND OF THE INVENTION

Small molecule regulation of the proteome constitutes one of the oldest methods of therapy known to humankind. However, despite entering an era of target-based therapy and personalized medicine, parallel advances in understanding the precise molecular outcomes of small molecule therapeutics remain under-developed. Currently, the state of the art involves attachment of small molecules to affinity handles and immobilization on a solid support, followed by in vitro affinity purification. Alternatively, target-based drug discovery evaluates the affinity of small molecules for a specific purified protein. These approaches fail to reveal the structural basis of the interaction (e.g., binding site), changes to protein-protein interactions (PPIs), and broader system-wide (e.g., proteome, interactome, or genome) effects. As a result, the vast majority of protein interactors are silently overlooked in current mechanism of action studies, leading to missed opportunities and incomplete toxicology profiles.

The primary bottleneck is the lack of an approach to globally reveal proteomic interactions (e.g., protein-protein interactions (PPIs)) mediated by a small molecule. Protein-protein interactions are implicated in thousands of diseases, and thus it is imperative to understand both normal and abnormal PPLs. For example, this gap is particularly notable in the case of the immunomodulatory drugs (IMIDs), thalidomide, lenalidomide, and pomalidomide, a class of pluripotent therapeutics that lack a defined mechanism of action. These, as well as other, IMIDs have been the focus of extensive time-consuming mechanism of action studies, which have inspired popular conclusions about the importance of enantioselectivity in drug discovery due to their single stereocenter. However, the IMIDs are rapidly racemized and metabolized in plasma, making any attempt at characterizing the phenotype behind a specific isoform inconclusive. A complete understanding of the role of IMID isoforms (e.g., R-lenalidomide versus S-lenalidomide) demands a molecular approach. A method to directly map the small molecule interactome has the potential to accelerate drug discovery by providing structural insight and instant validation of the binding interaction between a small molecule and its one or more target proteins, yet such global characterization is rarely performed due to the under-developed state of the current technology.

SUMMARY OF THE INVENTION

The present disclosure provides, in some aspects, compositions, techniques, methods, systems, and kits capable of mapping the direct and indirect effects of small molecules within the proteome. Some aspects of the present disclosure provide a small photo-click tag that enables efficient capture, enrichment, and characterization of small molecule binding sites on proteins. These small photo-click chemical tags can be incorporated into a variety of small molecules, including small molecule drugs, such as immunomodulatory drugs (e.g., lenalidomide, thalidomide, and pomalidomide) and non-steroidal anti-inflammatory drugs (NSAIDs) (e.g., naproxen, celecoxib, and indomethacin). The small size of these photo-click chemical tags ensures that small molecule binding does not perturb the native small molecule- or protein-protein interactions. After treatment of the whole cell proteome with the photo-click modified small molecule, the resulting interactions (e.g., small molecule-protein or protein-protein interactions) are captured (i.e., "frozen" in place) (see, e.g., FIG. 7 and FIG. 8). These interactions can be affinity enriched for characterization, for example, by mass spectrometry (MS) (e.g., mass-independent or isotope-targeted mass spectrometry). In addition to revealing the binding site of the small molecule, thus helping to elucidate its mechanism of action, the photo-click modified small molecules can also be used to reveal downstream effects of the small molecule on cellular pathways by mapping protein-protein interactions (see, e.g., FIG. 1). In addition to confirming mechanisms of action of small molecules through their interaction with known target proteins, this approach can be used to identify transient complexes formed with previously unidentified target proteins. This technique is typically referred to throughout the present disclosure as Small Molecule Interactome Mapping by Photo-Affinity Labeling (SIM-PAL), or Minimally-Interfering Photo-Affinity Labeling (MI-PAL) when the smallest exemplified photo-click chemical tags provided herein are employed. The binding site identification method provided by SIM-PAL and MI-PAL is a strategy capable of precisely defining binding preferences between enantiomers and metabolites of a small molecule of interest. Additionally, amino acid analogs comprising a photo-click tag enable the measurement of protein-protein interaction (PPI) perturbations in the presence of the small molecule of interest, allowing for the determination of a global "interactome" in the presence of the small molecule (e.g., drug).

Thus, in one aspect, the present disclosure provides photo-click tags that are readily incorporated into a small molecule scaffold. In general, the multi-functional photo-click tags comprise two functional moieties: a photo-conjugation moiety that can covalently capture the protein target (e.g., an enzyme that binds to a small molecule of interest, a receptor, an antibody, etc.), and a biocompatible handle (e.g., a click chemistry handle) for functionalization with a reporter molecule or affinity tag (e.g., a biotinylated affinity tag). In some embodiments, the photo-click tag comprises (a) a photo-conjugation moiety, and (b) a click chemistry handle. In some embodiments, the photo-conjugation moiety is a diazirine moiety. In some embodiments, the photo-click tag comprises (a) a diazirine moiety and (b) a click chemistry handle. In some embodiments, the click chemistry handle is an alkyne. In some embodiments, the photo-click tag comprises (a) a diazirine moiety and (b) an alkyne. In some embodiments, the photo-conjugation moiety forms a reactive species upon irradiation with light (i.e., forms an activated photo-click tag). In some embodiments, the diazirine forms a reactive carbene species upon irradiation with light. In some embodiments, the light has a wavelength of between about 10 nm and 400 nm. In some embodiments, the reactive species reacts with a C—C, C—H, N—H, or O—H bond of a protein. In some embodiments, a new covalent bond is formed between the activated photo-click tag and the protein.

In some embodiments, the photo-click tag comprises the structure:

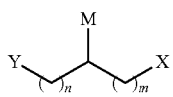

wherein Y, M, X, n, and m are as defined herein.

In some embodiments, the photo-click tag is of the formula:

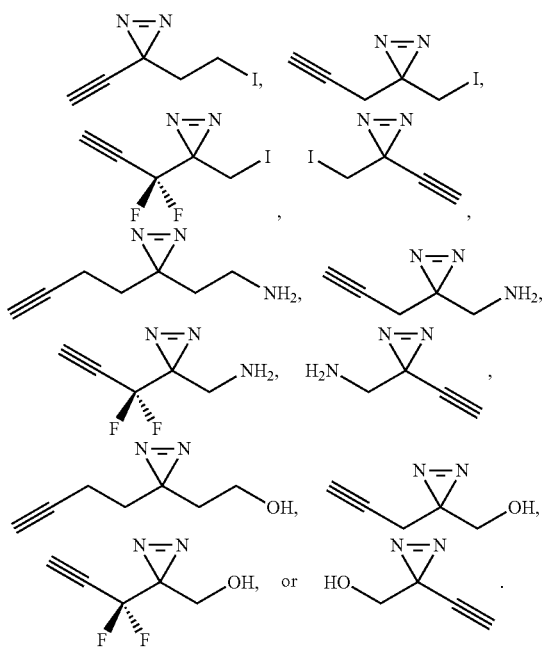

In another aspect, the present disclosure provides compounds that are covalently linked to any of the photo-click tags provided herein (i.e., photo-click conjugated compounds). In some embodiments, the compound is of Formula (I):

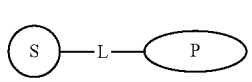

wherein S is a small molecule, P is a photo-click tag, and L is a linker, as provided herein.

In some embodiments, L comprises an ester, an ether, an amine, or an amide.

In some embodiments, S is an antibiotic, an anti-proliferative agent, an anti-cancer agent, a chemotherapeutic agent, an anti-angiogenesis agent, an anti-inflammatory agent, an immunosuppressant, an immunomodulatory agent, an anti-bacterial agent, an anti-viral agent, a cardiovascular agent, a cholesterol-lowering agent, an anti-diabetic agent, an anti-allergic agent, a contraceptive agent, or a pain-relieving agent. In some embodiments, S is an anti-inflammatory agent, or derivative thereof. In some embodiments, S is an immunomodulatory agent, or derivative thereof. In some embodiments, S is a chemotherapeutic agent, or derivative thereof.

In some embodiments, S is a steroid, or derivative thereof.

In some embodiments, the compound comprises one or more isotopically labeled atoms. In some embodiments, the isotopically labeled atom is $^{15}N$, $^{13}C$, $^{19}F$, or $^{2}H$.

In yet another aspect, provided herein are methods for using the photo-click tags and compounds conjugated to photo-click tags provided herein to determine, analyze, and evaluate small molecule-protein or protein-protein interactions. In some embodiments, the proteins are present in a cell, allowing for the determination of these interactions in the native cellular environment.

In one aspect, provided herein is a method for identifying a target protein of a small molecule. In some embodiments, the method comprises: (i) providing a compound comprising the small molecule connected to a photo-click tag via a linker, wherein the photo-click tag comprises (a) a diazirine moiety, and (b) a click chemistry handle; (ii) activating the diazirine moiety by irradiating the compound of (i) with a specific wavelength of light; (iii) contacting the target protein with the activated compound of (ii); (iv) forming a complex through a photo-induced covalent bond between the activated compound of (ii) and the protein; and (v) identifying the complex produced in (iv) that is bound to the compound, thereby identifying the target protein of the small molecule.

In another aspect, provided herein is a method for identifying the binding site of a small molecule on a protein. In some embodiments, the method comprises (i) providing a compound comprising the small molecule connected to a photo-click tag via a linker, wherein the photo-click tag comprises (a) a diazirine moiety, and (b) a click chemistry handle; (ii) activating the diazirine moiety by irradiating the compound of (i) with a specific wavelength of light; (iii) contacting the protein with the activated compound of (ii); (iv) forming a complex through a photo-induced covalent bond between the activated compound of (ii) and the protein; (v) digesting the protein of the complex into constitutive peptides in the presence of a protease; and (vi) identifying the one or more peptides produced in (iv) that is bound to the compound, thereby identifying the protein binding site of the small molecule.

In another aspect, provided herein is a method for identifying an interaction between a first protein and a second protein in a cell. In some embodiments, the method comprises: (i) providing the cell with an amino acid analog, wherein the amino acid analog comprises a photo-click tag comprising (a) a diazirine moiety, and (b) a click chemistry handle, and wherein the amino acid analog is incorporated into the first protein and/or the second protein during protein synthesis; (ii) activating the diazirine moiety of the amino acid analog by irradiating the cell with a specific wavelength of light; (iii) contacting the first protein or the second protein with the activated compound of (ii); (iv) forming a protein-protein complex through a photo-induced covalent bond between the activated amino acid analog of the first protein and an amino acid in the second protein; and (v) identifying the complex produced in (ii) that comprises the amino acid analog covalently linking the first protein and the second protein, thereby identifying the first protein and the second protein involved in the interaction.

Also provided herein are kits comprising any of the photo-click tags or photo-click tagged compounds provided herein. In addition, also provided herein are kits for use in performing any of the methods provided herein.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings, which constitute a part of this specification, illustrate several exemplary embodiments of the invention and together with the description, serve to explain certain principles of the invention. The embodiments disclosed in the drawings are exemplary and do not limit the scope of this disclosure.

FIG. 4A illustrates the types of changes induced by small molecule binding to a target protein. FIG. 4B summarizes the current state of the druggable proteome, with a particular focus on the large percentage of the druggable proteome that is characterized as "understudied." Adapted from Griffith et al. (2013) DGIdb: mining the druggable genome. *Nature Methods* 10, 1209-1210. FIG. 4C shows the predicted impact of technologies, such as SIM-PAL or MI-PAL as described herein, in uncovering druggable interactions that are currently considered "understudied" due to the lack of capable technology. SIM-PAL and MI-PAL represent strategies that are broadly translatable to any small molecule of interest.

FIG. 6A shows examples of minimally interfering photo-click probes that have been developed herein, along with the current standard for photo-click probes (See, Li et al. (2013) Design and Synthesis of Minimalist Terminal Alkyne-Containing Diazirine Photo-Crosslinkers and Their Incorporation into Kinase Inhibitors for Cell- and Tissue-Based Proteome Profiling. *Agnew Chem Int Ed*, 52, pp. 8551-8556). These smaller photo-click tags may lead to less perturbation of the small molecule and/or protein binding target, have superior photo-crosslinking properties, and/or have superior click chemistry rates compared to the current, larger photo-click probes. FIG. 6B shows improved copper (I)-catalyzed alkyne-azide cycloaddition (CuAAC) properties of the minimally interfering, electronically tuned "MI-PAL" photo-click tag. Asterisks (*) indicate isotopically labeled atoms.

FIG. 12A outlines the process in which photo-NSAIDs are applied in vivo (i.e., in cellulo) and conjugated to protein binding partners by photo-irradiation. Conjugated proteins are tagged by probe 10 using copper (I)-catalyzed alkyne-azide cycloaddition (CuAAC) and enriched to separately obtain the protein interactome and conjugated peptides representing binding site hotspots. Conjugated peptides are analyzed by isotope-targeted mass spectrometry (MS). FIG. 12B shows structures of NSAIDs naproxen (1), celecoxib (2), and indomethacin (3), their photo-NSAID analogs 4-6, and the negative controls tag 7, the orthogonal compound photoglutarimide 8, and the celecoxib analog 9. COX-2 $IC_{50}$ by ELISA is shown below each structure. FIG. 12C shows the structure of the cleavable biotin azide probe 10. Probe 10 is prepared as a 1:3 mixture of stable $^{12}C$:$^{13}C$ isotopes (highlighted in red).

FIG. 13A shows a fluorescence image of photo-NSAID binding to COX-2 and competitive displacement by the respective NSAID. COX-2 (125 ng) was incubated with photo-NSAIDS with or without the parent molecule, photo-crosslinked, and clicked with TAMRA-azide. FIG. 13B shows the docking structure of photonaproxen (4, red) and naproxen (1, blue) with COX-2. FIG. 13C shows the docking structure of photo-celecoxib (5, green) and celecoxib (2, blue) with COX-2. FIG. 13D shows the docking structure of photo-indomethacin (6, yellow) and indomethacin (3, blue). FIG. 13E shows the docking structure of diazirine tag 7 (purple) with COX-2. White box indicates part of COX-2 that is enlarged in sections 13B-13D. COX-2 (1 µg) was separately conjugated to each of the photo-NSAIDs (10 µM) or the diazirine tag 7 (10 µM), tryptically digested, and analyzed on an Orbitrap Elite. Conjugated peptides observed by MS are highlighted for each photo-NSAID. Docking structures were either the lowest desolvation energy or highest interface area size binding models created by Patchdock (October, 2017). Structure of COX-2 from PDB: 5KIR.

FIG. 14A shows protein enrichment of the photo-NSAIDs against the tag 7 based on PSMs. Proteins that were not statistically significant across the two biological replicates are displayed at a fold change of zero. FIG. 14B shows the overlap across the Jurkat photo-NSAID enriched proteome. FIG. 14C shows proteomic overlap between enriched proteins from Jurkat and K562 cells. FIG. 14D shows sub-cellular localization of the 1034 enriched proteins. FIG. 14E shows selected protein interaction networks captured by photo-NSAIDs. Color scheme: red=significantly enriched; pink=greater than 2-fold enriched; grey=identified in data; white=member of the protein complex not identified in data. Dashed border indicates direct observation of at least one conjugated peptide. Protein interaction networks were built using The Comprehensive Resource of Mammalian Protein Complexes (CORUM) as a reference. Half maximal effective concentration ($EC_{50}$) values for inhibition of the NF-κB pathway as determined by a NF-κB luciferase reporter described in Example 1.

FIG. 15A shows precursor pattern distribution (MS1) and database assignment (MS2) for a histone H2A peptide conjugated to each of the photo-NSAIDs. FIG. 15B shows a cluster diagram of histone protein complexes with at least one observed binding site to a photo-NSAID. High confidence interactions between two clusters made using STRING. FIG. 15C shows the structure of the nucleosome (PDB: 2CV5). Peptides from histone H2A (red) and histone H2B (blue) that were conjugated by all three photo-NSAIDs are highlighted. FIG. 15D shows competitive displacement of photo-NSAIDs by the parent compound. Jurkat cell lysates conjugated to the indicated compound with or without the parent compound were clicked with the biotin probe 10, captured on streptavidin-agarose, and probed for histone H2A, H2B, Ku70, NPM1, or NF-κB p65. FIG. 15E shows a cellular thermal shift assay performed on Jurkat cells in the presence of the indicated compound, probed for histone H2A.

FIG. 16D shows COX-2 $IC_{50}$ values for photo-NSAIDs and NSAIDs. $IC_{50}$ values were determined as described by the ELISA-based COX-2 inhibitor screening assay and performed in triplicate. Data is representative of two biological replicates.

FIG. 17D shows $IC_{50}$ values for NSAIDs and photo-NSAIDs in Jurkat cells. All dose-response curves were obtained in triplicate.

FIGS. 18A-18C show photo-NSAID dose-dependence and photo-irradiation-dependent labeling of Jurkat proteins. FIG. 18A shows dose-dependent labeling of Jurkat cells with the photo-NSAIDs, the tag 7, or photo-glutarimide 8. Jurkat cells were incubated with the small molecule at the indicated concentration for 1 hour at 37° C. and photoirradiated (30 minutes, 4° C.). Irradiated cells were lysed, clicked with tetramethylrhodamine-azide (TAMRA-azide), and visualized on gel. Coomassie blue staining shows equal protein loading. FIG. 18B shows anti-biotin Western blot from 250 μM of photo-NSAID or DMSO control treated Jurkat cells with (+) or without (−) UV irradiation for photo-naproxen (4), photo-celecoxib (5), and photo-indomethacin (6). Ponceau S staining shows equal amount of protein loading. FIG. 18C shows competition assay titration with photo-celecoxib (5) and the competitor celecoxib (2) at 1:1, 1:10, and 1:100 molar ratios. Jurkat cells were incubated with the tag 7, photo-celecoxib (5), or co-treated with photo-celecoxib (5) and the parent compound celecoxib (2) at 1:1, 1:10, and 1:100 molar ratios for 1 hour at 37° C., followed by photoirradiation (30 minutes, 4° C.) and cell lysis. Cell lysates were adjusted to 1.5 mg/mL, and were then clicked with 200 μM biotin azide probe 10, 300 μM copper (II) sulfate, 600 μM BTTP, and 2.5 mM freshly-prepared sodium ascorbate for 2 hours at 24° C. with rotation, followed by analysis by Western blotting using HRP-streptavidin conjugate. Ponceau S staining shows equal amount of protein loading.

FIG. 20A shows a Western blot probed for COX-2 of photo-NSAID captured proteins and competitive displacement by the parent compound in Jurkat whole cell lysates. Jurkat cells were incubated with photo-NSAIDs 1250 μM of photo-naproxen (4) and photoindomethacin (6); 50 μM of photo-celecoxib (5)] in the presence or absence of the parent compound (1:10 molar ratio) for 2 hours and photo-irradiated. Photo-irradiated proteins were lysed and clicked with the biotin azide probe 10 (load) and enriched on streptavidin-agarose (capture). FIG. 20B shows a cellular thermal shift assay probed for COX-2 in Jurkat cells in the presence of 50 μM of the tag 7, the celecoxib analog 9, celecoxib (2), or photo-celecoxib (5). Data are representative of two independent biological replicates. FIG. 20C shows quantification of COX-2 signal in cellular thermal shift assay using ImageJ and GraphPad Prism software. The solid lines represent the best fits of the data to the Boltzmann sigmoid equation, resulting in an apparent Ts of 27.6*0.6° C. for the tag 7, and 40.9*1.0° C. for the celecoxib analog 9, whereas both celecoxib (2) and photo-celecoxib (5) stabilized COX-2 at 50.5±0.6° C. and 52.2±1.0° C., respectively.

FIG. 21A shows relative protein abundance using peptide spectral matching (PSM) based label free quantification across the two Jurkat biological replicates collected at 250 μM photo-NSAIDs. FIG. 21B shows the overlap across one biological replicate of the Jurkat photo-NSAID enriched proteome at 50 μM photo-NSAIDs. FIG. 21C shows the proteomic overlap between enriched proteins from Jurkat cells exposed to 50 μM photo-celecoxib (5) or the celecoxib analog 9.

FIG. 30A shows photoconjugation of MI-PAL (3) to alpha-crystallin. FIG. 30B shows an example collision-induced dissociation (CID) mass spectra of a peptide from alpha-crystallin conjugated to MI-PAL (3). M represents the precursor mass. FIG. 30C shows visualization by Western blot of whole cell lysates from MM.1S (multiple myeloma) or K562 (chronic mylogenous leukemia) incubated with MI-PAL (3) and photoirradiated. Photoconjugated lysates were treated with biotin-azide and visualized by Western blot.

DEFINITIONS

Figure 1:
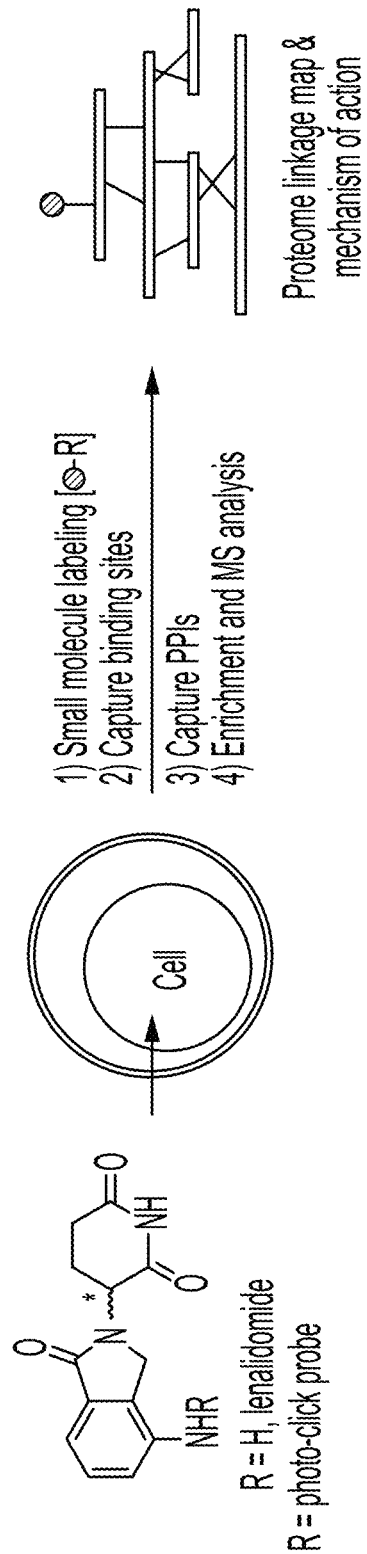
FIG. 1 is a generalized, non-limiting schematic showing how direct and indirect effects of a small molecule (lenalidomide is exemplified) on the whole cell proteome can be studied using the technology disclosed herein, such as SIM-PAL and MI-PAL.
Figure 2:
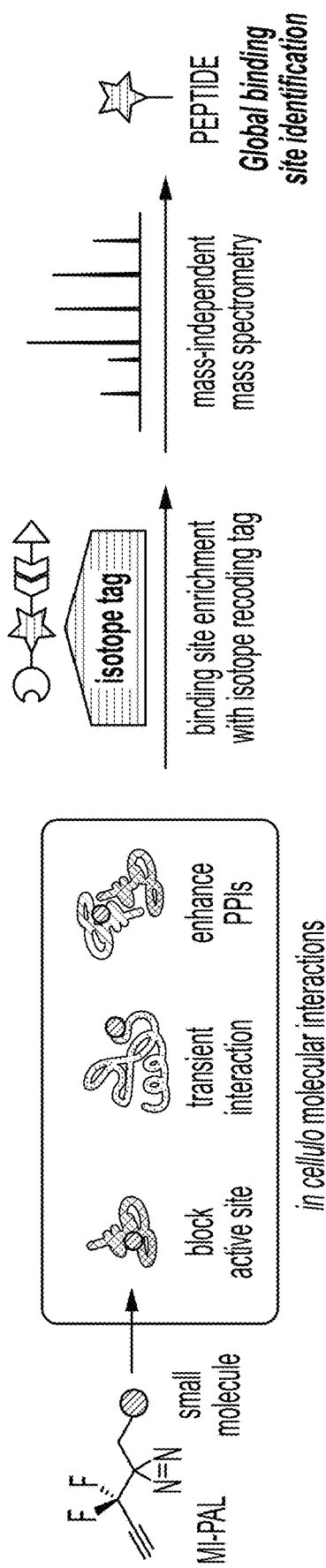
FIG. 2 is a generalized, non-limiting schematic outlining the MI-PAL global binding site mapping strategy.
Figure 3:
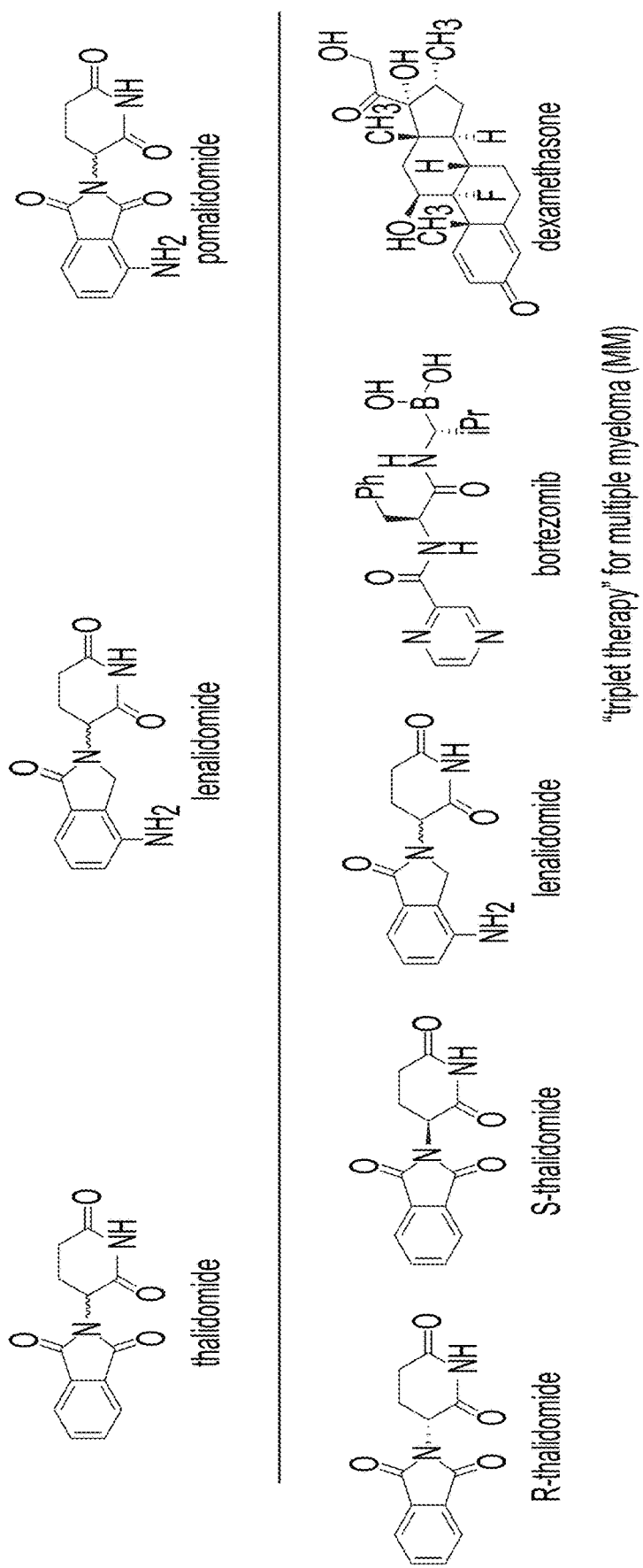
FIG. 3 shows immunomodulatory drugs (IMIDs) as a non-limiting example to illustrate the importance of chirality in drug discovery. Despite this, the current mechanism of action of these IMIDs, for example, lenalidomide, remains incomplete and demands elucidation by a molecular approach, such as SIM-PAL or MI-PAL.
Figure 4A:
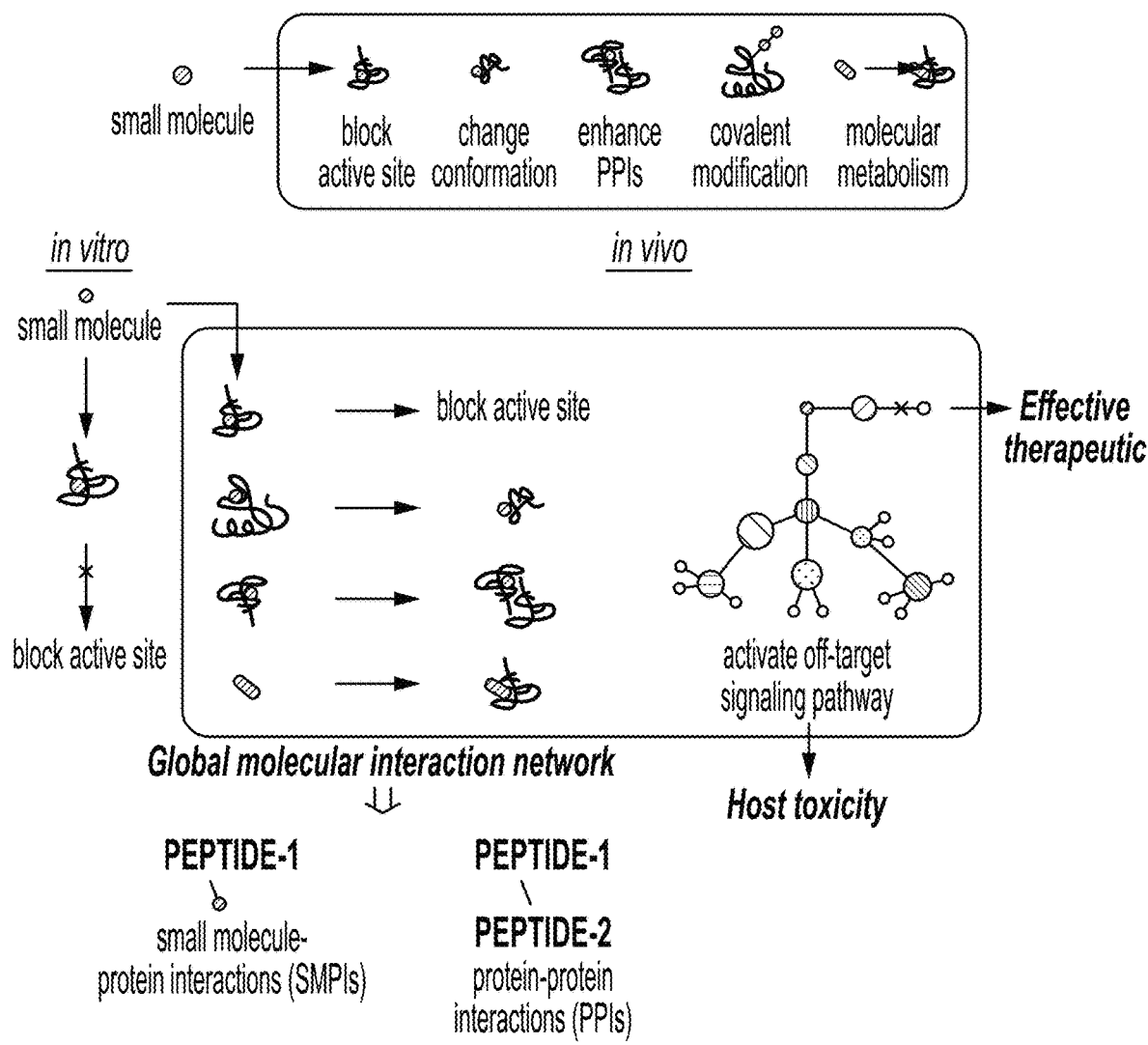
FIGS. 4A-4C shows a general schematic summarizing the gap in current technologies for analyzing small molecule-protein or protein-protein interactions.
Figure 4B:
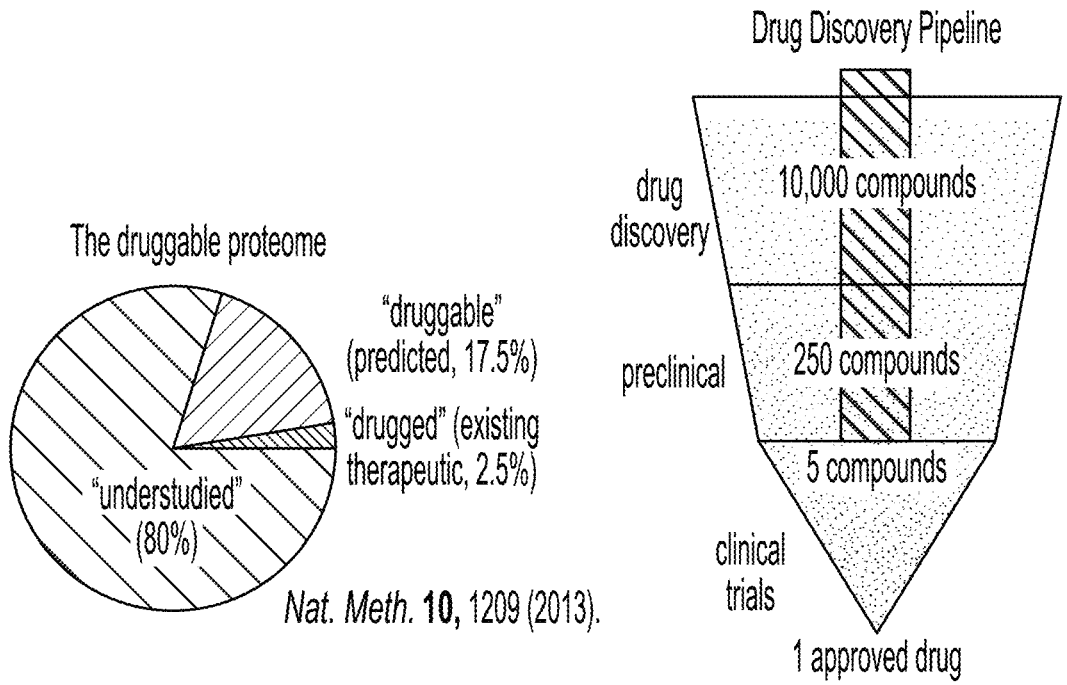
Figure 4C:
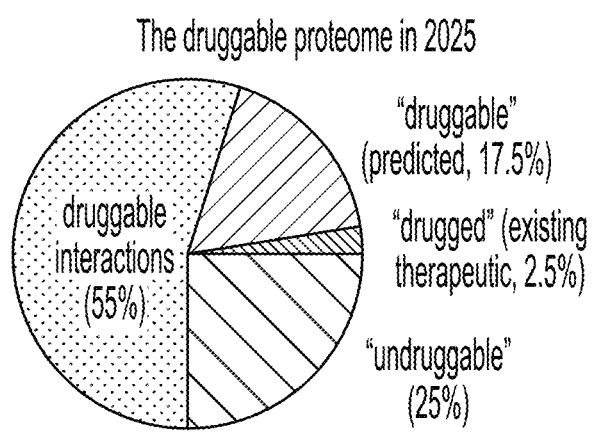
Figure 5:
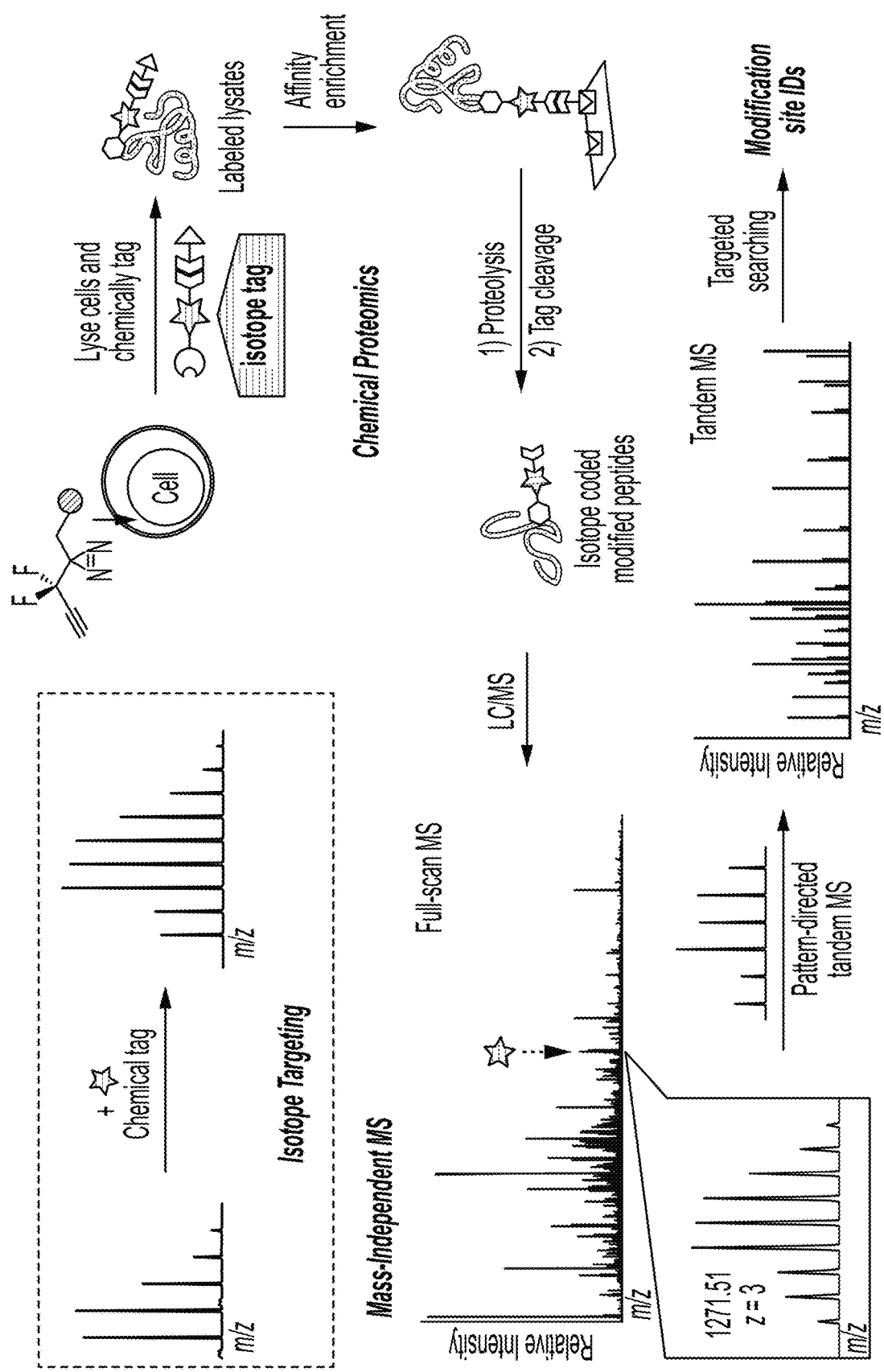
FIG. 5 shows a generalized, non-limiting schematic outlining the SIM-PAL global binding site mapping strategy.

Descriptions and certain information relating to various terms used in the present disclosure are collected herein for convenience.

As used herein and in the claims, the singular forms "a," "an," and "the" include the singular and the plural reference unless the context clearly indicates otherwise. Thus, for example, a reference to "an agent" includes a single agent and a plurality of such agents.

The term "agent" is used herein to refer to any substance, compound, small molecule, peptide, protein, nucleic acid), supramolecular complex, material, or combination or mixture thereof. A compound may be any agent that can be represented by a chemical formula, chemical structure, or sequence. Examples of agents include, e.g., small molecules, polypeptides, nucleic acids (e.g., RNAi agents, antisense oligonucleotide, aptamers), lipids, polysaccharides, etc. In general, agents may be obtained using any suitable method known in the art. In some embodiments, the agent is a small molecule. In some embodiments, the agent is an antibiotic, anti-proliferative agent, an anti-cancer agent, a chemotherapeutic agent, anti-angiogenesis agent, anti-inflammatory agent, immunosuppressant, immunomodulatory agent, antibacterial agent, anti-viral agent, cardiovascular agent, cholesterol-lowering agent, anti-diabetic agent, anti-allergic agent, contraceptive agent, or pain-relieving agent. In some embodiments, the agent is an anti-inflammatory agent. In some embodiments, the agent is an immunomodulatory drug. In some embodiments, the agent is a chemotherapeutic agent. These compounds may be conjugated to a photo-click tag provided herein. The ordinary skilled artisan will select an appropriate method for preparing a "photo-click conjugated agent" based, e.g., on the nature of the agent (e.g., the functional groups present in the agent) and the desired photo-click tag to be used. Examples of synthetic procedures for generating photo-click conjugated agents is provided in Examples 1 and 2 (also see FIGS. 26, 31, and 32). An agent may be at least partly purified. In some embodiments, an agent may be provided as part of a composition, which may contain, e.g., a counter-ion, aqueous or non-aqueous diluent or carrier, buffer, preservative, or other ingredient, in addition to the agent, in various embodiments. In some embodiments, an agent may be provided as a salt, ester, hydrate, or solvate. In some embodiments an agent is cell-permeable, e.g., within the range of typical agents that are taken up by cells and acts intracellularly, e.g., within mammalian cells, to produce a biological effect. Certain compounds may exist in particular geometric or stereoisomeric forms. Such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof are encompassed by this disclosure in various embodiments unless otherwise indicated. Certain compounds may exist in a variety or protonation states, may have a variety of configurations, may exist as solvates (e.g., with water (i.e., hydrates) or common solvents) and/or may have different crystalline forms (e.g., polymorphs) or different tautomeric forms. Embodiments exhibiting such alternative protonation states, configurations, solvates, and forms are encompassed by the present disclosure where applicable.

The term "amide," as used herein, refers to the group —C(=O)N($R^{X1}$)—, wherein each $R^{X1}$ is independently hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino. In some embodiments, $R^{X1}$ is hydrogen. In some embodiments, a photo-click tagged compound herein comprises a small molecule covalently linked to a photo-click tag by an amide.

The term "amine," as used herein, refers to the group —N($R^{X1}$)$_2$—, wherein each $R^{X1}$ is independently hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino. In some embodiments, $R^{X1}$ is hydrogen. In some embodiments, a photo-click tagged compound herein comprises a small molecule covalently linked to a photo-click tag by an amine.

The term "anti-inflammatory agent" refers to any compound (e.g., small molecule) that exhibits anti-inflammatory properties when administered to a subject in need thereof. The anti-inflammatory agent may be a steroidal anti-inflammatory agent or a nonsteroidal anti-inflammatory agent. In some embodiments, the anti-inflammatory agent is a nonsteroidal anti-inflammatory drug. The term "nonsteroidal anti-inflammatory drug" or "NSAID" as used herein refers to any compound (e.g., small-molecule) that can be classified as an NSAID. In general, an NSAID is a small molecule that reduces pain, reduces fever, prevents blood clots, and/or decreases inflammation, and the like. In general, NSAIDs work by inhibiting the activity of cyclooxygenase enzymes (COX-1 and/or COX-2). In cells, these enzymes are involved in the synthesis of key biological mediators, namely prostaglandins, which are involved in inflammation, and thromboxanes, which are involved in blood clotting. There are two types of NSAIDs available: non-selective and COX-2 selective. Non-selective NSAIDs inhibit the activity of both COX-1 and COX-2. In some embodiments, the anti-inflammatory agent is a steroidal anti-inflammatory agent. The term "steroidal anti-inflammatory agent" refers to any natural or synthetic agent that comprises the core structure of a steroid and exhibits an anti-inflammatory property when administered to a subject in need thereof.

In some embodiments, the reaction used to generate a photo-click conjugated agent is a click chemistry reaction. In some embodiments, the reaction used to conjugate the photo-click conjugated agent to a target protein is a click chemistry reaction. In some embodiments, the reaction used to conjugate (i.e., "click") a label onto the photo-click tag is a click chemistry reaction. It is to be understood that any "click chemistry" reaction known in the art can be used to this end. Click chemistry is a chemical philosophy introduced by Sharpless in 2001 and describes chemistry tailored to generate substances quickly and reliably by joining small units together. See, e.g., Kolb, Finn, and Sharpless, *Angew Chem Int Ed* (2001) 40: 2004-2021; Evans, Australian Journal of Chemistry (2007) 60: 384-395. The term "click chemistry" does not refer to a specific reaction or set of reaction conditions, but instead refers to a class of reactions (e.g., coupling reactions). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; and Michael additions (e.g., maleimide addition). Examples of click chemistry reactions can be found in, e.g., Kolb, H. C.; Finn, M. G. and Sharpless, K. B. *Angew. Chem. Int. Ed.* 2001, 40, 2004-2021. Kolb, H. C. and Sharpless, K. B. Drug Disc. Today, 2003, 8, 112-1137; Rostovtsev, V. V.; Green L. G.; Fokin, V. V. and Sharpless, K. B. *Angew. Chem. Int. Ed.* 2002, 41, 2596-2599; Tomoe, C. W.; Christensen, C. and Meldal, M. *J. Org. Chem.* 2002, 67, 3057-3064. Wang, Q. et al. *J. Am. Chem. Soc.* 2003, 125, 3192-3193; Lee, L. V. et al. *J. Am. Chem. Soc.* 2003 125, 9588-9589; Lewis, W. G. et al. *Angew. Chem. Int. Ed.* 2002, 41, 1053-41057; Manetsch, R. et al., *J. Am. Chem. Soc.* 2004, 126, 12809-12818; Mocharla, V. P. et al. *Angew. Chem., Int. Ed.* 2005, 44, 116-120; each of which is incorporated by reference herein. In some embodiments, the click chemistry reaction involves a reaction with an alkyne moiety comprising a carbon-carbon triple bond (i.e., an alkyne handle). In some embodiments, the click chemistry reaction is a copper (I)-catalyzed azide-alkyne cycloaddition (CuAAC) reaction. A CuAAC reaction generates a 1,4-disubstituted-1,2,3-triazole product (i.e., a 5-membered heterocyclic ring). See, e.g., Hein J E and Fokin V V (2010) Copper-catalyzed azide-alkyne cycloaddition (CuAAC) and beyond: new reactivity of copper (I) acetylides. *Chem Soc Rev*, 39(4), pp. 1302-1315; the contents of which is incorporated by reference herein. For example, as shown in Examples 1 and 2, a label (e.g., a biotinylated affinity label) comprising an azide moiety can be conjugated to a photo-click tag comprising an alkyne using a CuAAC reaction. In some embodiments, the click chemistry reaction is a photo-click reaction. As used herein, a "photo-click" reaction is a reaction in which a compound is activated upon irradiation with a specific wavelength of UV light (i.e., between about 10 nm and about 400 nm). The activated compound can then rapidly form a covalent bond with the nearest target molecule (e.g., chemical bonds present in a protein). In some embodiments, the compound comprises a diazirine, which forms a reactive carbene upon irradiation with UV light. The activated carbene can then react with a nearby C—C, C—H, N—H, O—H, or X—H (X=heteroatom) bond present in a protein, thus conjugating the diazirine to the protein. See, e.g., Dubnisky L et al (2011) Diazirine based photoaffinity labeling. *Bioorg Med Chem* 20, 554-570; which is incorporated herein by reference. The use of diazirines as photo-reactive crosslinking reagents, or photo-click reagents, has been described in, e.g., Sinz A. (2007) Investigation of Protein-Ligand Interactions by Mass Spectrometry. *Chem Med Chem*, 2, pp. 425-431; and Brunner J. (1993) New photolabeling and crosslinking methods. *Annu Rev Biochem.* 62, pp. 483-514; the entire contents of each of which are incorporated herein by reference.

The term "compound" as used herein encompasses any small molecule, peptide, nucleic acid, protein, or derivative thereof that can bind to and/or modulate (e.g., increase the activity of, decrease the activity of) a target of interest (e.g., a protein, e.g., an enzyme, receptor, reporter protein, etc.)). In some embodiments, the compound is a small molecule.

The term "ester," as used herein, refers to the group —C(=O)O—. In some embodiments, a photo-click tagged compound herein comprises a small molecule covalently linked to a photo-click tag by an ester.

The term "ether," as used herein, refers to the group —O—. In some embodiments, a photo-click tagged compound herein comprises a small molecule covalently linked to a photo-click tag by an ether.

The term "immunomodulatory drug" or "IMID" refers to any compound (e.g. small molecule) that can be classified as an immunomodulatory drug. In general, an immunomodulatory drug is an anti-inflammatory or antineoplastic compound that can modulate an immune response. Most immunomodulatory drugs are structurally and functionally similar to thalidomide. Thalidomide can exist as two enantiomers, R-thalidomide and S-thalidomide. Each enantiomer may exhibit a different function or interact with a specific drug target (e.g., protein). Thus, immunomodulatory drugs are often small molecule derivatives of R-thalidomide or S-thalidomide. Exemplary, non-limiting immunomodulatory drugs are (R/S)-lenalidomide, (R/S)-pomalidomide, and (R/S)-apremilast. In some embodiments, the immunomodulatory drug is thalidomide. In some embodiments, the immunomodulatory drug is lenalidomide. In some embodiments, the immunomodulatory drug is S-lenalidomide. In some embodiments, the immunomodulatory drug is R-lenalidomide. In some embodiments, the immunomodulatory drug is pomalidomide. In some embodiments, the immunomodulatory drug is S-pomalidomide. In some embodiments, the immunomodulatory drug is R-pomalidomide. In some embodiments, the immunomodulatory drug is apremilast. In some embodiments, the immunomodulatory drug is S-apremilast. In some embodiments, the immunomodulatory drug is R-apremilast.

The term "linker," as used herein, refers to a chemical group or a molecule linking two molecules or moieties, e.g., a small molecule and a photo-click tag. A linker may be, for example, a bond, an amino acid sequence, a peptide, or a polymer of any length and composition. In some embodiments, the linker is an organic molecule, functional group, polymer, or chemical moiety.

The term "photo-conjugation moiety," as used herein, refers to any moiety that forms a reactive intermediate upon irradiation with light (i.e., "photo-activation"). These moieties may be referred to as "photoreactive" moieties. Examples of photoreactive moieties are aryl azides, azidomethyl-coumarins, benzophenones, anthraquinones, diazo compounds, diazirines, and psoralen derivatives. For example, an aryl azide (e.g., phenyl azide, ortho-hydroxyphenyl azide, meta-hydroxyphenyl azide, tetrafluorophenyl azide, ortho-nitrophenyl azide, and meta-nitrophenyl azide) forms a reactive nitrene groups that can initiate addition reactions with double bonds, insertion into C—H and N—H bonds, or ring expansion in the presence of a nucleophile (e.g., a primary amine). In general, aryl azides are photoactived upon irradiation with UV light with a wavelength of about 250 nm to about 350 nm. Photo-conjugation moieties, their uses, and chemical reactions are discussed in *Bioconjugate Techniques*, 3$^{rd}$ Ed. (2013) by Hermanson; which is incorporated by reference herein.

The term "protease" refers to any enzyme capable of hydrolyzing a peptide bond. In general, a proteases catalyzes the hydrolysis of peptide bonds (i.e., digests the protein) through a unique mechanism based on the catalytic residue present in the active site of the protease. Exemplary, non-limiting proteases and their catalytic residues are serine poteases, which use a serine alcohol, cysteine proteases, which use a cysteine thiol, threonine proteases, which use a threonine secondary alcohol, aspartic proteases, which use an aspartate carboxylic acid, glutamic proteases, which use a glutamate carboxylic acid, metalloproteases, which use a metal (e.g., zinc), and asparagine peptide lyases, which use an asparagine to perform an elimination reaction and do not require water. In some embodiments, the protease is a serine protease. In some embodiments, the serine protease is trypsin. In some embodiments, the serine protease is chymotrypsin. In some embodiments, the protease is an aspartic protease. In some embodiments, the aspartic protease is pepsin. In some embodiments, one protease is used to digest a protein. In some embodiments, more than one protease is used to digest a protein.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. In some embodiments, a protein comprises a homodimer or a heterodimer. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain (e.g., the gRNA binding domain of Cas9 that directs the binding of the protein to a target site) and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein comprises a ligand binding domain. In some embodiments, a protein comprises an active site (e.g., site of biological or enzymatic activity). In some embodiments, a protein comprises an allosteric site (e.g., site of a protein that can bind to a ligand that can be remote from an active site). In some embodiments, the protein is an enzyme. In some embodiments, the protein is a receptor. In some embodiments, the protein is a reporter protein (e.g., GFP). Any of the proteins provided herein may be produced by any method known in the art. For example, the proteins provided herein may be produced via recombinant protein expression and purification. Methods for recombinant protein expression and purification are well known, and include those described by Green and Sambrook, *Molecular Cloning: A Laboratory Manual* (4$^{th}$ ed., Cold Spring Harbor Laboratory Press, Cold Spring Harbor, N.Y. (2012)), the entire contents of which are incorporated herein by reference. In some embodiments, the protein is present in vitro. In some embodiments, the protein is present in vivo. In some embodiments, the protein is present in a cell. In some embodiments, the protein is present in a cell lysate. In some embodiments, the protein is present in a whole proteome (i.e., the entire complement of proteins that is or can be expressed by a cell, tissue, or organism).

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydmiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "sample" may be used to generally refer to an amount or portion of something (e.g., a protein). A sample may be a smaller quantity taken from a larger amount or entity; however, a complete specimen may also be referred to as a sample where appropriate. A sample is often intended to be similar to and representative of a larger amount of the entity of which it is a sample. In some embodiments a sample is a quantity of a substance that is or has been or is to be provided for assessment (e.g., testing, analysis, measurement) or use. The "sample" may be any biological sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. In some embodiments a sample comprises cells, tissue, or cellular material (e.g., material derived from cells, such as a cell lysate, or fraction thereof). A sample of a cell line comprises a limited number of cells of that cell line. In some embodiments, a sample may be obtained from an individual who has been diagnosed with or is suspected of having a disease.

The term "small molecule," as used herein, is an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. In some embodiments, the small molecule is an NSAID, or a derivative thereof. In some embodiments, the small molecule is an immunomodulatory drug, or a derivative thereof. In some embodiments, the small molecule is a chemotherapeutic agent, or a derivative thereof.

The term "steroid," as used herein, refers to any compound with a core structure comprising four fused rings, wherein three of the four rings are cyclohexane rings and one of the four rings is a cyclopentane ring. Steroids can be classified functionally, such as corticosteroids or sex steroids. In some embodiments, the corticostemid is a glucocorticoid. In some embodiments, the corticosteroid is a mineralocorticoid. In some embodiments, the steroid is an androgen, an estrogen, or a progestogen. In some embodiments, the androgen is testosterone. In some embodiments, the estrogen is estradiol or beta-estradiol. In some embodiments, the progestogen is progesterone. Steroids can also be classified based on their chemical composition (i.e., the number of carbon atoms present in the steroid). Exemplary classifications are cholestanes (27 carbon atoms, e.g., cholesterol), cholanes (24 carbon atoms, e.g., cholic acid), pregnanes (21 carbon atoms, e.g., progesterone), androstanes (19 carbon atoms, e.g., testosterone), and estranges (18 carbon atoms, e.g., estradiol).

DETAILED DESCRIPTION OF CERTAIN EMBODIMENTS OF THE INVENTION

Small molecules are the most prominent class of agents that are used as therapeutics for the treatment of a variety of diseases and conditions, accounting for nearly 90% of the therapeutics available in the pharmaceutical market. Many agents (e.g., small molecules) elicit cell-type specific pharmacology that may increase therapeutic efficacy or yield off target toxicity. However, direct observation of the structures that underpin the global molecular associations between the proteome and even common therapeutics, such as the non-steroidal anti-inflammatory drugs (NSAIDs), remain little understood. Presented herein are photo-click tags, compounds, and methods useful for mapping the small molecule interactome of a small molecule of interest. These methods generally involve labeling of a target protein with a photo-click tag that is conjugated to the small molecule of interest, and may be referred to throughout the present disclosure as Small Molecule Interactome Mapping by Photo-Affinity Labeling (SIM-PAL), or Minimally-Interfering Photo-Affinity Labeling (MI-PAL) when the smallest exemplified photo-click chemical tags provided herein are employed.

These photo-click tags, photo-conjugated compounds, and methods can be applied in vivo to identify binding sites or protein-protein interactions within the complex cellular environment. For example, SIM-PAL uses (1) photochemical conjugation of small molecules throughout the whole proteome and (2) enrichment of the conjugated peptides for (3) targeted mass spectrometry-based assignment. In addition, these photo-click tags, photo-conjugated compounds, and methods amenable to map global binding sites for virtually any agent of interest.

Photo-Click Tags

The development of small, multi-functional photo-click tags that are readily incorporated into a small molecule scaffold has accelerated target identification for non-covalent agents that interact with one or more proteins in the proteome. In general, the multi-functional photo-click tags comprise two functional moieties: a photo-conjugation moiety that can covalently capture the protein target (e.g., an enzyme that binds to a small molecule of interest, a receptor, an antibody, etc.), and a biocompatible handle (e.g., a click chemistry handle) for functionalization with a reporter molecule or affinity tag (e.g., a biotinylated affinity tag). A biocompatible handle (e.g., a click chemistry handle) may be designed to study biological processes in their native environment (e.g., in living cells). The photo-conjugation moiety may comprise, for example, an aryl azide, benzophenone, or diazirine moiety, which can generate a short-lived, highly reactive intermediate (e.g., a nitrene, carbene, or diradical intermediate) that covalently attaches itself to a nearby biomolecule (e.g., a protein, nucleic acid, lipid). The biocompatible handle may be a click chemistry handle, for example, an alkyne, an alkene (e.g., a strained alkene or an activated alkene), a cyano moiety (—C≡N), or additional suitable click chemistry handles known in the art. Taken together, the photo-conjugation moiety and the click chemistry handle provide a multi-functional "photo-click tag". The photo-click tag may comprise the structure:

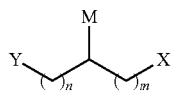

wherein
M is a photo-conjugation moiety;
Y is a click chemistry handle;
X is —OH, —NH$_2$, or a halogen; and
m and n are each independently integers between 1-10, inclusive.

In some embodiments, m is 0, 1, or 2. In some embodiments, n is 0, 1, or 2. In some embodiments, m and n taken together provide a photo-click tag fewer than 10 carbons in length (i.e., a $C_{1-10}$ alkyl), not including the click chemistry handle. In some embodiments, m and n taken together provide a photo-click tag fewer than 10 carbons in length (i.e., a $C_{1-7}$ alkyl), not including the click chemistry handle. In some embodiments, the photo-click tag comprises a $C_{1-10}$ alkyl. The term "alkyl" refers to a radical of a straight-chain or branched saturated hydrocarbon group having from 1 to 10 carbon atoms ("$C_{1-10}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$, n-octyl ($C_8$), and the like. In some embodiments, the photo-click tag comprises a $C_{3-7}$ alkyl, not including the click chemistry handle. In some embodiments, the photo-click tag comprises a $C_3$ alkyl, not including the click chemistry handle. In some embodiments, the photo-click tag comprises a $C_4$ alkyl, not including the click chemistry handle. In some embodiments, the photo-click tag comprises a $C_5$ alkyl, not including the click chemistry handle. In some embodiments, the photo-click tag comprises a $C_6$ alkyl, not including the click chemistry handle. In some embodiments, the photo-click tag comprises a $C_7$ alkyl, not including the click chemistry handle. For example, in some embodiments, m is 1 and n is 1 to provide a photo-click tag that is 3 carbon atoms in length ($C_3$ alkyl). Without wishing to be bound by any particular theory, photo-click tags with small scaffolds could provide the added benefit of reduced perturbation of small molecule binding to a protein target when the small molecule is bound to the photo-click tag. For example, integration of a small photo-click tag can preserve the native interaction between the small molecule conjugated to the photo-click tag and the target protein(s). See Examples 1 and 2.

In some embodiments, X is —OH. In some embodiments, X is —NH$_2$. In some embodiments, X is halogen. In some embodiments, X is chlorine (Cl). In some embodiments, X is iodine (I). In some embodiments, X is fluorine (F). In some embodiments, X is bromine (Br).

Thus, in one aspect, provided herein are photo-click tags comprising (a) a photo-conjugation moiety, and (b) a click chemistry handle. In some embodiments, the photo-conjugation moiety is a diazirine moiety. In some embodiments, the photo-click tag comprises (a) a diazirine moiety, and (b) a click chemistry handle. In some embodiments, the click chemistry handle is an alkyne. In some embodiments, the photo-click tag comprises (a) a diazirine moiety, and (b) an alkyne. An "alkyne" is a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkyne group has 2 to 9 carbon atoms ("$C_{2-9}$ alkyne"). In some embodiments, an alkyne has 2 to 8 carbon atoms ("$C_{2-8}$ alkyne"). In some embodiments, an alkyne has 2 to 7 carbon atoms ("$C_{2-7}$ alkynyl"). In some embodiments, an alkyne has 2 to 6 carbon atoms ("$C_{2-6}$ alkyne"). In some embodiments, an alkyne has 2 to 5 carbon atoms ("$C_2$0.5 alkyne"). In some embodiments, an alkyne has 2 to 4 carbon atoms ("$C_{2-4}$ alkyne"). In some embodiments, an alkyne has 2 to 3 carbon atoms ("$C_{2-3}$ alkyne"). In some embodiments, an alkyne has 2 carbon atoms ("$C_2$ alkyne"). The one or more carbon-carbon triple bonds can be internal (such as in 2-butyne) or terminal (such as in 1-butyne). Examples of $C_{2-4}$ alkynes include, without limitation, ethyne ($C_2$), 1-propyne ($C_3$), 2-propyne ($C_3$), 1-butyne ($C_4$), 2-butyne ($C_4$), and the like. Examples of $C_{2-6}$ alkynes include the aforementioned $C_{2-4}$ alkyne groups as well as pentyne (C), hexyne (C), and the like. Additional examples of alkynes include heptyne ($C_7$), octyne ($C_8$), and the like. Unless otherwise specified, each instance of an alkyne is independently unsubstituted (an "unsubstituted alkyne") or substituted (a "substituted alkyne") with one or more substituents. In certain embodiments, the alkyne is an unsubstituted $C_{2-10}$ alkyne. In certain embodiments, the alkyne is an unsubstituted $C_2$ alkyne. In certain embodiments, the alkyne is a substituted $C_{2-10}$ alkyne.

In some embodiments, any of the photo-click tags provided herein may be optionally substituted with one or more electronegative atoms. In some embodiments, the photo-click tag is optionally substituted with one electronegative atom. In some embodiments, the photo-click tag is optionally substituted with two electronegative atoms. The electronegative atoms may be attached to the same carbon, or the electronegative atoms may be attached to two different carbons, as valency permits. In some embodiments, one or more of the electronegative atoms is fluorine. In some embodiments, the photo-click tag is optionally substituted with one fluorine atom. In some embodiments, the photo-click tag is optionally substituted with two fluorine atoms. The fluorine atoms may be attached to the same carbon, or the fluorine atoms may be attached to two different carbons, as valency permits. Placing the one or more fluorine atoms in proximity to the diazirine moiety on the photo-click tag may improve photo-conjugation and/or click chemistry reaction kinetics, as photochemical carbene intermediates and click chemistry reaction kinetics are dependent on electronic substituent effects. See, e.g., Brunner J. et al. (1980) *J Biol Chem*, 255, pp. 3313-3318. Without wishing to be bound by any particular theory, electronically tuning the photo-click tag by placing one or more fluorine substituents on the carbon atom adjacent to the diazirine moiety could provide a more reactive photo-click tag, thereby increasing its utility as a photo-click tag, particularly in in vivo applications or applications in whole proteomes where there are a large number of proteins and other biomolecules present (e.g., in a cell, tissue, or organism). In some embodiments, the photo-click tag is of the formula:

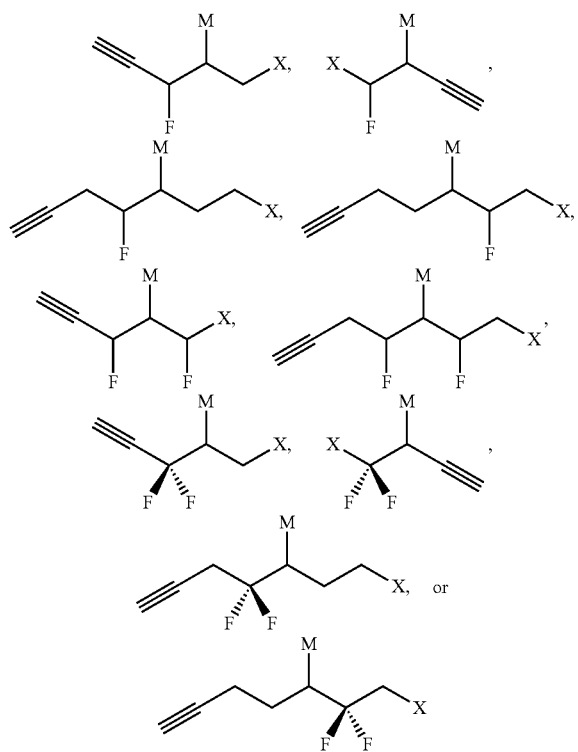

In some embodiments, the photo-conjugation moiety (M) is an aryl azide, azido-methyl-coumarin, benzophenone, anthraquinone, diazo compound, diazirine, or psoralen derivative. In some embodiments, the photo-conjugation moiety (M) is a diazirine moiety.

Diazirines are a class of organic small molecules comprising a carbon bound to two nitrogen atoms, wherein the two nitrogen atoms are double bonded to one another, thus forming a three-membered heterocyclic ring. In some embodiments, the diazirine moiety comprises the structure:

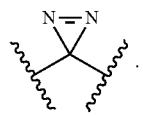 [SMILES: *C1(*)N=N1]

Upon irradiation with a specific wavelength of light (e.g., ultraviolet light), a diazirine forms a reactive carbene species (see Scheme I below). In some embodiments, the reactive carbene species comprises the structure

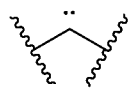

upon irradiation with a specific wavelength of light. In some embodiments, the reactive carbene species comprises at least two free electrons. In some embodiments, the specific wavelength of light is between about 10 nm and about 400 nm. In some embodiments, the specific wavelength of light is between about 355 nm and about 365 nm. In some embodiments, the specific wavelength of light is about 355 nm. In some embodiments, the specific wavelength of light is about 365 nm.

Scheme I

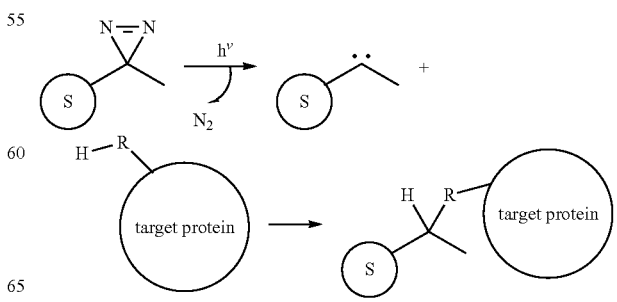

In some embodiments, the reactive carbene species reacts with a C—C, C—H, N—H, or O—H bond of a protein. Upon insertion of the reactive carbine species into a C—C, C—H, N—H, or O—H bond of a protein, a new covalent bond between the protein and photo-click tag is formed, thereby linking the photo-click tag to the protein (see, e.g., FIG. 30). This process may be referred to as photoaffinity labeling (PAL) (Dubinsky et al. (2011) Diazirine based photoaffinity labeling. *Bioorg Med Chem*, 20, pp. 554-570). A non-limiting example of a photo-conjugation of a photo-click tag, or a compound conjugated to a photo-click tag, to a target protein is shown below in Scheme II. The reaction in Scheme II can be performed in vitro or in vivo.

Scheme II

[S represents a small molecule conjugated to a group comprising a diazirine moiety (e.g., a photo-click tag), R represents an oxygen, nitrogen, or carbon atom in amino acid in the target protein]

In some embodiments, the photo-click tag is of the formula:

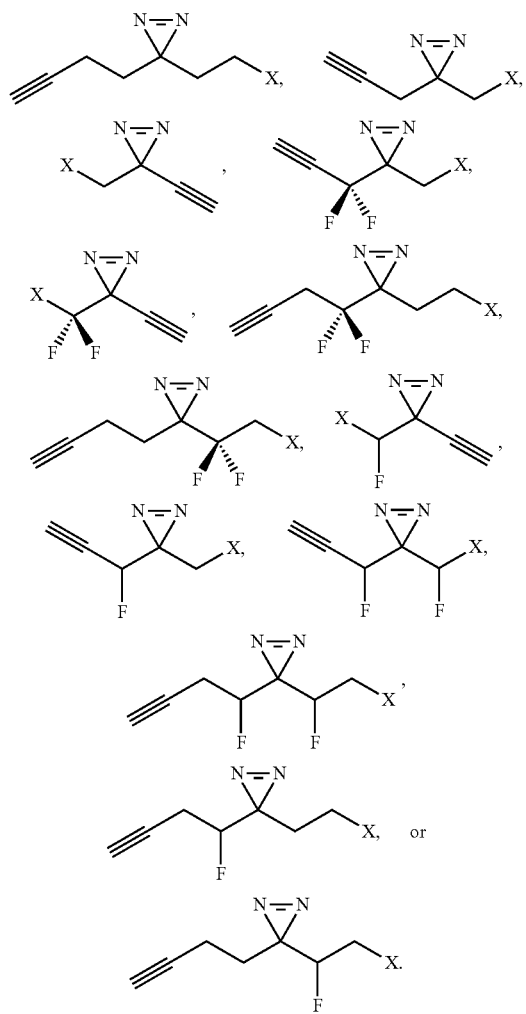

wherein,

X is —OH, —NH$_2$, or a halogen.

Figure 26:
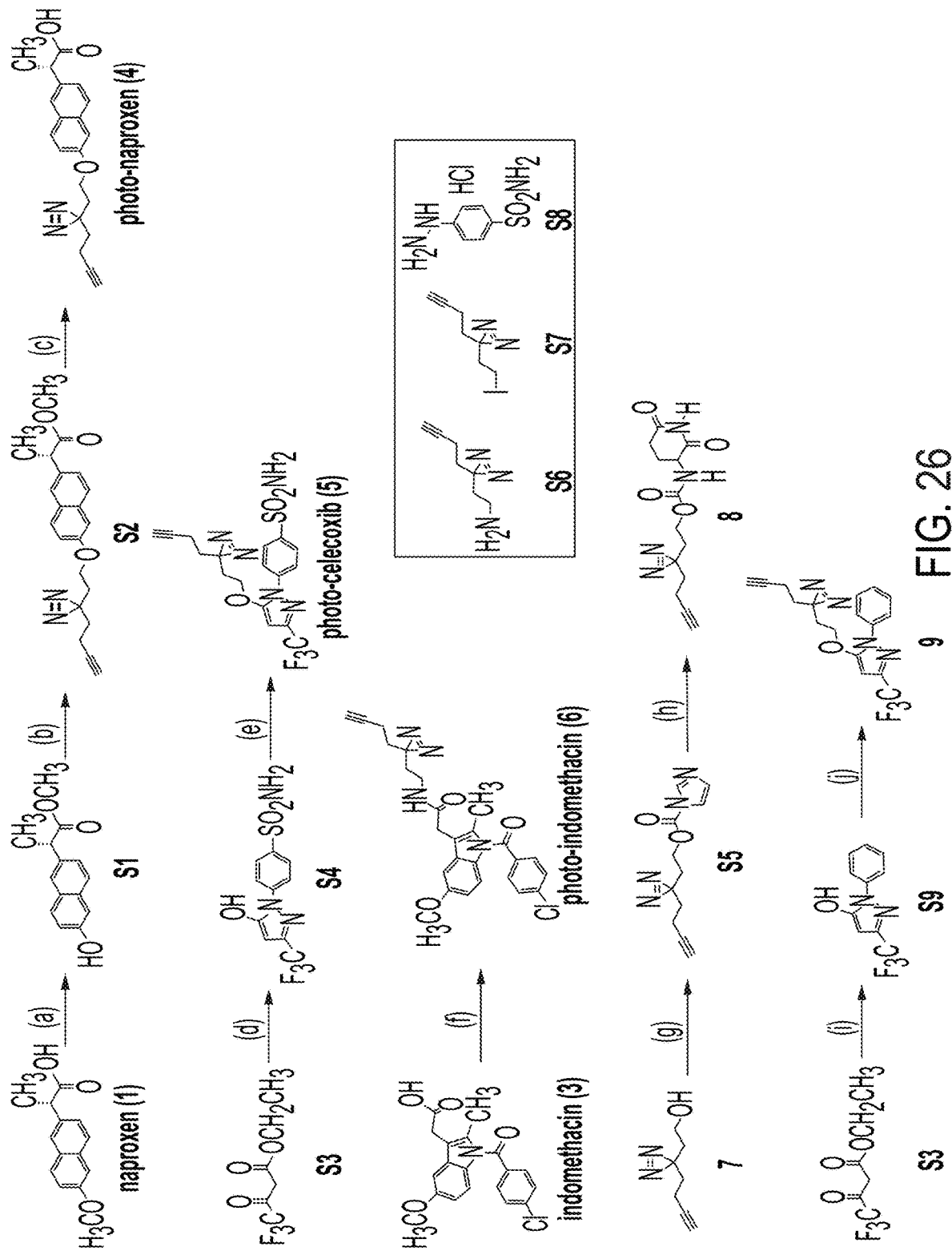
FIG. 26 shows a synthetic scheme for the synthesis of photo-NSAID analogs. Reagents and reaction conditions: (a) (i) HBr, 12 hours, reflux (ii) acetyl chloride, $CH_3OH$, 4 hours, reflux (95%, two steps); (b) $K_2COI$, S7, DMF, 12 hours, 24° C. (85%); (c) 1M NaOH, methanol, 4 hours, 24° C. (98%); (d) S8, ethanol, 12 hours, reflux (99%); (e) $K_2CO_3$, S7, DMF, 12 h, 24° C. (75%); (f) N-(3-dimethylaminopropyl)-N'-ethylcarbodiimide hydrochloride (EDC), triethyl amine, S6, DMAP, DMF, 12 hours, 24° C. (88%); (g) CDI, THF, 12 hours, 24° C. (95%); (h) 3-aminopiperidine-2,6-dione hydrochloride, DBU, DMF, 12 hours, 24° C. (86%); (i) phenylhydrazine, ethanol, 12 hours, reflux (92%); j) $K_2CO_3$, S7, DMF, 12 hours, 24° C. (68%).
Figure 27:
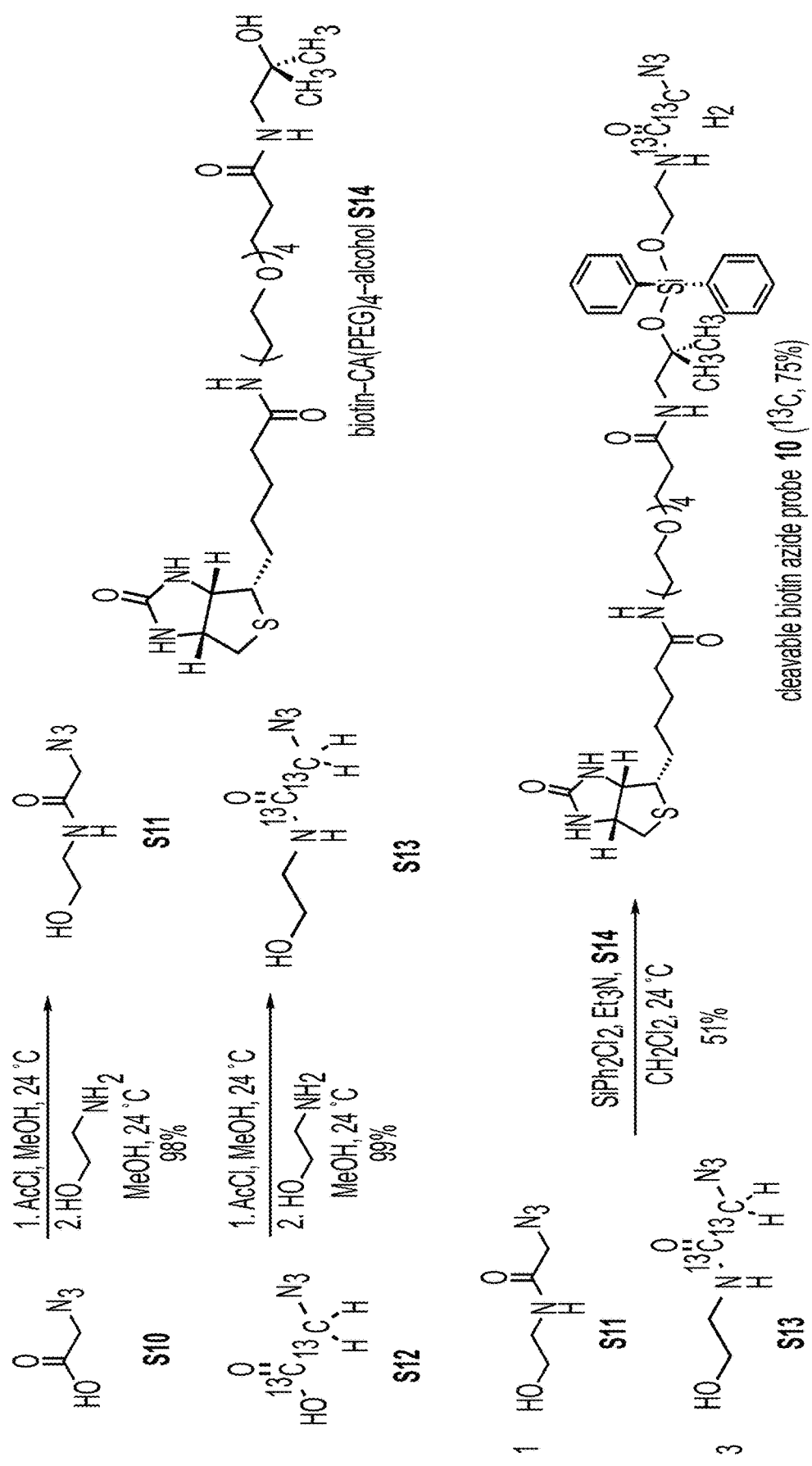
FIG. 27 shows a synthetic scheme for the synthesis of the cleavable biotin azide probe 10.

In some embodiments, X is —OH. In some embodiments, X is —NH$_2$. In some embodiments, X is halogen. In some embodiments, X is chlorine (Cl). In some embodiments, X is iodine (I). In some embodiments, X is fluorine (F). In some embodiments, X is bromine (Br). A person of skill in the art will recognize the appropriate X group for use in a photo-click tag in accordance with the present disclosure based on the functional groups present in the agent to be conjugated to the photo-click tag. For example, FIG. 26 shows exemplary synthetic schemes that can be used to conjugate a photo-click tag wherein X is —NH$_2$ to a small molecule comprising an —OH group, thereby generating a photo-conjugated agent comprising a —O— linker between the small molecule and the photo-click tag.

In some embodiments, wherein X is I, the photo-click tag is of the formula:

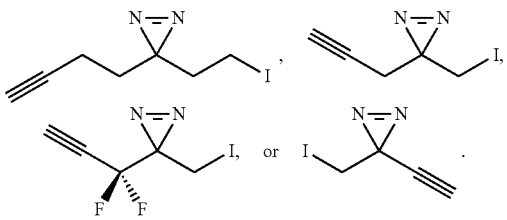

In some embodiments, wherein X is —NH$_2$, the photo-click tag is of the formula:

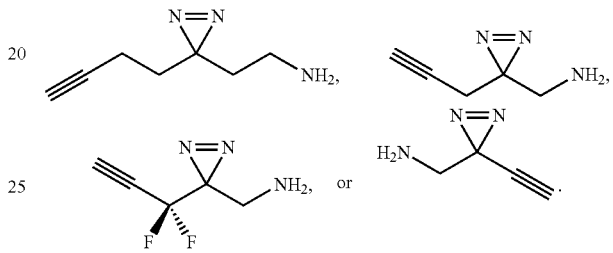

In some embodiments, the photo-click tag is of the formula:

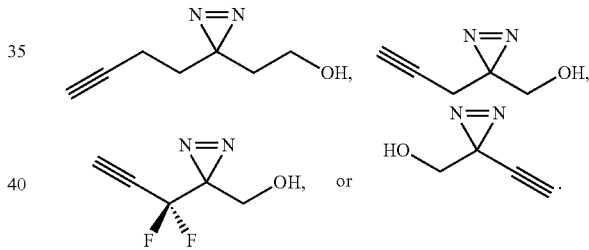

In some embodiments, the photo-click tag is of the formula:

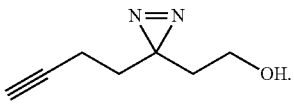

In some embodiments, the photo-click tag optionally comprises one or more electronegative atoms (e.g., fluorine).

In some embodiments, the photo-click tag is of the formula:

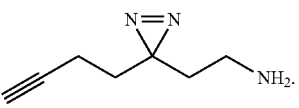

In some embodiments, the photo-click tag optionally comprises one or more electronegative atoms (e.g., fluorine).

In some embodiments, the photo-click tag is of the formula:

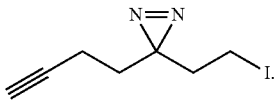

In some embodiments, the photo-click tag optionally comprises one or more electronegative atoms (e.g., fluorine).

In some embodiments, the photo-click tag is of the formula:

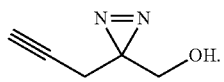

In some embodiments, the photo-click tag optionally comprises one or more electronegative atoms (e.g., fluorine).

In some embodiments, the photo-click tag is of the formula:

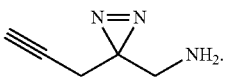

In some embodiments, the photo-click tag optionally comprises one or more electronegative atoms (e.g., fluorine).

In some embodiments, the photo-click tag is of the formula:

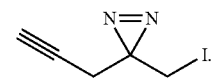

In some embodiments, the photo-click tag optionally comprises one or more electronegative atoms (e.g., fluorine).

In some embodiments, the photo-click tag is of the formula:

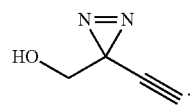

In some embodiments, the photo-click tag optionally comprises one or more electronegative atoms (e.g., fluorine).

In some embodiments, the photo-click tag is of the formula:

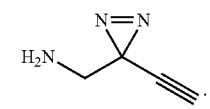

In some embodiments, the photo-click tag optionally comprises one or more electronegative atoms (e.g., fluorine).

In some embodiments, the photo-click tag is of the formula:

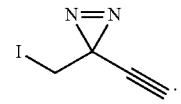

In some embodiments, the photo-click tag optionally comprises one or more electronegative atoms (e.g., fluorine).

In some embodiments, the photo-click tag is of the formula:

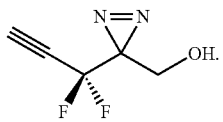

In some embodiments, for example, when the photo-click tag is associated with a small molecule of interest, the photo-click tag is coupled to the small molecule through a linker, as described below. Thus, in some embodiments, the photo-click tag is of the formula:

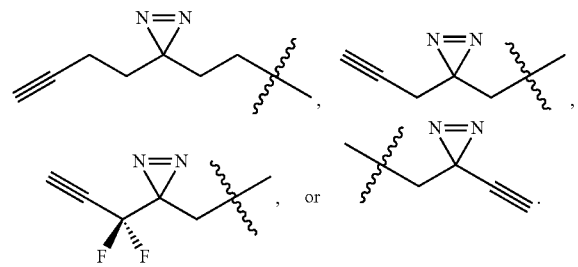

In some embodiments, the photo-click tag is less than about 10 Å in length. In some embodiments, the photo-click tag is less than about 9.5 Å in length. In some embodiments, the photo-click tag is less than about 9 Å in length. In some embodiments, the photo-click tag is less than about 8 Å in length. In some embodiments, the photo-click tag is less than about 7 Å in length. In some embodiments, the photo-click tag is less than about 6 Å in length. In some embodiments, the photo-click tag is between about 6 Å and about 9.5 Å in length. In some embodiments, the photo-click tag is between about 6 Å and about 8 Å in length. In some embodiments, the photo-click tag is between about 6 Å and about 7 Å in length. In some embodiments, the photo-click tag is about 7 Å in length. In some embodiments, the photo-click tag is about 6.9 Å in length.

Compounds Comprising Photo-Click Tags

As discussed above, the photo-click tags presented herein comprise a photo-conjugation moiety that can covalently capture (i.e., bind) the protein target (e.g., an enzyme that binds to a small molecule of interest, a receptor, an antibody, etc.), and a biocompatible handle (e.g., a click chemistry handle) for functionalization with a reporter molecule or affinity tag (e.g., a biotinylated affinity tag). Without wishing to be bound by any particular theory, the affinity can be used to enrich the target protein of interest, and aid in identifying the target protein bound to the photo-click tagged agent of interest. When attached to a compound (e.g., small molecule) of interest, these "photo-click tagged compounds"

can be used to map the interactions of the compound of interest with the target molecule (e.g., a protein). These photo-click tagged compounds are useful, for example, for mapping the interactions of the compound in a whole proteome, or for mapping the proteomic interactions mediated by the compound in vivo. Some compounds (e.g., small molecule drugs) can exist as stereoisomers (e.g., epimers, diastereomers, or enantiomers), wherein each stereoisomer may exhibit a different activity (e.g., bind to different target protein). In some embodiments, a compound exists as an enantiomer, wherein the S- and R-enantiomer interact differently with the same target protein. In some embodiments, a compound exists as an enantiomer, wherein the S- and R-enantiomer interact with unique target proteins. Thus, the compounds and methods of the present invention can be useful in determining the action of a specific enantiomer or other stereoisomer of a small molecule (e.g., an immunomodulatory drug). For example, the orientation of each enantiomer may place the photo-conjugation (e.g., diazirine) moiety in close proximity to one or more specific amino acids of the target protein (e.g., in the active site, in an allosteric site). A difference in the amino acids bound by the photo-conjugation moiety could indicate enantiomer-specific binding and interactions with the target protein.

Most small molecules can be covalently coupled to a photo-click tag provided herein by employing the appropriate organic chemistry reaction to couple the small molecule to the photo-click tag, for example, as shown in FIGS. 26, 70, and 71. Conjugation of the photo-click tag to the small molecule can be achieved by formation of an ester, ether, amine or amide to link the small molecule to the photo-click tag. For example, as shown in FIG. 26, an ether bond is formed when a photo-click probe comprising a free amine (NH$_2$) group reacts with a free hydroxyl (OH) group on the small molecule. As another example, an amide bond is formed when a photo-click probe comprising a free amine (NH$_2$) group reacts with a free carboxylic acid (—COOH) group on the small molecule (FIG. 26). A person of ordinary skill in the art will be able to determine the appropriate reaction conditions to use for coupling a small molecule to a photo-click tag (e.g., a triisopropyl ether (TIPS) protected photo-click tag) based on the functional groups present in the small molecule of interest, or portion of the small molecule that binds to a target protein or proteins. The photo-click tag should be placed on the molecule so as to not interfere with the small molecule-protein binding interaction. Thus, the resulting photo-click tagged compound may comprise the entire small molecule, or a portion of the small molecule. Where the photo-tagged compound comprises only a portion of the small molecule, this portion of the small molecule should be sufficient for maintaining the interaction between the small molecule and the target protein(s).

Thus, in some aspects, provided herein are compounds comprising the structure of Formula (I):

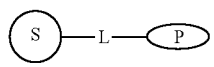

(I)

wherein
S is a small molecule, or derivative thereof;
P is a photo-click tag comprising (a) a photo-conjugation moiety (M), and (b) a click chemistry handle; and
L is a linker.

In some embodiments, the click chemistry handle is an alkyne. Thus, in some embodiments, P is

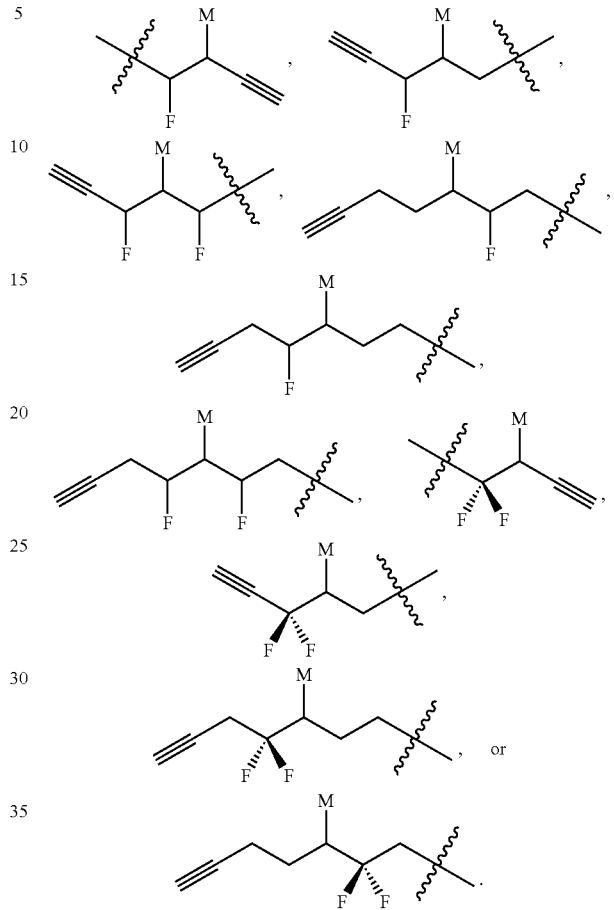

In some embodiments, the photo-conjugation moiety (M) is an aryl azide, azido-methyl-coumarin, benzophenone, anthraquinone, diazo compound, diazirine, or psoralen derivative. In some embodiments, the photo-conjugation moiety (M) is a diazirine moiety. In some embodiments. P comprises (a) a diazirine moiety, and (b) a click chemistry handle. In some embodiments, the click chemistry handle is an alkyne. In some embodiments, P comprises (a) a diazirine moiety, and (b) an alkyne.

In some embodiments, P is

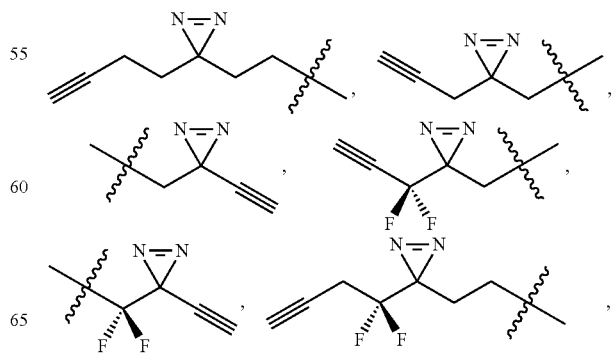

-continued

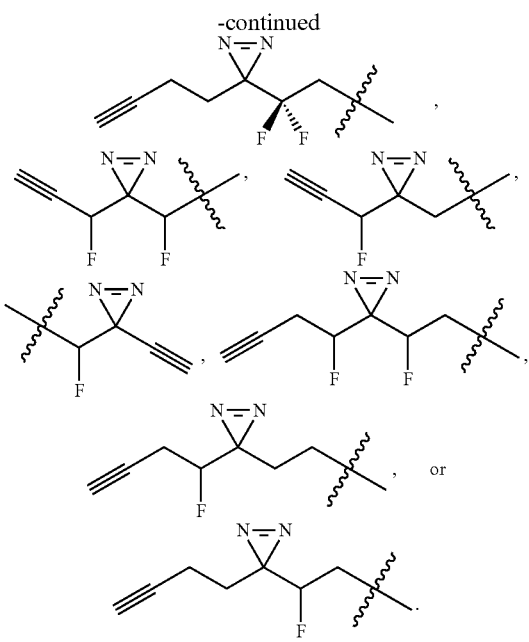

In some embodiments, P is

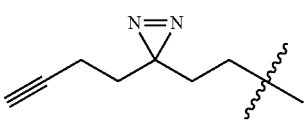

In some embodiments, P optionally comprises one or more electronegative atoms (e.g., fluorine).

In some embodiments. P is

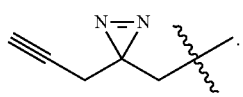

In some embodiments, P optionally comprises one or more electronegative atoms (e.g., fluorine).

In some embodiments, P is

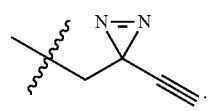 [SMILES: *CC1(C#C)N=N1]

In some embodiments, P optionally comprises one or more electronegative atoms (e.g., fluorine).

In some embodiments, P is

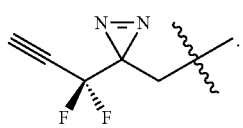

In some embodiments, L is a bond. In some embodiments, L comprises an ester, an ether, an amine, or an amide. In some embodiments, L comprises an ester. In some embodiments, L comprises an ether. In some embodiments, L comprises an amine. In some embodiments, L comprises an amide. In some embodiments, L is

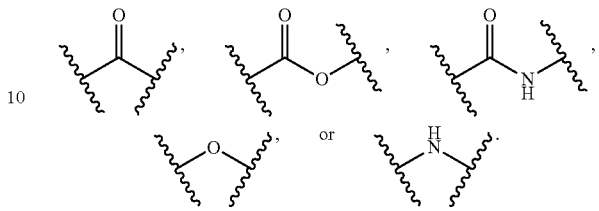

In some embodiments, L is

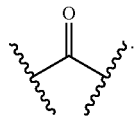

In some embodiments, L is

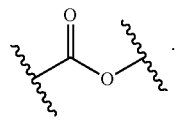 [SMILES: *OC(*)=O]

In some embodiments, L is

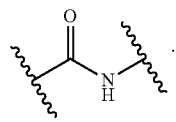

In some embodiments, L is

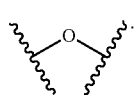

In some embodiments, L is

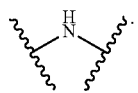

In some embodiments, S is an antibiotic, an anti-proliferative agent, an anti-cancer agent, a chemotherapeutic agent, an anti-angiogenesis agent, an anti-inflammatory agent, an immunosuppressant, an immunomodulatory agent, an anti-bacterial agent, an anti-viral agent, a cardiovascular agent, a cholesterol-lowering agent, an anti-diabetic agent, an anti-allergic agent, a contraceptive agent, or a pain-relieving agent.

In some embodiments, S is an anti-inflammatory agent, or derivative thereof. In some embodiments, the anti-inflammatory agent is a non-steroidal anti-inflammatory drug (NSAID), or derivative thereof. Exemplary, non-limiting examples of NSAIDs for use herein are aspirin (acetylsalicylic acid), diflunisal (dolobid), salicylic acid and other salicylates, salsalate (disalcid), ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, phenylbutazone (bute), mefenamic acid, meclofenamic acid, flufenamic acid, tolfenamic acid, celecoxib, rofecoxib, valdecoxib, parecoxib, lumiracoxib, etoricoxib, firocoxib, nimesulide, clonixin, licofelone, and derivatives thereof. In some embodiments, the NSAID is selected from the group consisting of acetaminophen, aspirin, bromefenac sodium, celecoxib, diclofenac, diclofenac potassium, diclofenac sodium, diflunisal, etodolac, fenoprofen calcium, flurbiprofen, ibuprofen, indomethacin, ketoprofen, magnesium salicylate, meclofenamate sodium, mefenamic acid, nabumetone, naproxen, naproxen sodium, oxaproxin, oxyohebutazone, phenylbutazone, piroxicam, rofecoxib, salsalate, sodium salicylate, sulindac, tometin sodium, valdexocib, and derivatives thereof.

In some embodiments, the NSAID is naproxen, or derivative thereof. In some embodiments, the NSAID is celecoxib, or derivative thereof. In some embodiments, the NSAID is indomethacin, or derivative thereof.

In some embodiments, the compound is of the formula:

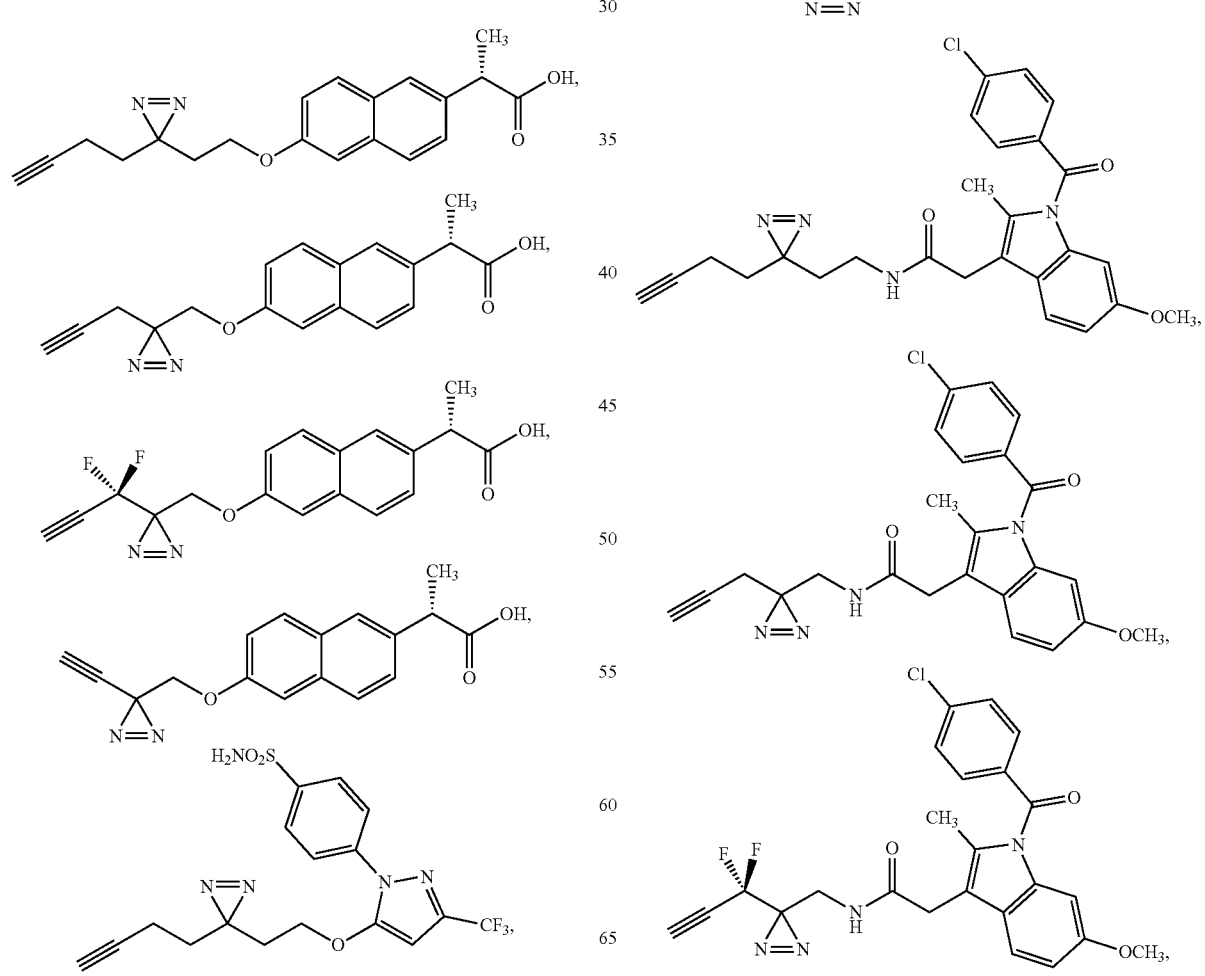

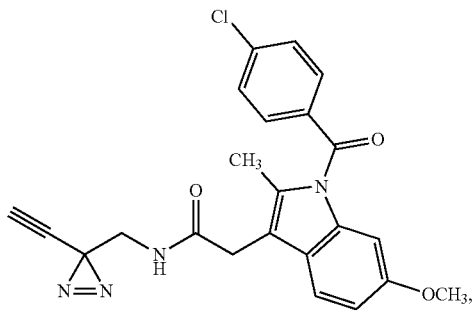

or a pharmaceutically acceptable salt thereof.

In some embodiments, the anti-inflammatory agent is a steroidal anti-inflammatory agent, or derivative thereof. In some embodiments, the steroidal anti-inflammatory agent is a corticosteroid, or derivative thereof. Exemplary, non-limiting corticosteroids suitable for use herein are 21-acetoxypregnenolone, alclometasone, alclometasone dipropionate, algestone, amcinonide, beclomethasone, betamethasone, betamethasone dipropionate, betamethasone sodium phosphate, betamethasone valerate, budesonide, chloroprednisone, ciclesonide, clobetasol, clobetasol-17-propionate, clobetasone-17-butyrate, clobetasone, clocortolone, cloprednol, corticosterone, cortisone, cortisone acetate, cortivazol, deflazacort, desonide, desoximetasone, dexamethasone, dexamethasone sodium phosphate, diflorasone, diflucortolone, difluprednate, enoxolone, fluazacort, flucloronide, flumethasone, fluocinonide, fluocinolone, fluocinolone acetonide, fluocinonide, fluocortin butyl, fluocortolone, fluocortolone caproate, fluocortolone pivalate, fluorometholone, flunisolide, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, hydrocortisone acetate, hydrocortisone-17-aceponate, hydrocortisone-17-buteprate, hydrocortisone-17-butyrate, hydrocortisone-17-valerate, loteprednol, mazipredone, medrysone, meprednisone, methylprednisolone, mometasone, mometasone furoate, paramethasone, paramethasone acetate, prednicarbate, prednisolone, prednisolone 25-diethylamino-acetate, prednisolone sodium phosphate, prednisone, prednival, prednylidene, rimexolone, tixocortol, tixocortol pivalate, triamcinolone, triamcinolone acetonide, triamcinolone alcohol, triamcinolone benetonide, triamcinolone hexacetonide, and derivatives thereof.

In some embodiments, S is an immunomodulatory drug, or derivative thereof. In some embodiments, the immunomodulatory drug is thalidomide, lenalidomide, pomalidomide, or derivative thereof. In some embodiments, the lenalidomide is R-lenalidomide. In some embodiments, the lenalidomide is S-lenalidomide. In some embodiments, the pomalidomide is R-pomalidomide. In some embodiments, the pomalidomide is S-pomalidomide.

In some embodiments, the compound is of the formula:

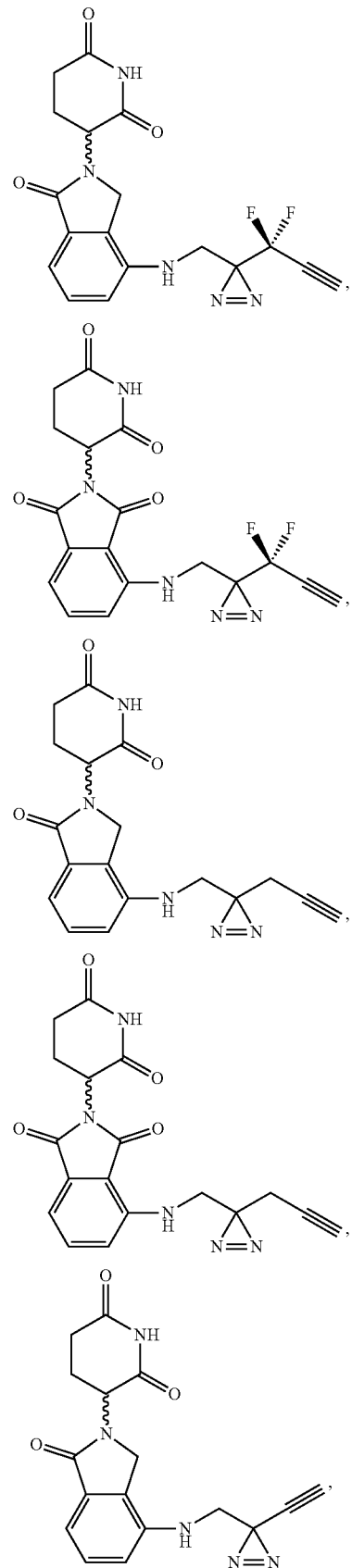

-continued
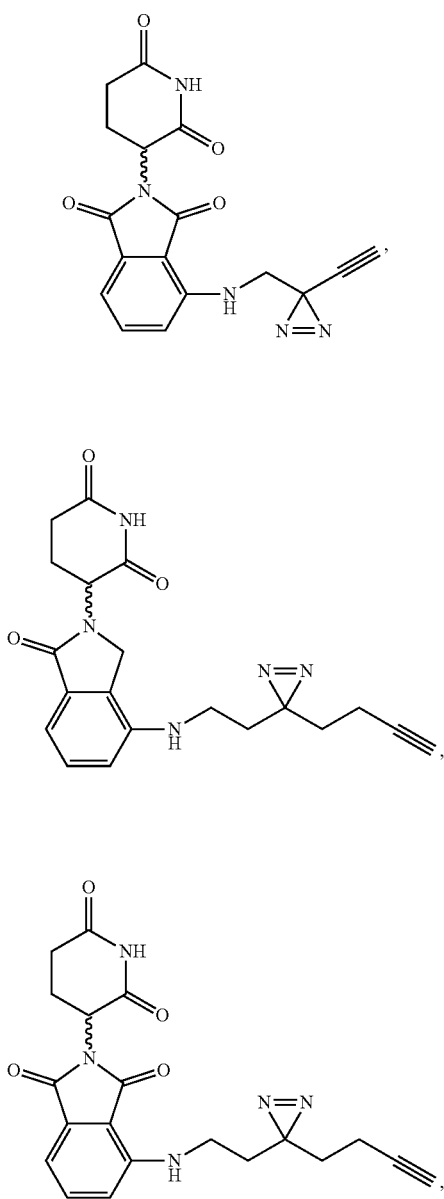
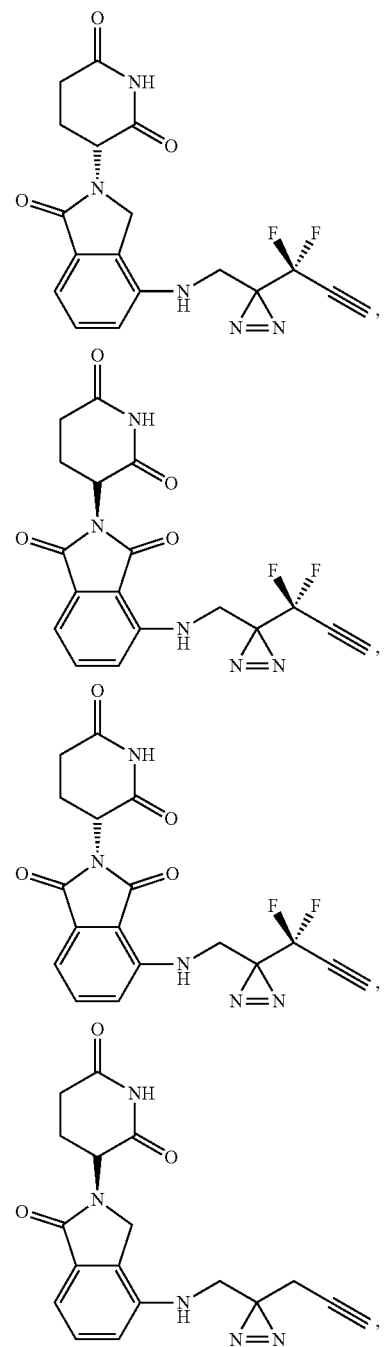
or a pharmaceutically acceptable salt thereof, wherein A represents a bond of un-specified stereochemistry.
In some embodiments, the compound is of the formula:
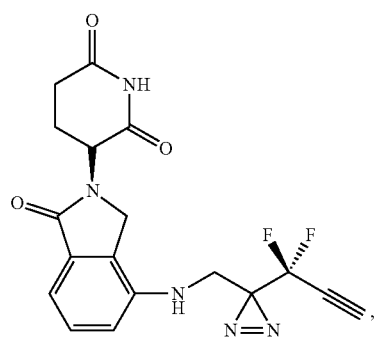
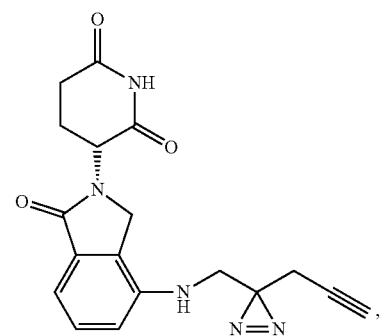

35
-continued
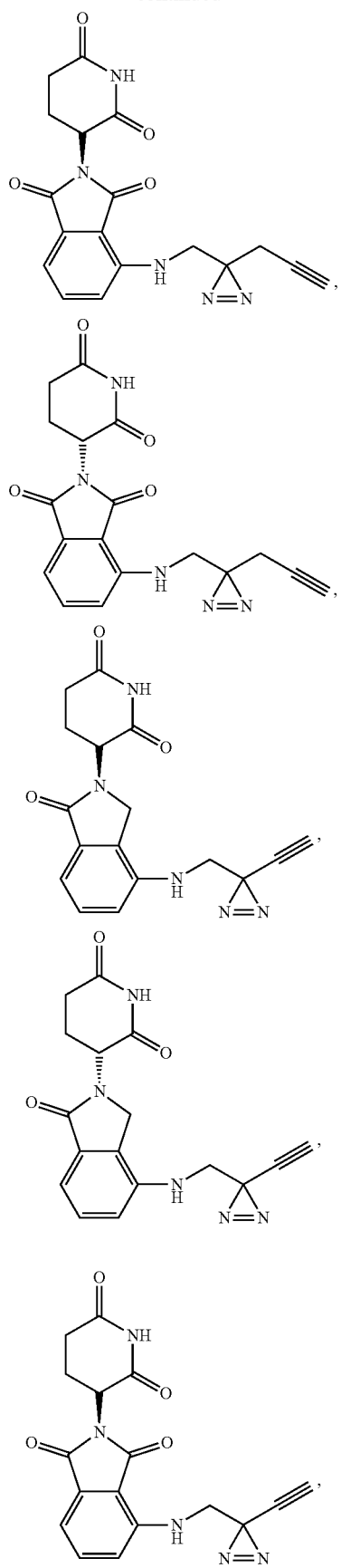
36
-continued
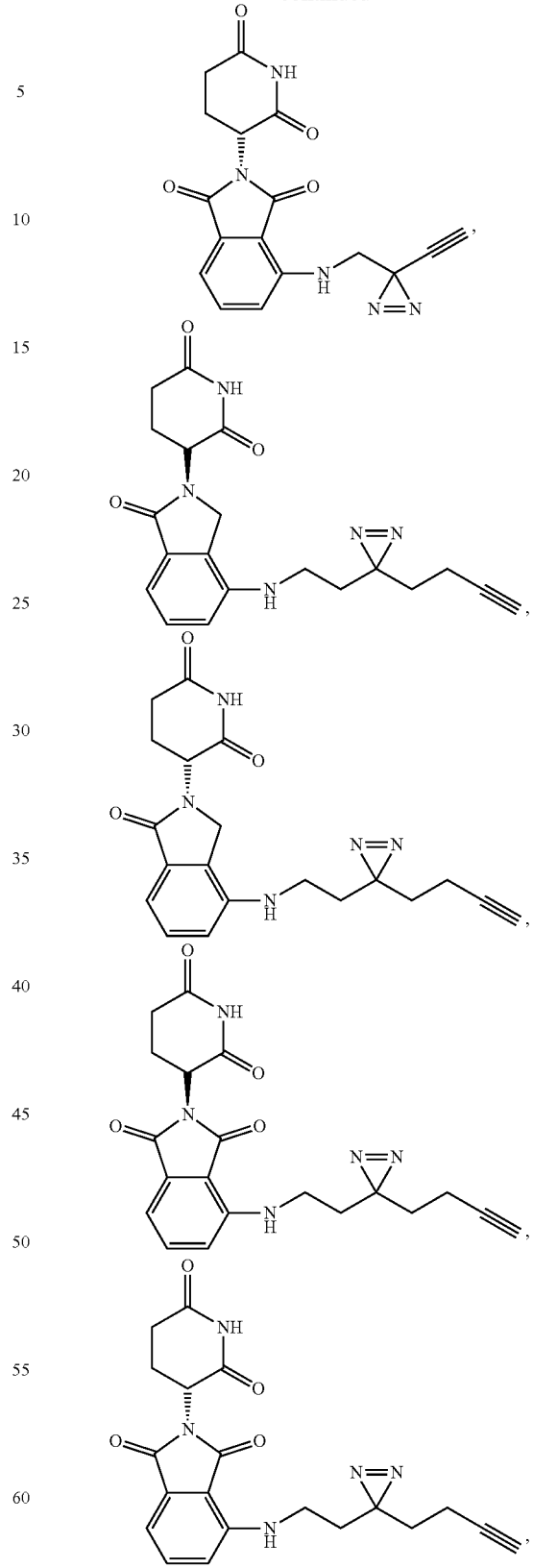
or a pharmaceutically acceptable salt thereof.
In some embodiments, S is a chemotherapeutic agent, or derivative thereof. Exemplary chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoportin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan. 9-aminocamptothecin, camptoirinotecan, irinotecan, crisnatol, mitomycin), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU 11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI, oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, hexamethyl melamine, and derivatives thereof.

In some embodiments, the chemotherapeutic agent is daunorubicin, or derivative thereof. In some embodiments, the chemotherapeutic agent is mitomycin, or derivative thereof.

In some embodiments, the compound is of the formula:

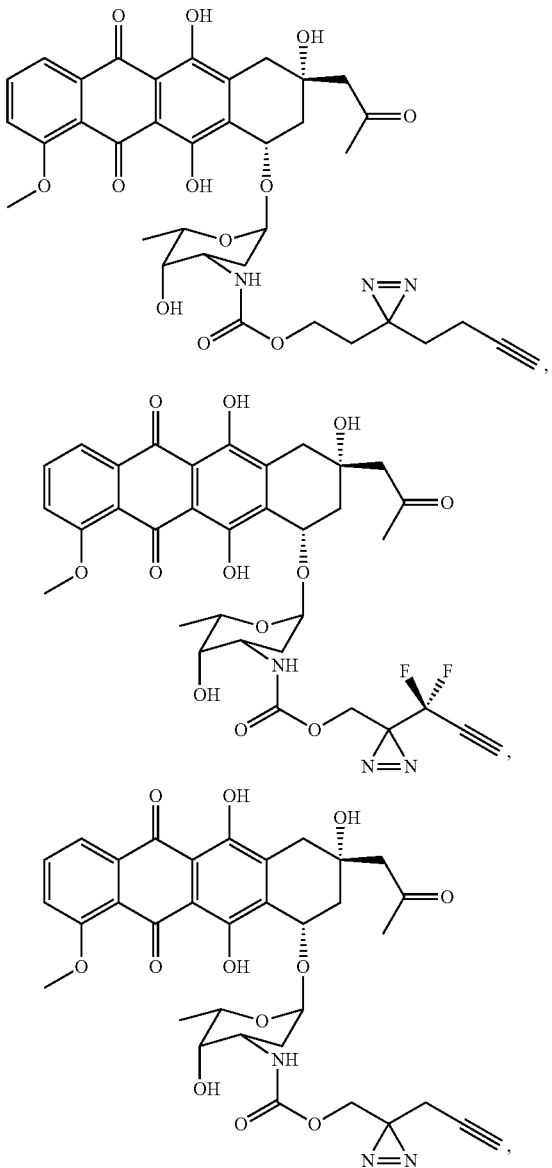

-continued

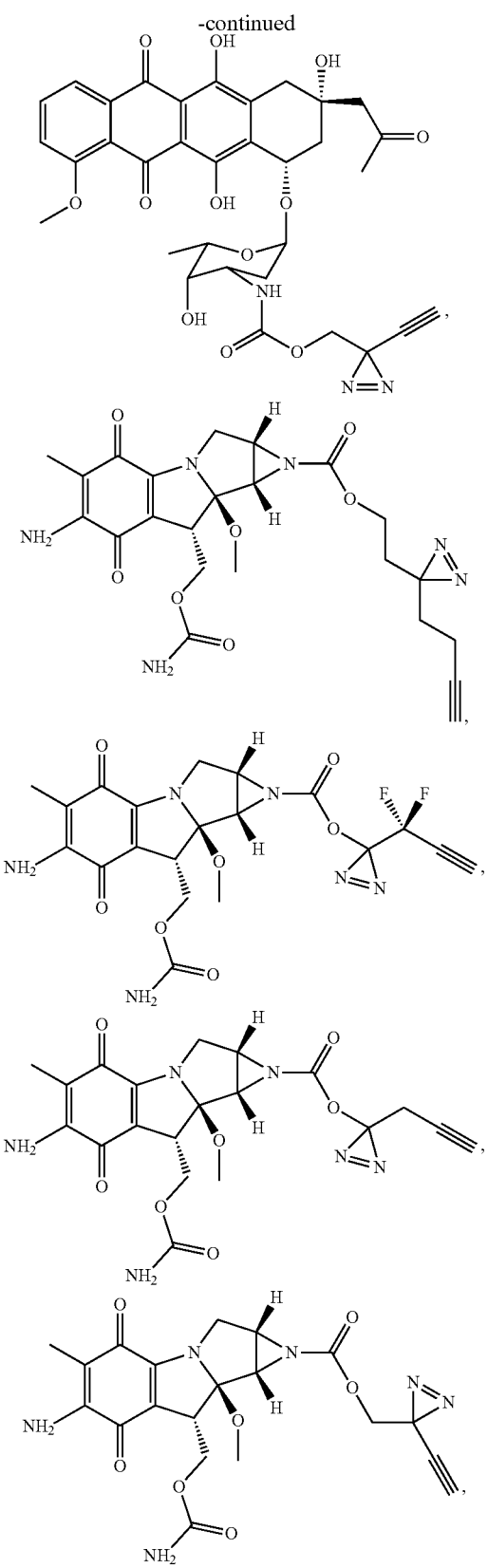

or a pharmaceutically acceptable salt thereof

In some embodiments, S is a steroid. In some embodiments, the steroid is a sex steroid, or derivative thereof. In some embodiments, the sex steroid is an estrogen, or derivative thereof. In some embodiments, the estrogen is estradiol or beta-estradiol, or derivative thereof.

In some embodiments, the compound is of the formula:

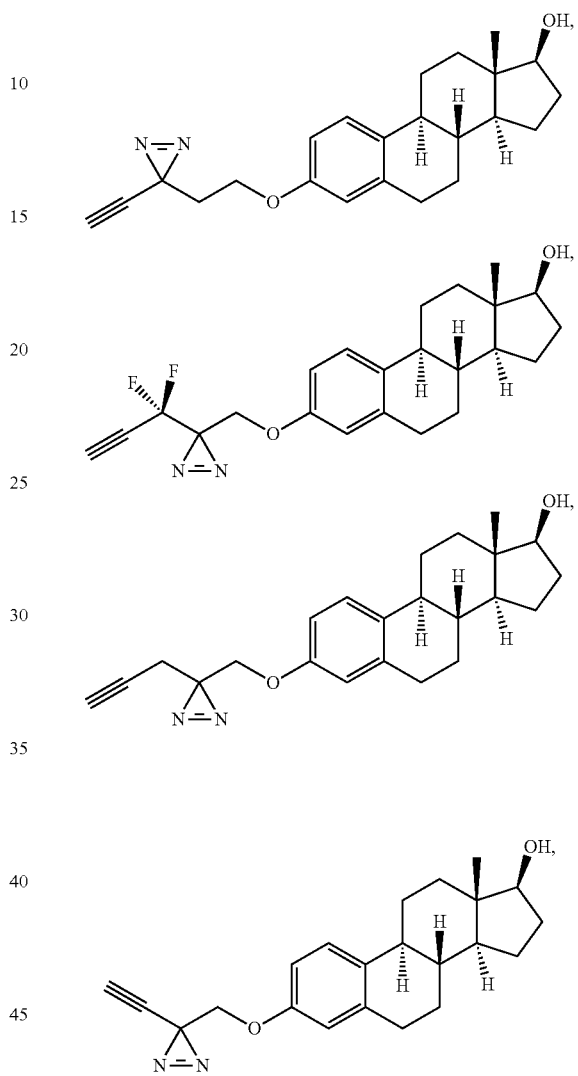

or a pharmaceutically acceptable salt thereof.

Figure 6A:
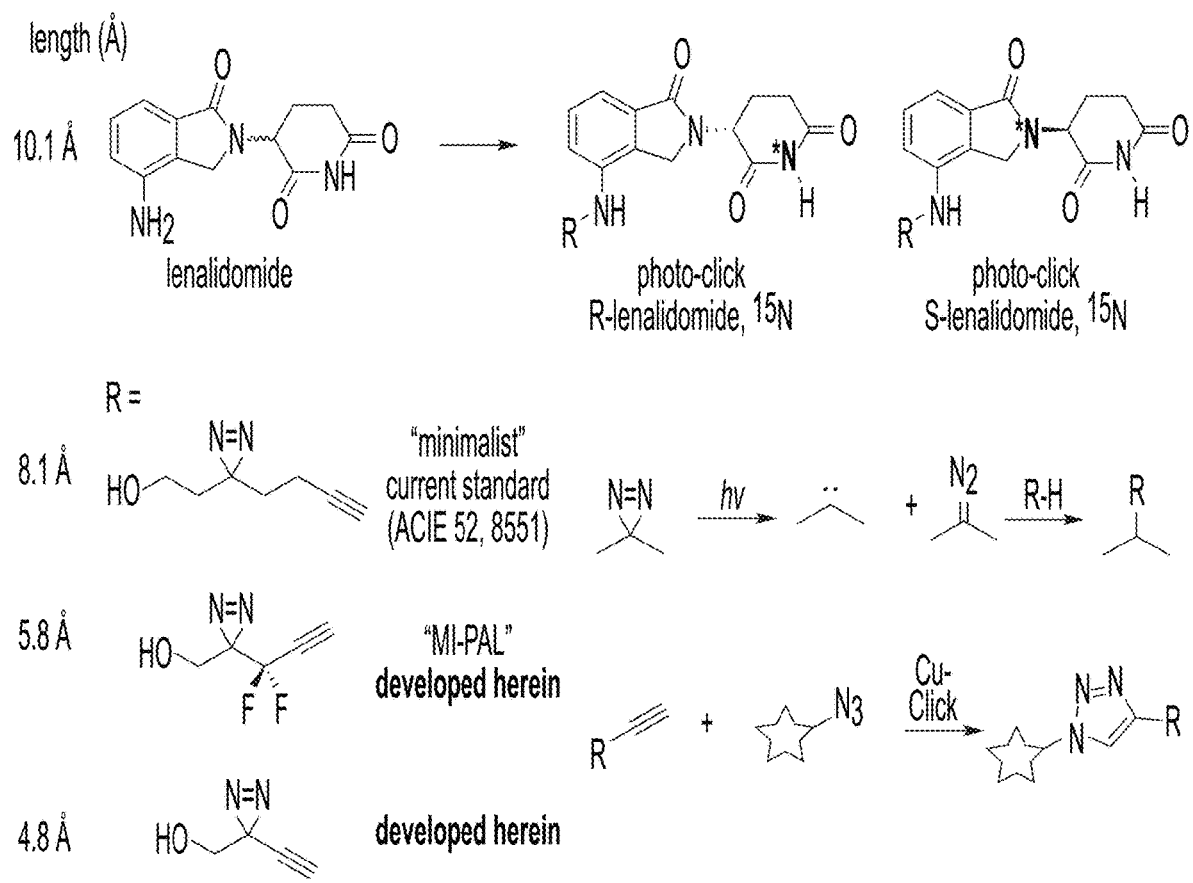
FIGS. 6A-6B shows a generalized strategy for developing photo-click conjugated small molecules (e.g., lenalidomide) as mechanistic probes.
Figure 6B:
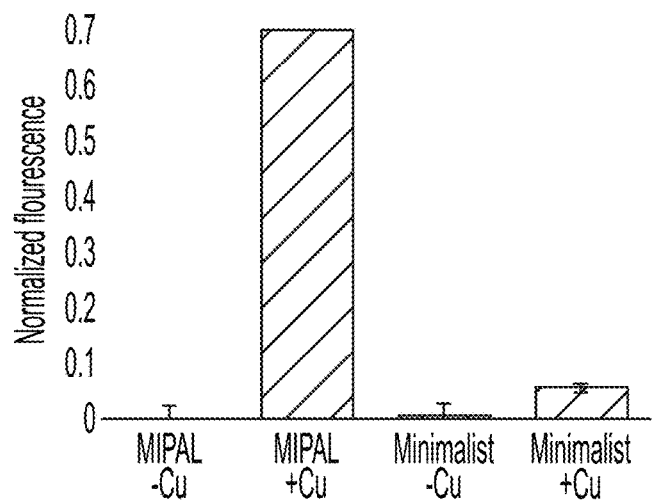
Figure 7:
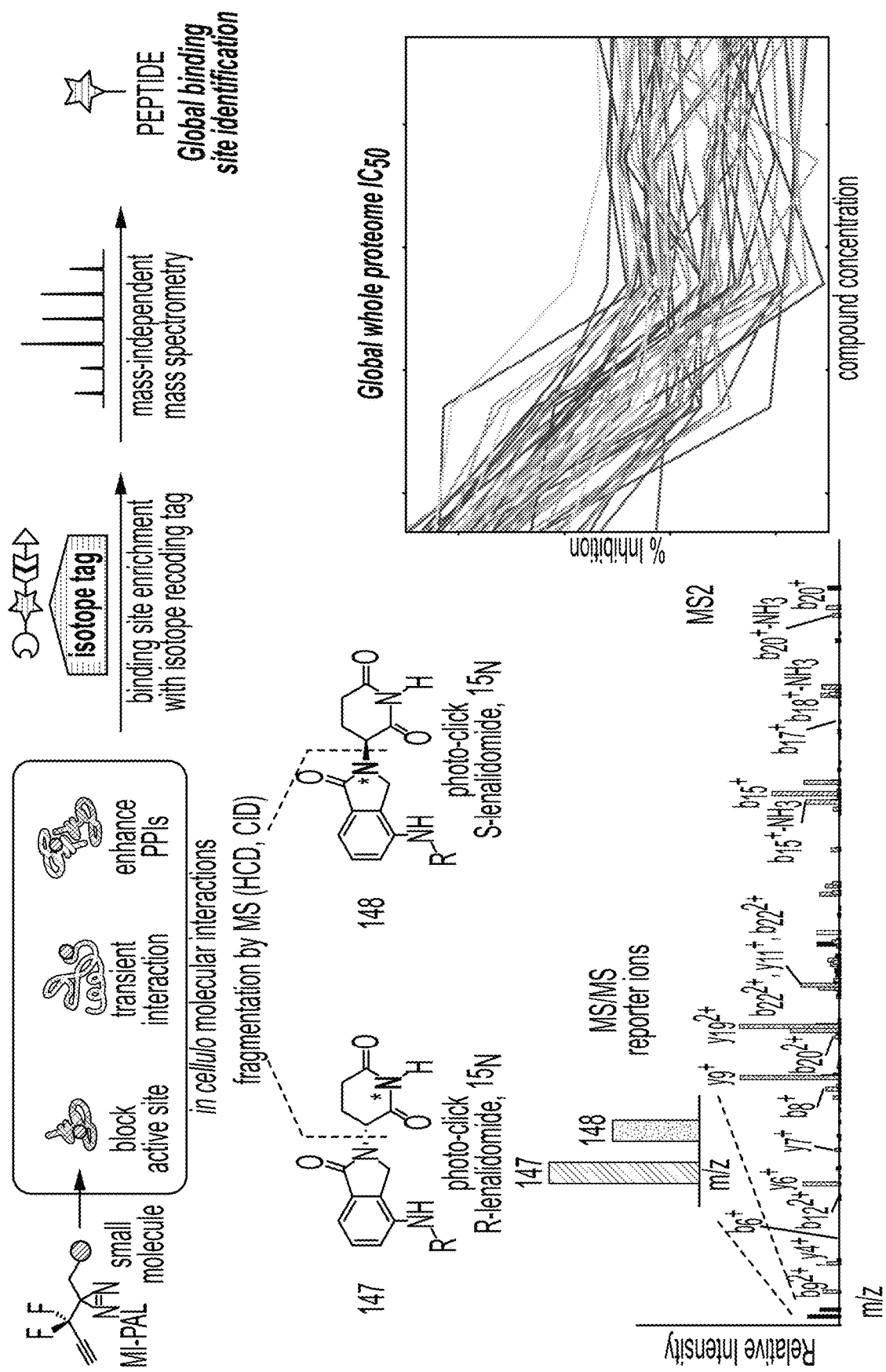
FIG. 7 shows a generalized strategy for applying the minimally-interfering "MI-PAL" photo-click tag to map small molecule binding sites in the whole multiple myeloma cell proteome. These results show that the binding and interactions of R-versus S-enantiomers can be elucidated using the SIM-PAL or MI-PAL technique described herein.
Figure 8:
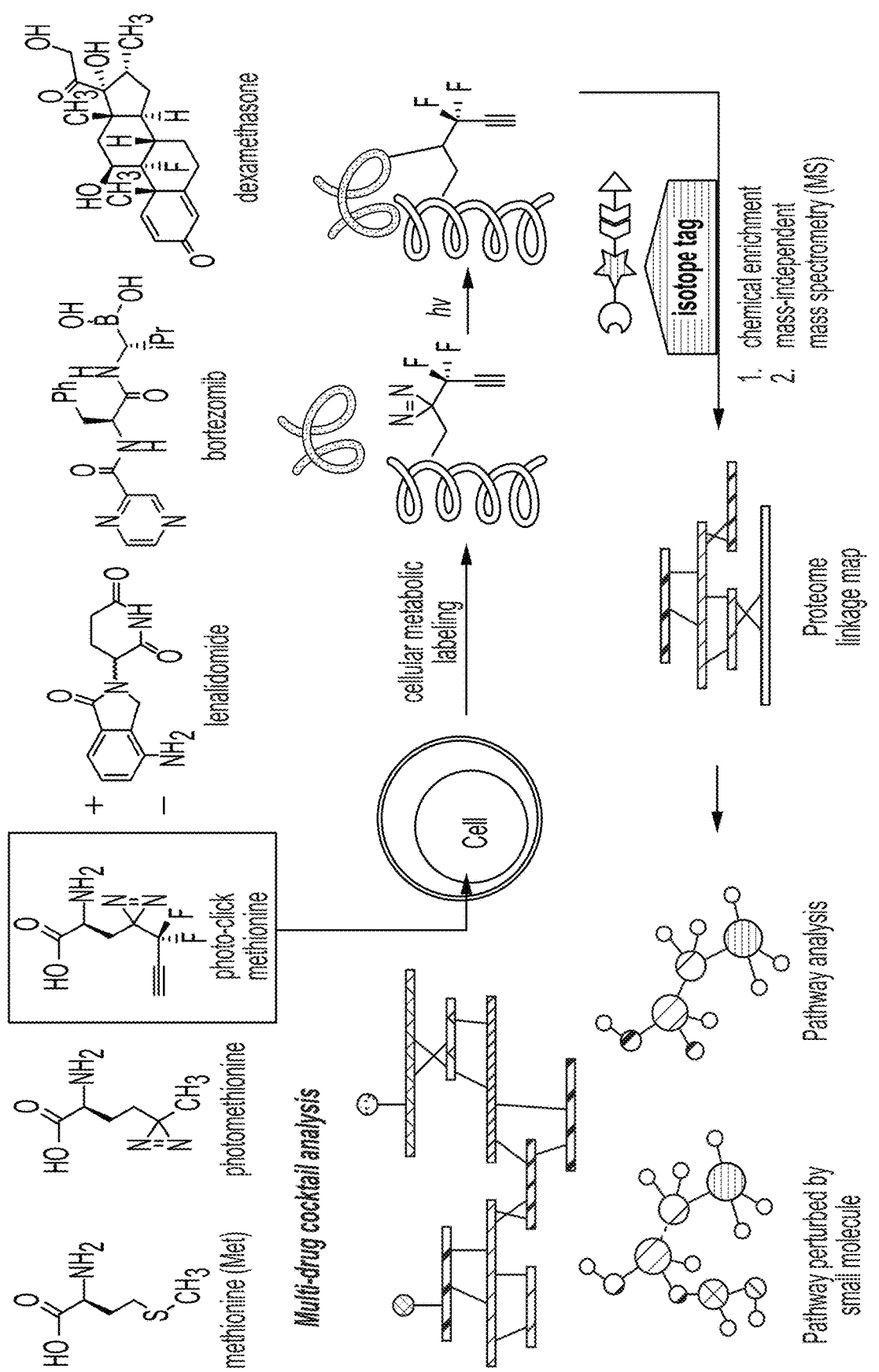
FIG. 8 shows a generalized, non-limiting schematic to study the effect on downstream protein-protein interactions in the presence of a small molecule (e.g., lenalidomide) or combination therapy. This method uses a photo-click labeled amino acid derivative to capture (e.g., "freeze") and identify protein-protein interactions, allowing for the generation of a proteome linkage map.
Figure 9:
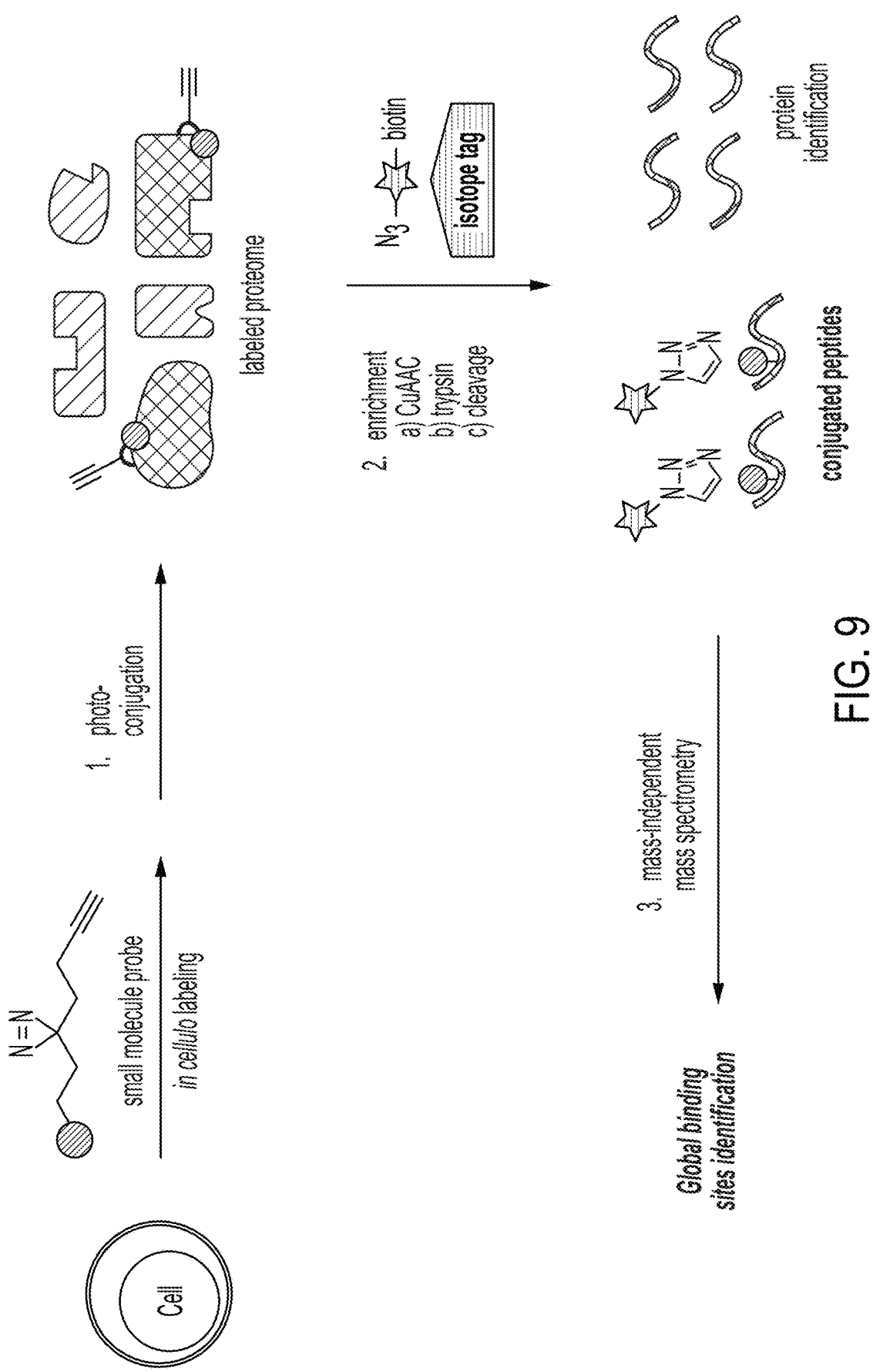
FIG. 9 shows a generalized, non-limiting schematic outlining the SIM-PAL global binding site mapping strategy using exemplary photo-click probes. See, e.g., Flaxman H A and Woo C M (2017) Mapping the Small Molecule Interactome by Mass Spectrometry. *Biochemistry*, 57(2), pp. 186-193.
Figure 10:
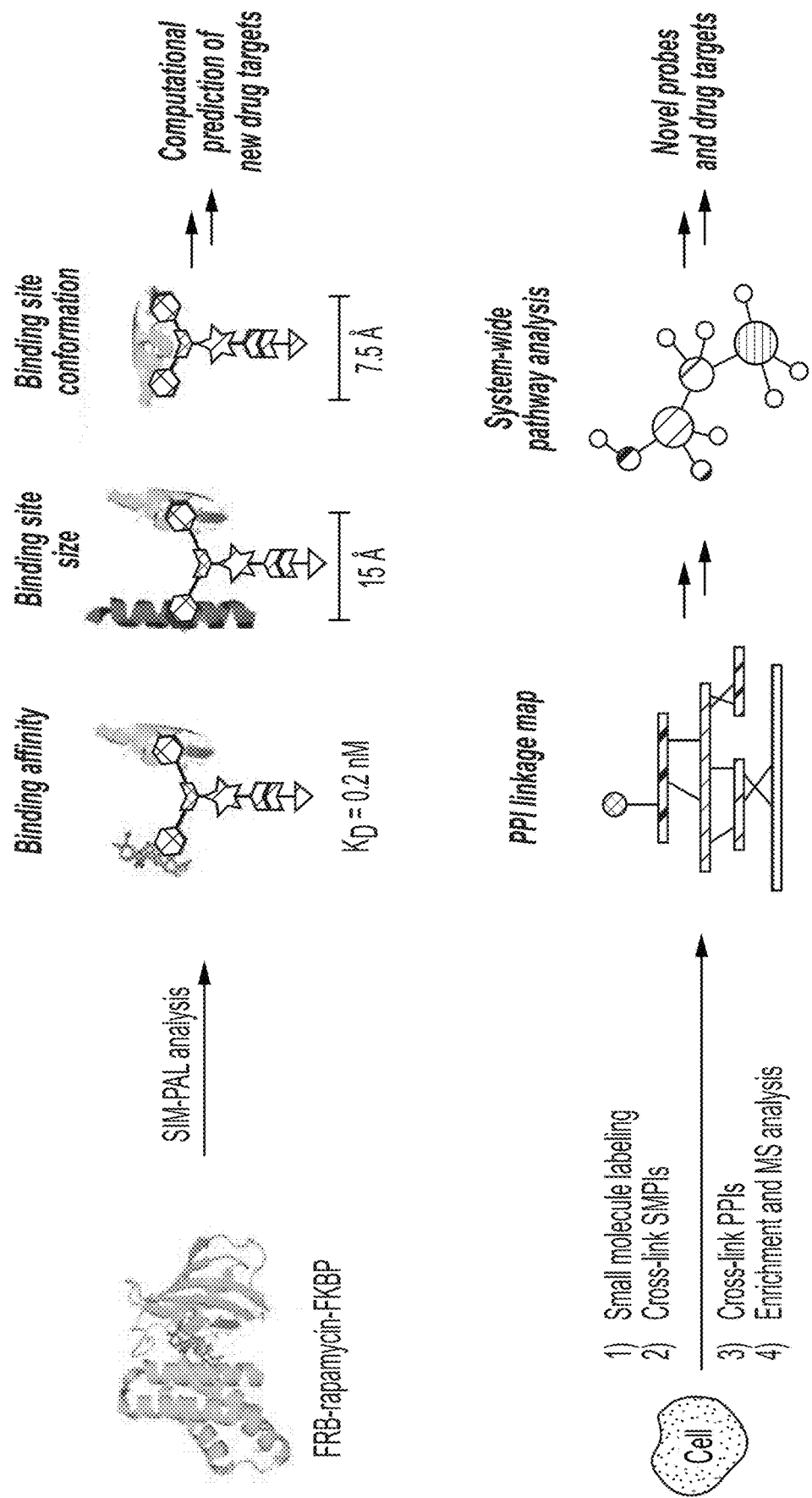
FIG. 10 shows a generalized, non-limiting schematic outlining system-level binding and pathway analysis in the presence of a small molecule of interest, such as a drug or drug candidate. SIM-PAL analysis can be used to predict new drug targets (i.e., proteins) or aid in the optimization of existing candidate molecules based on information, such as binding affinity, binding site size, and binding site conformation, given by the SIM-PAL analysis.
Figure 11:
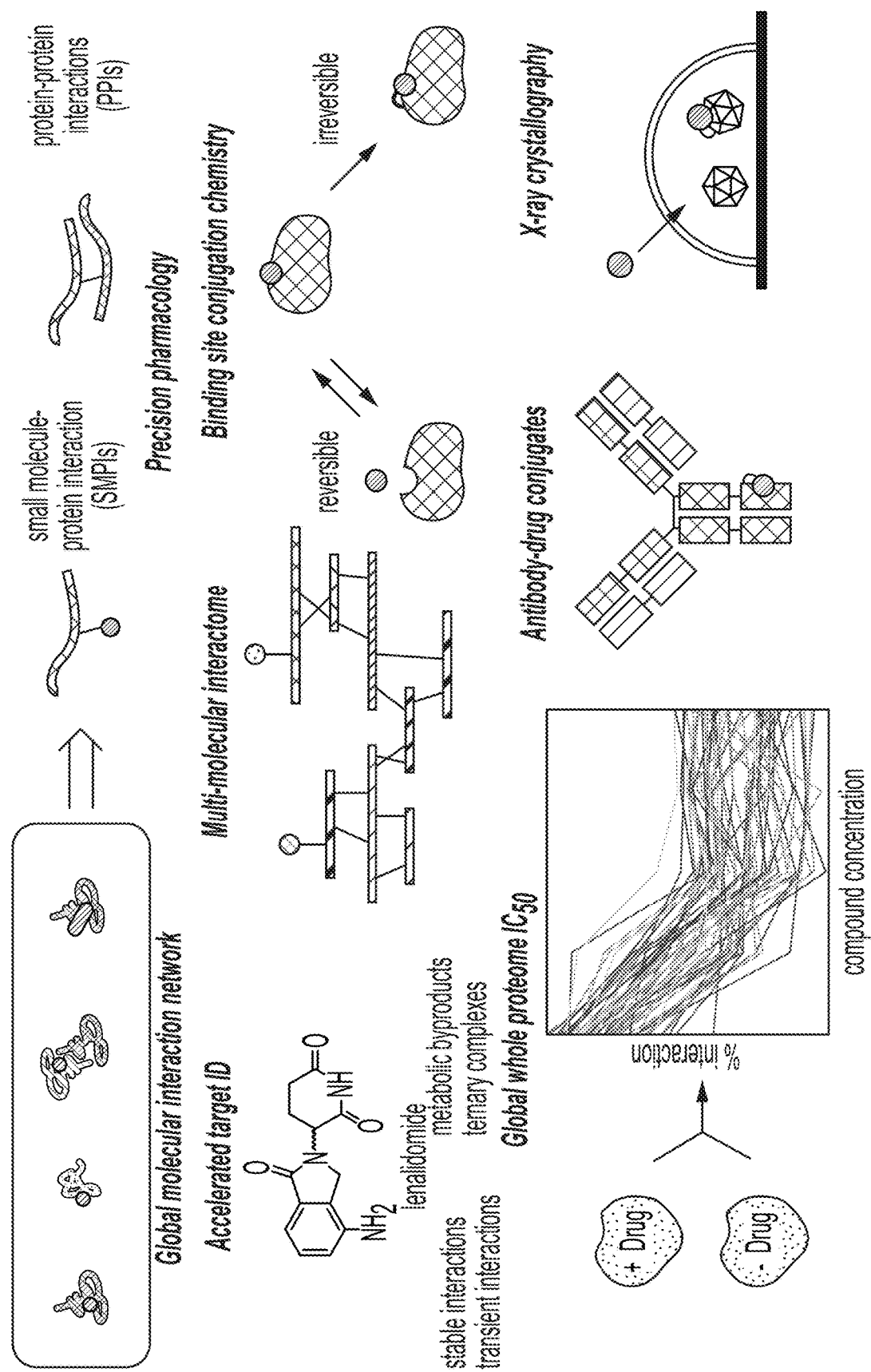
FIG. 11 shows potential, non-limiting applications of the SIM-PAL or MI-PAL technology. This technology can be used to discover and engineer molecular interactions (e.g., small molecule-protein interactions).

Any of the compounds presented herein can comprise one or more isotopically labeled atoms. In some embodiments, the isotopically labeled atom is $^{15}N$, $^{13}C$, $^{14}F$, or $^{2}H$. For example, as shown in FIG. 6A, nitrogen atoms labeled with astericks (*) indicate $^{15}N$ nitrogen atoms. Isotopic labeling of one or more atoms in the compound can facilitate identification of the compound through biophysical methods that are sensitive to isotopes, such as NMR. For example, NMR can be used to confirm the identity and structure of the appropriate photo-click tag or photo-click tagged compound product generated by the synthesis reaction (see, e.g., Examples 1 and 2). In addition, isotope-targeted mass spectrometry (MS) can be used to identify and assign the constitutive peptides of the target protein that are conjugated to the photo-click tagged compound (Example 1).

In another aspect, provided herein are amino acid analogs comprising the structure of Formula (II-a):

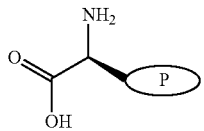
(II-a)

wherein
P is a photo-click tag comprising (a) a photo-conjugation moiety (M), and (b) a click chemistry handle.

In another aspect, provided herein are amino acid analogs comprising the structure of Formula (II-b):

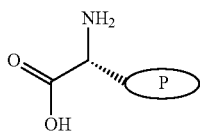
(II-b)

wherein
P is a photo-click tag comprising (a) a photo-conjugation moiety (M), and (b) a click chemistry handle.

In general, L-amino acids are incorporated into proteins in mammalian (e.g., human) cells. While L-amino acids represent all of the amino acids found in proteins during translation in the ribosome, D-amino acids are found in some proteins produced by enzyme posttranslational modifications after translation and translocation to the endoplasmic reticulum. Thus, in some embodiments, the amino acid analog comprises the structure of Formula (II-a). Alternatively, in some embodiments, the amino acid analog comprises the structure of Formula (II-b).

In some embodiments, the click chemistry handle is an alkyne. Thus, in some embodiments, P is

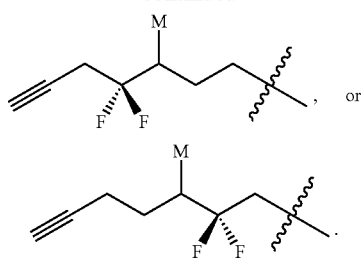

In some embodiments, the photo-conjugation moiety (M) is an aryl azide, azido-methyl-coumarin, benzophenone, anthraquinone, diazo compound, diazirine, or psoralen derivative. In some embodiments, the photo-conjugation moiety (M) is a diazirine moiety. In some embodiments, P comprises (a) a diazirine moiety, and (b) a click chemistry handle. In some embodiments, the click chemistry handle is an alkyne. In some embodiments, P comprises (a) a diazirine moiety, and (b) an alkyne.

In some embodiments. P is

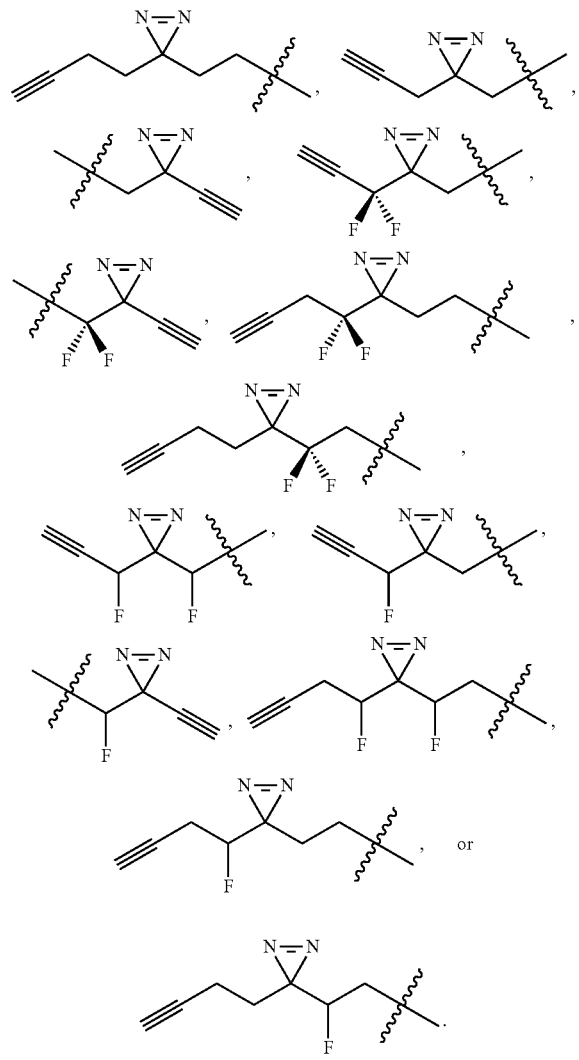

In some embodiments, P is

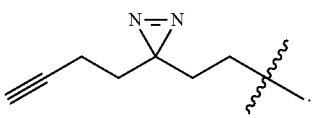 [SMILES: *CCC1(CCC#C)N=N1]

In some embodiments, P optionally comprises one or more electronegative atoms (e.g., fluorine).

In some embodiments, P is

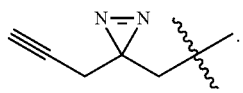 [SMILES: *CC1(CC#C)N=N1]

In some embodiments, P optionally comprises one or more electronegative atoms (e.g., fluorine).

In some embodiments, P is

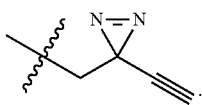 [SMILES: *CC1(C#C)N=N1]

In some embodiments, P optionally comprises one or more electronegative atoms (e.g., fluorine).

In some embodiments. P is

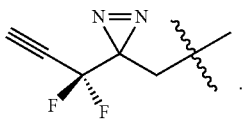

In some embodiments, the amino acid analog is of the formula:

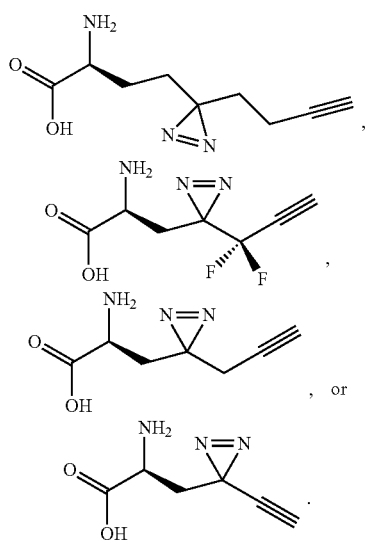

Also encompassed by the disclosure are kits. The kits provided may comprise a photo-click tag, a compound of Formula (I), or an amino acid analog of Formula (II-a) or (II-b), described herein; and a container (e.g., a vial, ampule, bottle, syringe, and/or dispenser package, or other suitable container). In some embodiments, the kit comprises a photo-click tag provided herein. In some embodiments, the kit comprises a compound of Formula (I) provided herein. In some embodiments, the kit comprises an amino acid analog of Formula (II-a) provided herein. In some embodiments, the kit comprises an amino acid analog of Formula (II-b) provided herein. In some embodiments, provided kits may optionally further include a second container comprising a pharmaceutical excipient for dilution or suspension of a photo-click tag or photo-tagged compound described herein. In certain embodiments, a kit described herein further includes instructions for using the kit. In certain embodiments, the kits and instructions provide for carrying out a method described herein.

Methods for Determining Small Molecule-Protein and Protein-Protein Interactions

As described above the photo-click tags and photo-click tagged compounds described herein are useful for mapping the direct and indirect effects of small molecules within the proteome. Some aspects of the present disclosure provide a small photo-click tag, wherein the photo-click tag is linked to a small molecule, that enables efficient capture, enrichment, and characterization of small molecule binding sites on a target protein or proteins. These methods can also be applied to determine the target protein of a small molecule, wherein the mechanism of action and/or the protein targeted by the small molecule is not known or well characterized. In addition, the methods and compositions provided herein are useful in determining a protein-protein interaction map, for example, in the presence of a small molecule to determine how the small molecule impacts cellular signaling and/or protein-protein interactions within a cell.

In one aspect, provided herein is a method for identifying the target protein of a small molecule. In some embodiments, the method comprises: (i) providing a compound comprising the small molecule connected to a photo-click tag via a linker, wherein the photo-click tag comprises (a) a photo-conjugation moiety and (b) a click chemistry handle; (ii) activating the photo-conjugation moiety by irradiating the compound of (i) with a specific wavelength of light; (iii) contacting the target protein with the activated compound of (ii); (iv) forming a complex through a photo-induced covalent bond between the activated compound of (ii) and the protein; and (v) identifying the complex produced in (iv) that is bound to the compound, thereby identifying the target protein of the small molecule. In some embodiments, the photo-conjugation moiety is a diazirine moiety. In some embodiments, the photo-click tag comprises (a) a diazirine moiety and (b) a click chemistry handle. In some embodiments, the click chemistry handle is an alkyne. In some embodiments, the photo-click tag comprises (a) a diazirine moiety and (b) an alkyne.

In another aspect, provided herein is a method for identifying the binding site of a small molecule to a protein. In some embodiments, the method comprises: (i) providing a compound comprising the small molecule connected to a photo-click tag via a linker, wherein the photo-click tag comprises (a) a photo-conjugation moiety, and (b) a click chemistry handle; (ii) activating the photo-conjugation moiety by irradiating the compound of (i) with a specific wavelength of light; (iii) contacting the protein with the activated compound of (ii); (iv) forming a complex through a photo-induced covalent bond between the activated compound of (ii) and the protein; (v) digesting the protein of the complex into constitutive peptides in the presence of a protease; and (vi) identifying the one or more peptides produced in (v) that are bound to the compound of (i), thereby identifying the protein binding site of the small molecule. In some embodiments, the photo-conjugation moiety is a diazirine moiety. In some embodiments, the photo-click tag comprises (a) a diazirine moiety, and (b) a click chemistry handle. In some embodiments, the click chemistry handle is an alkyne. In some embodiments, the photo-click tag comprises (a) a diazirine moiety, and (b) an alkyne.

In yet another aspect, provided herein is a method for identifying an interaction between a first protein and a second protein in a cell. In some embodiments, the method comprises: (i) providing a cell with an amino acid analog, wherein the amino acid analog comprises a photo-click probe comprising (a) a photo-conjugation moiety and (b) a click chemistry handle, and wherein the amino acid analog is incorporated into the first protein and/or the second protein during protein synthesis; (ii) activating the photo-conjugation moiety of the amino acid analog by irradiating the cell with a specific wavelength of light; (iii) contacting the first protein or the second protein with the activated compound of (ii); (iv) forming a protein-protein complex through a photo-induced covalent bond between the activated amino acid analog of the first protein and an amino acid in the second protein; and (v) identifying the complex produced in (ii) that comprises the amino acid analog covalently linking the first protein and the second protein, thereby identifying the first protein and the second protein involved in the interaction. In some embodiments, the photo-conjugation moiety is a diazirine moiety. In some embodiments, the photo-click tag comprises (a) a diazirine moiety and (b) a click chemistry handle. In some embodiments, the click chemistry handle is an alkyne. In some embodiments, the photo-click tag comprises (a) a diazirine moiety and (b) an alkyne. In some embodiments, the method further comprises digesting the protein-protein complex into constitutive peptides in the presence of a protease; and identifying a conjugated peptide that comprises a peptide comprising the amino acid analog covalently linking a peptide of the first protein to a peptide of the second protein. In some embodiments, the method further comprises contacting the cell with a small molecule, wherein the cell is contacted with the small molecule before the activating of step (ii). In some embodiments, the first protein and the second protein identified in the presence of the small molecule are compared to the first protein and the second protein identified in the absence of the small molecule. In some embodiments, a difference in the first protein and the second protein in the presence of the small molecule compared to the first protein and the second protein in the absence of the small molecule indicates modulation of a protein-protein interaction in the cell in the presence of a small molecule. In some embodiments, the first protein or the second protein is enriched in the presence of a small molecule. In some embodiments, the enrichment is at least 2-fold, at least 3-fold, at least 4-fold, or at least 5-fold compared to the amount of the first protein or the second protein in the absence of the small molecule. In some embodiments, the small molecule is an antibiotic, an anti-proliferative agent, an anti-cancer agent, a chemotherapeutic agent, an anti-angiogenesis agent, an anti-inflammatory agent, an immunosuppressant, an immunomodulatory agent, an anti-bacterial agent, an anti-viral agent, a cardiovascular agent, a cholesterol-lowering agent, an anti-diabetic agent, an anti-allergic agent, a contraceptive agent, or a pain-relieving agent. In some embodiments, the small molecule is an anti-inflammatory agent, an immunomodulatory drug, a chemotherapeutic agent, or a derivative thereof. In some embodiments, the small molecule is an anti-inflammatory agent, or derivative thereof. In some embodiments, the small molecule is an immunomodulatory drug, or derivative thereof. In some embodiments, the small molecule is a chemotherapeutic agent, or derivative thereof. In some embodiments, the small molecule is a steroid, or derivative thereof.

In some embodiments, the diazirine moiety forms a reactive carbene species upon irradiation with a specific wavelength of light. In some embodiments, the reactive carbene species reacts with a C—C, C—H, N—H, or O—H bond of a protein. Upon insertion of the reactive carbene species into a C—C, C—H, N—H, or O—H bond of a protein, a new photo-induced covalent bond between the protein and photo-click tag is formed, thereby linking the compound comprising the photo-click tag to the protein to generate a complex. In some embodiments, the specific wavelength of light is between about 10 nm and about 400 nm. In some embodiments, the specific wavelength of light is between about 355 nm and about 365 nm. In some embodiments, the specific wavelength of light is about 355 nm. In some embodiments, the specific wavelength of light is about 365 nm.

In some embodiments, the photo-click tag of (i) is of the formula:

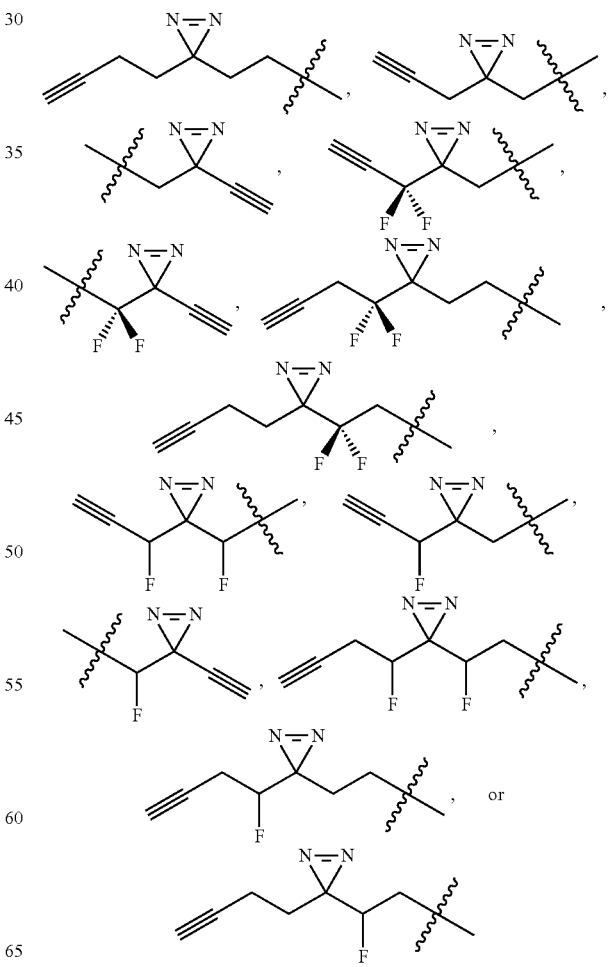

before irradiation with light. In some embodiments, the diazirine moiety

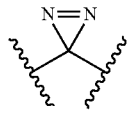

forms the reactive carbene species

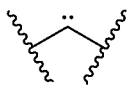

upon irradiation with light. In some embodiments, the photo-click tag of (ii) comprising the activated diazirine moiety is of the formula:

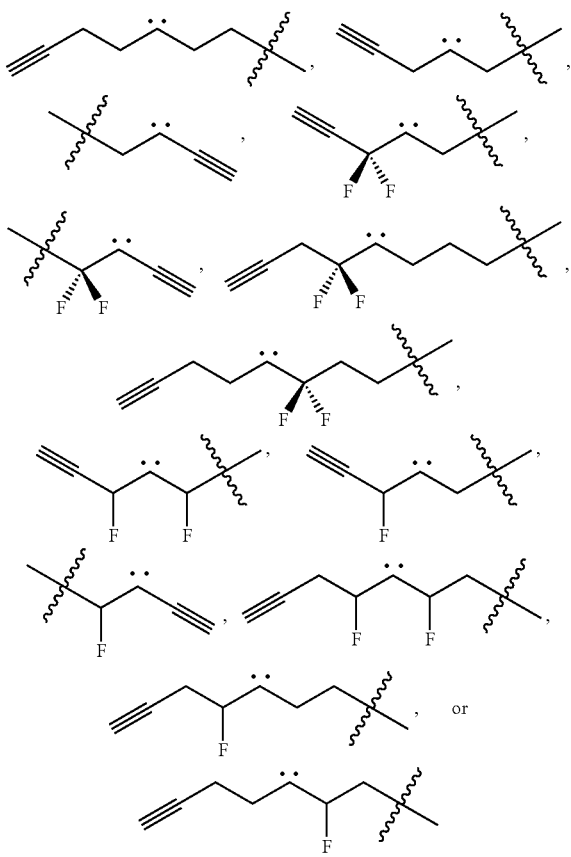

after irradiation with light. In some embodiments, the photo-click tag of (i) is of the formula

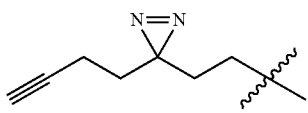 [SMILES: *CCC1(CCC#C)N=N1]

before irradiation with light, and is of the formula

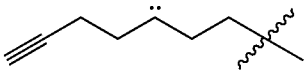

after irradiation with light. In some embodiments, the photo-click tag of (i) is of the formula

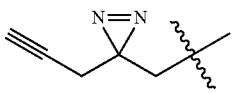 [SMILES: *CC1(CC#C)N=N1]

before irradiation with light, and is of the formula

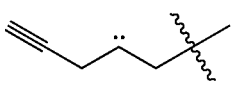

after irradiation with light. In some embodiments, the photo-click tag of (i) is of the formula

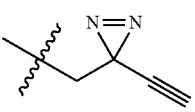 [SMILES: *CC1(C#C)N=N1]

before irradiation with light, and is of the formula

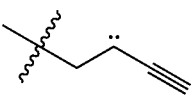

after irradiation with light. In some embodiments, the photo-click tag of (i) is of the formula

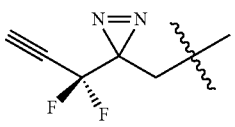

before irradiation with light, and is of the formula

after irradiation with light. In some embodiments, the photo-click tag of (i) is of the formula

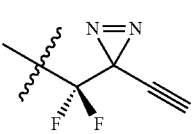

before irradiation with light, and is of the formula

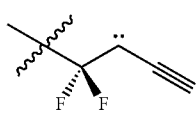

after irradiation with light. In some embodiments, the photoclick tag of (i) is of the formula

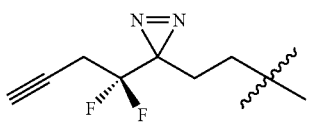

before irradiation with light, and is of the formula

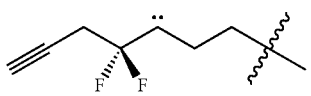

after irradiation with light. In some embodiments, the photoclick tag of (i) is of the formula

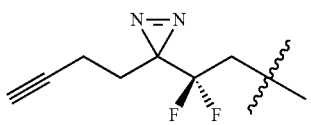

before irradiation with light, and is of the formula

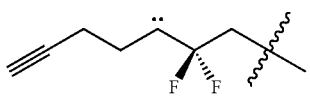

after irradiation with light. In some embodiments, the photoclick tag of (i) is of the formula

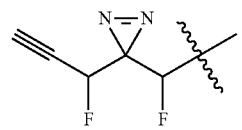 [SMILES: *C(F)C1(C(F)C#C)N=N1]

before irradiation with light, and is of the formula

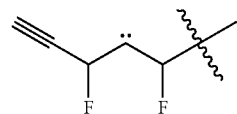

after irradiation with light. In some embodiments, the photoclick tag of (i) is of the formula

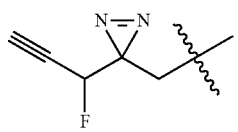 [SMILES: *CC1(C(F)C#C)N=N1]

before irradiation with light, and is of the formula

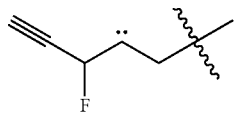

after irradiation with light. In some embodiments, the photoclick tag of (i) is of the formula

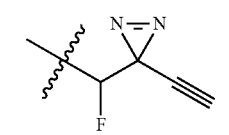 [SMILES: *C(F)C1(C#C)N=N1]

before irradiation with light, and is of the formula

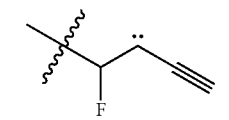

after irradiation with light. In some embodiments, the photoclick tag of (i) is of the formula

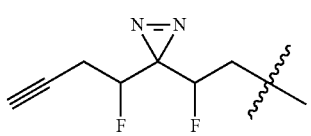 [SMILES: *CC(F)C1(C(F)CC#C)N=N1]

before irradiation with light, and is of the formula

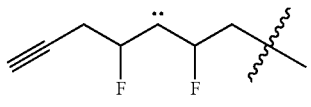

after irradiation with light. In some embodiments, the photoclick tag of (i) is of the formula

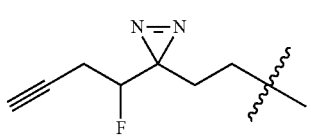 [SMILES: *CCC1(C(F)CC#C)N=N1]

before irradiation with light, and is of the formula

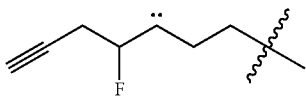

after irradiation with light. In some embodiments, the photo-click tag of (i) is of the formula

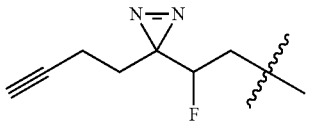 [SMILES: *CC(F)C1(CCC#C)N=N1]

before irradiation with light, and is of the formula

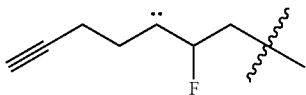

after irradiation with light. In some embodiments, the light has a wavelength between about 10 nm and about 400 nm. In some embodiments, the light has a wavelength between about 355 nm and about 365 nm. In some embodiments, the light has a wavelength of about 355 nm. In some embodiments, the light has a wavelength of about 365 nm.

Some embodiments of the method comprise contacting the protein conjugated to the compound comprising the small molecule and photo-click tag or the protein-protein complex formed in the presence of an amino acid analog with a protease to digest the proteins into constitutive peptides. Without wishing to be bound by any particular theory, protease digestion is a step often employed before analysis and identification of the protein using mass spectrometry (MS). Digestion of the protein into constitutive peptides allows for MS analysis of individual peptides, which can allow for the identification of peptides bound to photo-click tag and thus the small molecule or protein partner (i.e., protein-protein interaction partner) of interest. This method is also used, for example, to identify protein post-translational modifications. See, e.g., Gundry R L, et al. (2009) Preparation of Proteins and Peptides for Mass Spectrometry Analysis in a Bottom-Up Proteomics Workflow. Curr Protoc Mol Biol, doi:10.1002/0471142727.mb1025s88; which is incorporated by reference herein. In some embodiments, the protease is a serine protease, cysteine protease, threonine protease, aspartic protease, glutamic protease, metalloprotease, or an asparagine peptide lyase. In some embodiments, the protease is a serine protease. In some embodiments, the serine protease is trypsin. In some embodiments, the serine protease is chymotrypsin. In some embodiments, the protease is an aspartic protease. In some embodiments, the aspartic protease is pepsin. In some embodiments, one protease maybe used to digest a protein. In some embodiments, more than one protease maybe used to digest a protein. In some embodiments, the digesting of step (v) is performed under conditions suitable for the protease to catalyze the cleavage of peptide bonds in the protein. Upon cleavage with a protease, the protein, which is covalently bound to the photo-tagged compound, is digested into constitutive peptides based on the specificity of the chosen protease or combination of proteases, thus providing a plurality of peptides comprising peptides that are covalently bound to the photo-tagged compound (i.e., conjugated peptides) and native peptides (i.e., peptides that are not covalently bound to the photo-tagged compound).

In some embodiments, the step of identifying comprises performing mass spectrometry to identify the protein that is bound to the compound. Mass spectrometry (MS) has been used for the identification of protein-ligand interactions, see, for example, Sinz A. (2007) Investigation of Protein-Ligand Interactions by Mass Spectrometry. Chem Med Chem, 2, 425-431. In particular, peptide mixtures are generally separated before introduction into the mass spectrometer, such as through liquid chromatography (LC) or capillary electrophoresis (CE). In some embodiments, the mass spectrometry used in the step of identifying is intact mass spectrometry. Intact mass spectrometry may also be referred to as "native mass spectrometry", as this MS method generally involves preservation of the native protein or complex shape and structure. See, e.g., Doerr A. (2012) Mass spectrometry of intact protein complexes. Nature Methods, 10, doi:10.1038/nmeth.2298.

In some embodiments, when the method involves a digesting step, the identifying step comprises performing mass spectrometry to identify the peptides that are bound to the compound. In some embodiments, the mass spectrometry used in the identifying step is mass-independent mass spectrometry (MS). Without wishing to be bound by any particular theory, mass-independent MS generally involves the mass-independent assignment of peptides, which uses a pattern-searching algorithm to direct tandem MS analysis to isotopically labeled species (e.g., a compound comprising one or more isotopically labeled atoms). See, e.g., Woo C M, et al. (2015) Isotope-targeted glycoproteomics (IsoTaG): a mass-independent platform for intact N- and O-glycopeptide discovery and analysis. Nat Methods, 12(6), 561-567. Mass-independent MS can overcome traditional MS barriers in detection of low abundance species by enhancing the detection of the species of interest (e.g., the isotopically labeled species) even in a background of unmodified species (e.g., unmodified peptides that do not comprise an isotopically labeled atoms). Mass-independent mass spectrometry may also be referred to interchangeable as isotope-targeted mass spectrometry.

In some embodiments, the identification of the peptide or protein species of interest (e.g., the peptide or protein conjugated to the photo-click tagged compound) can be enhanced by performing an enrichment step before the identifying step to increase the abundance (i.e., enrich) the conjugate (e.g., the protein conjugated to the photo-click tagged compound, the peptide conjugated to the photo-click tagged compound, the protein-protein complex conjugated by the amino acid analog, or a peptide of the first protein conjugated to a peptide of the second protein by the amino acid analog) present in the sample for analysis. Thus, in some embodiments, the method further comprises a step of enriching the conjugate formed when the photo-activated compound covalently binds to a protein. In some embodiments, the step of enriching is performed before the digesting step. In some embodiments, the step of enriching is performed after the digesting step. In some embodiments, the step of enriching is performed without digesting the protein before or after the enriching step. In some embodiments, the step of enriching comprises covalently attaching a label to the click chemistry handle of the photo-click tag. In some embodiments, the label comprises a click chemistry handle that can be conjugated (i.e., "clicked") to the click chemistry handle of the photo-click tag. In some embodiments, the label comprises an azide (N) moiety. In some embodiments, the label is covalently attached to the click chemistry handle of the photo-click tag using copper(i)-catalyzed azide-alkyne cycloaddition (CuAAC) reaction conditions. The CuAAC is a click chemistry reaction that involves the copper-catalyzed reaction of an azide with an alkyne to form a 5-membered heteroatom ring. An exemplary scheme outlining a CuAAC reaction is shown below in Scheme III.

Scheme III

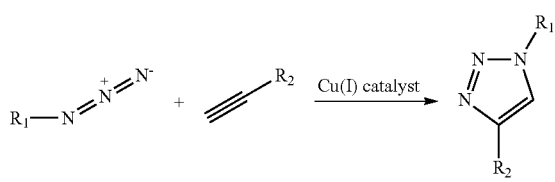

While a CuAAC reaction requires an alkyne and an azide, a person of ordinary skill in the art is capable of determining appropriate reaction conditions for attaching a label to a click chemistry handle, wherein the label and the click chemistry handle do not comprise an azide or an alkene. See, e.g., Hein, C D et al (2008) Click Chemistry, a Powerful Tool for Pharmaceutical Sciences. *Pharm Res*, 25, 2216-2230, which is incorporated by reference herein.

In some embodiments, the label comprises an affinity tag. An affinity tag can be used to efficiently separate the protein or peptides covalently linked to the photo-click tagged compound (i.e., conjugated protein or conjugated peptides) from native proteins or peptides (i.e., proteins or peptides that are not covalently linked to the photo-click tagged compound). The term "affinity tag" refers to any moiety that can be used to separate a species of interest (e.g., a protein or peptide) from a complex mixture. Exemplary affinity tags include, but are not limited to, peptide tags (e.g., AviTag (GLNDIFEAQKIEWHE), Calmodulin-tag (KRRWKKN-FIAVSAANRFKKISSSGAL), polyglutamate tag (EE-EEEE), E-tag (GAPVPYPDPLEPR) FLAG-tag (DYKDDDDK), HA-tag (YPYDVPDYA), His-tag (5-10 histidines, e.g., HHHHHH), Myc-tag (EQKLISEEDL), NE-tag (TKENPRSNQEESYDDNES), S-tag (KETAAAKFER-QHMDS), SBP-tag (MDEKTTGWRGGHVVEG-LAGELEQLRARLEHHPQGQREP), Softag 1 (SLAELLNAGLGGS), Softag 3 (TQDPSRVG), Strep-tag (Strep-tag II: WSHPQFEK), TC tag (CCPGCC), Ty tag (EVHTNQDPLD), V5 tag (GKPIPNPLLGLDST), VSV-tag (YTDIEMNRLGK), Xpress tag (DLYDDDDK), and derivatives thereof, covalent peptide tags (e.g., Isopeptag (TDKDMTITFTNKKDAE), SpyTag (AHIVMV-DAYKPTK), SnoopTag (KLGDIEFIKVNK), SnoopTagJr (KLGSIEFIKVNK), DogTag (DIPATYEFTDGKHYIT-NEPIPPK), and derivatives thereof), protein tags (e.g., BCCP (Biotin Carboxyl Carrier Protein), Glutathione-S-transferase-tag, Green fluorescent protein-tag, HaloTag. Maltose binding protein-tag, Nus-tag, Thioredoxin-tag, Fc-tag, Designed Intrinsically Disordered tags, chitin binding protein (CBP), thioredoxin (TRX), and derivatives thereof), biotin, avidin (e.g., streptavidin), carbohydrates (e.g., lectins), and glutathione. Affinity tags are often added to a species of interest (e.g., a protein or peptide) to facilitate separation, for example, using affinity chromatography, by taking advantage of the specific interaction between two moieties (e.g., antigen and antibody, enzyme and substrate, receptor and ligand, or protein and nucleic acid). In some embodiments, the affinity tag is biotin. In some embodiments, the label is of the formula:

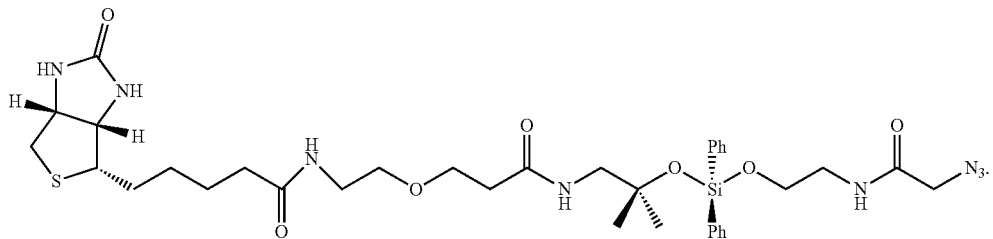

In some embodiments, the method further comprises separating the protein or peptides covalently linked to the photo-click tagged compound, wherein the photo-click tagged compound is covalently attached to the label. In some embodiments, when the label comprises biotin, the conjugated protein or conjugated peptide can be separated from native proteins or peptides by streptavidin-coupled beads. Once the conjugated protein or conjugated peptide is captured by the interaction between the biotin of the label and the streptavidin of the beads and separated from the native proteins or peptides, the conjugated protein or conjugated peptide can be cleaved from the beads, for example, using acidic cleavage conditions, thereby releasing the conjugated protein or conjugated peptide and generating an enriched sample for identification of the protein or peptide covalently bound to the photo-click tag. Additional suitable label/derivative-bead combinations will be apparent to those of skill in the art based on this disclosure and knowledge in the field, and are within the scope of this disclosure.

In some embodiments, the protein is present in a whole proteome. In some embodiments, the protein is present in vitro. For example, the methods can be performed on a sample consisting essentially of the protein of interest (e.g., the protein that binds to a small molecule of interest), such as in a purified protein sample. The methods can also be performed on a sample comprising a mixture of proteins in a sample (e.g., a cell lysate). In some embodiments, the protein is present in a cell lysate. In some embodiments, the protein is present in vivo. In some embodiments, the protein is present in a cell. In some embodiments, the cell is a mammalian (e.g., human) cell. In some embodiments, the cell is a human cell. In some embodiments, the cell is a human cell derived from a subject with a disease (e.g., cancer).

EXAMPLES

In order that the invention described herein may be more fully understood, the following examples are set forth. The examples described in this application are offered to illustrate the methods, compositions, and systems provided herein and are not to be construed in any way as limiting their scope.

Example 1-Small Molecule Interactome Mapping by Photo-Affinity Labeling (SIM-PAL) Reveals Binding Site Hotspots for the NSAIDs Many therapeutics elicit cell-type specific polypharmacology that may increase therapeutic efficacy or yield off target toxicity. However, direct observation of the structures that underpin the global molecular associations between the proteome and even common therapeutics, such as the nonsteroidal anti-inflammatory drugs (NSAIDs), remain little understood. Presented here is a platform termed small molecule interactome mapping by photo-affinity labeling (SIM-PAL) and apply it to the in vivo characterization of the NSAID interactome to yield identification of specific binding sites. SIM-PAL uses (1) photochemical conjugation of NSAID derivatives in the whole proteome and (2) enrichment of the conjugated peptides for (3) targeted mass spectrometry-based assignment. Using SIM-PAL, the NSAID interactome consisting of over 1000 enriched proteins was identified and nearly 200 conjugated peptides representing direct binding interactions in Jurkat and K562 cells were directly characterized. The enriched proteins were often identified as parts of complexes, including known targets of NSAID activity (e.g., NF-κB) and novel interactions (e.g., AP-1, proteasome). These data further revealed a binding site hotspot on histones H2A and H2B where the three photo-NSAIDs, but not fragment-based small molecules, interacted. The binding interaction of the NSAIDs stabilized COX-2 and histone H2A by cellular thermal shift assay. Since protein-protein stabilization is a gain of function regulatory mechanism, it is conceivable that NSAIDs affect biological processes through these broader proteomic interactions. SIM-PAL enabled characterization of NSAID binding site hotspots and is amenable to map global binding sites for virtually any molecule of interest.

Introduction

Polypharmacology, wherein one drug interacts with multiple protein targets, is a common phenomenon in drug discovery. Polypharmacology manifests in increased efficacy when properly exploited or tragic unanticipated off-target effects when not fully understood. Many pharmaceuticals in diverse therapeutic areas possess either known or uncharacterized polypharmacology,[1] such as the nonsteroidal anti-inflammatory drugs (NSAIDs),[2] the immunomodulatory drugs.[3] or the opioids.[4] Proteomic differences across cell types are the basis for molecular interactions that culminate in an observed phenotype,[5] suggesting that with a map of the protein-ligand interaction network throughout the whole proteome, these polypharmacology outcomes may eventually be predicted.[6,7]

A method to directly map the small molecule interactome has the potential to accelerate drug discovery by providing structural insight and instant validation of the binding interaction, yet such global characterization is rarely performed. Common analytical methods to structurally reveal small molecule binding sites, such as X-ray crystallography or NMR spectroscopy, are constrained to the measurement of stable interactions between a single compatible protein and small molecule pair in vitro. Global proteomic profiles are now commonly obtained using mass spectrometry (MS), and with a small molecule affinity purification strategy can be used to identify binding proteins.[8] However, the vast majority of proteomics studies stop short of obtaining direct structural evidence for the molecular interaction, due to inherent challenges in mapping the binding sites of a small molecule on the whole proteome. Small molecule interactions occur over a range of concentrations that require a general mechanism for capture and enrichment prior to MS analysis. The chemistry selected to capture the binding event must be rapid and general for unbiased covalent bond formation at the small molecule binding site. Yet, the demand for a general chemical strategy to covalently conjugate a small molecule locally to the protein interaction site poses great challenges to spectral assignment by database searching. Database searching methods are not adapted to the computational complexity yielded by amino acid residue-agnostic modifications to the whole proteome. Without the complexity of the whole proteome, binding sites of small molecules to defined protein isolates can be determined by application of photo-affinity labeling (PAL) to conjugate the small molecule to the protein prior to MS analysis.[9]

Translation of MS-based binding site identification from a single protein to the whole proteome thus requires (1) a selective chemical workflow to isolate the conjugated peptide and (2) a targeted MS technique for confident characterization. PAL covalently conjugates small molecules to the proteome for stringent enrichment of interacting proteins.[10] Application of cleavable enrichment handles enables recovery of the small molecule-conjugated peptide.9 Critically, a targeted MS strategy, wherein unique isotopic markers are installed specifically to the small molecule conjugated peptide, provides an orthogonal handle for detection and validation that proves transformative during database assignment of peptides carrying heterogeneous modifications by MS.[11] Recent strides have enabled the identification of fragment-based small molecule ligands to the whole proteome.[12]

The knowledge gap caused by the lack of a small molecule interactome map extends to common pharmaceuticals like the nonsteroidal anti-inflammatory drugs (NSAIDs). The NSAIDs are potently suppress inflammation, pain, and fever and have been further explored as potential treatments for cancer[2,13] and Alzheimer's disease.[14] NSAID mechanisms have been primarily characterized through inhibition of the enzymes cyclooxygenase-1 and -2 (COX-1, COX-2, respectively).[15] Inhibition of COX-2, the primary cyclooxygenase involved in inflammation, prevents the production of prostaglandins, thereby reducing inflammation. However, a wealth of biomedical evidence points to broader COX-2-independent mechanisms of NSAIDs involved in anti-cancer activity for which a molecular basis remains poorly defined.[16-18] Prior studies suggest that specific NSAIDs inhibit the nuclear factor-κB (NF-κB) pathway[19] and caspases.[20] A detailed understanding of broader NSAID mechanisms is constrained by the absence of a global understanding of NSAID-protein interactions and their underlying structures.

Figure 12A:
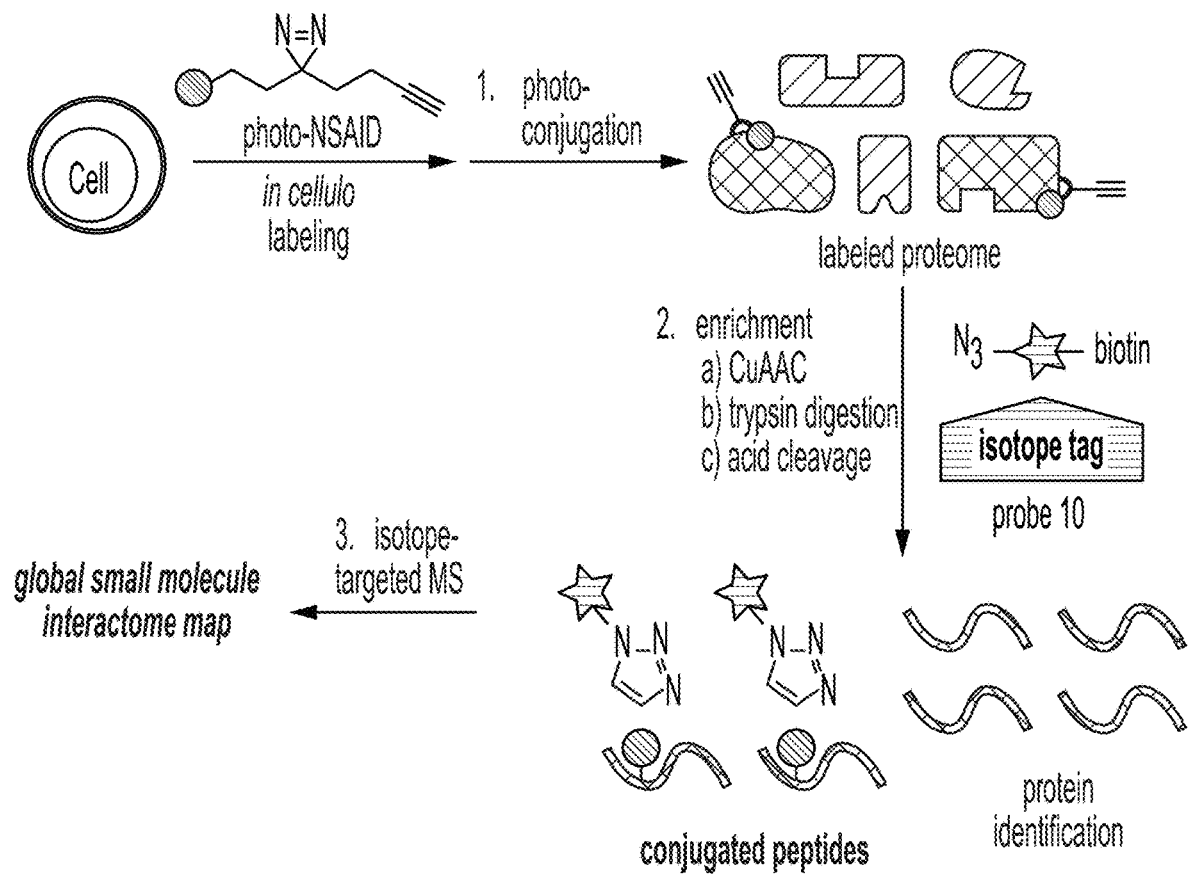
FIGS. 12A-12C show a general strategy to profile the NSAID interactome using SIM-PAL.

Herein, the development of a platform termed small molecule interactome mapping by photo-affinity labeling (SIM-PAL) and its application to the NSAIDs is reported. SIM-PAL is designed to directly characterize the protein interactions and binding site hotspots of a small molecule in a whole cell proteome using a PAL-based enrichment strategy coupled to isotope-targeted MS (FIG. 12A). Our platform involves: (1) photo-conjugation of NSAID derivatives in cells, (2) enrichment and isotopic recoding of NSAID-labeled peptides, and (3) isotope-targeted assignment of the conjugated peptides. Photo-NSAID derivatives are effective reporters of NSAID binding sites with recombinant COX-2 and the global whole cell proteome, as shown herein. Photo-NSAIDs displayed overlapping protein interactions in Jurkat and K562 cell lines. By virtue of direct characterization of the conjugated peptide, we localized the photo-NSAIDs to a specific binding hotspot on the interface of histones H2A and H2B. Histone H2A was stabilized by interacting with the NSAIDs by cellular thermal shift assay. SIM-PAL revealed the precise binding interactions for the photo-NSAIDs via an approach that is readily translated to broad classes of small molecules.

Results

Development of Photo-NSAIDs as Reporters of NSAID Binding Sites

Figure 12B:
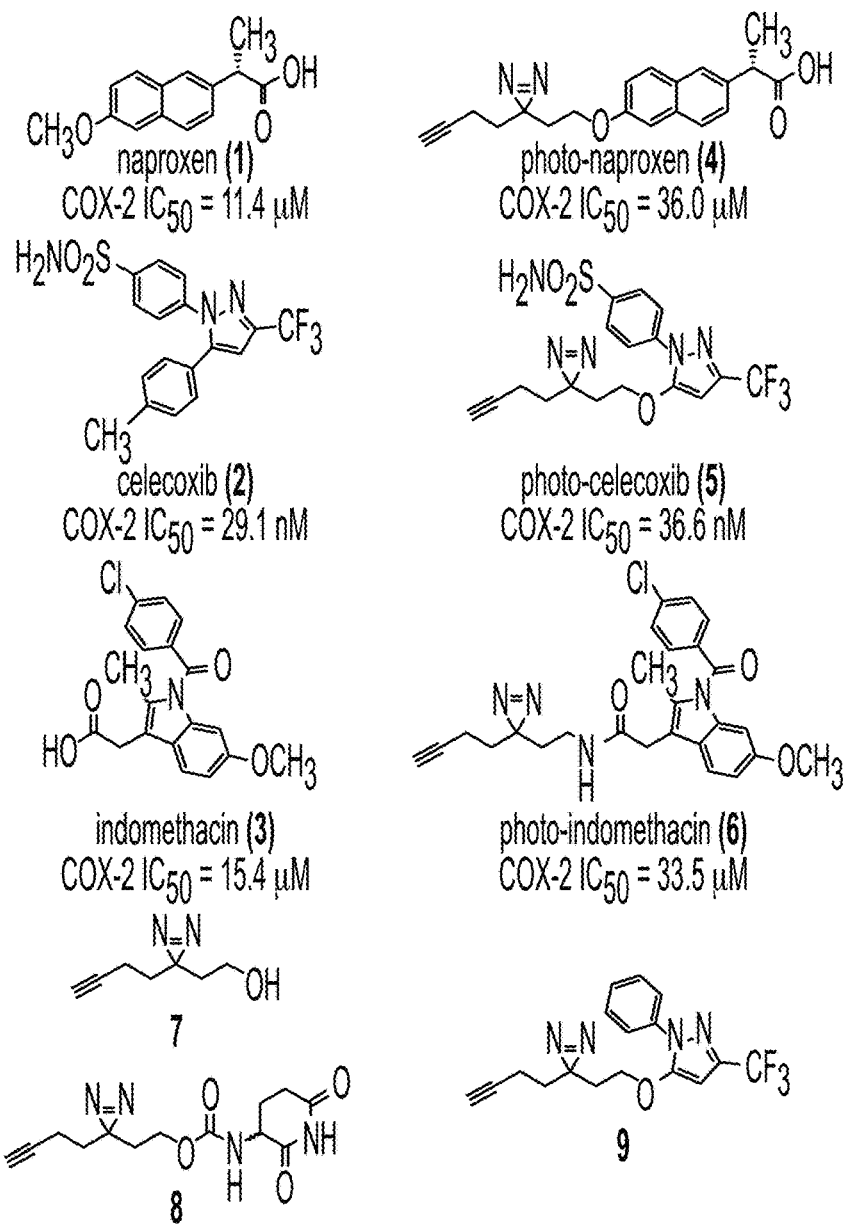
Figure 12C:
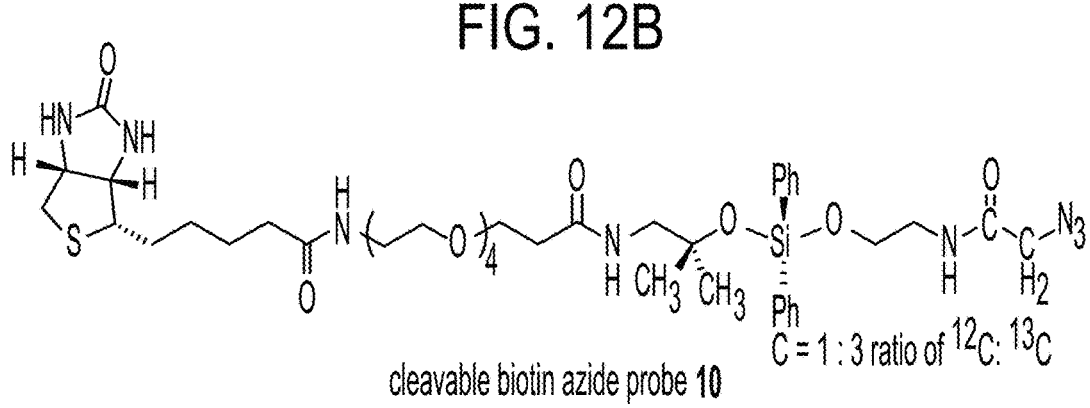

Three NSAIDs, naproxen (1), celecoxib (2), and indomethacin (3), were conjugated to diazirine-based photo-affinity labels ("photo-NSAIDs") to serve as reporters for NSAID binding sites (FIG. 12B). These NSAIDs were selected for their different structure-activity relationship (SAR) between COX-1 and COX-2.[21,22] Naproxen (1) is a nonselective COX-1 and COX-2 inhibitor, but is commonly employed for chronic use due to low rates of gastrointestinal side effects.[23] Celecoxib (2) is a selective COX-2 inhibitor developed by Pfizer, yet possesses off-target cardiovascular and gastrointestinal complications.[24] Indomethacin (3) is a member of the indole class of NSAIDs and possesses known COX-2-independent anti-inflammatory mechanisms.[16] The design of photo-NSAIDs were based upon previous SAR studies[25,26] and the crystal structure between mouse COX-2 and indomethacin (3).[27] During our studies, a crystal structure of a NSAID with human COX-2 was reported.[28] In addition to photo-NSAIDs 4-6, the tag 7,[29] a structurally orthogonal photoglutarimide 8, and a celecoxib analog 9, was developed to assess selectivity of the binding site identification assay (FIG. 26).

Figure 13A:
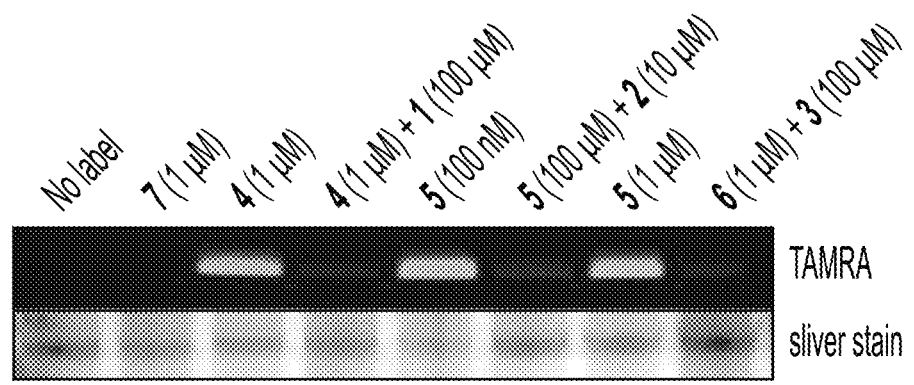
FIGS. 13A-13E show a comparative analysis of NSAIDs and photo-NSAIDs with recombinant COX-2.

All three photo-NSAIDs maintained COX-2 inhibition by ELISA (FIG. 12B, FIGS. 16A-16D), although some variation in activity was observed. Photo-celecoxib (5) was the most potent ($IC_{50}$=36.6 nM) and photo-naproxen (4) was the least potent ($IC_{50}$=36.0 µM). All photo-NSAIDs possessed antiproliferative properties within 1.3-1.4-fold of their parent compound in Jurkat cells (FIGS. 17A-17D). Elimination of the sulfonamide from celecoxib (2) to give the analog 9 is known to reduce COX-2 inhibition[26] and we found additionally attenuated anti-proliferative activity of the analog 9 in activated Jurkat cells (FIGS. 17A-17D). Furthermore, all photo-NSAIDs were competitively displaced from recombinant COX-2 by the native NSAID (FIG. 13A). COX-2 was separately incubated with each of the photo-NSAIDs with or without a 100-fold excess of the parent compound as a competitor.[10] The samples were photo-irradiated, tagged with the fluorophore TAMRA-azide by copper-mediated azide alkyne cycloaddition (CuAAC), or click chemistry, and fluorescently visualized to reveal selective and reversible binding of COX-2 to the photo-NSAIDs. The tag 7 did not produce observable conjugation to COX-2 by fluorescence.

Photo-NSAIDs Possess Known and Transient Binding Sites with COX-2

Recombinant COX-2 was used to validate fragmentation patterns of conjugated NSAIDs to a protein and determine binding site selectivity for each of the photo-NSAIDs. Small molecule modification on a peptide may perturb MS fragmentation pathways in unexpected ways, rendering the spectra unable to be assigned by database searching. To evaluate this possibility, photo-NSAIDs (10 µM) were incubated with recombinant COX-2 for 30 minutes and photo-irradiated. The irradiated samples were appended to the cleavable biotin azide probe 10 to simulate the conjugated species ultimately observed after enrichment (FIG. 12O. The probe 10 is a multifunctional probe developed to possess a biotin affinity enrichment handle, an acid-labile diphenylsilane, and a stable isotope-coded azidoacetate for click chemistry and isotope-targeted MS. We previously established the compatibility of a similar cleavable probe scaffold in targeted MS experiments.[11] Following click chemistry, the samples were trypsin-digested and the probe was cleaved in situ (2% formic acid). The resulting peptides were analyzed by LC-MS/MS. MS data was searched by SEQUEST and Byonic against recombinant COX-2 with the photo-NSAID as a modification on any amino acid (Table 2). Due to the nature of photochemical conjugation, a binding site will be represented by multiple conjugated peptide structures and potentially multiple surrounding peptides in the MS data. All peptide spectral matches (PSMs) assigned to a conjugated peptide were manually validated.

Photo-NSAIDs were readily assigned by database searching. Manual inspection of these PSMs indicated that in the case the photo-NSAIDs 4-6, no irregular fragmentation pathways were observed. As expected, at a consistent dose of 10 µM across all photo-NSAIDs, photo-celecoxib (5) possessed the highest number of observed conjugated peptides (seven conjugated peptides from 14 PSMs), including within the active site of COX-2. Analysis of COX-2 treated by photonaproxen (4) and photo-indomethacin (6) revealed six conjugated peptides across 19 PSMs and eight PSMs, respectively (Table 2). By contrast, the tag 7 was found conjugated to one peptide, which was not marked by the photo-NSAIDs. Within each peptide, the specific conjugation site localized to a range of 2-4 amino acid residues that reflect the specificity of the photochemical conjugation event.

Figure 13B:
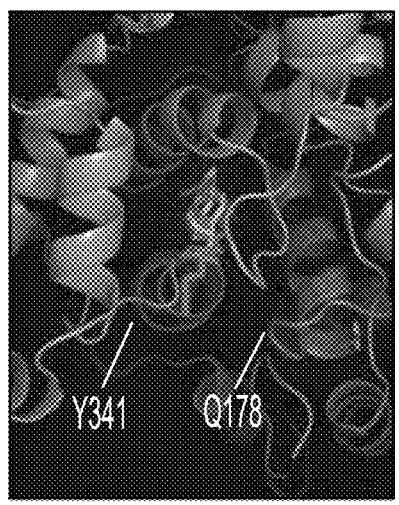
Figure 13C:
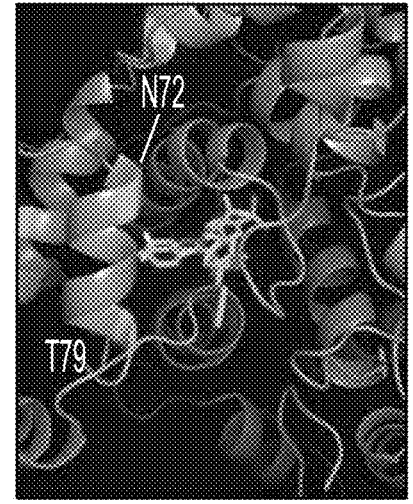
Figure 13D:
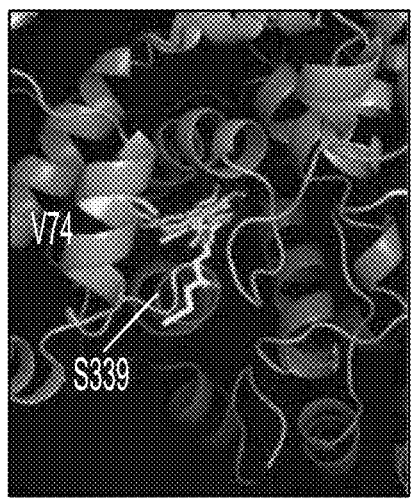
Figure 13E:
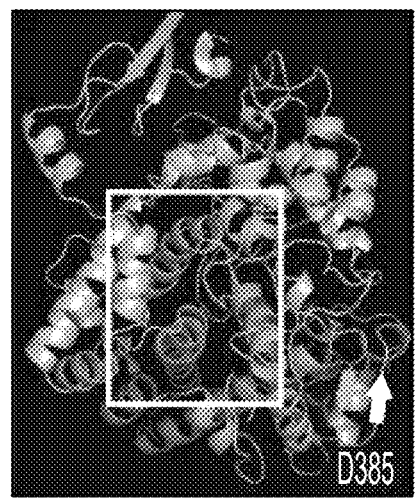

The photo-NSAIDs, the parent compounds, and the tag 7 were structurally minimized [Gaussian 16, basis set: HF 3-21g(d)] and individually docked in the crystal structure of human COX-2 (PDB: 5KIR).[28] Docking was performed using Patchdock, a molecular docking algorithm based on shape complementarity using rigid structures.[30] Structures with the lowest desolvation energy or highest interface area size docked the photo-NSAID or parent compound to the same interaction site, although the orientations within each pair of compounds differed (FIGS. 13B-13D). The docked structure of photo-naproxen (4, red), photo-celecoxib (5, green), and photo-indomethacin (6, yellow) overlaid with their respective parent compound (blue). Conjugated amino acid residues within 5 Å of the docked photo-NSAID are highlighted in FIGS. 13B-13D. The orientation of each of the photo-NSAIDs positioned the diazirine in close proximity to one or two specific amino acids on a conjugated peptide observed by MS. Other marked residues were located on solvent exposed areas of the protein. As photo-chemistry captures dynamic processes and the photochemical tag is structurally flexible, the additional conjugation events on recombinant COX-2 may represent transient interactions with COX-2 in vitro, which may not be observed in cellulo. The tag 7 was additionally docked and, in combination with the observed MS data, was shown to transiently bind to an orthogonal region of COX-2 (FIG. 13E). No conjugated peptides from amino acids near to the canonical binding site were observed.

Characterization of the NSAID Interactome in Jurkat and K562 Cells

Figure 19:
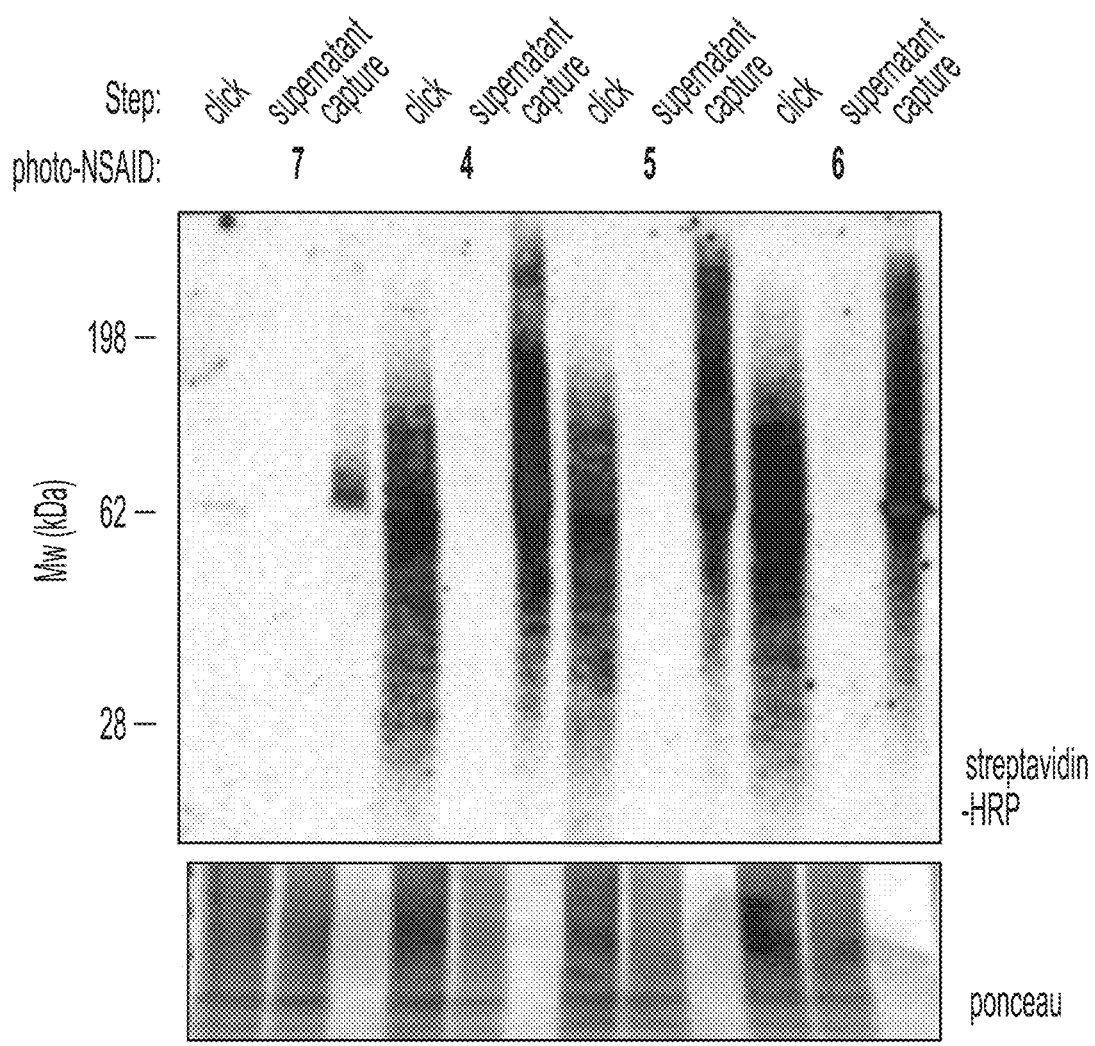
FIG. 19 shows an anti-biotin Western blot for enriched small molecule conjugated proteins from Jurkat cells. Jurkat cells were treated with a photo-NSAID or the tag 7, photo-irradiated and clicked with the cleavable biotin azide probe 10 (click). Biotinylated proteins were enriched on streptavidin-agarose beads, and the beads were washed (1% RapiGest, 6M urea, PBS). The biotin-depleted whole proteome (supernatant) and the beads (capture) were analyzed by gel. Ponceau S staining shows protein loading.
Figure 20A:
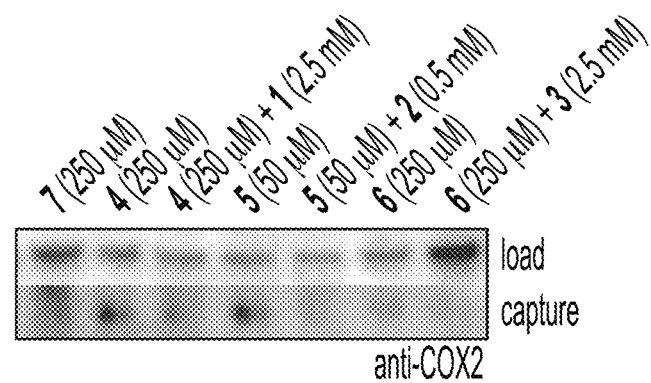
FIGS. 20A-20C show photo-NSAID interactions with COX-2 in Jurkat cells.
Figure 20B:
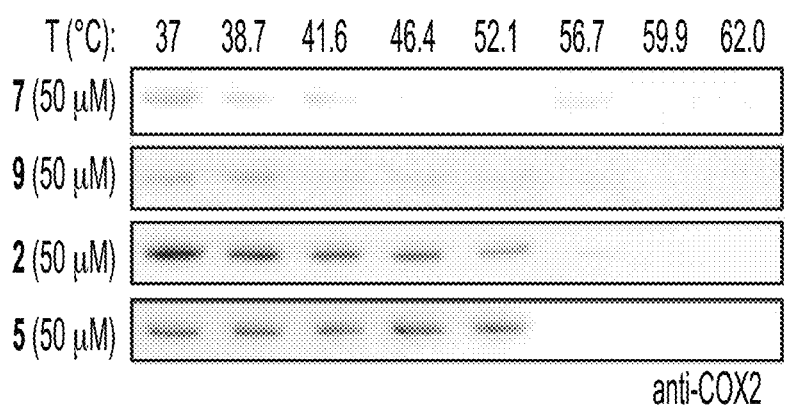
Figure 20C:
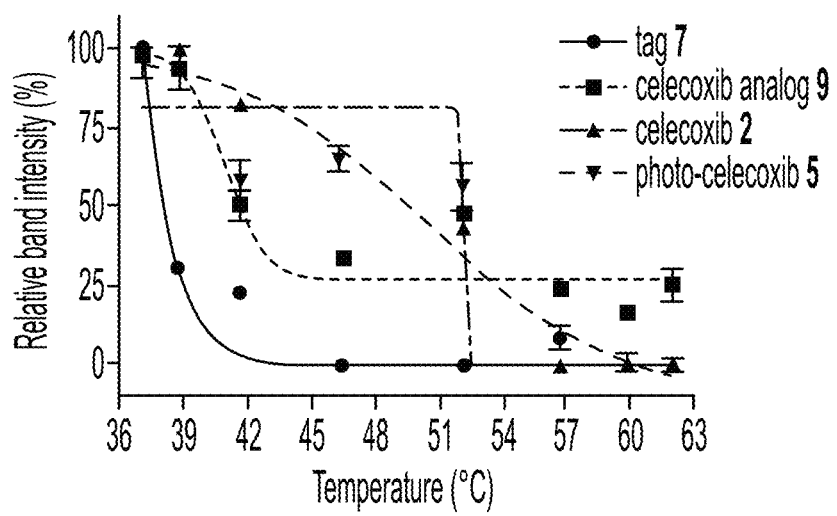

Confident that photo-NSAIDs were producing defined linkages with COX-2 that recapitulated NSAID activity, we next sought to characterize global NSAID interactions within the whole cell proteome. Photo-NSAIDs, the tag 7, and the photo-glutarimide 8 were added to activated Jurkat T cells as a model system for inflammation. Small molecule dose-dependent and photo-irradiation-dependent labeling of the proteome peaked at 250 µM. Competitive displacement of the tightest COX-2 binder photo-celecoxib (5) by the parent compound occurred at a 1:10 molar ratio (FIGS. 18A-18C). Jurkat cells were stimulated with phorbol myristyl acetate and ionomycin for 18 hours prior to photo-NSAID exposure.[31] The stimulated Jurkat cells were exposed to each compound (250 µM, 1 hour) and photo-irradiated in situ to conjugate the small molecule to the proteome. The resulting NSAID-conjugated proteins were enriched using the probe 10 in a biotin-dependent manner (FIG. 19). COX-2 from Jurkat cells was enriched by photo-NSAIDs and this enrichment was abrogated by competition with the parent compound, as indicated by Western blot (FIG. 20A). Cellular thermal shift assay, an orthogonal mechanism to validate protein-ligand interactions,[32] showed that COX-2 was stabilized by celecoxib (2) and photo-celecoxib (5) by over 10° C. relative to the tag 7 (FIG. 20B-C).

Figure 14A:
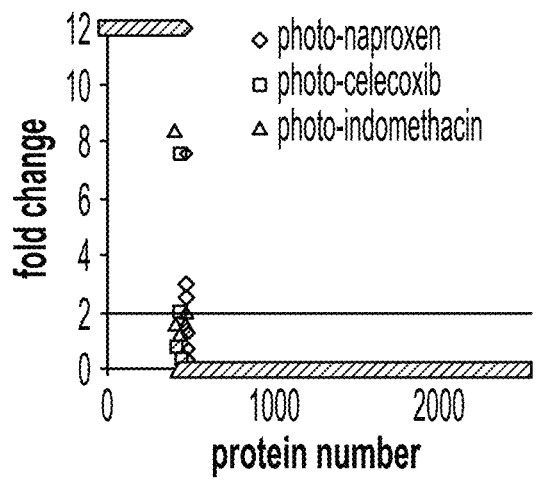
FIGS. 14A-14E show the photo-NSAID (250 µM) protein interactome.
Figure 14B:
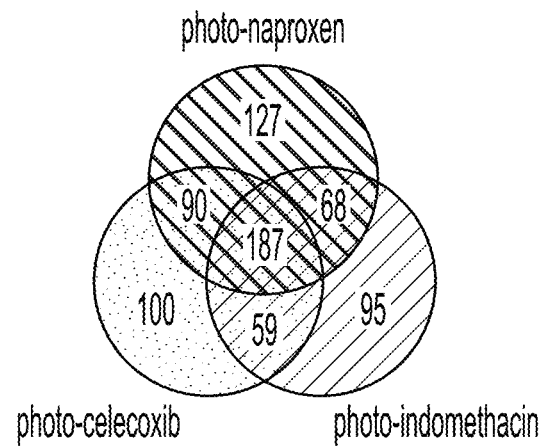
Figure 21A:
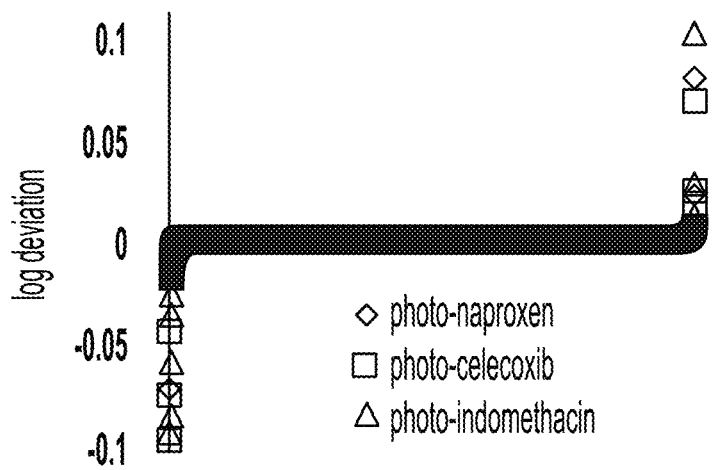
FIGS. 21A-21C show proteomics data reproducibility and protein overlap of analyzed compounds.
Figure 21B:
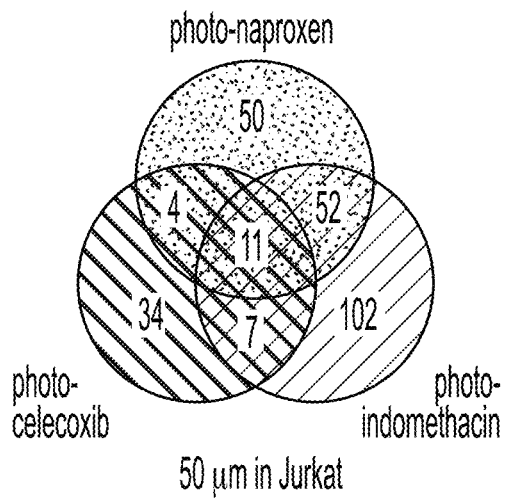

The enriched proteomes were digested with trypsin and the released peptides were analyzed by LC-MS/MS on an Orbitrap Fusion Tribrid with collision induced dissociation (CID) and higher energy CID (HCD) fragmentation modes. MS data were assigned by SEQUEST HT. Two biological replicates were collected for each of the photo-NSAIDs that displayed high reproducibility across the enriched proteome (>60%) and protein abundance (FIG. 21A). Using PSM-based label free quantification,[33] proteins that were greater than 2-fold enriched and statistically significant (t-test, p-value<0.05) were considered selectively enriched by the photo-NSAID relative to the control tag 7 (FIG. 14A). This analysis yielded approximately 700 proteins significantly enriched by at least one of the photo-NSAIDs (Table 3). High proteomic overlap amongst photo-NSAIDs, but not negative controls 7 and 8, was observed. Across each of the three compounds, at least 40% of the identified photo-NSAID-binding proteins were enriched by all three photo-NSAIDs and 53% of the proteins were enriched by at least two photo-NSAIDs (FIG. 14B). By comparison, 140 proteins that were statistically enriched by any photo-NSAID were also enriched by the photoglutarimide 8 (24%).

Figure 21C:
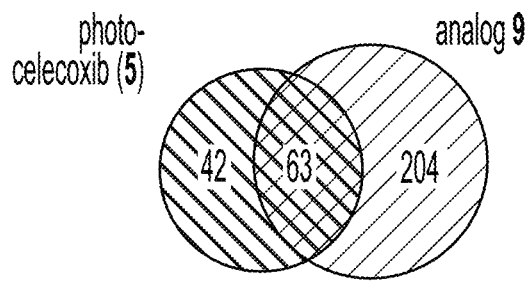

Jurkat cells were initially dosed with a concentration of 250 µM of each photo-NSAID to maximize downstream observation of conjugated peptides by MS. Although naproxen (1) enters blood plasma at concentrations that surpass 250 µM,[34] our $IC_{50}$ data against Jurkat cells showed a range of 23-216 µM across the NSAIDs and their derivatives (FIG. 17A-17D). We thus examined the NSAID interactome at 50 µM and identified 260 proteins enriched by the three photo-NSAIDs and not by the tag 7 (Table 4). At 50 µM the proteomic overlap between the photo-NSAIDs was lower, indicative of higher selectivity between the molecular structures (Figure S6B). A majority of proteins identified at 50 µM were likewise identified at 250 µM for each photo-NSAID (86-92%). The celecoxib analog 9 (50 µM) was additionally tested in activated Jurkat cells and displayed moderate proteomic overlap with photo-celecoxib (5) (FIG. 21C).

Figure 14C:
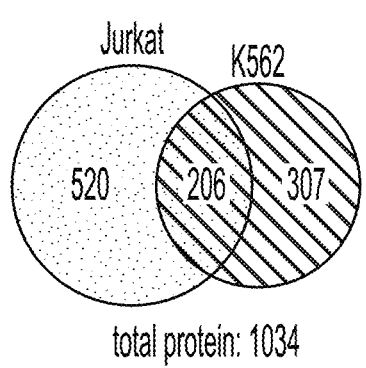
Figure 22:
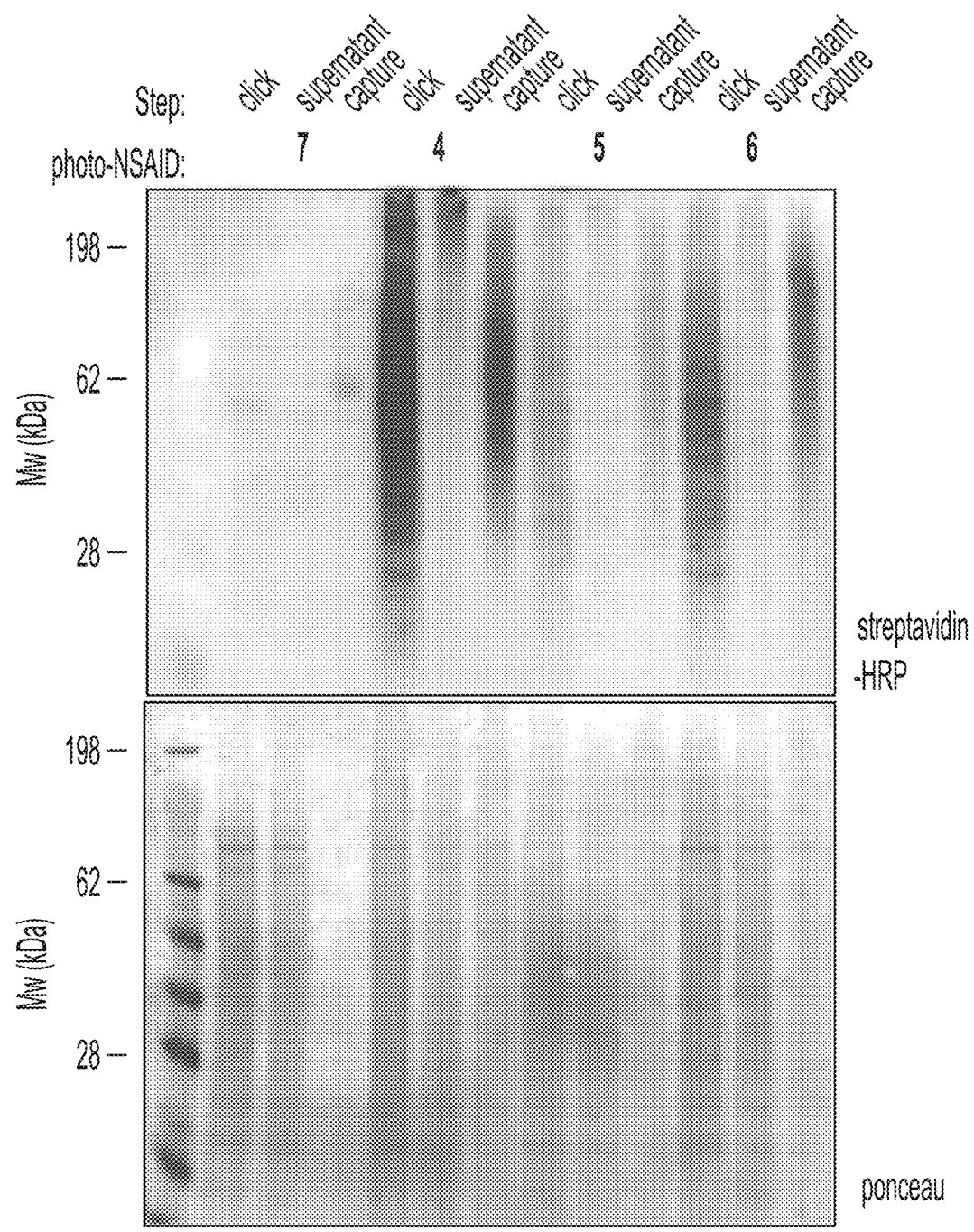
FIG. 22 shows an anti-biotin Western blot for enriched small molecule conjugated proteins from K562 cells. K562 cells were treated with a photo-NSAID or the tag 7, photo-irradiated and clicked with the cleavable biotin azide probe 10 (click). Biotinylated proteins were enriched on streptavidin-agarose beads, and the beads were washed (1% RapiGest, 6 M urea, PBS). The biotin-depleted whole proteome (supernatant) and the beads (capture) were analyzed by gel. Ponceau S staining shows protein loading.
Figure 23:
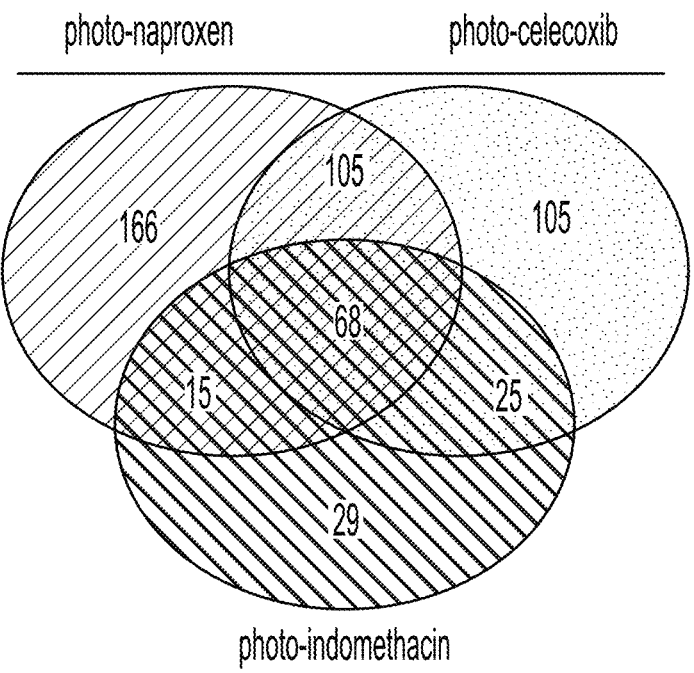
FIG. 23 shows a venn diagram of statistically-enriched photo-NSAID (250 µM) protein interactome from K562 cells across two biological replicates.

To determine the generality of these observations, photo-NSAIDs were additionally tested against K562 cells, a human chronic myeloid leukemia cell line. Several lines of evidence point to NSAID-dependent inhibition and apoptosis of K562 cells.[35] A total of 513 proteins were significantly enriched across two biological replicates from K562 cells, of which 42% of the proteins were enriched by at least two of the three photo-NSAIDs (FIGS. 22 and 23). Significantly enriched proteins from K562 cells possessed a moderate overlap with proteins from Jurkat cells (206 proteins), indicating a high degree of specificity across cell lines (FIG. 14C). In sum, a total of 1034 proteins were enriched from Jurkat and K562 cells by photo-NSAIDs (Table 3).

Figure 14D:
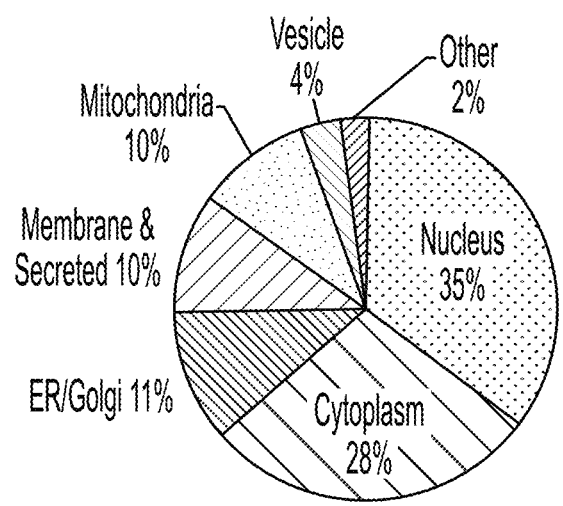

Photo-NSAIDs interacted with proteins distributed throughout the cell (FIG. 14D). Approximately two thirds of the NSAID interactome localized to the nucleus and cytoplasm. Photo-NSAIDs additionally captured proteins annotated as localized to the mitochondria (10%), endoplasmic reticulum and Golgi (11%), and membrane or secreted proteins (10%). These data are a close reflection of the natural distribution of proteins throughout the cell.[36] Only 30% of these proteins were previously annotated as interacting with a small molecule, let alone one of the NSAIDs (BindingDB, ChEMBL, DrugBank). This gap may be in part due to the broader range of interactions captured by photo-conjugation as compared to existing target identification strategies. Comparison of photo-NSAID interactions with proteomics profiles derived from fragment-based small molecules[12] revealed a 60% overlap. Thus, photo-NSAIDs possess a protein interaction profile that is specific to molecular structure and cell type. These data point to a broader range of molecular interactions that remain to be revealed by the reported profiling approach.

Figure 14E:
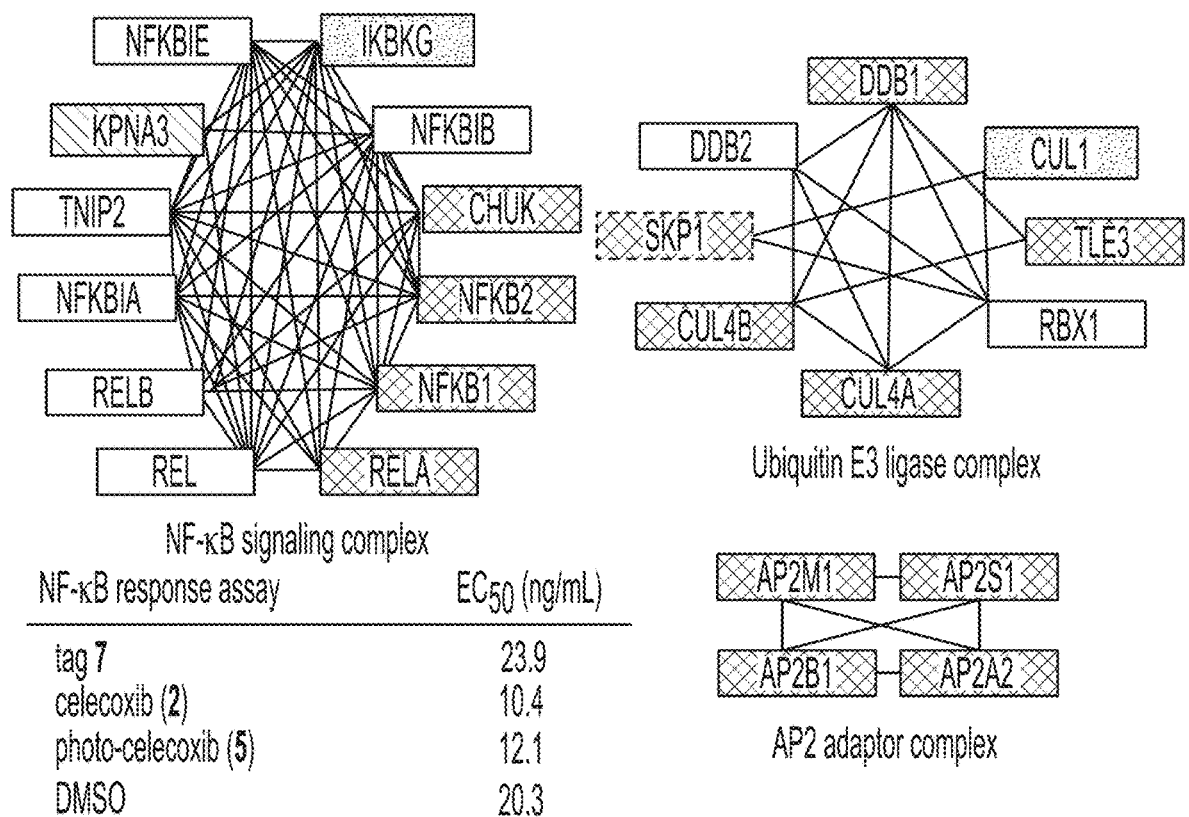
Figure 24:
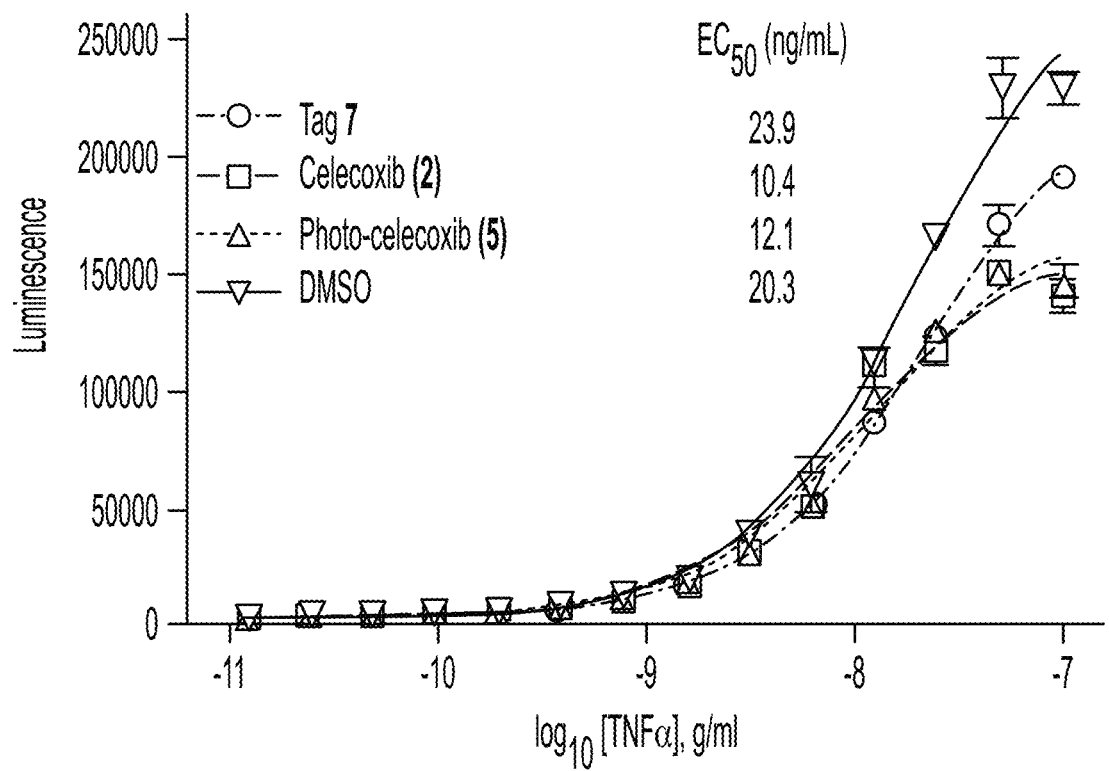
FIG. 24 shows a TNF-α titration curve for NF-κB-RE-luc2P HEK293 cells treated with 5 µM of the tag 7, celecoxib (2), photo-celecoxib (5), and DMSO. The luminescence was quantified using the ONE-Glo Luciferase Assay System Reagent on a microplate reader FilterMax F3. All data were obtained in triplicate, data representative of two independent experiments.

In line with evidence for capture of a broader range of associated proteins, a number of protein complexes were selectively enriched. Comparison of enriched proteins to CORUM37 revealed that NF-κB subunits (NFKB1, NFKB2) in complex with the inhibitor of NF-κB (IKKA) are directly interacting with the photo-NSAIDs, confirming their known inhibition of the NF-κB pathway[2] and was revalidated for celecoxib (2) and photo-celecoxib (5) via a NF-κB luciferase reporter assay (FIGS. 14E and 24). Additional protein complexes that were nearly completely enriched include the proteasome and the adaptor protein complex 2 (FIG. 14E). These proteins may have existed as complexes leading to photo-NSAID conjugation by virtue of proximity, indicative of a binding site hotspot for the photo-NSAIDs within specific families of proteins, or were enriched due to associative protein interactions. While protein complexes can be enriched through associative protein-protein interactions, our use of strong dissociative detergents to prepare cell lysates (1% Rapigest, sonication) does not typically lead to observation of protein complexes following enrichment.[11]

Direct Photo-NSAID Interaction Mapping Reveals Binding Site Hotspots

Following tryptic digestion of the photo-NSAID proteome, the probe 10 was acid cleaved to release the conjugated peptides from the enrichment media for separate isolation. The conjugated peptides were analyzed by application of mass-independent MS. A unique isotopic signature was embedded to the probe 10 using a carbon-13-derived stable isotope ratio of 1:3 over [M:M+2] spacing to perform mass-independent MS. During click chemistry, the unique isotopic signature was exclusively transferred to the photo-NSAIDs conjugated to the proteome. The isotopic signature is therefore only found on small molecule-conjugated peptides and is used during mass-independent MS to overcome traditional MS barriers in detection of low abundance species and validation of modified peptides against a background of unmodified peptides. During data collection, the isotopically recoded species is immediately recognizable by full scan MS and may be selected for fragmentation by use of an inclusion list.[38,39] This selection process increases the fraction of isotopically recoded, small molecule-conjugated peptides selected for fragmentation.[11]

More critically, the isotope signature played a crucial role in manual validation of database search assignments due to the ambiguity of the amino acid modification site. Database searching was performed against the SwissProt human protein database with each of the photo-NSAIDs as a modification on any amino acid residue. Small molecule conjugation to any amino acid drastically increases the size of the protein database. For example, a single modification increases the size of the fully tryptic human protein database by 60-fold, while two modifications increase the database size by 1000-fold. This exponential increase in the tryptic peptide database leads to a breakdown in false discovery rate (FDR).[40] Thus, a two-tier validation process was used for confident assignment of conjugated peptides. First, modified peptides at 5% FDR were filtered based on visual inspection of the MS2 spectral assignment. Second, each of the precursor spectra was individually validated for the isotopic signature in the MS1. Based on this analysis, 575 PSMs, corresponding to 194 individual conjugated peptides, were characterized across the photo-NSAIDs, tag 7, and photo-glutarimide 8 (Table 5). The top ten most frequently observed conjugated peptides are displayed in Table 1.

TABLE 1

Selected conjugated peptides observed with high PSM frequency across photo-NSAIDs, the tag 7 and the photo-glutarimide 8. Presented data is in aggregate across Jurkat and K562 cells. For the full dataset, see Table 5.

| | Conjugated Peptide | Protein (Gene) | Count of PSMs | | | | |
|---|---|---|---|---|---|---|---|
| | | | 4 | 5 | 6 | 7 | 8 |
| 1 | AMGIMNSFVNDIFER (SEQ ID NO: A1) | Histone H2B type 1-K (HIST1H2BK) | 41 | 12 | 1 | | |
| 2 | VGAGAPVYLAAVLEYLTAEILELAGNAAR (SEQ ID NO: A2) | Histone H2A type 2-B (HIST2H2AB) | 8 | 28 | 9 | | |
| 3 | VAPEEHPVLLTEAPLNPK (SEQ ID NO: A3) | Actin, cytoplasmic 1 (ACTB) | 3 | 14 | 3 | | |
| 4 | VGAGAPVYMAAVLEYLTAEILELAGNAAR (SEQ ID NO: A4) | Histone H2A type 2-A (HIST2H2AA3) | 2 | 12 | 5 | | |
| 5 | MSVQPTVSLGGFEITPPVVLR (SEQ ID NO: A5) | Nucleophosmin (NPM1) | 7 | 7 | 1 | | |
| 6 | NLEALALDLMEPEQAVDLTLPK (SEQ ID NO: A6) | X-ray repair cross-complementing 6 (XRCC6) | 7 | 3 | | 1 | 2 |
| 7 | IHFPLATYAPVISAEK (SEQ ID NO: A7) | Tubulin alpha-1A chain (TUBA1A) | | 13 | | | |
| 8 | VGAGAPVYLAAVLEYLTAEILELAGNAARDNKK (SEQ ID NO: A8) | Histone H2A type 2-B (HIST1H2AB) | 5 | 8 | | | |
| 9 | ISGLIYEETR (SEQ ID NO: A9) | Histone H4 (HIST1H4A) | 2 | 10 | 1 | | |
| 10 | VETGVLKPGMVVTFAPVNVTTEVK (SEQ ID NO: A10) | Elongation factor 1-alpha 1 (EEF1A1) | 5 | 7 | | | |
| 11 | AIGAVPLIQGEYMIPCEK (SEQ ID NO: A11) | Cathepsin D (CTSD) | 4 | 2 | 3 | | |

The individual peptides derived from a total of 150 proteins, of which over 90% of the proteins were greater than two-fold enriched, but did not necessarily pass statistical significance, by at least one of the photo-NSAIDs than by the tag 7. A number of isotopically-coded species that were either not selected or not confidently assigned by SEQUEST were also observed. Detection of enriched conjugated species using a pattern searching algorithm[39] revealed nearly 1000 isotopically coded precursor ions in the MS1 spectra across our photo-NSAID conjugated peptide data.

The observed interaction frequency and overlap was specific to the small molecule. Photo-celecoxib (5) and photonaproxen (4) represented the bulk of the identified interactions and were found conjugated to 93 and 85 peptides, respectively. Photo-indomethacin (6) was conjugated to 34 peptides in total. A degree of overlap between the photo-NSAID conjugated peptides was observed, where 30 peptides were identified by at least two of the three photo-NSAIDs. Of these, a single conjugated peptide on Ku70, a member of the DNA repair pathway, was observed by two photo-NSAIDs, the tag 7 and photo-glutarimide 8 (entry 6, Table 1). The remaining 14 conjugated peptides detected by the tag 7 and nine conjugated peptides from the photo-glutarimide 8 were detected exclusively by that compound.

Figure 15A:
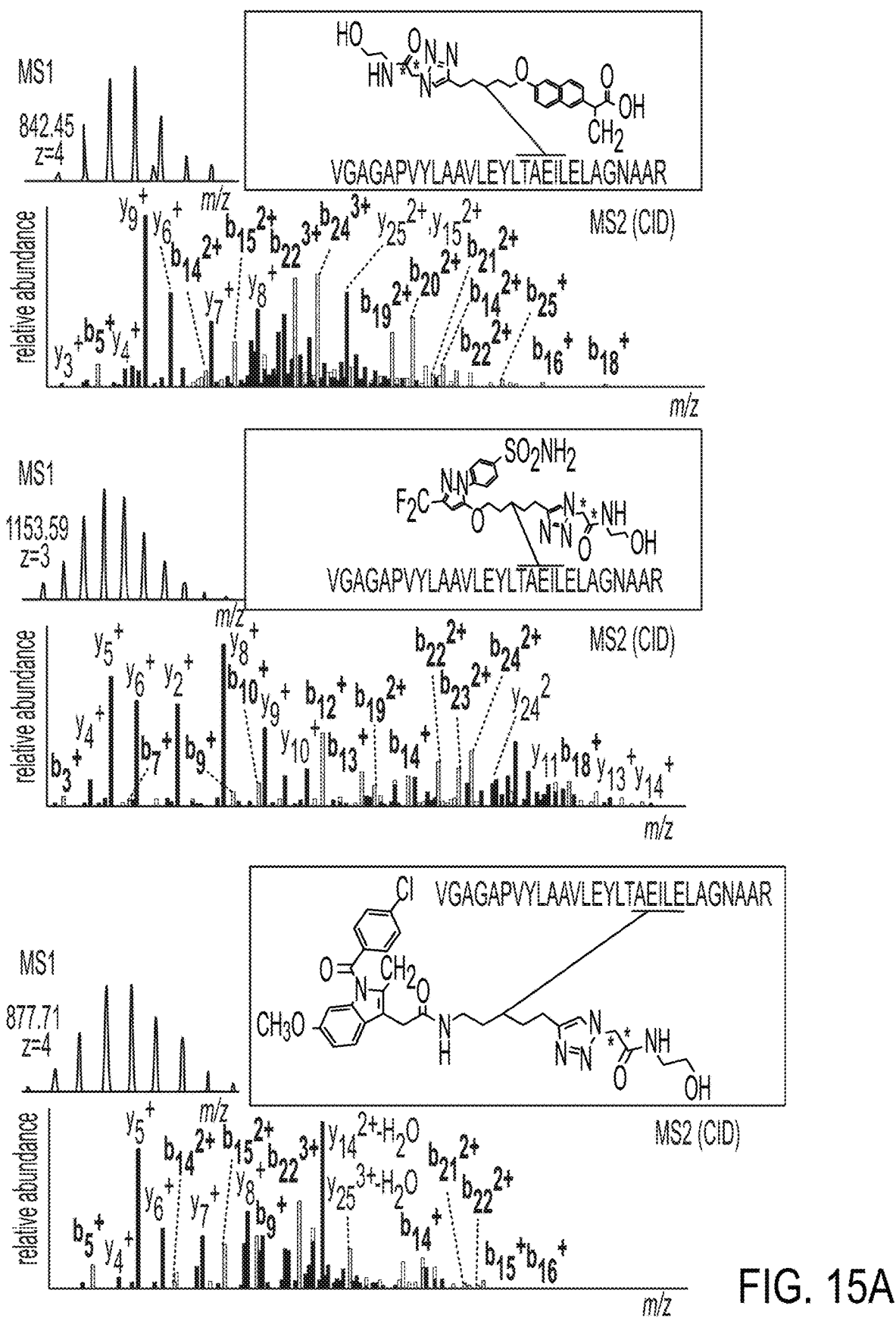
FIGS. 15A-15E show the evaluation of photo-NSAID binding site hotspots identified by SIM-PAL.
Figure 15B:
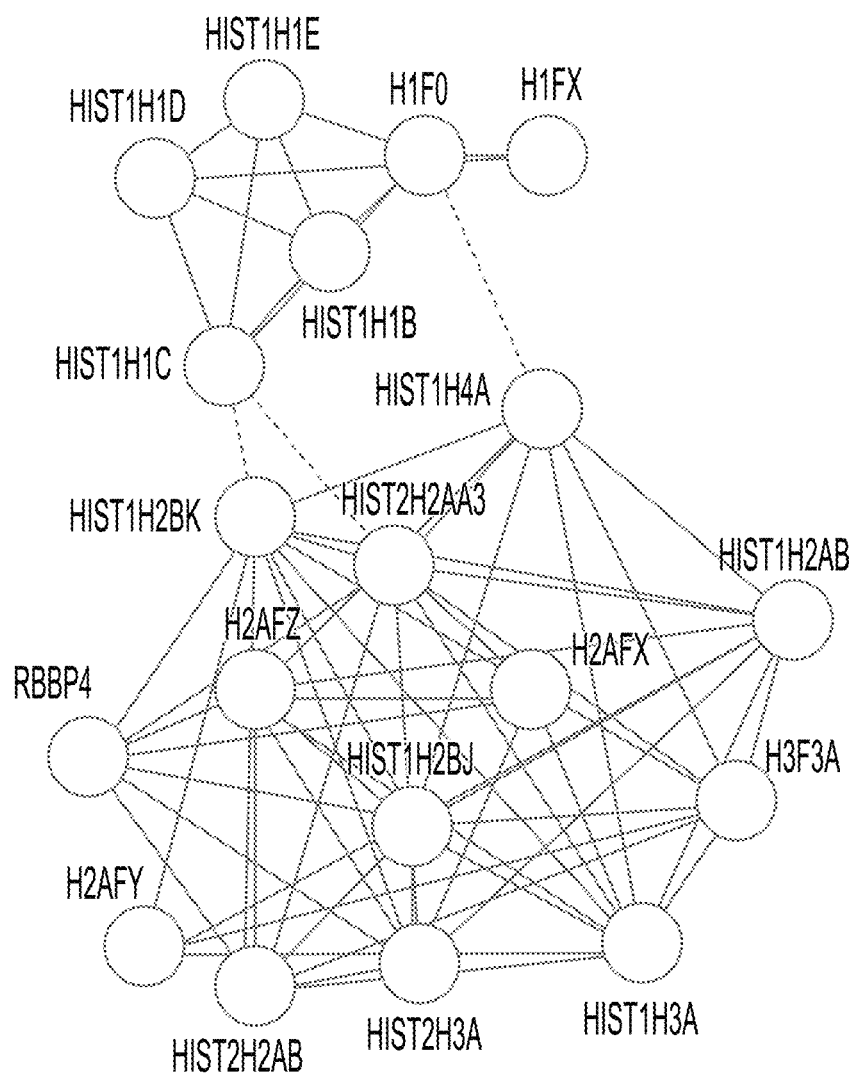
Figure 15C:
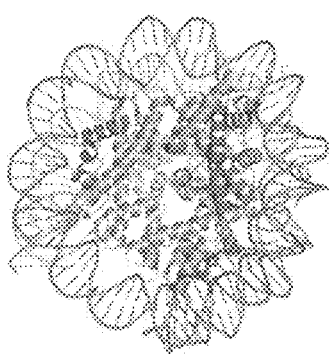
Figure 25:
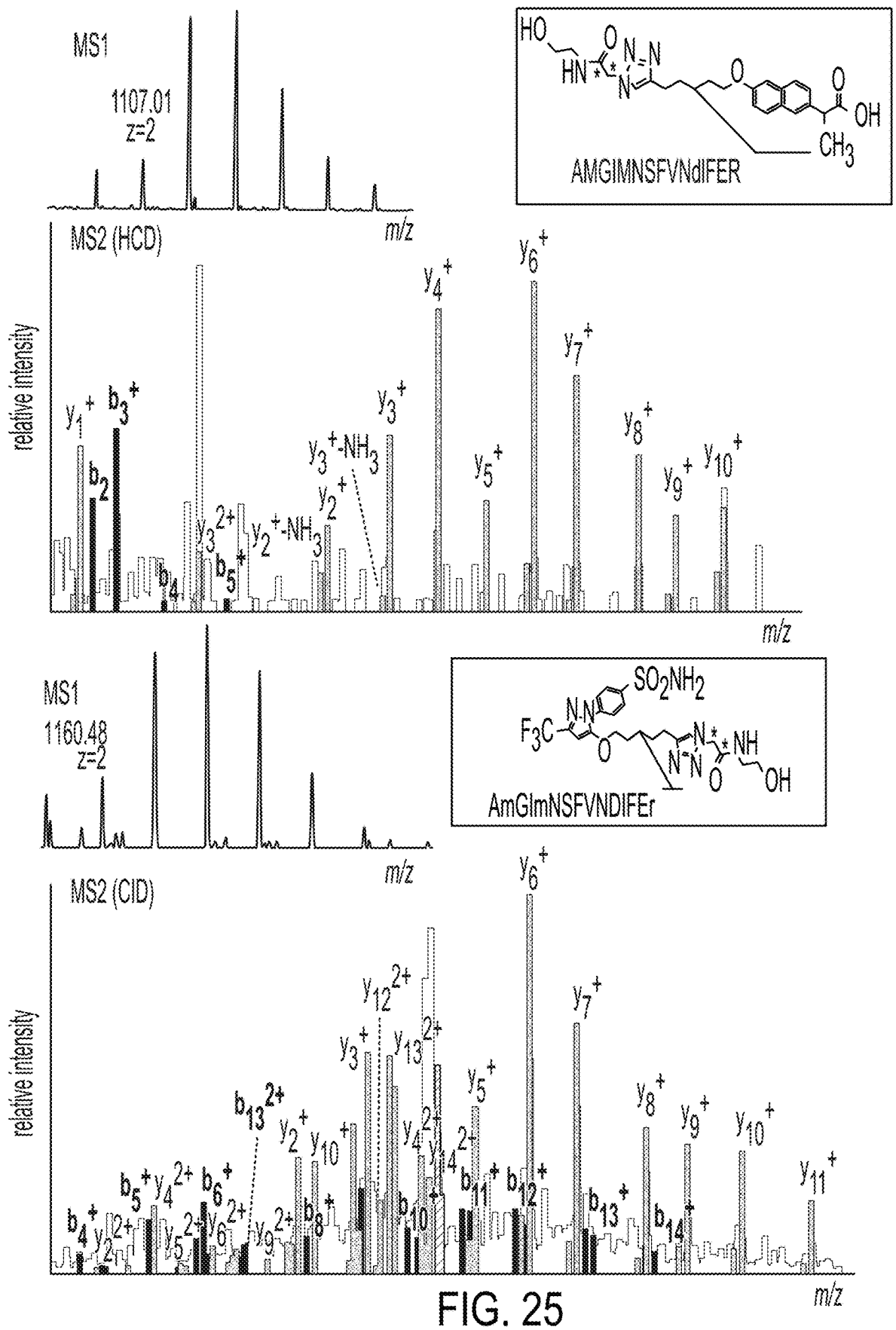
FIG. 25 shows example spectra of photo-naproxen (4) and photo-celecoxib (5) conjugated to a peptide from histone H2B. Spectra were validated for isotopic pattern (MS1) and spectral assignment (MS2) by SEQUEST HT.

We found a significant number of PSMs assigned to NSAID-conjugated histone peptides (FIG. 15A, FIG. 25). All directly observed histone interactions were highly interconnected and imply significantly upregulated conjugation of histone complexes by the photo-NSAIDs (FIG. 15B). These proteins were enriched in photo-NSAID proteomic data as compared to the tag 7, but were not considered statistically significant. In particular, two peptides from histone H2A and histone H2B were primarily detected. The histone H2B peptide was detected in a total of 54 PSMs across our datasets, predominantly by photo-naproxen (4, entry 1, Table 1). Histone H2A type 2-A and type 2-B were detected in a total of 62 and 19 PSMs, respectively (entries 2, 4, and 8. Table 1), predominantly in Jurkat cells. These PSMs related to peptides conjugated to photo-celecoxib (5), followed by photonaproxen (4) and to a lesser degree photo-indomethacin (6). By virtue of directly observing the conjugated peptide, photo-NSAIDs were mapped to a specific binding site hotspot around these two peptides, which are in close proximity in structures of the nucleosome (FIG. 15C).[41] Conjugated peptides from nucleophosmin and elongation factor 1-alpha 1 (entries 6 and 10, Table 1) were also observed.

Figures 15D, 15E:
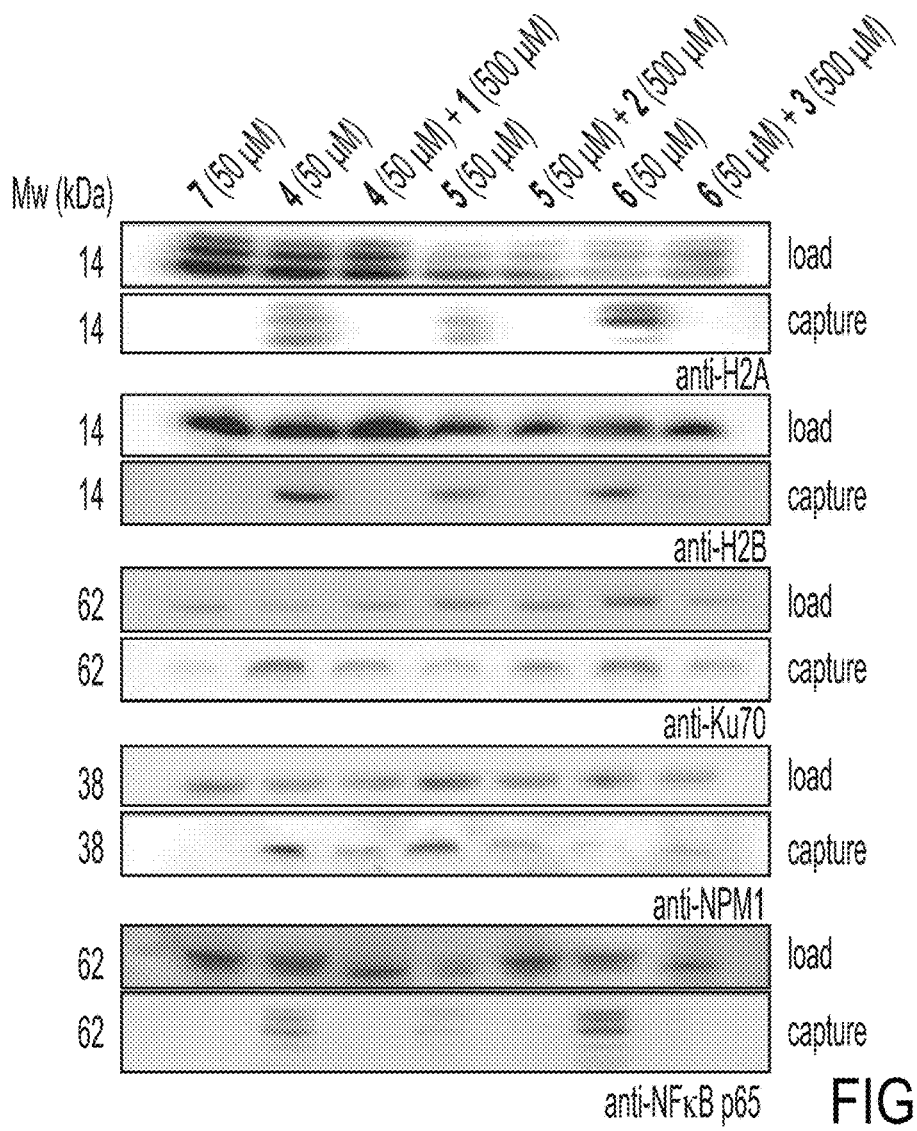
Figure 16A:
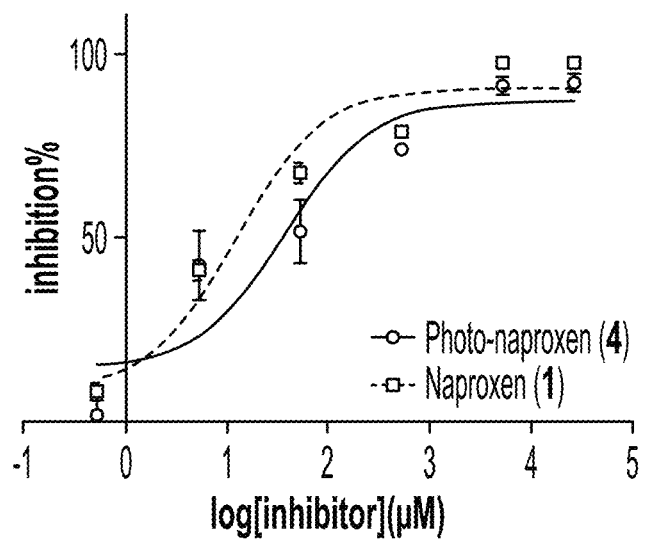
FIGS. 16A-16D show inhibition of COX-2 by (FIG. 16A) photo-naproxen (4) and naproxen (1), (FIG. 16B) photo-celecoxib (5) and celecoxib (2), and (FIG. 16O) photo-indomethacin (6) and indomethacin (3).
Figure 16B:
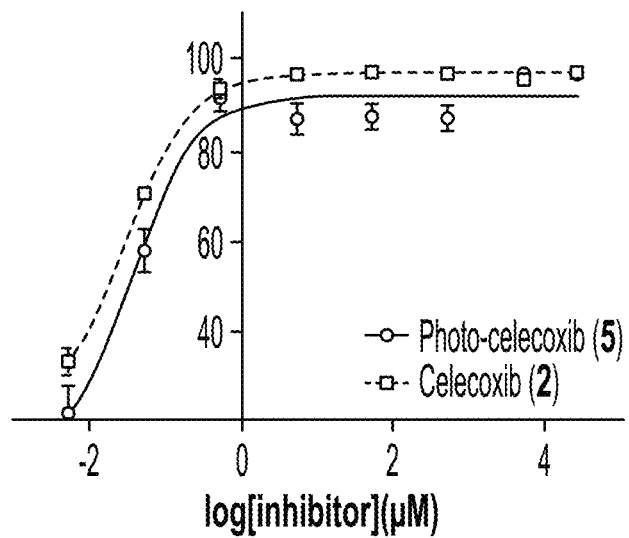
Figures 16C, 16D:
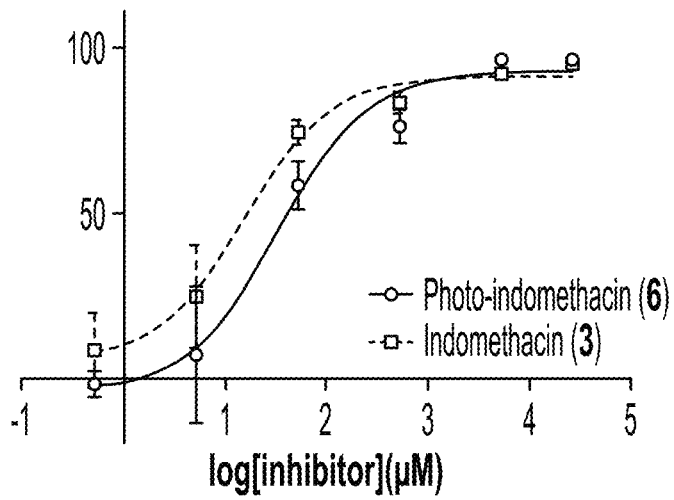
Figure 17A:
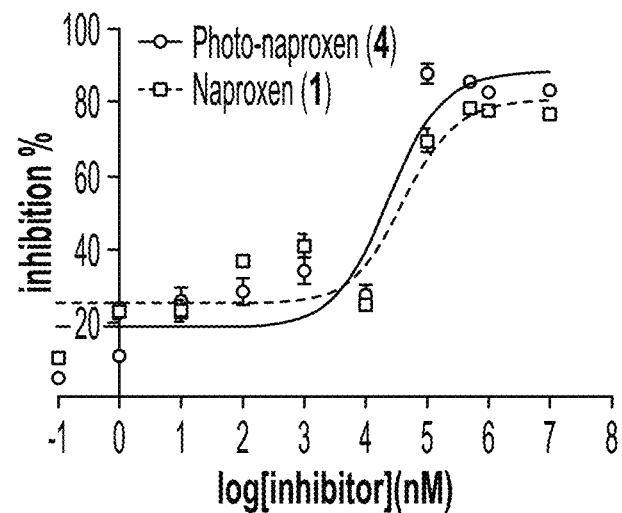
FIGS. 17A-17D show MTT cell viability assay for photo-NSAIDs and NSAIDs in Jurkat cells. Dose-response curves for (FIG. 17A) photo-naproxen (4) and naproxen (1), (FIG. 17B) celecoxib (2), photo-celecoxib (5) and celecoxib analog 9, and (FIG. 17C) photo-indomethacin (6) and indomethacin (3).
Figure 17B:
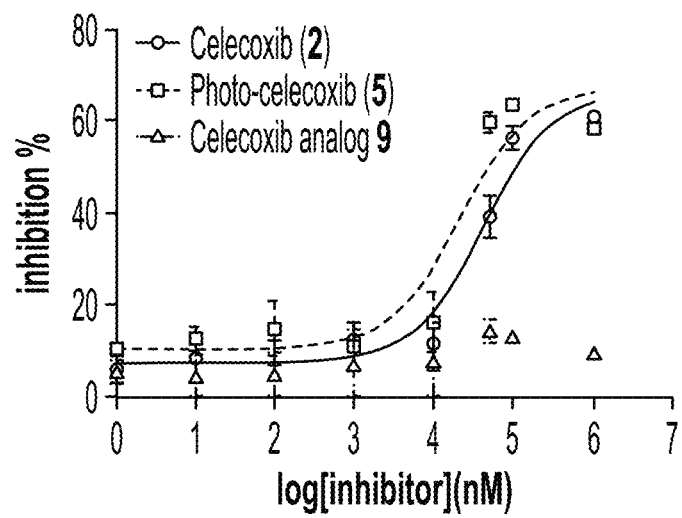
Figures 17C, 17D:
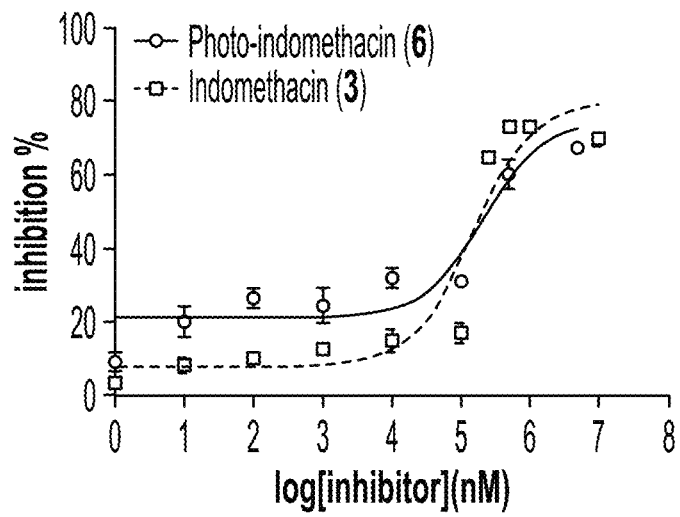

Validation of SIM-PAL by competition assay revealed that binding of all three photo-NSAIDs with histone H2A and H2B was competitively exchanged with the parent compound by Western blot (FIG. 15D). The interaction of photo-NSAIDs with NF-κB p65 was additionally completely displaced by the parent compound. Selective photo-conjugation and partial competition was observed when probing for Ku70 or nucleophosmin. The tag 7 and photo-NSAIDs labeled elongation factor 1-alpha 1 and rho GDP-dissociation inhibitor 2 similarly, although partial competition was still observed in some cases (data not shown). Cellular thermal shift assay in Jurkat cells showed stabilization of histone H2A by all three NSAIDs and the celecoxib analog 9 relative to the tag 7 by 10-15° C. (FIG. 15E). Photo-naproxen (4) and photo-celecoxib (5) also stabilized histone H2A, while photo-indomethacin (6) did not. These data are in line with the PSM frequency in Table 1. Characterization of these binding sites for biological function will be pursued.

Discussion

The development and application of SIM-PAL to enable characterization of the small molecule interactome and direct binding interactions was described (FIG. 12A). SIM-PAL provides several key advantages, including: (1) instant validation of the interaction by virtue of direct observation, (2) measurement of a range of interactions between transient and highly specific binding events, and (3) structural information about the binding site and the small molecule structure. These advantages are highlighted by our analysis of three NSAIDs for their binding sites with a single protein (COX-2) and against the whole proteome from Jurkat and K562 cells.

We applied SIM-PAL to three NSAIDs, naproxen (1), celecoxib (2), and indomethacin (3), due to their different structures yet similar anti-inflammatory effects. Variation in their off-target toxicity and the affected COX-2-independent anti-inflammatory pathways has been reported with a limited molecular basis for these effects. For example, celecoxib was the result of a medicinal chemistry optimization for COX-2 selectivity relative to COX-1,[22] yet additional COX-2 independent mechanisms have been subsequently reported.[18] To illuminate the molecular driving force behind NSAID biology, we developed a set of photo-NSAIDs (4-6, FIG. 12B) that recapitulated the activity of the parent compounds and demonstrated their direct binding interaction with COX-2 (FIGS. 13A-13E). Due to the dynamic nature of PAL, we identified additional transient interactions with COX-2 in vitro and the broader proteome in cellulo. These data report on access and molecular recognition of the compounds to the proteome and afford a structural basis for further functional analysis or protein degradation strategies.[42] A systematic study of the kinetics of PAL will provide concrete measurement of the range of transient interactions observable by SIM-PAL.

Application of the photo-activated compounds 4-8 to stimulated Jurkat and K562 cells revealed specific protein interactions that were more homologous across the three photo-NSAIDs than with the tag 7 or the photo-glutarimide 8. The photo-NSAID interactome revealed entire protein complexes of both known and novel interactions. For example, specific proteins in the NF-κB pathway are now identified as direct interactors (FIGS. 14E and 24). Enrichment of several protein complexes also indicates that the photo-conjugation event is dynamic and highly specific to the local environment of the small molecule at the time of activation. Novel interactions with the proteasome and the adaptor protein complex 2 were also notable. These results provide insight to the molecular interactions within the proteome generated by the NSAIDs, which may or may not possess direct biological function. Selection of proteins for follow up functional studies may be based on existing biological relevance, relative abundance, or dose dependence. Further studies may reveal functional relevance and the basis for some of the poorly-understood biological effects of NSAIDs.

We elected to evaluate a specific conjugation event that was observed on an interface between histone H2A and H2B in the nucleosome due to the high frequency of PSMs in our MS data. The two peptides are within 6 Å of each other in a crystal structure of the nucleosome, indicative of a binding site hotspot recognized by the photo-NSAIDs.41 While all three photo-NSAIDs were able to conjugate these peptides, photonaproxen (4) conjugation to histone H2B was observed the most frequently, while conjugation of photo-celecoxib (5) was most frequently observed conjugated to histone H2A. Comparison of these data to fragment-based small molecule interaction sites revealed that a diazirine-tagged coumarin, most structurally similar to photo-naproxen (4), likewise conjugated a similar peptide from histone H2AZ.[12] The interaction of photo-NSAIDs with histones was competitively displaced by the parent compound by Western blot (FIG. 15D). These data point to the existence of a binding site hotspot in the nucleosome. Although functional relevance cannot be inferred simply due to observation of an interaction, celecoxib (2) and photo-celecoxib (5) stabilized histone H2A by cellular thermal shift assay (FIG. 15E). Stabilization of protein complexes leading to downstream signaling changes is reminiscent of other immunomodulators, including cyclosporin, FK506, and rapamycin,[43] and the immunomodulatory drug lenalidomide.[44,45] The photo-NSAIDs reported here are validated probes that may be applied to additional biological studies.

While the photo-NSAIDs interacted with and stabilized COX-2 in cellulo, COX-2 was only observed in PSMs at a FDR>1% that were thus removed from the final dataset (Table 3). Furthermore, conjugated peptides from only a fraction of the enriched proteins were identified. These detection differences reflect the increased challenge in seeking to perform site-specific identification of a single conjugated peptide as opposed to protein identification that may derive from multiple peptides from the same protein. Deeper analysis of the NSAID interactome may be obtained by increasing protein inputs, increasing chromatographic separation, application of additional fragmentation methods, or use of a second protease (e.g., chymotrypsin).

SIM-PAL represents the culmination of advances in chemical enrichment strategies coupled to MS technology and a computational pattern searching algorithm to lay the groundwork for rapid progress in direct structural characterization of small molecule interactions within the whole proteome. Recent work in profiling small molecule modification sites has begun to expand the number of interactions that are known to occur throughout the proteome and enable a deeper understanding of the molecular underpinnings of polypharmacology. SIM-PAL revealed the global interaction map for the three NSAIDs profiled and is readily translated to other clinically relevant agents. For example, the immunomodulatory drugs have widely established pluripotent activity and the mechanism of action is only partly understood.[3] Alternatively, metformin is widely used to treat diabetes with little understanding of the underlying mechanism.[46] SIM-PAL is poised for broad application to bioactive small molecules for identification of proteomic interactions using an unbiased whole cell assay.

TABLE 2

Summary of conjugated peptides representative of binding sites of photo-NSAIDs on recombinant COX-2.

| photo-NSAID | Position | Annotated Sequence | m/z [Da] | MH+ [Da] | Theo. MH+ [Da] |
|---|---|---|---|---|---|
| photo-naproxen | 175 | FlpDPQ | 892.92743 | 1784.84758 | 1784.84982 |
| | 176 | FlPdPQ | 738.85565 | 1476.70403 | 1476.70858 |
| | 177 | KFIPDpQGSNMMFAFFAQHFTH | 763.76746 | 3814.80817 | 3814.79016 |
| | 178 | FIPDPqGS | 738.85217 | 1476.69707 | 1476.69734 |
| | 179 | KFIPDPQgSNMMFAFFAQHFTH | 763.76904 | 3814.81611 | 3814.79016 |
| | 179 | RKFIPDPQgSNMMFA | 888.42743 | 2663.26773 | 2663.27851 |
| | 179 | LRRKFIPDPQgSNMMF | 754.37665 | 2261.11539 | 2261.12457 |
| | 180 | KFIPDPQGs | 875.94287 | 1750.87847 | 1750.87268 |
| | 181 | SnMMFAFFAQHFTHQFFK | 1014.7923 | 3042.36234 | 3042.37822 |
| | 185 | FIPDPQGSNMMFaFFA | 872.06433 | 2614.17844 | 2614.17091 |
| | 188 | FIPDPQGSNMMFAFFaQHFTHQ | 1028.7958 | 3084.37278 | 3084.38075 |
| | 188 | FIPDPQGSNMMFAFFaQHFTHQF | 767.1568 | 3831.75489 | 3831.73672 |
| | 250 | YQIIDGEMYPpTVK | 659.99353 | 1977.96604 | 1977.95543 |
| | 250 | YQIIDGEMYPpTVKDT | 1089.526 | 2178.04473 | 2178.03513 |
| | 341 | LSGyHFKLK | 700.88739 | 1400.7675 | 1400.76128 |
| | 343 | LSGYHfKLK | 700.88556 | 1400.76384 | 1400.76128 |
| | 449 | SQASIDQSRQMKYQSfNEYR | 930.77051 | 2790.29697 | 2790.2828 |
| | 461 | yESFEELTGEK | 820.37549 | 1639.7437 | 1639.74139 |
| | 507 | tMVEVGAPFSLK | 793.90698 | 1586.80669 | 1586.81748 |
| photo-celecoxib | 72 | LFLKPTPnTVHYILTHFKGFWNVV | 763.96851 | 3815.81342 | 3815.82412 |
| | 79 | LFLKPTPNTVHYILtHFKGFWNVV | 763.56281 | 3813.78492 | 3813.80847 |
| | 101 | NAIMSyVLTSR | 835.3681 | 1669.72893 | 1669.73245 |
| | 101 | NAIMSyVLTSR | 835.3681 | 1669.72893 | 1669.73245 |
| | 165 | QLPDSNEIVeK | 908.90686 | 1816.80644 | 1816.81459 |
| | 165 | QLPDSNEIVeK | 835.87292 | 1670.73857 | 1670.73422 |
| | 166 | QLPDSNEIVEk | 907.90515 | 1814.80303 | 1814.79894 |
| | 248 | YQIIDGEMyPPTVK | 1099.9956 | 2198.98393 | 2198.98609 |
| | 248 | YQIIDGEMyPPTVK | 1026.9542 | 2052.90117 | 2052.90572 |
| | 320 | LILIGeTIKIVIEDYV | 973.80646 | 2919.40482 | 2919.40067 |
| | 446 | yQSFNEYR | 826.32996 | 1651.65264 | 1651.65697 |
| | 446 | yQSFNEYR | 753.28943 | 1505.57158 | 1505.5766 |
| | 455 | rFMLKPYESFEELTGEKEMSA | 979.75653 | 2937.25504 | 2937.27554 |
| | 566 | GCPFTSfSVPDPELIKTVTINASSSRSGLDD | 866.58209 | 4328.88135 | 4328.89089 |
| photo-indomethacin | 74 | LFLKPTPNTvHYILTHFK | 921.81818 | 2763.43998 | 2763.45766 |
| | 93 | ILTHFKGFWNVVNNIPfLR | 921.81226 | 2763.42221 | 2763.43652 |
| | 113 | pPTYNADYGYK | 941.91199 | 1882.8167 | 1882.82019 |
| | 339 | LILIGETIKIVIEDYVQHLsGYHFKLKF | 901.47186 | 4503.33021 | 4503.32663 |
| | 343 | VIEDYVQHLSGYHfK | 761.69812 | 2283.07981 | 2283.06763 |
| | 423 | SFTRQIAGRVAGgR | 962.49585 | 1923.98442 | 1923.97434 |
| | 586 | TVTINASSSRs | 785.87128 | 1570.73528 | 1570.73031 |
| | 597 | SGLDDINPTVLl | 852.92023 | 1704.83318 | 1704.82863 |

Amino acids that were identified as the conjugation site by SEQUEST HT searching are denoted in bold lowercase letter.
COX-2 tryptic digests were analyzed on an Orbitrap Elite and assigned to tryptic or semi-tryptic peptides using SEQUEST HT.

Lengthy table referenced here
US11912664-20240227-T00001

Please refer to the end of the specification for access instructions.

Lengthy table referenced here
US11912664-20240227-T00002

Please refer to the end of the specification for access instructions.

Lengthy table referenced here
US11912664-20240227-T00003

Please refer to the end of the specification for access instructions.

REFERENCES (1) Lounkine, E.; Keiser, M. J.; Whitebread. S.; Mikhailov, D.; Hamon, J.; Jenkins, J. L.; Lavan, P.; Weber, E.; Doak, A. K.; Cote, S.; Shoichet, B. K.; Urban, L. Nature 2012, 486, 361.
(2) Jana, N. R. Cell Molec Life Sci 2008, 65, 1295.
(3) Zhu, Y. X.; Kortuem, K. M.; Stewart, A. K. Leuk Lymphoma 2013, 54, 683.
(4) Pasternak, G. W. Neuropharmacology 2014, 76 Pt B, 198.
(5) Hopkins, A. L. Nat Chem Bio 2008, 4, 682.
(6) Keiser. M. J.; Setola, V.; Irwin, J. J.; Laggner, C.; Abbas, A. I.; Hufeisen, S. J.; Jensen, N. H.; Kuijer, M. B.; Matos, R. C.; Tran, T. B.; Whaley, R.; Glennon, R. A.; Hert, J.; Thomas, K. L. H.; Edwards, D. D.; Shoichet, B. K.; Roth, B. L. Nature 2009, 462, 175.
(7) Paolini, G. V.; Shapland, R. H. B.; van Hoorn, W. P.; Mason, J. S.; Hopkins, A. L. Nat Biotech 2006, 24, 805.
(8) Schenone, M.; Dancik, V.; Wagner, B. K.; Clemons, P. A. Nat Chem Biol 2013, 9, 232.
(9) Gertsik, N.; Am Ende, C. W.; Geoghegan, K. F.; Nguyen, C.; Mukherjee, P.; Mente, S.; Seneviratne, U.; Johnson, D. S.; Li, Y. M. Cell Chem Biol 2017, 24, 3.
(10) Mackinnon, A. L.; Taunton, J. Curr Protoc Chem Biol 2009, 1, 55.
(11) Woo, C. M.; Iavarone, A. T.; Spiciarich, D. R.; Palaniappan, K. K.; Bertozzi, C. R. Nat Meth 2015, 12, 561.
(12) Parker, C. G.; Galmozzi, A.; Wang, Y.; Correia, B. E.; Sasaki, K.; Joslyn, C. M.; Kim, A. S.; Cavallaro, C. L.; Lawrence, R. M.; Johnson, S. R.; Narvaiza, I.; Saez, E.; Cravatt, B. F. Cell 2017, 168, 527.
(13) Zha, S.; Yegnasubramanian, V.; Nelson, W. G.; Isaacs, W. B.; De Marzo, A. M. Cancer Lett 2004, 215, 1.
(14) Stewart, W. F.; Kawas, C.; Corrada, M.; Metter, E. J. Neurology 1997, 48, 626.
(15) Vane, J. R. Nat New Biol 1971, 231, 232.
(16) Tegeder, I.; Pfeilschifter, J.; Geisslinger, G. Faseb J 2001. 15, 2057.
(17) Hanif, R.; Pittas, A.; Feng, Y.; Koutsos, M. I.; Qiao, L.; Staiano-Coico, L.; Shiff, S. I.; Rigas, B. Biochem Pharmacol 1996, 52, 237.
(18) Jones, M. K.; Wang, H. T.; Peskar, B. M.; Levin, E.; Itani, R. M.; Sarfeh, 1. J.; Tarnawski, A. S. Nat. Med. 1999, 5, 1418.
(19) Yin, M.-J.; Yamamoto, Y.; Gaynor, R. B. Nature 1998, 396, 77.
(20) Smith, C. E.; Soti, S.; Jones, T. A.; Nakagawa, A.; Xue, D.; Yin, H. Cell Chem Biol 2017, 24, 281.
(21) Mitchell, J. A.; Akarasereenont, P.; Thiemermann, C.; Flower, R. J.; Vane, J. R. Proc. Natl. Acad. Sci. U.S.A 1993, 90, 11693.
(22) Flower, R. J. Nat Rev Drug Discov 2003, 2, 179.
(23) Schnitzer, T. J.; Burmester, G. R.; Mysler, E.; Hochberg, M. C.; Doherty, M.; Ehrsam, E.; Gitton, X.; Krammer, G.; Mellein, B.; Matchaba, P.; Gimona, A.; Hawkey, C. J.; Grp, T. S. Lancet 2004, 364, 665.
(24) McGettigan, P.; Henry, D. JAMA-J. Am. Med. Assoc. 2006, 296, 1633.
(25) Kalgutkar, A. S.; Crews, B. C.; Rowlinson, S. W.; Marnett, A. B.; Kozak, K. R.; Remmel, R. P.; Marnett, L. J. Proc Natl Acad Sci USA 2000, 97, 925.
(26) Chandna, N.; Kumar, S.; Kaushik, P.; Kaushik, D.; Roy, S. K.; Gupta, G. K.; Jachak, S. M.; Kapoor, J. K.; Sharma, P. K. Bioorg Med Chem 2013, 21, 4581.
(27) Kurumbail, R. G.; Stevens, A. M.; Gierse, J. K.; McDonald, J. J.; Stegeman, R. A.; Pak, J. Y.; Gildehaus, D.; iyashiro, J. M.; Penning, T. D.; Seibert, K.; Isakson, P. C.; Stallings, W. C. Nature 1996, 384, 644.
(28) Orlando, B. J.; Malkowski, M. G. Acta Crystallogr F Struct Biol Commun 2016, 72, 772.
(29) Li, Z.; Hao, P.; Li, L.; Tan, C. Y. J.; Cheng, X.; Chen, G. Y. J.; Sze, S. K.; Shen, H.-M.; Yao, S. Q. Angew Chem Int Ed 2013, 52, 8551.
(30) Schneidman-Duhovny, D.; Inbar, Y.; Nussinov, R.; Wolfson, H. J. Nucleic Acids Res 2005, 33, W363.
(31) Iñiguez, M. A.; Punzón, C.; Fresno, M. J Immunol 1999, 163, 111.
(32) Jafari, R.; Almqvist, H.; Axelsson, H.; Ignatushchenko, M.; Lundbuck, T.; Nordlund, P.; Molina, D. M. Nat. Protocols 2014, 9, 2100.
(33) Zhang, Y.; Wen, Z.; Washburn, M. P.; Florens, L. Anal Chem 2010, 82, 2272.
(34) Zhou, D.; Zhang, Q.; Lu, W.; Xia, Q.; Wei, S. J Clin Pharmacol 1998, 38, 625.
(35) Dharmapuri, G.; Doneti, R.; Philip, G. H.; Kalle, A. M. Leuk Res 2015, 39, 696.
(36) Thul, P. J.; Åkesson, L.; Wiking, M.; Mahdessian, D.; Geladaki, A.; Ait Blal, H.; Alm, T.; Asplund, A.; Bjork, L.; Breckels, L. M.; Bäckström, A.; Danielsson, F.; Fagerberg, L.; Fall, J.; Gatto, L.; Gnann, C.; Hober, S.; Hjelmare, M.; Johansson, F.; Lee, S.; Lindskog, C.; Mulder, J.; Mulvey, C. M.; Nilsson, P.; Oksvold, P.; Rockberg, J.; Schutten, R.; Schwenk, J. M.; Sivertsson, Å.; Sjöstedt, E.; Skogs, M.; Stadler, C.; Sullivan, D. P.; Tegel, H.; Winsnes, C.; Zhang, C.; Zwahlen, M.; Mardinoglu, A.; Pontén, F.; von Feilitzen, K.; Lilley, K. S.; Uhlén. M.; Lundberg, E. Science 2017, 356.
(37) Ruepp, A.; Waegele, B.; Lechner, M.; Brauner, B.; Dunger-Kaltenbach, I.; Fobo, G.; Frishman, G.; Montrone, C.; Mewes, H. W. Nucleic Acids Res 2010, 38, D497.
(38) Palaniappan, K. K.; Pitcher, A. A.; Smart, B. P.; Spiciarich, D. R.; Iavarone, A. T.; Bertozzi, C. R. ACS Chem Biol 2011, 6, 829.
(39) Woo, C. M.; Felix, A.; Byrd, W. E.; Zuegel, D. K.; Ishihara, M.; Azadi, P.; Iavarone, A. T.; Pitteri, S. J.; Bertozzi, C. R. J Proteome Res 2017, 16, 1706.
(40) Bern, M.; Kil, Y. J.; Becker, C. Curr Protoc Bioinformatics 2012, Chapter 13, Unit13 20.
(41) Tsunaka, Y.; Kajimura, N.; Tate, S.-i.; Morikawa, K. Nucleic Acids Res 2005, 33, 3424.

(42) Lu, J.; Qian, Y.; Altieri, M.; Dong, H.; Wang, J.; Raina, K.; Hines, J.; Winkler, James D.; Crew, Andrew P.; Coleman, K.; Crews, Craig M. Chem Biol 2015, 22, 755.
(43) Schreiber, S. Science 1991, 251, 283.
(44) Kronke, J.; Udeshi, N. D.; Narla, A.; Grauman, P.; Hurst, S. N.; McConkey, M.; Svinkina, T.; Heckl. D.; Comer, E.; Li, X.; Ciarlo, C.; Hartman, E.; Munshi, N.; Schenone, M.; Schreiber, S. L.; Carr, S. A.; Ebert, B. L. Science 2014, 343, 301.
(45) Lu, G.; Middleton, R. E.; Sun, H.; Naniong, M.; Ott, C. J.; Mitsiades, C. S.; Wong, K.-K.; Bradner, J. E.; Kaelin, W. G. Science 2014, 343, 305.
(46) Pernicova, I.; Korbonits, M. Nat. Rev. Endocrinol. 2014, 10, 143.

Supplemental Information
Methods

General Experimental Procedures. All reactions were performed in single-neck, oven-dried, roundbottomed flasks fitted with rubber septa under a positive pressure of nitrogen, unless otherwise noted. Air- and moisture-sensitive liquids were transferred via syringe or stainless steel cannula. Organic solutions were concentrated by rotary evaporation at 30-33° C. Normal and reverse phase flash-column chromatography was performed as described by Still and co-workers.[1] Normal phase purifications employ silica gel (60 Å. 40-63 μm particle size) purchased from Silicycle (Quebec, Canada). Analytical thin-layer chromatography (TLC) was performed using glass plates pre-coated with silica gel (0.25 mm, 60 Å pore size) impregnated with a fluorescent indicator (254 nm). TLC plates were visualized by exposure to ultraviolet light (UV), iodine ($I_2$), and/or submersion in ninhydrin followed by brief heating with a heat gun (10-15 seconds).

Chemical Materials. Commercial solvents and reagents were used as received with the following exceptions. Dichloromethane and N,N-dimethylformamide were purified according to the method of Pangborn and co-workers.[2] Triethylamine was distilled from calcium hydride under an atmosphere of nitrogen immediately before use. 3-aminopiperidine-2,6-dione hydrochloride was obtained from Ark Pharm. RapiGest was prepared according to the method of Lee and co-workers.[3] 3-[4-({Bis[(1-tert-butyl-1H-1,2,3-triazol-4-yl)methyl]amino}methyl)-1H-1,2,3-triazol-1-yl]propanol (BTTP) was prepared according to the method of Wu and co-workers.[4] 3-(4,5-Dimethylthiazol-2-yl)-2,5-diphenyltetrazolium bromide (MTT) was obtained from Sigma Aldrich. Biotin-CA(PEG)$_4$-alcohol S14 was synthesized according to the method of Tirrell and co-workers.[5]

Biological Materials. COX-2 polyclonal antibody (PA5-16817), histone H2A polyclonal antibody (PA5-35893) and high sensitivity streptavidin-HRP (21130) were purchased from Thermo Fisher Scientific and used in 1:100, 1:500 and 1:10,000 dilutions, respectively. Anti-Histone H2B monoclonal antibody (12364) was purchased from Cell Signaling Technology and diluted to 1:1000 in Western Blot detection. Nucleophosmin (NPM1/B23) monoclonal antibody (sc-271737), Ku-70 (XRCC6) monoclonal antibody (sc-56129), NFκB p65 monoclonal antibody (sc-8008), Ly-GDI monoclonal antibody (sc-376473), EF-1 α1 monoclonal antibody (sc-21758), Cathepsin D monoclonal antibody (sc-377299) and secondary antibody m-IgGκ BP-HRP (sc-516102) were provided by Santa Cruz, and used in 1:500, 1:200, 1:500, 1:500, 1:100, 1:200 and 1:1000 dilutions, respectively. ONE-Glo Luciferase Assay System (E6110) was purchased from Promega Corporation.

Cell Culture Materials. K562 and Jurkat cell lines were obtained from the American Type Culture Collection (ATCC) and maintained in RPMI-1640 medium supplemented with 10% fetal bovine serum (FBS) and 1% penicillin/streptomycin at 37° C. and 5% $CO_2$ in a water-saturated incubator. EDTA-free protease inhibitor cocktail was obtained from Roche Diagnostics. Streptavidin-agarose beads were obtained from Thermo Scientific and washed with PBS prior to use. The GloResponse NF-κB-RE-luc2P HEK293 Cell Line, a clonal derivative of Human Embryonic Kidney 293 (HEK293), was provided by Choudhary lab, and maintained in DMEM medium supplemented with 10% FBS and 1% penicillin/streptomycin at 37° C. and 5% $CO_2$ in a water-saturated incubator.

Chemical Instrumentation. Proton nuclear magnetic resonance spectra ($^1$H NMR) were recorded at 400 or 500 MHz at 24° C., unless otherwise noted. Chemical shifts are expressed in parts per million (ppm, δ scale) downfield from tetramethylsilane and are referenced to residual protium in the NMR solvent [$CHCl_3$, δ 7.26; $CHD_2OD$, δ 3.31; $(CHD_2)(CD_3)SO$, δ 2.491. Data are represented as follows: chemical shift, multiplicity (s=singlet, d=doublet, t=triplet, q=quartet, quin=quintet, m=multiplet and/or multiple resonances, br=broad, app=apparent), integration, coupling constant in Hertz, and assignment. Proton-decoupled carbon nuclear magnetic resonance spectra ($^{13}$C NMR) were recorded at 125 MHz at 24° C., unless otherwise noted. Chemical shifts are expressed in parts per million (ppm, δ scale) downfield from tetramethylsilane and are referenced to the carbon resonances of the solvent ($CDCl_3$, δ 77.0; $CD_3OD$, δ 49.0; $(CD_3)_2SO$, δ 39.0). $^{13}$C NMR and data are represented as follows: chemical shift, carbon type. Chemical shifts are expressed in parts per million (ppm, δ scale) downfield from tetramethylsilane. Infrared (IR) spectra were obtained using a Shimadzu 8400S FT-IR spectrometer referenced to a polystyrene standard. Data are represented as follows: frequency of absorption ($cm^{-1}$), intensity of absorption (s=strong, m=medium, w=weak, br=broad). High-resolution mass spectrometry (HRMS) measurements were obtained at the Chemistry and Chemical Biology Department, Harvard University Mass Spectrometry Facility using a Bruker microTOF-Q II hybrid quadrupole-time of flight, Agilent 1260 UPLC-MS. Low-resolution mass spectrometry (LRMS) measurements were obtained on Waters ACQUITY UPLC equipped with SQ Detector 2 mass spectrometer. The samples were photoirradiated with UVP Blak-Ray B-100AP high-intensity UV lamp (UVP LLC, Upland, CA). The absorbance was measured on a multi-mode microplate reader FilterMax F3 (Molecular Devices LLC, Sunnyvale, CA). TAMRA-fluorescence and chemiluminescence were detected by scanning the gel on Azure Imager $C_{600}$ (Azure Biosystems, Inc., Dublin, CA).

Experimental Procedures with COX-2

COX-2 inhibitor screening assay by ELISA. The COX-2 inhibitor screening assay kit (701080, Cayman Chemical, Ann Arbor, MI) was used to determine the inhibitory concentration of COX-2 in the presence of photo-NSAIDs or NSAIDs. The effect of inhibitors on COX-2-mediated prostaglandin production was measured in triplicate with several concentration gradients of photo-NSAIDs or NSAIDs. Non-specific binding (NSB), maximum binding (BO), 100% initial activity (IA), background COX-2 (BC) and blank samples, in duplicate, were also measured. A prostaglandin screening standard curve was obtained by plotting the data as $\ln[B/B(I-B/B_0)]$ versus log concentrations of prostaglandin and performing a linear regression fit. The concentration of prostaglandin for each inhibitor sample was calculated by using the prostaglandin standard curve. The curve of percent inhibition by the inhibitor concentration was fitted and analyzed to determine the $IC_{50}$ value for inhibitors using GraphPad Prism (GraphPad Software, San Diego, CA).

Competitive analysis of NSAIDs and photo-NSAIDs with isolated COX-2. Recombinant human COX-2 (125 ng, 12036-H08B, Sino Biological Inc., Beijing, China) was separately incubated with each of the photo-NSA IDs with or without a 100-fold excess of the parent compound as a competitor for 2 hours at 37° C. The samples were photo-irradiated for 30 minutes at 4° C., tagged with TAMRA-azide (760765, Sigma-Aldrich, St. Louis. MO) by copper-click chemistry for 2 hours at 24° C., and detected by fluorescence spectroscopy (Azure imager C600, Azure Biosystems) with Cy3 excitation.

Molecular docking of the structure of COX-2 with photo-NSAIDs and the tag 7. The photo-NSAIDs, the parent compounds, and the tag 7 were structurally minimized using Gaussian 16.0 with a basis set of HF 3-21g(d). The energetically minimal structures were used in a geometry-based molecular docking algorithm PatchDock (https://bioinfo3d.cs.tau.ac.il/PatchDock/) to calculate docking transformations that based on a scoring function and atomic desolvation energy. The structures with the lowest desolvation energy and highest interface area size were used in FIG. 13. The receptor molecule was obtained from the crystal structure of human COX-2 (PDB: 5KIR).

In-vitro photolabeling of COX-2 with photo-NSAIDs and analysis by LC-MS/MS. Recombinant COX-2 (1 µg) was separately incubated with each of the photo-NSAIDs (10 µM) or the tag 7 (10 µM) for 30 minutes at 37° C., and photo-irradiated for 15 minutes at 4° C. The samples were then tagged with the cleavable biotin azide probe 10 by copper-click chemistry for 3 hours at 24° C., followed by sample digestion with trypsin for 12 hours at 37° C., and probe cleavage with 2% formic acid. The resulting peptides were analyzed by LC-MS/MS. MS data was searched in Proteome Discoverer v2.2 with SEQUEST HT or Byonic v2.1 against the recombinant COX-2.

Experimental Procedures with Whole Cells

Cell growth assay (MTT) with photo-NSAIDs and NSAIDs. Jurkat cells were seeded in a 96-well flatbottomed cell culture plate (Falcon) in RPMI with 10% FBS and 1% penicillin/streptomycin at a density of $1\times10^5$ cells/mL and maintained for 24 hours at 37° C. and 5% $CO_2$ atmosphere. Cells were treated with photo-NSAIDs or NSAIDs in triplicate at different doses and incubated for 24 hours at 37° C. MTT solution (10 µL, 5 mg/mL) was added to each well and gently mixed. The cells were incubated for 4 hours at 37° C., followed by addition of 0.1 mL isopropanol with 0.04 N HCl to each well. The resulting mixture was mixed thoroughly by repeated pipetting. The absorbance was measured within 1 hour on a multi-mode microplate reader with a wavelength of 620 nm.

In-situ photo-labeling of K562 or Jurkat cells with photo-NSAIDs. K562 cells or PMA/Ionomycin activated Jurkat cells (~97% cell viability) were suspended in FBS-free RPMI at the indicated concentration of photo-NSAIDs or negative controls tag 7 the photo-glutarimide 8, or the analog 9 for 2 hours at 37° C., followed by UV irradiation at 365 nm for 30 minutes at 4° C. In competition experiments, cell lysates were co-treated with the photo-NSAIDs and their parent compounds in 10-fold excess. The photoirradiated samples were pelleted, lysed with 1% RapiGest and EDTA-free protease inhibitor and briefly sonicated with a probe tip sonicator. Sonicated cell lysates were cleared by centrifugation and the concentration of the soluble proteins was determined using the BCA protein assay. Protein concentrations were adjusted to a final concentration of 2.5 mg/mL. Cell lysates (500 µL) were reacted with pre-mixed click reagents at a final concentration of 200 µM biotin azide probe 10, 300 µM copper (II) sulfate, 600 µM BTTP and 2.5 mM freshly-prepared sodium ascorbate for 5 hours at 24° C. with rotation. The proteins were precipitated with methanol (1 mL) for 1 hour at −80° C., pelleted by centrifugation (15,000 g) for 10 minutes at 4° C., and air dried for 10 minutes at 24° C.

Enrichment of photo-crosslinked proteins for LC-MS/MS. Biotinylated protein pellets were resuspended in 1% RapiGest in PBS (400 µL) and briefly sonicated. Streptavidin-agarose resin (200 µL, washed 3×1 mL PBS) was added to the suspended proteins and incubated for 12 hours at 24° C. The beads were centrifuged for 3 minutes at 3000×g and the supernatant was removed. The beads were washed with 1% RapiGest (1 mL), urea (6M, 3×1 mL), and PBS (2×1 mL) in succession. The washed beads were resuspended in PBS (200 µL). The proteins on beads were reduced with 5 mM dithiothreitol (DTT) for 30 minutes at 24° C. and alkylated with 10 mM iodoacetamide for 30 minutes at 24° C. in the dark. The beads were pelleted by centrifugation and resuspended in 0.5 M urea/PBS (200 µL) and trypsin (1.5 µg) digested for 12 hours at 37° C. with rotation. The supernatant digest was collected and the beads were washed with PBS (200 µL) and water (2×200 µL). The washes were combined to obtain the "trypsin fraction". Cleavage of the probe 10 and recovery of the conjugated peptide was performed in 2% formic acid in water (200 µL) for 30 minutes at 24° C. The cleavage solution was collected and the beads were washed with 80% acetonitrile in water (400 µL) and the fractions were combined to afford the "cleavage fraction". The trypsin and cleavage fractions were concentrated to dryness using a SpeedVac concentrator heated at 40° C., and stored at −20° C. until analysis by LC-MS/MS.

Cell thermal shift assay (CETSA) with photo-NSAIDs and NSAIDs. Jurkat cells in 15 mL of FBSfree RPMI at a density of $2.5\times10^6$ cells/mL were incubated with 50 µM of tag 7, photo-NSAIDs or NSAIDs for 2 hours in a 5% $CO_2$ atmosphere at 37° C. The cell suspension was then collected and centrifuged for 3 minutes at 300×g and the culture medium was aspirated. The cell pellets were re-suspended and washed with PBS (2×15 mL) by centrifugation. PBS (1 mL) supplemented with EDTA-free protease inhibitors (1×) was added to each tube, and the resulting cell suspension was equally distributed into eight different 0.2 mL PCR tubes. The PCR tubes were heated over a temperature gradient (37-62° C.) for 20 minutes in a 96-well thermal cycler, followed by repeated freeze-thaw cycles (5×). The PCR tubes containing the resulting cell lysates were centrifuged at 20,000×g for 30 minutes at 4° C. to pellet cell debris together with precipitated and aggregated proteins. Each supernatant with the soluble protein fraction was transferred carefully to a new tube and analyzed by Western blot. The Western blot bands were quantified by ImageJ, and the data were fitted to obtain apparent Tagg values using the Boltzmann Sigmoid equation within GraphPad Prism.

Luciferase reporter assay for NF-κB pathway. The Glo-Response NF-κB-RE-luc2P HEK293 cell line contains a luciferase gene (luc2P) under the control of a minimal TATA promoter with multiple nuclear factor-KB response elements (NF-κB-REs). A total of 10,000 NF-κB-RE-luc2P HEK293 cells per well were dispensed into a 384-well plate, and incubated respectively with 5 µM of tag 7, celecoxib (2), photocelecoxib (5) and DMSO for 1 hour at 37° C. followed by addition of two-fold serial dilutions of TNF-α to induce reporter gene expression. After 5 hours of induction in a tissue culture incubator at 37° C., luminescence was quantified using the ONE-Glo Luciferase Assay System Reagent on a multi-mode microplate reader FilterMax F3 (read for 0.5 second/well). The TNF-α titration curve was fitted and analyzed to determine the half maximal effective concentration ($EC_{50}$) using GraphPad Prism.

Mass Spectrometry Procedures

Mass spectrometry procedures. The desalted samples were resuspended in 0.1% formic acid in water (15 μL). The sample (4.0 μL) was loaded onto a C18 trap column (3 cm, 3 μm particle size C10 Dr. Maisch 150 μm LD) and then separated on an analytical column (Thermo Scientific Acclaim PepMap 100, 2 μm particle size, 250 mm length, 75 μm internal diameter) at 150 nL/min with a Thermo Scientific EASY-nLC 1000 system connected in line to a Thermo Scientific Orbitrap Fusion Tribrid or Orbitrap Elite. The column temperature was maintained at 50° C. The tryptic peptides were separated via a stepwise gradient from 5% to 98% of 0.1% formic acid in acetonitrile over 120 minutes (0-1 minutes, 0-5%; 1-91 minutes, 5-27%; 91-115 minutes, 27-98%; 115-120 minutes, 98%-4%). The cleavage peptides were separated via a step-wise gradient from 5% to 98% of 0.1% formic acid in acetonitrile over 130 minutes (0-1 minutes, 0-5%; 1-81 minutes, 5-28%; 81-100 minutes, 28-98%; 100-135 minutes, 98%-0%). Survey scans of peptide precursors were performed at 120K FWHM resolution (m/z=200). Tandem MS was performed on the most abundant precursors exhibiting a charge state from 2 to 5 at a resolving power settings of 15K and fragmentation energy of 36V. HCD/CID fragmentation was applied with 35% collision energy and resulting fragments detected using the normal scan rate in the ion trap.

Data analysis procedures. Data analysis was performed with Proteome Discoverer v2.2 using SEQUEST HT, allowing for variable modifications (methionine oxidation: +15.995 Da; cysteine alkylation: +57.021 Da; photo-naproxen: +452.206 Da, +454.222 Da; photo-celecoxib: +543.151 Da, +545.167 Da; photo-indomethacin: +592.220 Da, +594.236 Da), two missed cleavages and mass tolerance of 10 ppm for the precursor ion, 0.02 Da and 0.6 Da for fragment ions from HCD and CID, respectively. For binding sites of photo-NSAIDs to COX-2 (Table 2), MS data was searched by SEQUEST HT and Byonic against the recombinant COX-2 with the photo-NSAID before and after click chemistry as a modification on any amino acid and assigned to tryptic or semi-tryptic peptides. For the proteomic analysis of K562 and Jurkat cells (Table 3, 4), MS/MS raw files of the tryptic digests were searched against the Swiss-Prot human database (downloaded in 2016) and a contaminant protein database. The statistically significant enriched proteome were determined according to the procedure of Washburn and co-workers.[6] Briefly, the normalized spectral abundance factor (NSAF) was calculated as the number of spectral counts divided by the protein's length, and then divided by the sum of spectral counts for all proteins in the experiment. The zero NSAF values were replaced by the minimum measured NSAF value and the natural log transformation of NSAF values was used for evaluation with the statistical t-test. Normalized protein assignments at 1% FDR were considered statistically significantly enriched if the fold change was greater than two and the associated p-value was <0.05 (t-test) in labeled samples than in samples treated with the tag 7. For experiments where biological replicates were not obtained, enrichment was determined by subtraction of all proteins observed in the samples treated with the tag 7. MS/MS data from cleavage fractions were searched against the entire proteome identified in tryptic digests for direct binding site characterization (Table 5). All calculations were performed in Microsoft Excel and all peptide spectral matches (PSMs) at 5% FDR were manually validated for precursor isotopic pattern in the MS1 and spectral assignment in the MS2.

Synthetic Procedures

Synthesis of methyl (S)-2-(6-hydroxynaphthalen-2-yl)propanoate (S1)

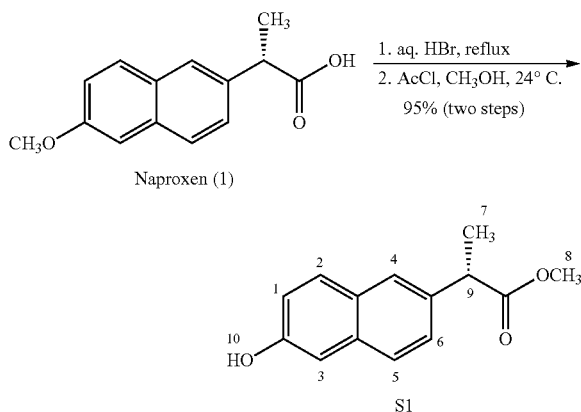

Step 1: Naproxen (1, 5.00 g, 21.7 mmol, 1 equiv) was added to aqueous HBr (48% w/w, 35 mL, 309 mmol, 14.2 equiv) in a round bottom flask fitted to a reflux condenser. The reflux condenser was connected to a vented trap containing saturated aqueous sodium bicarbonate solution. The mixture was stirred for 12 hours at reflux. The product mixture was cooled over 30 minutes to 24° C. The cooled solution was poured in deionized (DI) water (200 mL) and cooled in an ice bath until a visible white precipitate was formed. The precipitate was filtered through a fritted funnel, washed with DI water (3×30 mL) and dried for 2 hours in air.

Step 2: The crude white powder was dissolved in methanol (40 mL). Acetyl chloride (2.30 mL, 32.6 mmol, 1.50 equivalents) was added to the resulting solution at 0° C. and the mixture was heated for 4 hours at reflux. The product mixture was cooled over 30 minutes to 24° C. and evaporated to dryness. The resulting material was azeotroped with benzene (2×20 mL) to afford compound S1 as an off-white solid (4.70 g, 95%).

$R_f$=0.30 (20% ethyl acetate-hexane; UV). $_1$H NMR (500 MHz, DMSO-$d_6$): δ 9.71 (s, 1H, $H_{10}$), 7.73 (d, 1H, J=7.2 Hz, $H_2$), 7.65-7.63 (m, 2H, $H_4$/$H_5$), 7.31 (d, 1H, J=8.0 Hz, 66), 7.11-7.09 (m, 2H, $H_1$/$H_3$), 3.90 (q, 1H, J=7.3 Hz. $H_9$), 3.58 (s. 3H, $H_8$), 1.46 (d, 3H, J=7.3 Hz, $H_7$). $^{13}$C NMR (125 MHz, DMSO-$d_6$): δ 174.9 (C), 155.7 (C), 135.2 (C), 134.1 (C), 129.6 (CH), 128.1 (C), 126.8 (CH), 126.4 (CH), 126.1 (CH), 119.3 (CH), 108.9 (CH), 52.2 ($OCH_3$), 44.8 (CH) 18.9 ($CH_3$). IR (ATR-FTIR), $cm^{-1}$: 3348 (br), 2982 (m), 2957 (m), 2940 (m), 1703 (s), 1637 (s), 1613 (s), 1509 (s), 1486 (s), 1437 (m), 1338 (s), 1208 (m), 1171 (m), 1147 (m), 927 (m), 857 (m), 808 (m), 558 (m), 471 (m). LRMS-ESI (m/z): [M+H]$^+$ calculated for $C_{14}H_{15}O_3$, 231.1; found, 231.2.

The $^1$H NMR and $^{13}$C NMR of S1 prepared by the above procedures were in agreement with those reported previously.[7]

Synthesis of methyl (S)-2-(6-(2-(3-(but-3-yn-1-yl)-3H-diazirin-3-yl)ethoxy)naphthalen-2-ylpropanoate (S2)

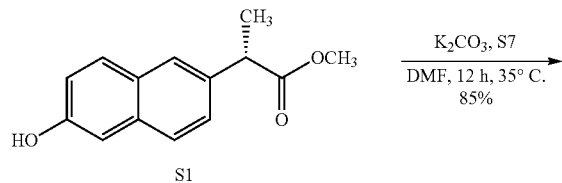

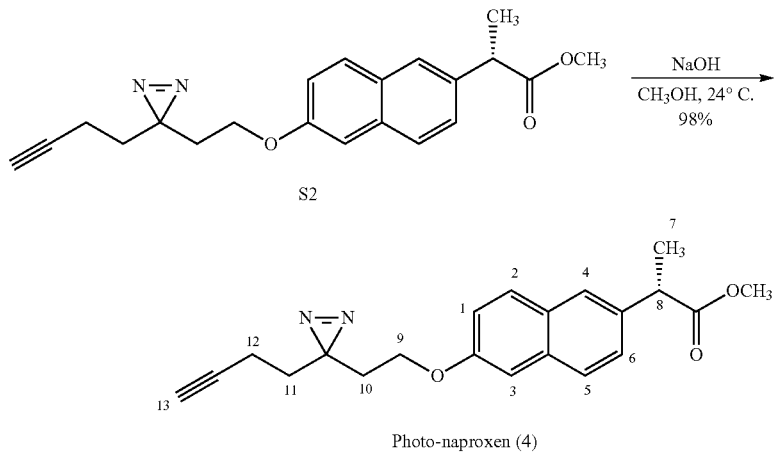

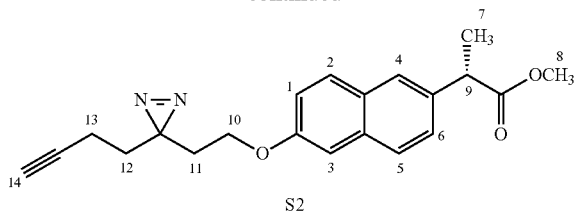

Potassium carbonate (300 mg, 2.17 mmol, 2.10 equiv) and iodide S7 (350 mg, 1.40 mmol, 1.00 equiv) was added to a solution of S (250 mg, 1.04 mmol, 1 equiv) in DMF (6.0 mL). The mixture was stirred for 12 hours at 35° C. The product mixture was poured into a separatory funnel containing DI water (15 mL) and diethyl ether (30 mL). The organic portion was separated, washed with brine and dried over magnesium sulfate. The magnesium sulfate was filtered off and the ethereal solution was concentrated in vacuo to afford a waxy material. The material was purified using flash-column chromatography (eluting with 0-40% ethyl acetate-hexane, two steps) to afford the diazirine S2 (310 mg, 85%).

$R_f$=0.37 (20% ethyl acetate-hexane; UV). $^1$H NMR (500 MHz, CDCl$_3$): δ 7.74 (d, 1H. J=8.5 Hz, H$_2$). 7.71 (d, 1H, J=8.2 Hz, H$_8$), 7.68 (s, 1H, H$_4$), 7.43 (dd, 1H. J=8.5, 1.8 Hz, H$_6$), 7.18 (dd, 1H, J=8.9, 2.5 Hz, H$_1$). 7.10 (d, 1H, J=2.4 Hz, H$_3$), 3.97 (t, 2H, J=7.2 Hz, H$_{10}$), 3.87 (q, 1H, J=7.2 Hz, H$_9$), 3.68 (s, 3H, H$_8$), 2.11 (td, 2H, J=8.1, 5.0 Hz, H$_{13}$), 2.02 (t, 1H, J=5.0 Hz, H$_{14}$), 1.98 (t, 2H, J=7.2 Hz, H$_{11}$), 1.78 (t, 2H, J=7.2 Hz, H$_{12}$), 1.60 (d, 3H, J=7.1 Hz, H$_7$). $^{13}$C NMR (125 MHz, CDCl$_3$): δ 175.1 (C), 156.4 (C), 135.9 (C), 133.6 (C), 129.4 (CH), 129.1 (C), 127.2 (CH), 126.3 (CH), 125.9 (CH), 119.1 (CH), 106.6 (CH). 82.8 (C), 69.2 (CH), 62.6 (OCH$_2$), 52.1 (OCH$_3$), 45.4 (CH), 32.9 (CH$_2$), 32.7 (CH$_2$), 26.7 (CN$_2$), 18.6 (CH$_3$), 13.3 (CH$_2$). IR (ATR-FTIR), cm$^{-1}$: 3295 (br), 2922, 2852, 2940, 1705 (s), 1634 (s), 1468 (m), 1510 (w), 1468 (m), 1393 (m), 1209 (m), 1180 (m), 939 (m), 811 (m), 640 (m), 475 (m), 1172 (m), 1147 (m), 930 (m), 857 (m), 808 (m), 560 (m), 490 (m). HRMS-ESI (m/z): [M+H]$^+$ calculated for C$_{21}$H$_{23}$N$_2$O$_3$, 351.1709; found, 351.1710.

Synthesis of (S)-2-(6-(2-(3-(but-3-yn-1-yl)-3H-diazirin-3-yl)ethoxy)naphthalen-2-yl)propanoic acid [photo-naproxen (4)]

Compound S2 (200 mg, 570 μmol, 1 equiv) was added to a 1M NaOH in methanol (3.0 mL). The mixture was stirred for 4 hours at 24° C. The product material was concentrated in vacuo. The residue obtained was acidified to pH 2, with KHSO$_4$ (1M) and the resulting mixture was added to ethyl acetate. The organic portion was separated, dried over anhydrous sodium sulfate, filtered and concentrated in vacuo to afford photo-naproxen (4) as a waxy solid (190 mg, 98%).

$^1$H NMR (500 MHz, CDCl$_3$): δ 7.72 (m, 3H, H$_2$/H$_4$/H$_5$), 7.45 (dd, 1H, J=8.2, 1.8 Hz, H$_6$), 7.18 (dd, 1H, J=8.5, 2.4 Hz, H$_1$), 7.09 (d, 1H, J=2.4 Hz, H$_3$), 3.97 (t, 2H, J=7.0 Hz, H$_9$), 3.90 (t, 1H, J=7.1 Hz, H$_8$), 2.13 (td, 2H, J=7.9, 2.9 Hz, H$_{12}$), 2.02 (t, 1H. J=2.6 Hz, H$_{13}$), 1.98 (t, 2H, J=7.1 Hz, H$_{10}$), 1.80 (t, 2H, J=7.5 Hz, H$_{11}$), 1.62 (d, 3H, 7.2 Hz, H$_7$). $^{13}$C NMR (125 MHz, CDCl$_3$): δ 180.1 (C), 156.5 (C), 135.2 (C), 133.7 (C), 129.4 (CH), 129.1 (C), 127.2 (CH), 126.3 (CH), 126.1 (CH), 119.1 (CH), 106.6 (CH), 82.8 (C), 69.2 (CH), 62.6 (OCH$_2$), 45.2 (CH), 32.9 (CH$_2$), 32.7 (CH$_2$). 26.7 (CN$_2$), 18.2 CH$_3$), 13.3 (CH$_2$). IR (ATR-FTIR), cm$^{-1}$: 3295 (br), 2921 (w), 2852 (m), 1703 (s), 1633 (s), 1605 (s), 1468 (m), 1393 (m), 1263 (m), 1208 (m), 1180 (w), 939 (w), 853 (w), 812 (w), 641 (w), 475 (w). HRMS-ESI: [M+Na]$^+$ calculated for C$_{20}$H$_{20}$N$_2$NaO$_3$, 359.1372; found, 359.1372.

Synthesis of 4-(5-hydroxy-3-(trifluoromethyl)-1H-pyrazol-1-yl)benzenesulfonamide (S4)

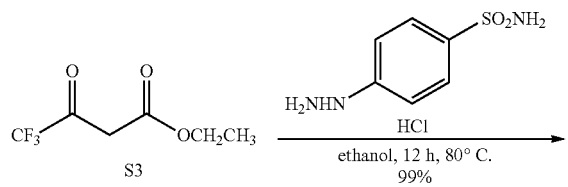

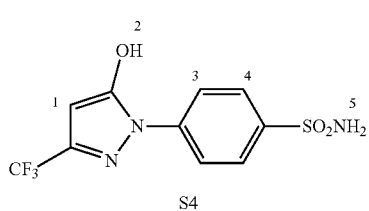

Ethyl 4, 4, 4-trifluoro-3-oxobutanoate (S3, 2.00 g, 10.9 mmol, 1 equiv) and 4-hydrazineylbenzenesulfonamide (2.40 g, 10.9 mmol, 1.00 equiv) were dissolved in ethanol (10 mL) and the resulting mixture was stirred for 12 hours at reflux. The product mixture was cooled for 30 minutes to 24° C. The solvent was evaporated in vacuo and the residue was poured into DI water (15 mL). The solution was acidified to pH 2 and a white precipitate formed. The precipitate was filtered through a frit funnel, the precipitate was filtered through a fritted funnel and dried for 2 hours in air to afford the benzenesulfonamide S4 as a slight yellow powder (3.30 g, 99%).

$^1$H NMR (500 MHz, DMSO-$d_6$): δ 12.86 (s, 1H, H$_2$), 7.96 (m, 4H, H$_3$/H$_4$), 7.46 (m, 2H, H$_5$), 5.97 (s, 1H, H$_1$). $^{13}$C NMR (125 MHz, DMSO-$d_6$): δ 154.8 (C), 142.7 (CH), 141.9 (q, 2JCF=37.2 Hz, C), 140.6 (CH), 127.3 (CH), 122.7 (q, 1JCF=267.4 Hz, CF$_3$), 122.3 (C), 86.4 (C). $^{19}$F NMR (375 MHz, DMSO-$d_6$): δ −61.5. IR (ATR-FTIR), cm$^{-1}$: 3449 (br), 3383 (w), 3280 (w), 2983 (w), 2940 (m), 1703 (s), 1637 (s), 1613 (m), 1589 (m), 1579 (m), 1556 (w), 1535 (m), 1436 (m), 1408 (m), 1208 (m), 1102 (m), 991 (m), 927 (w), 895 (w), 848 (w), 795 (w), 778 (m), 706 (w), 541 (w), 470 (w).

Synthesis of 4-(5-(2-(3-(but-3-yn-1-yl)-3H-diazirin-3-yl)ethoxy)-3-(trifluoromethyl)-1H-pyrazol-1-yl)benzenesulfonamide (5)

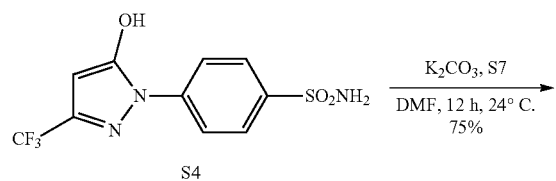

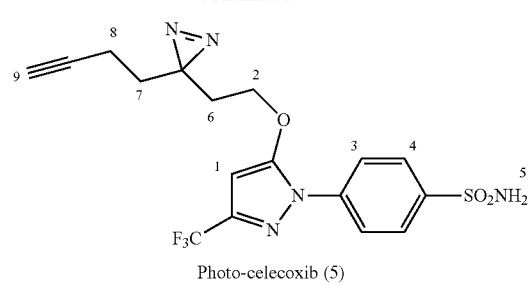

Photo-celecoxib (5)

A mixture of compound S4 (90.0 mg. 286 μmol, 1 equiv), and iodo-diazirine S7 (70.0 mg, 286 μmol, 1.00 equiv) was dissolved in DMF (3.0 mL) at 24° C. To this mixture, was added potassium carbonate (40.0 mg, 286 μmol, 1.00 equiv) and stirred for 12 hours at 24° C. The reaction mixture was partitioned between ethyl acetate (30 mL) and DI water (15 mL) and the organic portion was separated and washed with brine (3×15 mL). The combined organic portion was dried over anhydrous sodium sulfate, filtered and concentrated in vacuo to afford an off white powder. The powder was purified by flash column chromatography (30-60% ethyl acetate-hexane, three steps) to afford photo-celecoxib (5) as a white powder (92.0 mg, 75%).

$R_f$=0.20 (40% ethyl acetate-hexane; UV). $^1$H NMR (500 MHz, CDCl$_3$): δ 8.05 (d, 2H, J=8.2 Hz, H$_3$), 8.02 (d, 2H, J=8.1 Hz, H$_4$), 5.95 (s, 1H, H$_1$), 5.13 (br, 2H, H$_8$), 4.04 (t, 2H, J=7.2 Hz, H$_2$), 2.05-2.03 (m, 5H, H$_6$/H$_8$/H$_9$), 1.71-1.69 (m, 2H, H$_7$). $^{13}$C NMR (125 MHz, CDCl$_3$): δ 154.6 (C), 143.0 (q, 2JCF=38.8 Hz, CH), 141.1 (C), 140.4 (C), 127.6 (CH), 122.5 (CH), 121.7 (q, 1JCF=267.5 Hz CF$_3$), 85.3 (C), 82.4 (C), 69.7 (CH), 67.6 (OCH$_2$). 32.4 (CH$_2$), 32.1 (CH$_2$), 26.1 (CN$_2$), 13.2 (CH$_3$). $^{19}$F NMR (375 MHz, CDCl$_3$): δ −63.6. IR (ATR-FTIR), cm$^{-1}$: 3277 (br), 1590 (s), 1563 (m), 1512 (m), 1490 (w), 1416 (m), 1380 (w), 1335 (w), 1246 (m), 1151 (m), 1101 (m), 968 (w), 908 (w), 840 (w), 743 (w), 715 (w), 626 (m), 543 (w). HRMS-ESI (m/z): [M+H]$^+$ calculated for C$_{17}$H$_{17}$F$_3$N$_5$O$_3$S, 428.0999; found, 428.0949.

Synthesis of N-(2-(3-(but-3-yn-1-yl)-3H-diazirin-3-yl)ethyl)-2-(1-(4-chlorobenzoyl-5-methoxy-2-methyl-1H-indol-3-yl)acetamide (6)

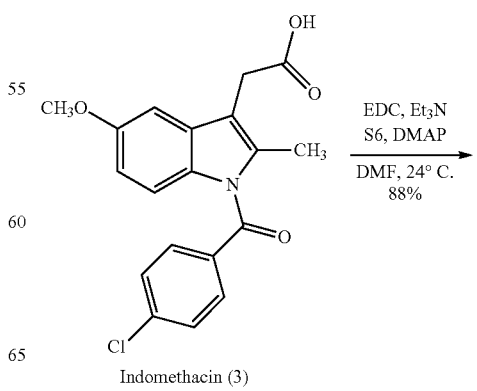

Indomethacin (3)

Synthesis of the Photo-Glutarimide 8

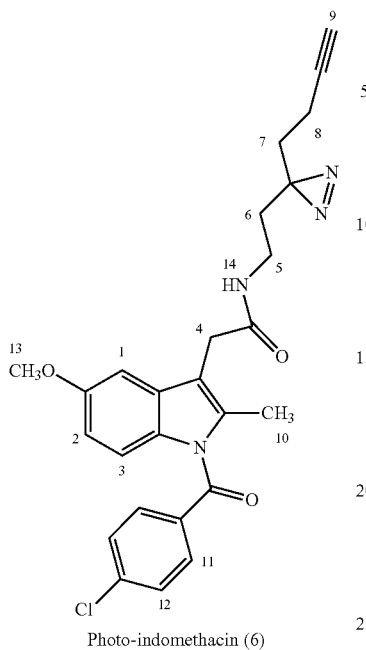

Photo-indomethacin (6)

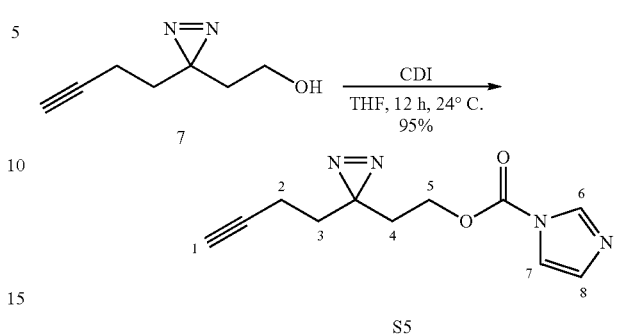

N-(3-Dimethylaminopropyl)-N'-ethylcarbodiimide hydrochloride (418 mg, 2.19 mmol, 1.50 equiv), triethyl amine (400 μL, 2.98 mmol. 2.00 equiv), N,N'-dimethylaminopyridine (36.0 mg, 290 μmol, 0.20 equiv) and the amine S6 (200 mg, 1.46 mmol, 1.00 equiv) were added in sequence to a solution of indomethacin (3, 522 mg, 1.46 mmol, 1 equiv) in DMF (10 mL) at 24° C. The reaction mixture was stirred for 12 hours at 24° C. and then quenched by addition of potassium hydrogen sulfate (1M, 10 mL). The mixture was transferred into a separatory funnel containing ethyl acetate (50 mL). The organic portion was separated, washed with brine (3×10 mL) and the dried over anhydrous sodium sulfate. The sodium sulfate was filtered and the eluent was concentrated in vacuo to afford a crude residue. The crude residue was dissolved in ethyl acetate and crystallized from hexane to afford photo-indomethacin (6) as a white solid (615 mg, 88%).

$^1$H NMR (500 MHz, CDCl$_3$): δ 7.70 (d, 2H, J=8.0 Hz, H$_{11}$), 7.49 (d, 2H, J=7.8 Hz, H$_{12}$), 6.92 (s, 1H, H$_1$), 6.9 (d, 1H, J=9.0 Hz, H$_3$), 6.72 (d, 1H, J=9.0 Hz, H$_2$), 5.78 (s, 1H, H$_{14}$), 3.83 (s, 3H, H$_{13}$), 3.65 (s, 2H, H$_4$), 3.11 (t, 2H, J=7.2 Hz, H$_5$), 2.42 (s, 3H, H$_{10}$), 1.88 (dd, 2H, J=7.5, 2.4 Hz, H$_8$), 1.84-1.83 (m, 1H, H$_9$) 1.62 (t, 2H, t, J=7.0 Hz, H$_6$), 1.53 (t. 2H, J=7.2 Hz, H$_2$). $^{13}$C NMR (125 MHz, CDCl$_3$): δ 169.9 (C), 168.2 (C), 156.2 (C), 139.4 (C-Cl), 136.4 (C), 133.5 (=C—CH$_3$), 131.1 (CH), 130.9 (CH), 130.3 (C), 129.1 (=C—NR2), 115.1 (CH), 112.6 (CH), 112.2 (C), 100.9 (CH), 82.5 (C), 69.3 (CH), 55.7 (OCH$_3$), 34.6 (CH$_2$), 32.4 (CH$_2$), 32.1 (CH$_2$), 31.8 (CH), 26.7 (CN$_2$), 13.3 (CH$_2$), 12.9 (CH$_3$). IR (ATR-FTIR), cm$^{-1}$: 3297 (br), 3066 (w), 2930 (w), 2835 (w), 1673 (s), 1650 (m), 1590 (w), 1525 (s), 1476 (m), 1455 (m), 1356 (m), 1314(s), 1222 (s), 1148 (w), 1088 (m), 1065 (w) 909 (w), 833 (w), 728 (w), 644 (w) 481(w). HRMS-ESI (m/z): [M+H]$^+$ calculated for C$_{26}$H$_{26}$ClN$_4$O$_3$, 477.1693; found, 477.1660.

Step 1. Synthesis of 2-(3-(but-3-yn-1-yl)-3H-diazirin-3-yl)ethyl 1H-imidazole-1-carboxylate (S5): To a solution of 2-(3-(but-3-yn-1-yl)-3H-diazirin-3-yl) ethan-1-ol (200 mg, 1.45 mmol, 1 equiv) in tetrahydrofuran (10 mL) at 24° C., was added carbonyldiimidazole (950 mg, 5.80 mmol. 4.00 equiv). The mixture was allowed to stir for 12 hours at 24° C. The product mixture was concentrated in vacuo to a solid residue. The residue was directly loaded to a hexane-equilibrated silica gel column and the desired material was eluted using a 50-100% ethyl acetate-hexane solvent, two steps). The imidazole S5 was isolated as colorless oil after concentration of the residual solvent (320 mg, 95%).

R$_f$=0.15 (40% ethyl acetate-hexane; UV). $^1$H NMR (500 MHz, CDCl$_3$): δ 8.13 (s, 1H, H$_6$) 7.42-7.41 (m, 1H, H$_7$), 7.03-7.02 (m, 1H, H$_8$), 4.26-4.23 (t, 2H, J=7.1 Hz, H$_8$), 1.99-1.96 (m, 3H, H$_2$/H$_1$), 1.91-1.88 (t, 2H, J=6.9 Hz, H$_4$), 1.66-1.63 (t, 2H, J=7.1 Hz, H$_3$). $^{13}$C NMR (125 MHz, CDCl$_3$): δ 148.3 (C). 137.1 (CH), 130.7 (CH), 117.1 (CH). 82.3 (C), 69.6 (CH), 62.9 (OCH$_2$), 32.1 (CH$_2$), 32.0 (CH$_2$), 26.0 (CN$_2$), 13.1 (CH$_2$). IR (ATR-FTIR), cm$^{-1}$: 3291 (br), 3158 (w), 3132 (m), 2960 (w), 2921 (m), 2858 (m), 1758 (s), 1588 (s), 1525 (m), 1473 (m), 1444 (m), 1404 (m), 1380 (w), 1316 (w), 1282 (w), 1240 (w), 1173 (w), 1095 (m), 1058 (m), 1003 (w), 898 (m), 833 (w), 768 (w), 749 (w), 649 (w), 598 (w), 526 (w). HRMSESI (m/z): [M+H]$^+$ calculated for C$_{11}$H$_{13}$N$_4$O$_2$, 233.1039; found, 233.1064.

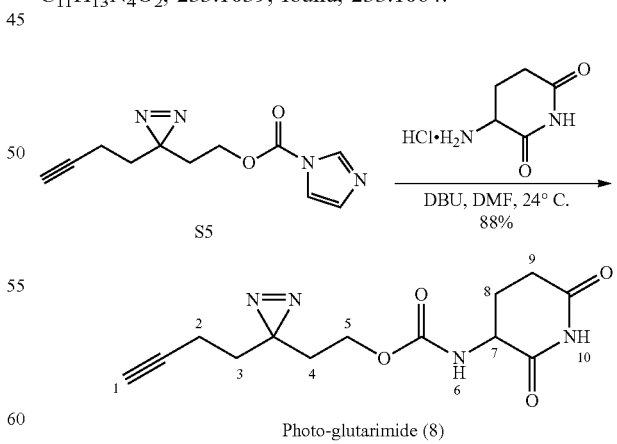

Photo-glutarimide (8)

Step 2. Synthesis of 2-(3-(but-3-yn-1-yl)-3H-diazirin-3-yl)ethyl (2,6-dioxopiperidin-3-yl)carbamate (8): 1,8-Diazabicyclo[5.4.0]undec-7-ene (650 mg, 4.31 mmol, 5.30 equiv) and 3-aminopiperidine-2,6-dione hydrochloride (600 mg, 2.58 mmol, 3.14 equiv) were added in sequence to a stirred solution of 2-(3-(but-3-yn-1-yl)-3H-diazirin-3-yl) ethyl 1H-imidazole-1-carboxylate (200 mg, 820 µmol, 1 equiv) in DMF (10 mL). The mixture was stirred for 12 hours at 24° C. The product mixture was partitioned between ethyl acetate (30 mL) and DI water (20 mL). The organic portion was separated and the aqueous portion was extracted with ethyl acetate (2×20 mL). The combined organic portion was washed with DI water (4×10 mL) then with brine (10 mL). The solution was dried over anhydrous sodium sulfate, filtered and concentrated in vacuo to afford the crude material. The crude was purified by silica gel flash chromatography (using 20-60% ethyl acetate-hexanes, two steps) to afford the photo-glutarimide 8 as an oil (220 mg, 86%).

$R_f$=0.20 (40% ethyl acetate-hexane). $^1$H NMR (500 MHz, CDCl$_3$): δ 8.60 (m, 1H, H$_{10}$), 5.72 (m, 1H, H$_6$), 4.41-4.36 (m, 1H, H$_2$), 4.02 (t, 2H, J=5.7 Hz, H$_8$), 2.84-2.49 (m, 4H, H$_8$/H$_9$), 2.04-1.91 (m, 3H, H$_2$/H$_1$). 1.78 (t, 2H, J=6.2 Hz, H$_4$), 1.70 (t, 2H, J=7.2 Hz, H$_3$). $^{13}$C NMR (125 MHz, CDCl$_3$): δ 171.6 (C), 171.4 (C), 155.9 (C), 82.6 (C), 69.4 (CH), 65.1 (CH), 60.2 (OCH$_2$), 32.5 (CH$_2$), 32.2 (CH$_2$), 31.2 (CH$_2$), 25.2 (CN$_2$), 13.2 (CH$_2$). IR (ATR-FTIR), cm$^{-1}$: 3283 (br), 3107 (w), 2958 (w), 2918 (m), 2858 (w), 1694 (s), 1587 (s), 1527 (m), 1356 (m), 1331 (m), 1302 (m), 1197 (m), 1082 (w), 1063 (m), 1037 (m), 991 (w), 776 (m), 650 (m), 472 (m). HRMS-ESI (m/z): [M+Na]$^+$ calculated for C$_3$H$_{16}$N$_4$NaO$_4$, 315.1069; found, 315.1076.

Synthesis of 1-phenyl-3-(trifluoromethyl)-1H-pyrazol-5-ol (S9)

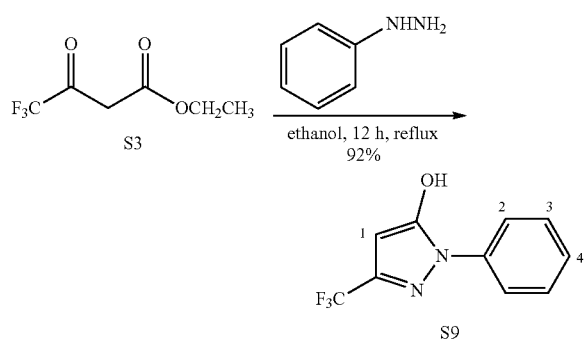

Ethyl 4, 4, 4-trifluoro-3-oxobutanoate (S3, 200 µL, 1.37 mmol, 1 equiv) and phenylhydrazine (148 µL, 1.37 mmol, 1.00 equiv) were dissolved in ethanol (1.4 mL) and the resulting mixture was stirred for 12 hours at reflux. The reaction mixture was cooled to 24° C. and the solvent was evaporated in vacuo. The residue was dissolved into ethyl acetate (3 mL) and washed with 1N HCl (3×3 mL). The organic layer was dried over sodium sulfate, filtrated and concentrated in vacuo. The resulting material was washed with dichloromethane (5 mL) to afford the compound as orange solid (289 mg. 92%).

$R_f$=0.25 (30% ethyl acetate-hexanes; UV). $^1$H NMR (500 MHz, DMSO-d$_6$): δ 7.71 (d, 2H, H$_2$, J=8.0 Hz), 7.51 (dd, 2H, J=8.0 Hz, H$_3$), 7.38 (t, 1H, J=8.0 Hz, H$_4$), 5.94 (s, 1H, H$_1$). $^{13}$C NMR (125 MHz, DMSO-d$_6$): δ 153.7 (C), 140.4 (q, 2JCF=37.4 Hz, C), 137.7 (C), 129.1 (CH), 127.2 (CH), 122.3 (CH), 121.3 (q, 1JCF=266.9 Hz. CF$_3$), 85.6 (q, 3JCF=1.6 Hz, CH). $^{19}$F NMR (375 MHz, DMSO-d$_6$): δ −61.8. IR (ATR-FTIR), cm$^{-1}$: 3373 (br), 1599 (m), 1505 (m), 1491 (m), 1456 (m), 1407 (m), 1151 (s), 1119 (s), 984 (s), 758 (s), 691 (s). HRMS-ESI (m/z): [M+H]$^+$ calculated for C$_{10}$H$_8$F$_3$N$_5$O, 229.0583; found, 229.0598.

Synthesis of 5-(2-(3-(but-3-yn-1-yl)-3H-diazirin-3-yl)ethoxy)-1-phenyl-3-(trifluoromethyl)-1H-pyrazole (9)

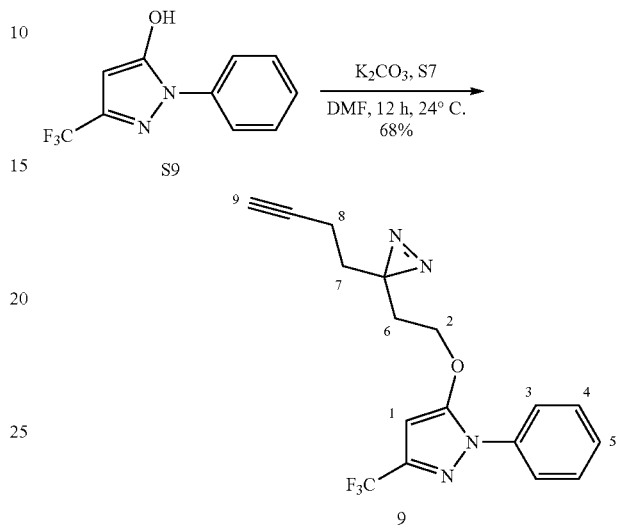

A mixture of compound S9 (38.1 mg, 167 µmol, 1 equiv) and iodo-diazirine S7 (41.4 mg, 178 µmol, 1.00 equiv) was dissolved in DMF (1.7 ML) at 24° C. Potassium carbonate (46.1 mg, 334 µmol, 2.00 equiv) was added to the resulting mixture. The reaction mixture was stirred for 12 hours at 50° C. then cooled for 30 minutes to 24° C. and partitioned between ethyl acetate (5 mL) and DI water (5 mL). The organic portion was separated and washed with brine (3×5 mL). The organic portion was dried over anhydrous sodium sulfate, filtered and concentrated in vacuo to afford an off white powder. The powder was purified by flash column chromatography (20% ethyl acetate-hexanes) to afford the celecoxib analog 9 as a pale yellow oil (39.4 mg, 68%).

$R_f$=0.58 (20% ethyl acetate-hexanes; UV). $^1$H NMR (500 MHz, CDCl$_3$): δ 7.74 (d, 2H, J=7.6 Hz, H), 7.48 (dd, 2H, J=7.6, 7.6 Hz, H$_4$), 7.36 (t, 1H, J=7.6, 7.6 Hz, H). 5.92 (s, 1H, H$_1$), 3.99 (t, 2H, J=6.0 Hz, H$_2$), 2.01-1.95 (m, 5H, H$_6$/H$_8$/H$_9$), 1.66 (t, 2H, J=6.8 Hz, H$_7$). $^{13}$C NMR (125 MHz, CDCl$_3$): δ 154.0 (C), 141.8 (q, 2JCF=38.4 Hz, CH), 137.5 (C), 129.0 (CH), 127.7 (CH), 123.0 (CH), 120.9 (q, 1JCF=267.3 Hz CF$_3$), 84.7 (q, 3JCF=2.1 Hz, CH), 82.4 (C), 69.4 (CH), 67.1 (OCH$_2$), 32.6 (CH$_2$), 32.3 (CH$_2$), 26.1 (CN$_2$), 13.2 (CH$_3$). $^{19}$F NMR (375 MHz, CDCl$_3$): δ −63.3 ppm. IR (ATR-FTIR), cm$^{-1}$: 3303 (s), 1594 (m), 1562 (m), 1508 (m), 1488 (m), 1457 (m), 1243 (s), 1126 (s), 1099 (s), 968 (s), 759 (s), 639 (s) cm-1. HRMS-ESI (m/z): [M+H]$^+$ calculated for C$_{17}$H$_{16}$F$_3$N$_4$O, 349.1271; found, 349.1276.

Synthesis of 2-aminoethyl 2-azidoacetate (S11)

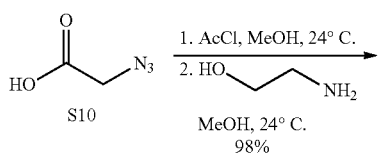

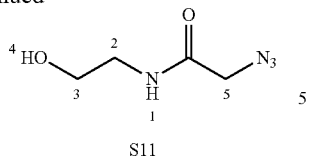

S11

Step 1. Acid chloride formation: Azidoacetic acid (S10. 154 mg, 1.49 mmol, 1 equiv) was dissolved in methanol (10 mL) at 24° C. Acetyl chloride (211 µL, 2.49 mmol, 2.00 equiv) was added dropwise to the stirred solution at 24° C. The resulting mixture was stirred for 6 hours at 24° C. The product mixture was evaporated to dryness and used directly in the following step.

Step 2. Synthesis of 2-aminoethyl 2-azidoacetate (S11): The azido-acetyl chloride (151 mg. 1.49 mmol, 1 equiv) obtained in the previous step was dissolved in methanol (10 mL) at 24° C. Aminoethanol (450 µL, 7.47 mmol, 5.00 equiv) was added dropwise to the stirred solution at 24° C. The resulting mixture was stirred for 16 hours at 24° C. The product mixture was concentrated to dryness. The residue obtained was purified by flash-column chromatography (eluting with 10% ethyl acetate-hexanes, grading to 20% ethyl acetate-hexanes, one step) to afford 2-aminoethyl 2-azidoacetate (S11) as clear yellow oil (209 mg, 98%).

$R_f$=0.60 (10% methanol-dichloromethane; ninhydrin). $^1$H NMR (500 Hz, CDCl$_3$): δ 7.01 (br s, 1H, H$_1$), 3.96 (s. 2H, H$_5$), 3.68 (t, 2H, J=5.0 Hz, H$_3$), 3.57 (br s, 1H, H$_4$), 3.41 (td, 2H, J=5.5, 5.0 Hz, H$_2$). $^{13}$C NMR (125 Hz, CDCl$_3$): δ 167.7 (C), 62.0 (CH$_2$), 52.8 (CH$_2$), 42.3 (CH$_2$). IR (ATR-FTIR), cm$^{-1}$: 3306 (s), 2107 (s), 1655 (s), 1548 (m). HRMS-ESI (m/z): [M+H]$^+$ calculated for C$_4$H$_9$N$_4$O$_2$, 145.0726; found, 145.0720.

Synthesis of 2-aminoethyl 2-azidoacetate (S13)

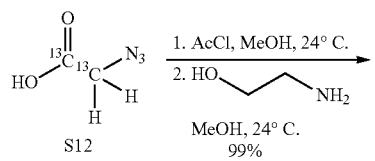

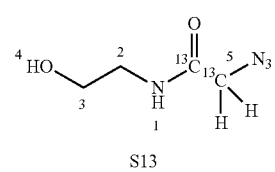

S13

Step 1. Acid chloride formation: Azidoacetic acid-13C2 (S12, 146 mg, 1.42 mmol, 1 equiv) was dissolved in methanol (10 mL) at 24° C. Acetyl chloride (200 µL, 2.84 mmol, 2.00 equiv) was added dropwise to the stirred solution at 24° C. The resulting mixture was stirred for 6 hours at 24° C. The product mixture was evaporated to dryness and used directly in the following step.

Step 2. Synthesis of 2-aminoethyl 2-azidoacetate (S13): The azidoacetyl chloride-$^{13}$C$_2$ (172 mg, 1.42 mmol, 1 equiv) obtained in the previous step was dissolved in methanol (10 mL) at 24° C. Aminoethanol (427 µL, 7.10 mmol, 5.00 equiv) was added dropwise to the stirred solution at 24° C. The resulting mixture was stirred for 16 hours at 24° C. The product mixture was concentrated to dryness. The residue obtained was purified by flash-column chromatography (eluting with 10% ethyl acetate-hexanes, grading to 20% ethyl acetate-hexanes, one step) to afford 2-aminoethyl 2-azidoacetate-$^{13}$C$_2$ (S13) as clear yellow oil (207 mg, 99%).

$R_f$=0.60 (10% methanol-dichloromethane; ninhydrin). $^1$H NMR (500 MHz, CDCl$_3$): δ 6.73 (br s, 1H, H$_1$), 4.17-3.87 (dd, 2H, JCH=144.1, 5.8 Hz, H$_5$), 3.76 (t, 2H, J=5.5 Hz, H$_3$), 3.48 (td, 2H, J=5.5, 2.0 Hz, H$_2$), 2.30 (br s, 1H, H$_4$). $^{13}$C NMR (125 MHz, CDCl$_3$): δ 167.7 (d, JCC=54.9 Hz, 13C), 62.1 (CH$_2$), 52.9 (d, JCC=54.9 Hz, 13CH$_2$), 42.3 (CH$_2$). IR (ATR-FTIR), cm$^{-1}$: 3272 (s), 2946 (s), 2017 (s), 1654 (s). HRMS-ESI (m/z): [M+H]$^+$ calculated for C$_2$$_3$C$_2$H$_9$N$_4$O$_2$, 147.0793; found, 147.0789.

Synthesis of the Cleavable Biotin Azide Probe 10

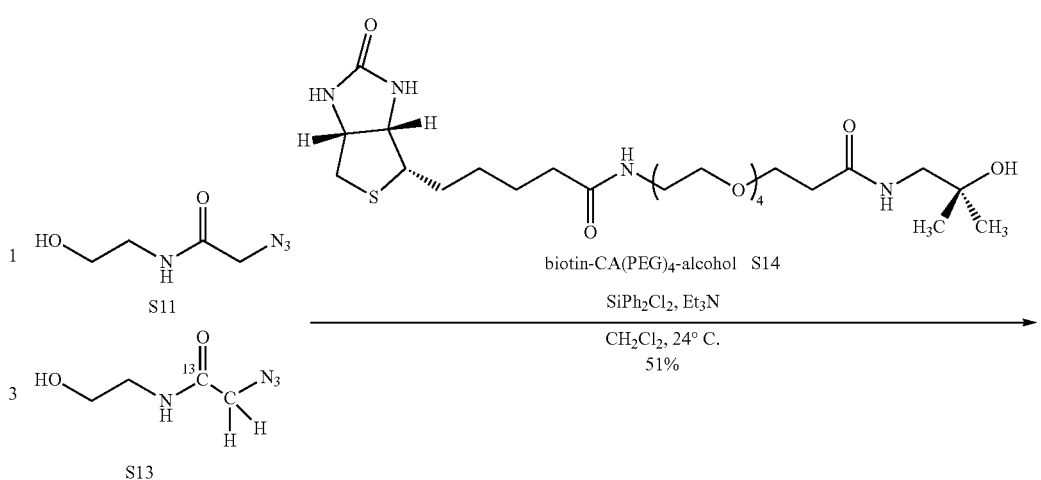

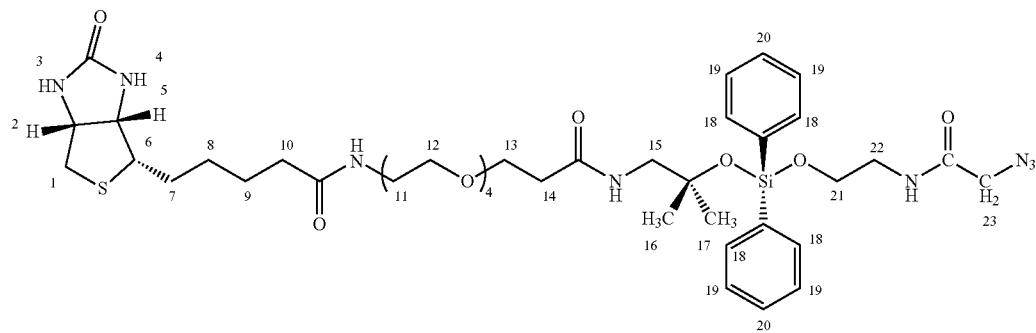

cleavable biotin azide probe 10

Triethylamine (102 μL, 736 μmol, 20.0 equiv) and dichlorodiphenylsilane (38.8 μL, 184 μmol. 5.00 equiv) were added in sequence to a stirred solution of the biotin-CA (PEG)$_4$-alcohol S14[5] (20.7 mg, 36.8 μmol, 1 equiv) in dichloromethane (370 μL). The resulting solution was stirred for 2 hours at 24° C. A 1:3 mixture of the azide S11 and the azide-$^{13}C_2$ S13 (53.0 mg, 368 μmol, 10.0 equiv) was added to the stirred solution. The resulting solution was stirred for an additional 12 hours at 24° C. The product mixture was diluted sequentially with dichloromethane (3 mL) and saturated aqueous sodium bicarbonate solution (3 mL). The resulting biphasic mixture was transferred to a separatory funnel and the layers that formed were separated. The aqueous layer was extracted with dichloromethane (3·3 mL), and the organic layers were combined. The combined organic layers were dried over sodium sulfate. The dried solution was filtered, and the filtrate was concentrated by rotary evaporation. The residue obtained was purified by flash-column chromatography (eluting with 1% methanol-dichloromethane, grading to 10% methanol-dichloromethane, 3 steps) to afford the IsoTaG azido silane probe 10 as a clear oil (16.6 mg, 51%).

$R_f$=0.43 (5% methanol-dichloromethane; 12). $^1$H NMR (600 MHz, CD$_3$OD): δ 7.66 (d, 4H, J=6.6 Hz, His), 7.43 (t, 2H, J=7.2 Hz, H$_2$a), 7.37 (t, 4H, J=7.8 Hz, H$_{19}$), 4.47 (dd, 1H, J=7.8, 5.4 Hz, H$_2$), 4.29 (dd, 1H, J=7.8, 4.2 Hz, H$_5$), 3.94 (d, 0.5H, J=4.8 Hz, H$_{23}$), 3.85-3.83 (m, 1.5H, H$_{23}$), 3.71 (t, 2H, J=6.0 Hz, H$_{11}$), 3.61-3.55 (m, 18H, H$_{11}$/H$_{12}$/H$_{15}$), 3.52 (t, 2H, J=6.5 Hz, H$_{21}$), 3.44-3.41 (m, 0.5H, H$_{22}$), 3.35 (t, 1.5H, J=5.0 Hz, H$_{22}$), 3.19 (dt, 1H, J=5.0, 4.5 Hz, H$_6$), 2.92 (dd, 1H, J=12.6, 5.4 Hz, H$_{10}$), 2.69 (d, 1H, J=12.6 Hz, H$_1$), 2.45 (t, 2H, J=6.0 Hz, H$_{14}$), 2.21 (t, 2H, J=7.5 Hz, H$_{10}$), 1.75-1.55 (m, 4H, H$_7$/H$_9$), 1.44 (quint, 2H, J=7.5 Hz, H$_8$), 1.25 (s, 6H, H$_{16}$/H$_{17}$). $^{13}$C NMR (151 MHz, CD$_3$OD): δ 176.1 (C), 174.1 (C), 170.2 (d, JCC=52.8 Hz, 13C), 166.1 (C), 136.1 (4×CH), 135.6 (2×C), 131.4 (2×CH), 128.9 (4×CH), 77.0 (CH$_2$), 71.6 (CH$_2$), 71.5 (3×CH$_2$) 71.3 (2×CH$_2$), 70.6 (CH$_2$), 68.4 (CH$_2$), 63.4 (CH), 62.7 (CH$_2$) 61.6 (CH), 57.0 (CH$_2$), 52.97 (d, Jcc=52.8 Hz, $^{13}$CH$_2$), 51.6 (CH$_2$), 42.6 (CH$_2$), 41.1 (CH$_2$), 40.4 (CH$_2$), 37.8 (CH$_2$), 36.7 (CH$_2$), 29.8 (CH$_2$), 29.5 (CH$_2$), 28.2 (2×CH$_3$), 26.8 (CH$_2$). IR (ATR-FTIR), cm$^{-1}$: 3296 (br), 2927 (m), 2103 (s), 1683 (s), 1644 (s), 1116 (s). HRMS-ESI (m/z): [M+Na]+ calculated for C$_{41}$H$_{62}$N$_8$O$_{10}$SSiNa/ C$_{39}$$^{13}$C$_2$H$_{62}$N$_8$O$_{10}$SSiNa, 909.3977/911.4044; found, 909.3932/911.3986.

ADDITIONAL REFERENCES FOR METHODS (1) Still, W. C.; Kahn, M.; Mitra, A. J. Org. Chem. 1978, 43, 2923.
(2) Pangborn, A. B.; Giardello, M. A.; Grubbs, R. H.; Rosen, R. K.; Timmers. F. J. Organometallics 1996, 15, 1518.
(3) Lee, P. J. J.; Compton, B. J.; Patent, U. S., Ed.; Waters Investments Limited: USA, 2007; Vol. 7229539.
(4) Wang, W.; Hong, S.; Tran, A.; Jiang, H.; Triano, R.; Liu, Y.; Chen, X.; Wu, P. Chem Asian J 2011, 6, 2796.
(5) Szychowski, J.; Mahdavi, A.; Hodas, J. J. L.; Bagert, J. D.; Ngo, J. T.; Landgraf, P.; Dieterich, D. C.; Schuman, E. M.; Tirrell, D. A. J. Am. Chem. Soc. 2010, 132, 18351.
(6) Zybailov, B.; Mosley, A. L.; Sardiu, M. E.; Coleman, M. K.; Florens, L.; Washburn, M. P. J Proteome Res 2006, 5, 2339.
(7) Mésangeau, C.; Pérès, B.; Descamps-Franeois, C.; Chavatte, P.; Audinot, V.; Coumailleau, S.; Boutin, J. A.; Delagrange, P.; Bennejean, C.; Renard, P.; Caignard, D. H.; Berthelot, P.; Yous. S. Bioorg Med Chem 2010, 18, 3426.

Example 2: Synthesis of an Electronically-Tuned Minimally Interfering Alkynyl Photo-Affinity Label to Measure Small Molecule-Protein Interactions Reported herein is the synthesis of an electronically-tuned minimally interfering photoaffinity label (MI-PAL), a compact five-carbon tag functionalized with an alkyl diazirine and alkyne handle. MI-PAL is compatible with protein photo-conjugation, click chemistry and mass spectrometry and readily installed to complex molecules for biological target identification.

The development of small multifunctional chemical tags that are readily embedded to a small molecule has accelerated target identification for non-covalent ligands. These chemical tags typically possess two primary functions: first, photo-conjugation chemistry to covalently capture the protein target and second, a reporter group for characterization of the liganded proteome.[1,2] Photo-affinity labels (PALs) like the aryl azide, benzophenone, and diazirine generate short-lived highly reactive nitrene, carbene or diradical intermediates, respectively, that insert to nearby biomolecules.[3-5] The covalent conjugation event facilitates subsequent ligand-dependent detection of the biomolecule. To allow for the greatest flexibility in detection, a biocompatible handle (e.g., alkyne) is commonly embedded to the chemical tag for versatile functionalization with a reporter molecule via copper-catalyzed azide-alkyne cycloaddition (CuAAC).[4]

Figure 28:
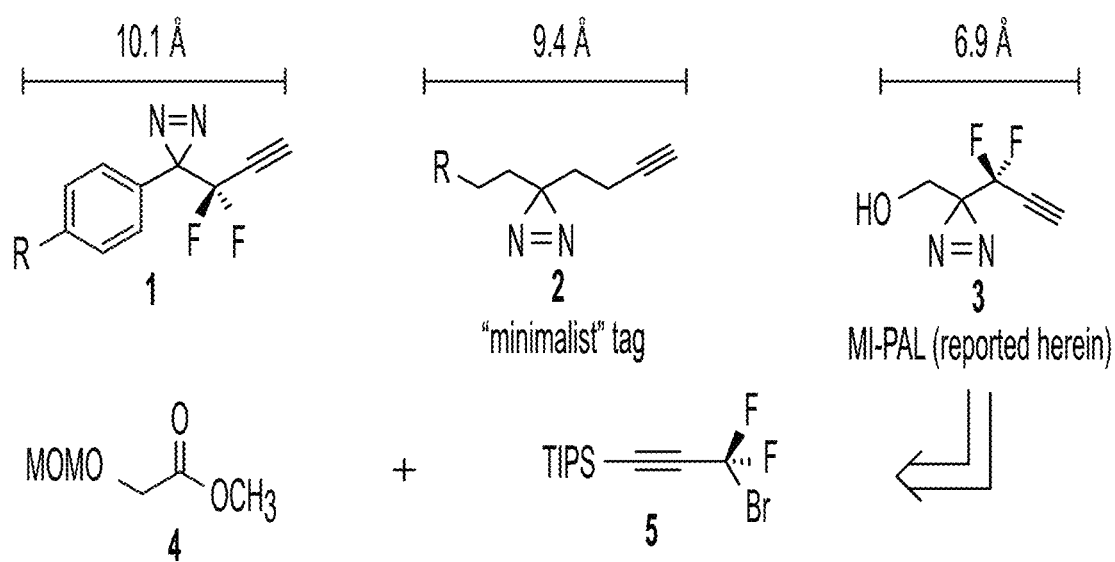
FIG. 28 shows structures of arylalkyne 1, "minimalist" tag 2, and MI-PAL (3), chemical tags that possess a diazirine functional group and alkyne reporter handle. Retrosynthesis of 3 proceeds through the ester 4 and alkyne 5.

Equally important is the facile integration of the chemical tag to the ligand in a minimally perturbative manner in order to preserve the native interactions of the ligand with the proteome. Thus, of the available PALs, the diazirine has seen recent application in numerous target identification studies due to its small size.[6-8] Integration of the diazirine with an alkyne reporter handle have yielded chemical tags like the aryl diazirine 1,[9] 10.1 Å in length, or the "minimalist" tag (2),[10] 9.4 Å in length (FIG. 28). The minimalist tag (2) has been applied to drug on-target[11] and off-target identification.[12,11] fragment based screening,[13] and binding site mapping.[14,13]

Synthesis of an electronically-tuned five carbon tag, such as the diazirine 3, would afford a smaller alkyl tag scaffold (6.9 Å)[15] with universally improved photoconjugation and CuAAC properties (FIG. 28). Photochemical carbene intermediates and CuAAC reaction kinetics are strongly dependent on electronic substituent effects. Electronic stabilization of the reactive carbene by fluorine was first demonstrated with 3-trifluoromethyl-3-phenyldiazirine, which possessed superior stability and selectivity as compared to alkyl diazirines.[16] Reactive carbenes formed from diazirines can produce intramolecular and intermolecular products that may differ based on the substituents adjacent to the carbene.[5] Electronic tuning of the alkyne with fluorine likewise accelerates strain-promoted azide-alkyne cycloaddition[7] and CuAAC, with measured improvements in reaction rates of 18-fold greater for the difluoropropyne relative to the dihydropropyne.[18] Based on these data, we hypothesized that strategic placement of fluorine adjacent to the alkyne and diazirine functional groups would improve the essential properties required for the chemical tag and provide synthetic access to a minimally-interfering photo-affinity label (MI-PAL, 3). The tag was retrosynthetically accessed by coupling the ester 4 to a monobromodifluoroalkyne 5, followed by installation of the diazirine.

Figure 29:
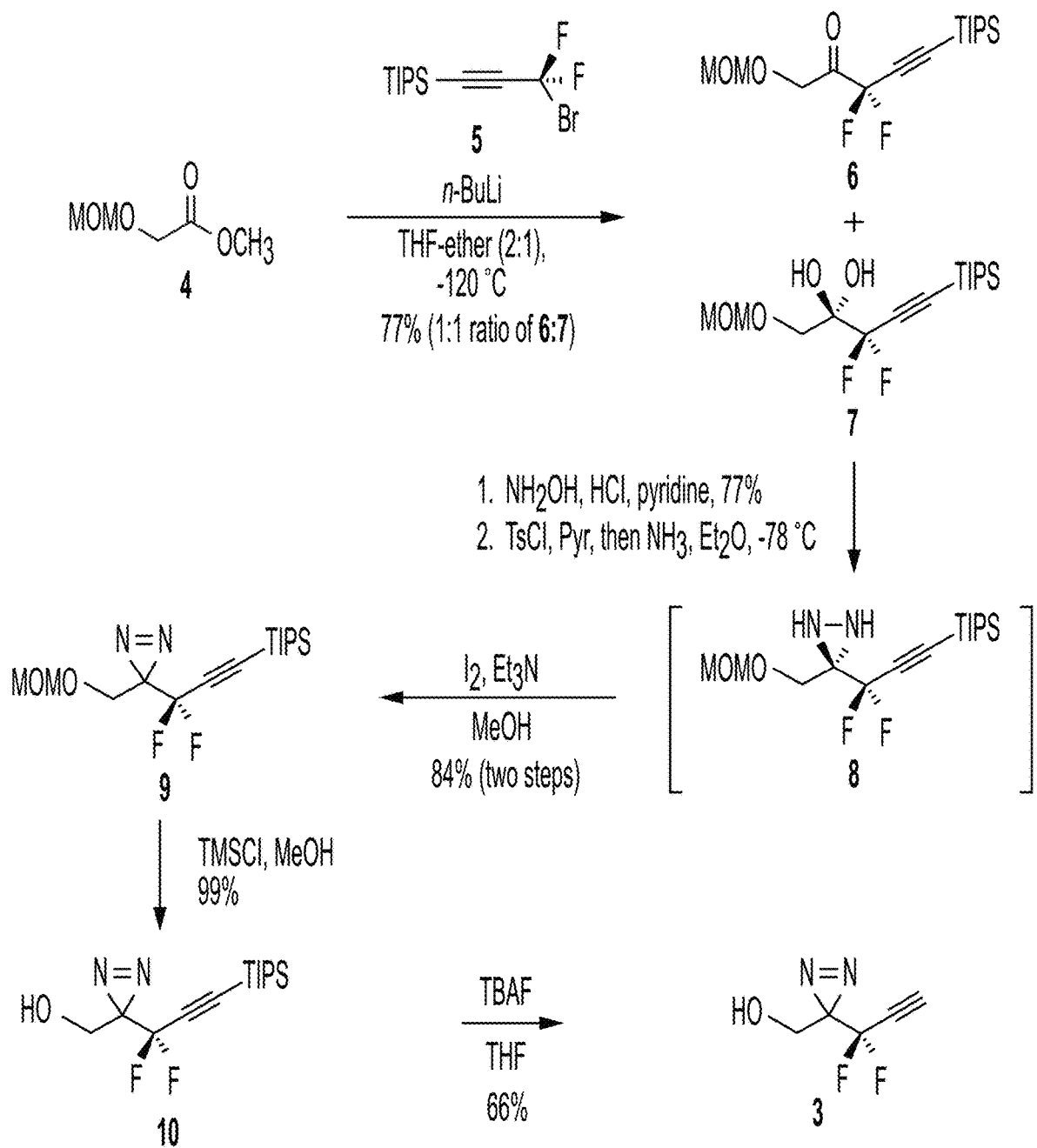
FIG. 29 shows the synthetic scheme used for the synthesis of MI-PAL (3) from the ester 4 and the alkyne 5.

Synthesis of MI-PAL (3) commenced from the ester 4 and the monobromodifluoroalkyne 5 (FIG. 29). The nucleophilic addition of the monobromodifluoroalkyne 5 to the alphahydroxyethyl ester 4 afforded the desired difluoroketone 6 and the hydrate 7 in 77% yield as a 1:1 mixture. The hydrate 7 was formed in situ due to the electrophilicity of the difluoropropyne. A brief investigation of the scope of the initial coupling step revealed that the desired reaction was promoted by the methoxymethyl ester forming a lithium chelate complex preventing collapse to the ketone at low temperatures. The equimolar mixture of ketone 6 and hydrate 7 was then treated with hydroxylamine, followed by a sequence of tosylchloride in pyridine and ammonia in ether to install the diaziridine 8. Elaboration of the ketone 6 to the diaziridine 8 was enabled by the difluoropropyne protected with triisopropylsilane (TIPS) to prevent undesired nucleophilic or deprotonation pathways promoted by basic ammonia. Oxidation (iodine, trimethylamine) of the diaziridine 8 afforded the diazirine 9 in 65% overall yield from the mixture of 6 and 7. Acid deprotection (TMSCI, MeOH) of the diazirine 9 revealed the alcohol 10 (99%). The alcohol 10 could be further desilylated to yield MI-PAL (3) itself (66%). However, we found that MI-PAL (3) was relatively volatile (boiling point=86° C.) and thus in practice rarely removed the TIPS protecting group until after incorporation of MI-PAL (3) to a small molecule of interest. The advanced alcohol intermediate 10 was thus prepared by a four-step sequence in high overall yields (49% overall).

Figure 30A:
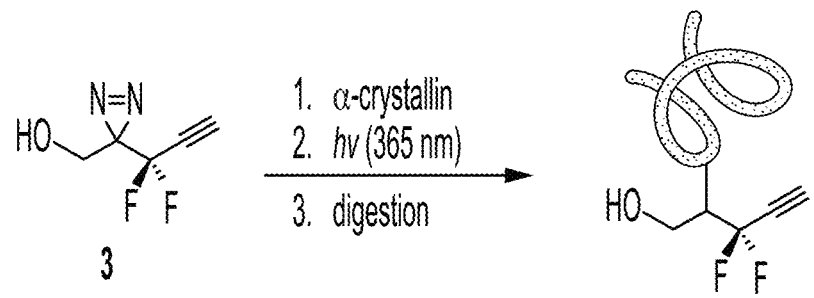
FIGS. 30A-C show photo-conjugation and CuAAC with MI-PAL (3) to the proteome.
Figure 30B:
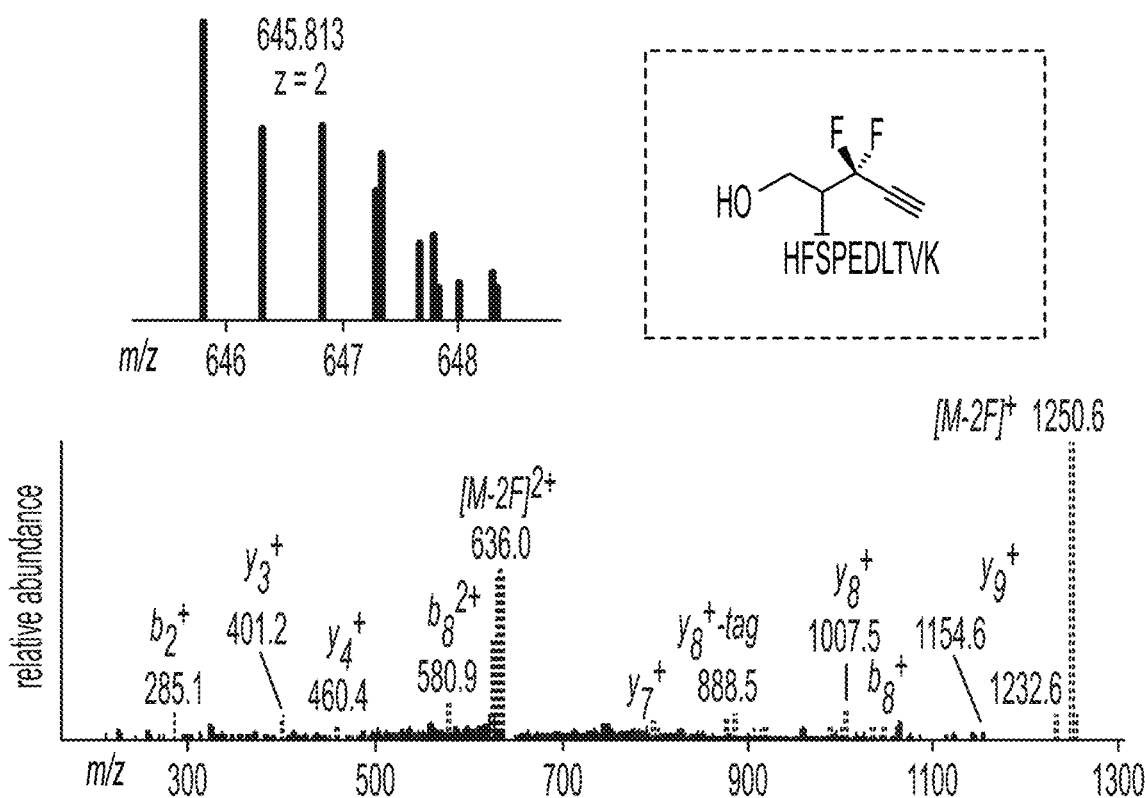
Figure 30C:
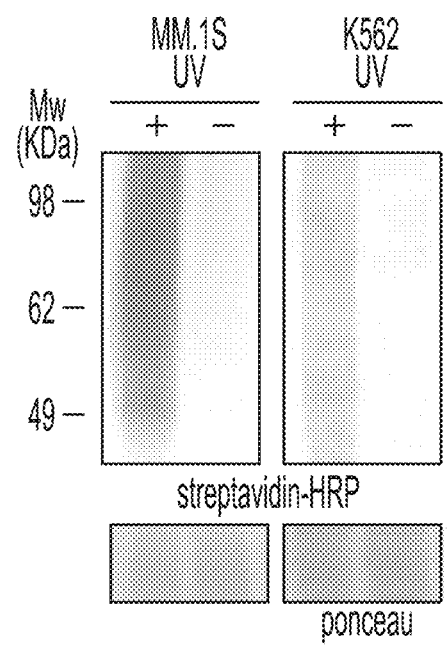

With MI-PAL (3) in hand, we next evaluated the photochemical and CuAAC properties by bmass spectrometry and Western blot. MI-PAL (3, 10 µM) was incubated with an isolated protein, alpha-crystallin, and photo-irradiated (365 nm) for 15 minutes (FIG. 30A). The conjugated protein was trypsin digested and analyzed by liquid chromatography-tandem mass spectrometry on an Orbitrap Elite by collision induced dissociation (CID). Tandem mass spectra of MI-PAL (3) conjugated-peptides obtained by CID displayed characteristic alkyl fluorine ion losses as diagnostic markers.[19] An example peptide conjugated to MI-PAL (3) is shown in FIG. 30B. To test both photo-conjugation and CuAAC properties, 100 µM of MI-PAL (3) was incubated with MM.1S or K562 whole cell lysates and photo-irradiated (30 minutes). The MI-PAL photo-conjugated lysates were treated by CuAAC with biotin-azide as a reporter and visualized by Western blot. A UV-specific signal due to biotinylation from samples photo-conjugated to MIPAL (3) was observed (FIG. 30C).

Figure 31:
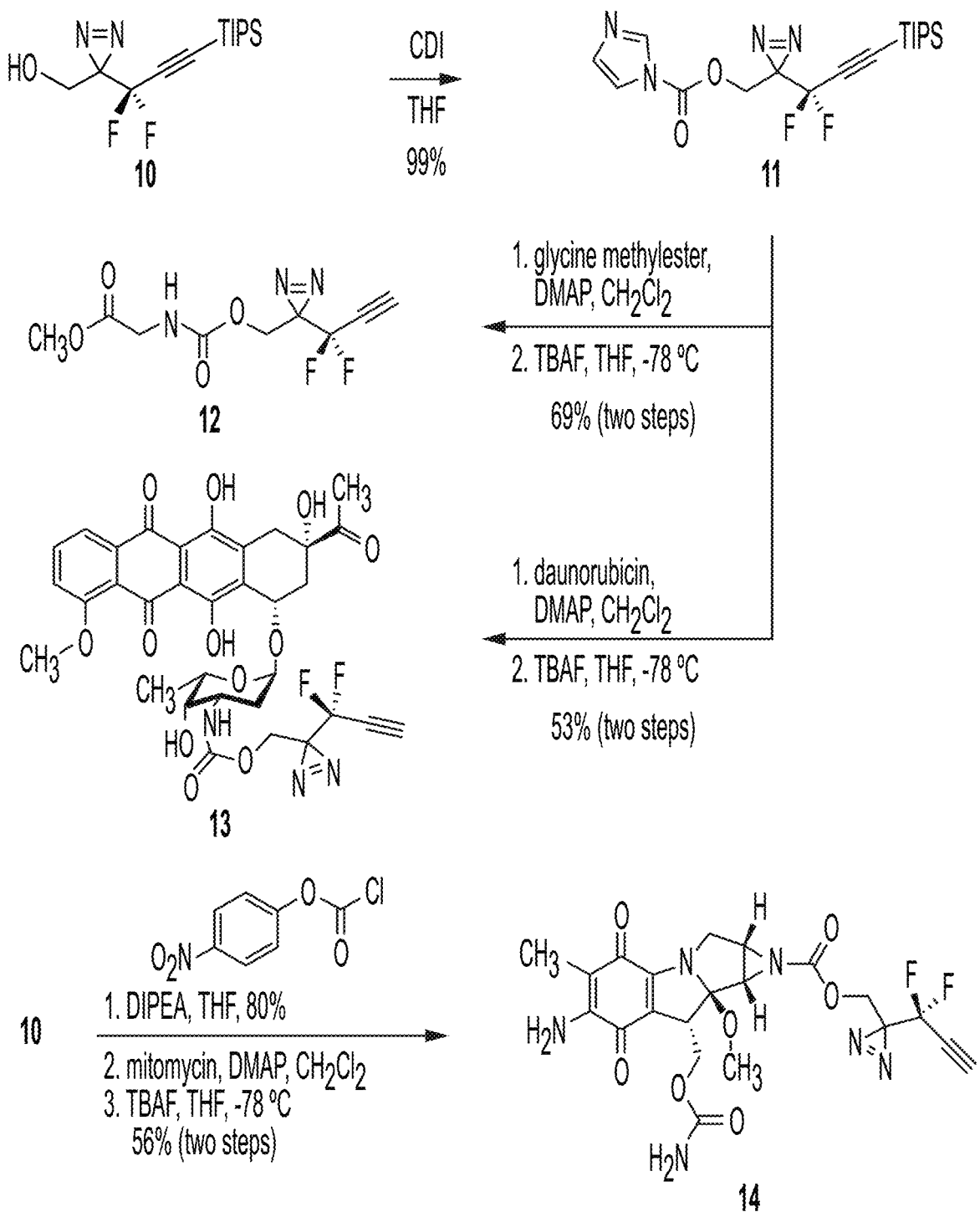
FIG. 31 shows the synthetic scheme used for the synthesis of the MI-PAL-tagged glycine methylester 12, the MI-PAL-tagged daunorubicin 13, and the MI-PAL-tagged mitomycin 14.
Figure 32:
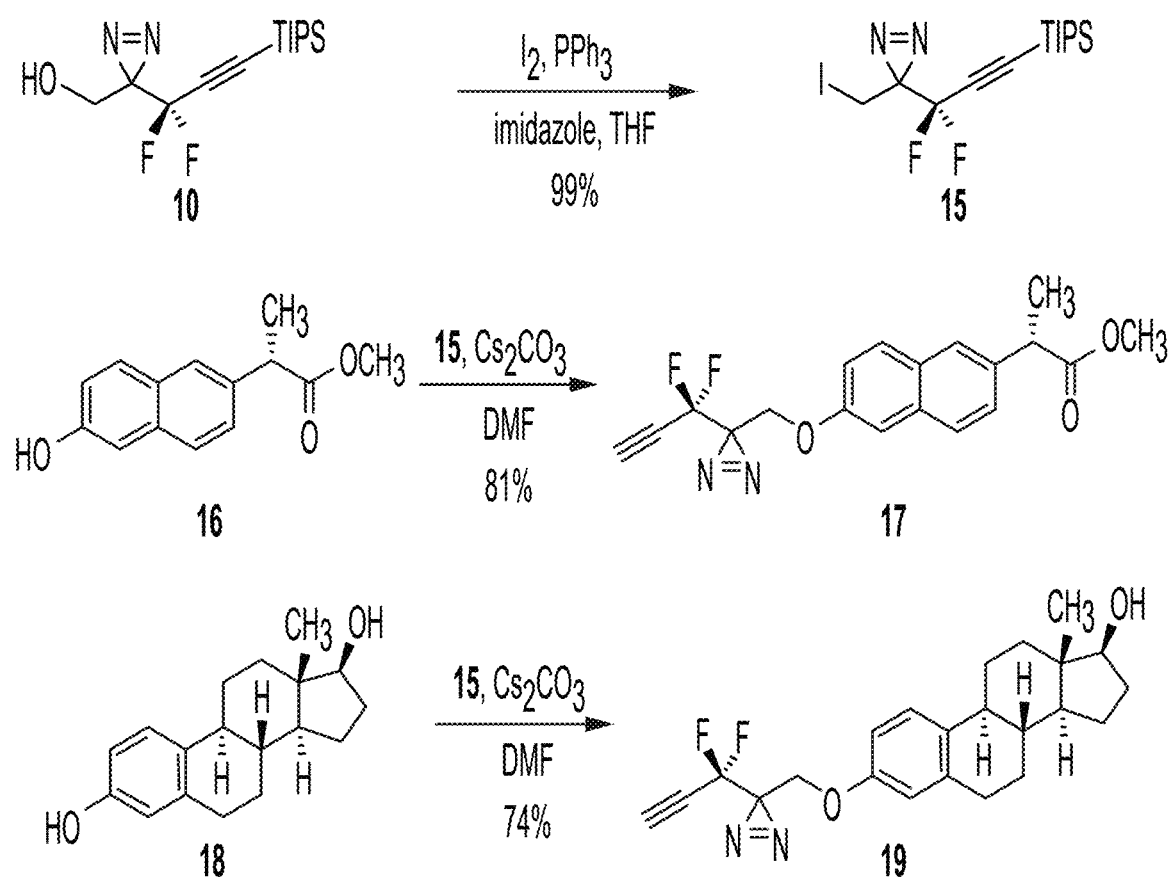
FIG. 32 shows the synthetic scheme used for the synthesis of the MI-PAL-tagged naproxen analog 16 and the MI-PAL-tagged β-estradiol 17 from the iodide 15.

MI-PAL (3) was readily incorporated to a range of small molecules (FIGS. 31 and 32). The alcohol 10 was activated with carbonyldiimidazole (CDI) in quantitative yield to afford the carbamate 11 (FIG. 31). The carbamate 11 was treated with several coupling partners of increasing complexity followed by removal of the TIPS protecting group to reveal the terminal alkyne. The MI-PAL-tagged glycine methylester 12 was formed in 69% yield over two steps. Daunorubicin was readily modified by the carbamate 11 to afford the MI-PAL-tagged daunorubicin 13 in 53% yield over two steps. The alcohol 10 was additionally activated with 4-nitrophenyl chloroformate and installed to mitomycin to prepare the tagged mitomycin analog 14. In all cases, desilylation with TBAF proceeded smoothly following conjugation of MI-PAL to a small molecule. Mitomycin and the MI-PAL-tagged mitomycin 14 displayed similar anti-proliferative activity against K562 cells ($EC_{50}$=34.9 µM and 40.6 µM, respectively).

We additionally tested the participation of MI-PAL in direct $S_N2$ displacement to modify small molecule ligands (FIG. 32). The alcohol 10 was transformed to the iodide 15 in the presence of iodine and triphenylphosphine in excellent yield (99%). The iodide 15 was then elaborated to the naproxen analog 16 in the presence of cesium carbonate in N,N-dimethylformamide. In situ deprotection of the alkyne by cesium carbonate afforded the MI-PAL-tagged naproxen analog 17 in 81% yield. Mixtures of the iodide 15 and cesium carbonate with β-estradiol (18) additionally provided the MI-PAL-tagged β-estradiol 19 in 74% yield. Thus, MI-PAL is readily functionalized to a range of complex ligands to accelerate target identification.

Characterization of the small molecule interactome is dramatically accelerated by chemical tags that enable measurement of the non-covalent interaction between the ligand and its biomolecular targets. Integration of photo-activatable functional groups with a handle for CuAAC in a short chemical tag is arguably the most likely to preserve the native interactions of the small molecule with the protein targets, although the design of a reporter for a small molecule will be structure-dependent. Functional assays to compare the modified small molecule to the parent compound are necessary to validate the preservation of biological activity, including phenotype assays (e.g., cell viability) or in vitro binding assays if the target is known (e.g., fluorescence polarization, SPR, or ITC). Reported herein is the development of an electronically-tuned five carbon tag 3 as a novel minimally-interfering photo-affinity label. MIPAL (3) possesses a diazirine appended directly to a difluoropropyne that enables facile synthetic access to the tag and its essential functions in photo-conjugation and CuAAC. We demonstrated the photo-conjugation with a single protein and whole proteome, UV-dependent CuAAC with a biotin-azide reporter, and measurement by mass spectrometry, as well as incorporation of MI-PAL (3) into several complex small molecules. MI-PAL (3) thus constitutes a small electronically-tuned alkyl diazirine alkyne tag for application in non-covalent ligand target identification studies

REFERENCES

1. Flaxman, H. A.; Woo, C. M. Biochemistry 2017.
2. Ziegler, S.; Pries, V.; Hedberg, C.; Waldmann, H. Angew Chem Int Ed 2013, 52, 2744-2792.
3. Hatanaka, Y. Chem Pharm Bull (Tokyo) 2015, 63, 1-12.
4. Mackinnon, A. L.; Taunton, J. Curr Protoc Chem Biol 2009, 1, 55-73.
5. Korneev, S. M. Eur J Org Chem 2011, 2011, 6153-6175.
6. Das, J. Chem Rev 2011, 111, 4405-17.
7. Dubinsky, L.; Krom, B. P.; Meijler, M. M. Bioorg Med Chem 2012, 20, 554-70.
8. Moss, R. A. Acc Chem Res 2006, 39, 267-272.
9. Kumar, N. S.; Young, R. N. Bioorg Med Chem 2009, 17, 5388-95.
10. Li, Z.; Hao, P.; Li, L.; Tan, C. Y. J.; Cheng, X.; Chen. G. Y. J.; Sze, S. K.; Shen, H.-M.; Yao, S. Q. Angew Chem Int Ed 2013, 52, 8551-8556.
11. Su, Y.; Pan, S.; Li, Z.; Li, L.; Wu, X.; Hao, P.; Sze, S. K.; Yao, S. Q. Sci Rep 2015, 5, 7724.
12. Pan, S.; Jang, S.-Y.; Wang, D.; Liew, S. S.; Li, Z.; Lee, J.-S.; Yao, S. Q. Angew Chem 2017, 129, 11978-11983.
13. Parker, C. G.; Galmozzi, A.; Wang, Y.; Correia, B. E.; Sasaki, K.; Joslyn, C. M.; Kim, A. S.; Cavallaro, C. L.; Lawrence, R. M.; Johnson, S. R.; Narvaiza, I.; Saez, E.; Cravatt, B. F. Cell 2017, 168, 527-541.e29.
14. Gao, J.; Mfuh, A.; Amako, Y.; Woo, C. M. Manuscript under review 2018.
15. The longest linear distance were measured in Gaussian 16 from structures minimized with the Hartree Fock basis set 6-31g(d).
16. Brunner, J.; Senn, H.; Richards, F. M. J Biol Chem 1980, 255, 3313-3318.
17. Baskin, J. M.; Prescher, J. A.; Laughlin, S. T.; Agard, N. J.; Chang, P. V.; Miller, I. A.; Lo, A.; Codelli, J. A.; Bertozzi, C. R. Proc Natl Acad Sci 2007, 104, 16793-16797.
18. Grée, D.; Grée, R. Tet Lett 2010, 51, 2218-2221.
19. Lau, K. S.; Sadilek, M.; Khalil, G. E.; Gouterman, M.; Bruckner, C. J Am Soc Mass Spectrom 2005, 16, 1915-20.

EQUIVALENTS AND SCOPE

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

Section headings used herein are not to be construed as limiting in any way. It is expressly contemplated that subject matter presented under any section heading may be applicable to any aspect or embodiment described herein.

LENGTHY TABLES

The patent contains a lengthy table section. A copy of the table is available in electronic form from the USPTO web site (https://seqdata.uspto.gov/?pageRequest=docDetail&DocID=US11912664B2). An electronic copy of the table will also be available from the USPTO upon request and payment of the fee set forth in 37 CFR 1.19(b)(3).

What is claimed is:

1. A compound of Formula (I):

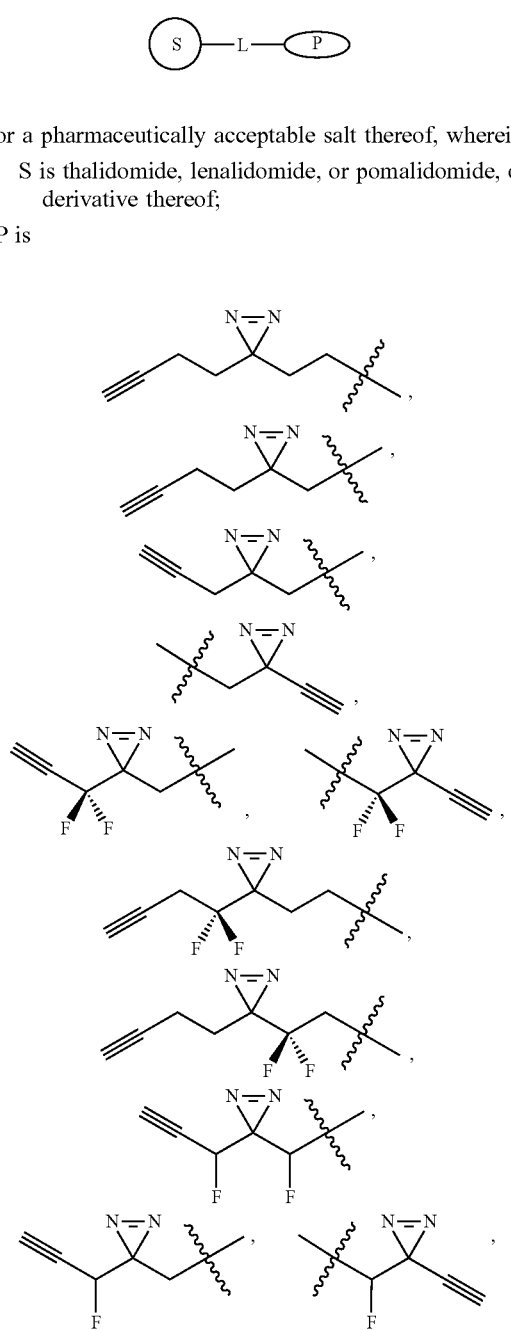

or a pharmaceutically acceptable salt thereof, wherein

S is thalidomide, lenalidomide, or pomalidomide, or a derivative thereof;

P is

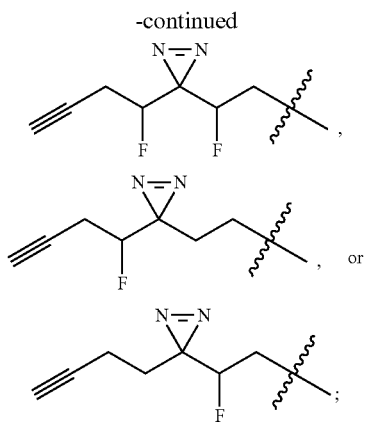

and

L is a bond,

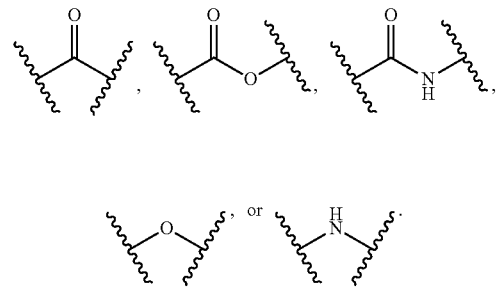

2. The compound of claim 1, or a pharmaceutically acceptable salt thereof, wherein the immunomodulatory agent is thalidomide, lenalidomide, or pomalidomide.

3. The compound of claim 1, wherein the compound is of the formula:

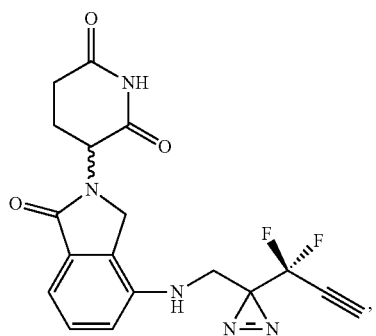

411
-continued
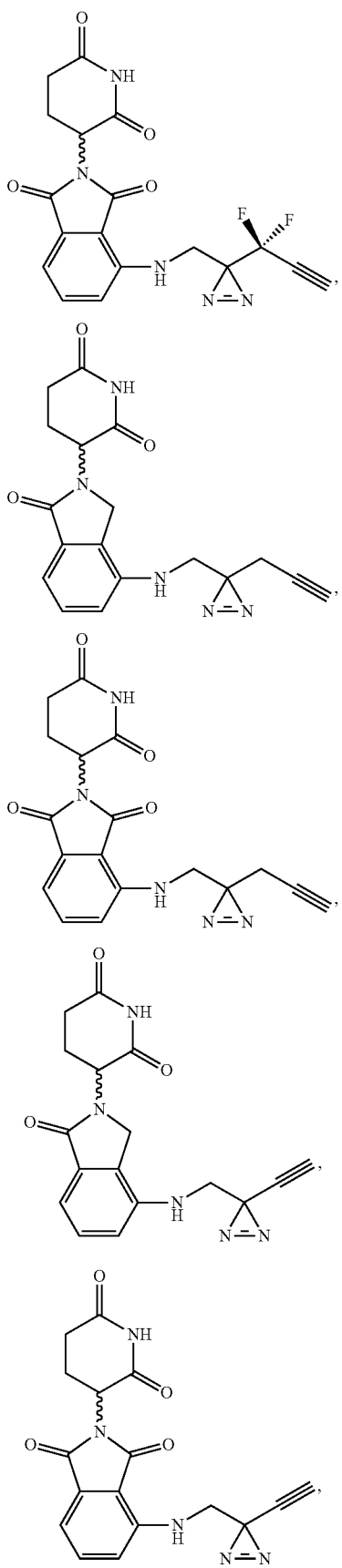
412
-continued
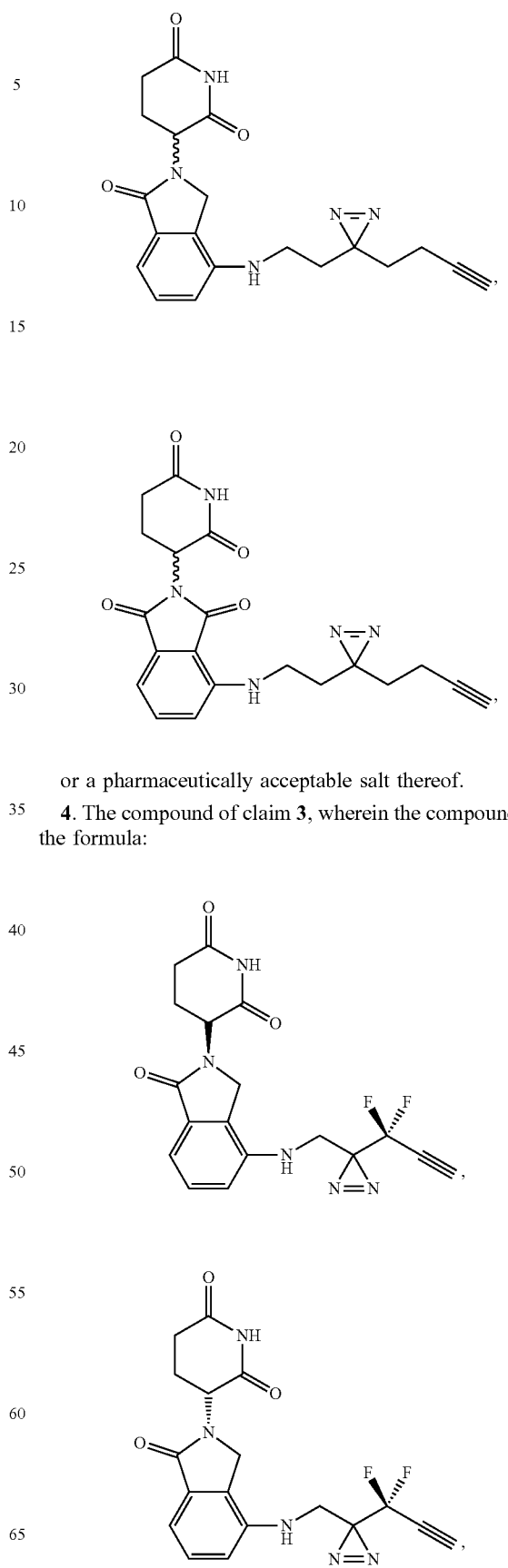
or a pharmaceutically acceptable salt thereof.
4. The compound of claim 3, wherein the compound is of the formula:

413
-continued
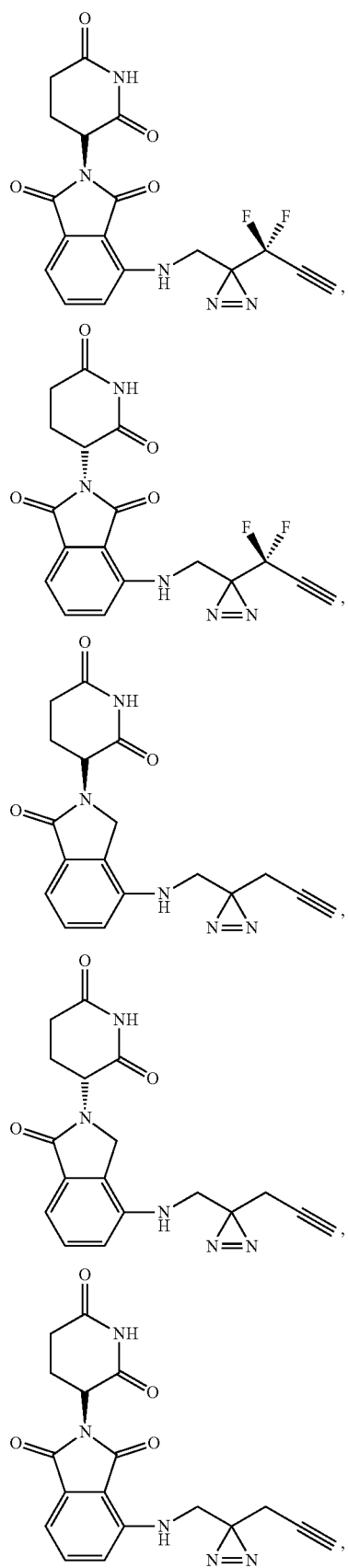
414
-continued
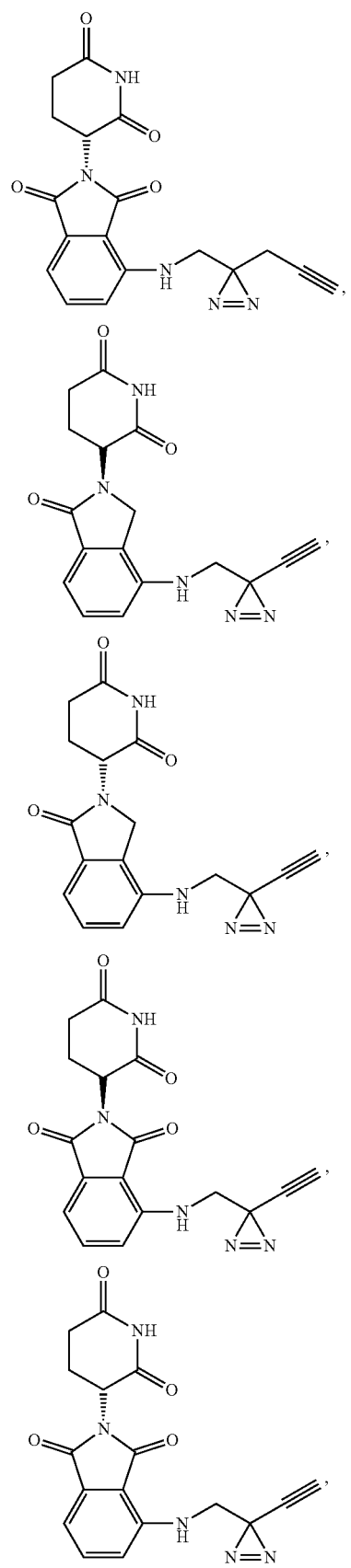

-continued

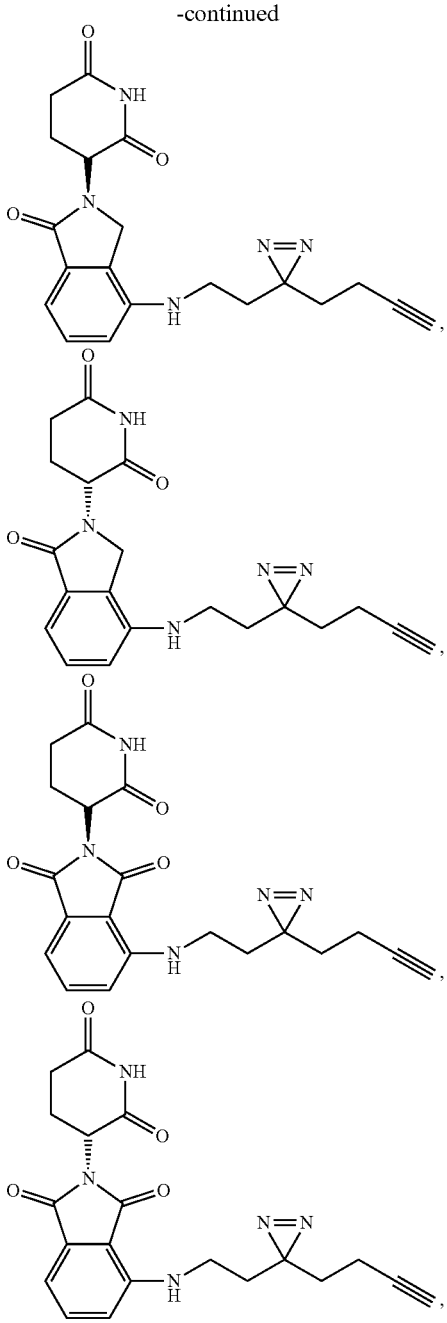

or a pharmaceutically acceptable salt thereof.

5. A method for identifying a target protein of a small molecule, the method comprising:
   (i) providing the compound of claim 1, or a pharmaceutically acceptable salt thereof;
   (ii) activating the diazirine moiety by irradiating the compound of (i) with a specific wavelength of light;
   (iii) contacting the target protein with the activated compound of (ii);
   (iv) forming a complex through a photo-induced covalent bond between the activated compound of (ii) and the protein; and
   (v) identifying the complex produced in (iv) that is bound to the compound, thereby identifying the target protein of the small molecule.

6. A method for identifying the binding site of a small molecule on a protein, the method comprising:
   (i) providing the compound of claim 1, or a pharmaceutically acceptable salt thereof;
   (ii) activating the diazirine moiety by irradiating the compound of (i) with a specific wavelength of light;
   (iii) contacting the protein with the activated compound of (ii);
   (iv) forming a complex through a photo-induced covalent bond between the activated compound of (ii) and the protein;
   (v) digesting the protein of the complex into constitutive peptides in the presence of a protease; and
   (vi) identifying the one or more peptides produced in (iv) that is bound to the compound, thereby identifying the protein binding site of the small molecule.

7. The compound of claim 1, or a pharmaceutically acceptable salt thereof, wherein L is:

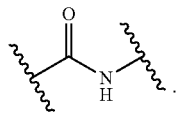

8. The compound of claim 1, or a pharmaceutically acceptable salt thereof, wherein L is

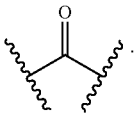 [SMILES: *C(*)=O]

9. The compound of claim 1, or a pharmaceutically acceptable salt thereof, wherein P is:

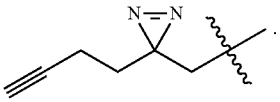 [SMILES: *CC1(CCC#C)N=N1]

10. The compound of claim 1, or a pharmaceutically acceptable salt thereof, wherein S is:

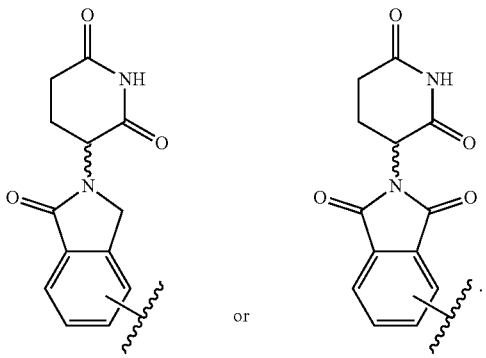

11. The compound of claim 1, or a pharmaceutically acceptable salt thereof, wherein S is:

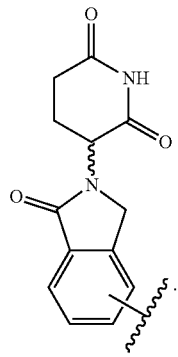

12. The compound of claim 1, or a pharmaceutically acceptable salt thereof, wherein:

L is

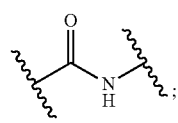

and

P is

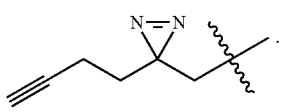 [SMILES: *CC1(CCC#C)N=N1]

13. The compound of claim 1, or a pharmaceutically acceptable salt thereof, wherein:

L is

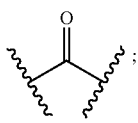

and

P is

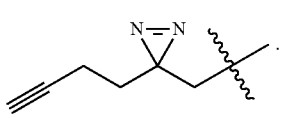 [SMILES: *CC1(CCC#C)N=N1]

14. The compound of claim 1, or a pharmaceutically acceptable salt thereof, wherein S is

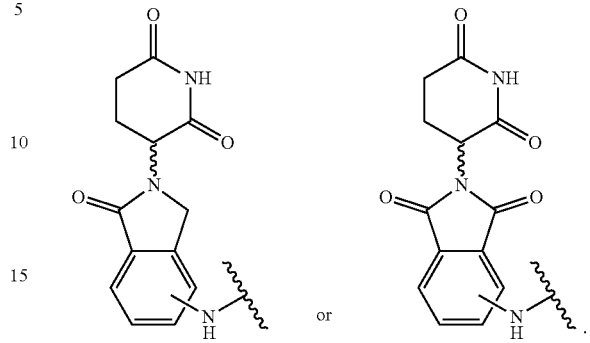

15. The compound of claim 1, or a pharmaceutically acceptable salt thereof, wherein S is

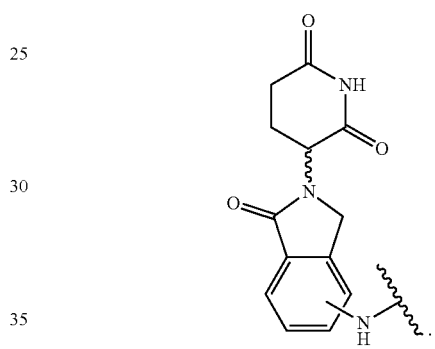

16. The compound of claim 1, or a pharmaceutically acceptable salt thereof, wherein:

S is

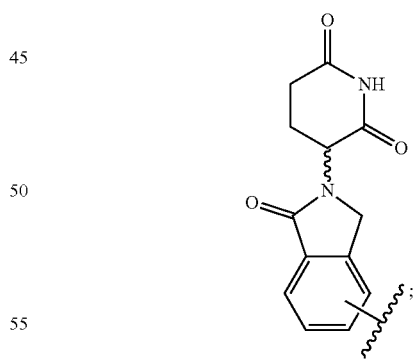

L is

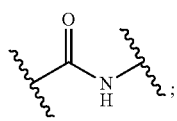

P is
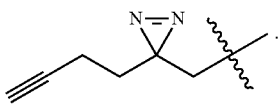 [SMILES: *CC1(CCC#C)N=N1]
17. The compound of claim 1, or a pharmaceutically acceptable salt thereof, wherein:
S is
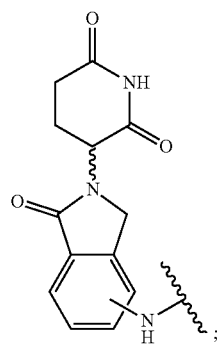
L is
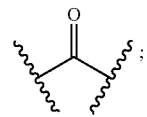 [SMILES: *C(*)=O]
and
P is
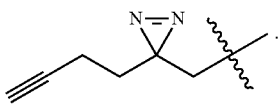 [SMILES: *CC1(CCC#C)N=N1]
* * * * *